US010100371B2

(12) United States Patent
De Framond et al.

(10) Patent No.: US 10,100,371 B2
(45) Date of Patent: *Oct. 16, 2018

(54) CORN EVENT 5307

(71) Applicant: Syngenta Participations AG, Basel (CH)

(72) Inventors: Annick Jeanne De Framond, Research Triangle Park, MO (US); Moez Rajabali Meghji, St. Louis, MO (US); Stephen L. New, Cary, NC (US); Anna Underwood Prairie, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 417 days.

This patent is subject to a terminal disclaimer.

(21) Appl. No.: 14/815,345

(22) Filed: Jul. 31, 2015

(65) Prior Publication Data

US 2015/0329922 A1 Nov. 19, 2015

Related U.S. Application Data

(62) Division of application No. 13/140,429, filed as application No. PCT/US2009/067873 on Dec. 14, 2009, now Pat. No. 9,133,474.

(60) Provisional application No. 61/122,885, filed on Dec. 16, 2008.

(51) Int. Cl.
| | | |
|---|---|---|
| C12N 15/11 | (2006.01) | |
| C12Q 1/6895 | (2018.01) | |
| C07K 14/415 | (2006.01) | |
| C12N 15/82 | (2006.01) | |

(52) U.S. Cl.
CPC .......... *C12Q 1/6895* (2013.01); *C07K 14/415* (2013.01); *C12N 15/8286* (2013.01); *Y02A 40/162* (2018.01)

(58) Field of Classification Search
None
See application file for complete search history.

(56) References Cited

U.S. PATENT DOCUMENTS

| | | | | |
|---|---|---|---|---|
| 5,495,068 A | * | 2/1996 | Foley ........................ | A01H 5/10 435/412 |
| 5,736,131 A | | 4/1998 | Bosch et al. | |
| 8,466,346 B2 | * | 6/2013 | DeFramond ......... | C07K 14/415 435/419 |
| 9,133,474 B2 | * | 9/2015 | DeFramond ......... | C07K 14/415 |
| 2006/0141495 A1 | | 6/2006 | Wu et al. | |
| 2010/0017914 A1 | | 1/2010 | Hart et al. | |

FOREIGN PATENT DOCUMENTS

| | | |
|---|---|---|
| EP | 0942985 B1 | 9/2004 |
| WO | WO9822595 | 5/1998 |
| WO | 2007/142840 A2 | 12/2007 |
| WO | WO2007142840 A2 | 12/2007 |
| WO | WO2008121633 A1 | 9/2008 |
| WO | WO2011041256 A2 | 4/2011 |

OTHER PUBLICATIONS

R. K. Wilson, Sep. 2013, GenBank Accession No. AC202955.4 (version 4), National Center for Biotechnology Information, National Institutes of Health, U.S.A.*
Fu et al 2002, Proceedings of the National Academy of Science USA 99(14): 9573-9578.*
Grimanelli et al., "Timing of the Maternal-to-Zygotic Transition during Early Seed Development in Maize," The Plant Cell, vol. 17, 1061-1072, Apr. 2005, Supplementary Table 1.
Corresponding to GenBank/EMBL Accession No. T14727 [Retrieved from the internet Oct. 18, 2013: in entirety, 59 pp.
Genbank AC202540.4. Zea mays chromosome 3 clone ZMMBBb-133C10; ZMMBBb0133c10, * Sequencing in Progress *, 4 unordered pieces. Jun. 27, 2008. [Retrieved from the internet Oct. 5, 2011. in entirety.
Genbank AC208695.3. Zea mays chromosome 4 clone ZMMBBb-318B2; ZMMBBb0318B02, * Sequencing in Progress *, 4 unordered pieces. Jun. 27, 2008 [Retrieved from the internet Oct. 5, 2011: in entirety.
Song, Rentao and Messing, Joachim, Gene expression of a gene family in maize based on noncollinear haplotypes, Proceedings of the National Academy of Sciences of the United States of America (PNAS), Jul. 22, 2003, vol. 100, No. 15, pp. 9055-9060, ISSN: 0027-8424.
Genbank AC125584.2. Rattus norvegicus cloe CH230-1F2. 9Oc2002. [Retrieved from the internet Apr. 6, 2010: in entirety.
GenBank. Accession AC125584. 2002.

\* cited by examiner

*Primary Examiner* — David H Kruse
(74) *Attorney, Agent, or Firm* — Karen A. Magri

(57) ABSTRACT

A novel transgenic corn event designated 5307, is disclosed. The invention relates to DNA sequences of the recombinant constructs inserted into the corn genome and of genomic sequences flanking the insertion site that resulted in the 5307 event. The invention further relates to assays for detecting the presence of the DNA sequences of event 5307, to corn plants and corn seeds comprising the genotype of and to methods for producing a corn plant by crossing a corn plant comprising the event 5307 genotype with itself or another corn variety.

6 Claims, 2 Drawing Sheets

Specification includes a Sequence Listing.

Plasmid map of pSYN12274.

Insert map of Event 5307.

CORN EVENT 5307

This application is a divisional of, and claims priority to U.S. patent application Ser. No. 13/140,429 filed Jun. 16, 2011, which is a national stage filing under 35 U.S.C. § 371 of International Application No. PCT/US2009/67873, filed Dec. 14, 2009 and published Jul. 8, 2010 as WO 2010/077816, which claims the benefit of U.S. Provisional Application Ser. No. 61/122,885, filed Dec. 16, 2008, the contents of each of which are incorporated herein by reference in their entireties.

STATEMENT REGARDING ELECTRONIC SUBMISSION OF A SEQUENCE LISTING

A substitute sequence listing in ASCII text format, submitted under 37 C.F.R. § 1.821, entitled "71922-US-REG-D-P-2_SEQ LIST_ST25.txt", 446 kB in size, generated on Mar. 21, 2018, and filed via EFS-Web is provided in lieu of a paper copy. This sequence listing is hereby incorporated by reference into the specification for its disclosures.

FIELD OF THE INVENTION

The invention relates generally to the field of plant molecular biology, plant transformation, and plant breeding. More specifically, the invention relates to insect resistant transgenic corn plants comprising a novel transgenic genotype and to methods of detecting the presence of the corn plant DNA in a sample and compositions thereof.

BACKGROUND

Plant pests are a major factor in the loss of the world's important agricultural crops. About $8 billion are lost every year in the U.S. alone due to infestations of non-mammalian pests including insects. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

The expression of foreign genes in plants can to be influenced by their chromosomal position, perhaps due to chromatin structure or the proximity of transcriptional regulation elements close to the integration site (See for example, Weising et al., 1988, "Foreign Genes in Plants," Ann. Rev. Genet. 22:421-477). Therefore, it is common to produce hundreds of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

The invention includes an insect resistant transgenic corn event that has incorporated into its genome a FR8a gene, disclosed in International Publication No. WO 08/121633, published Oct. 9, 2008, which is herein incorporated by reference, encoding a FR8a insecticidal toxin, useful in controlling *Diabrotica* spp. insect pests. The transgenic corn event also has incorporated in its genome a PMI gene, encoding a phosphomannose isomerase enzyme (PMI), disclosed in U.S. Pat. No. 5,767,378, which is herein incorporated by reference, useful as a selectable marker, which allows the plant to utilize mannose as a carbon source. The invention further includes novel isolated nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample.

SUMMARY

The invention is drawn to a transgenic corn event, designated 5307, comprising a novel transgenic genotype that comprises a FR8a gene and a PMI gene which confers insect resistance and the ability to utilize mannose as a carbon source, respectively, to the 5307 corn event and progeny thereof. The invention also provides transgenic corn plants comprising the genotype of the invention, seed from transgenic corn plants comprising the genotype of the invention, and to methods for producing a transgenic corn plant comprising the genotype of the invention by crossing a corn inbred comprising the genotype of the invention with itself or another corn line of a different genotype. The transgenic corn plants of the invention may have essentially all of the morphological and physiological characteristics of the corresponding isogenic non-transgenic corn plant in addition to those conferred upon the corn plant by the novel genotype of the invention. The invention also provides compositions and methods for detecting the presence of nucleic acids from event 5307 based on the DNA sequence of the recombinant expression cassettes inserted into the corn genome that resulted in the 5307 event and of genomic sequences flanking the insertion site. The 5307 event can be further characterized by analyzing expression levels of FR8a and PMI proteins as well as by testing efficacy against corn rootworm.

According to one aspect, the invention provides a preferably isolated nucleic acid molecule comprising at least 10 contiguous nucleotides of a heterologous DNA sequence inserted into the corn plant genome of corn event 5307 and at least 10 contiguous nucleotides of a corn plant genome DNA flanking the point of insertion of a heterologous DNA sequence inserted into the corn plant genome of corn event 5307. The preferably isolated nucleic acid molecule according to this aspect may comprise at least 20 or at least 50 contiguous nucleotides of a heterologous DNA sequence inserted into the corn plant genome of corn event 5307 and at least 20 or at least 50 contiguous nucleotides of a corn plant genome DNA flanking the point of insertion of a heterologous DNA sequence inserted into the corn plant genome of corn event 5307.

According to another aspect, the invention provides a preferably isolated nucleic acid molecule comprising at least one junction sequence of event 5307 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the 5307 event.

According to another aspect, the invention provides a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and complements thereof.

According to another aspect, the invention provides a preferably isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting event 5307 are provided. Such flanking sequence primers comprise a preferably isolated nucleic acid sequence comprising at least 10-15 contiguous nucleotides from nucleotides 1-1348 as set forth in SEQ ID NO: 5 (arbitrarily designated herein as the 5' flanking sequence), or the complements thereof, also disclosed as SEQ ID NO: 111. In one embodiment of this aspect the flanking sequence primers are selected from the group consisting of SEQ ID NO: 9 through SEQ ID NO: 14, and complements thereof.

In another aspect of the invention, the flanking sequences primers comprise a preferably isolated nucleic acid sequence comprising at least 10-15 contiguous nucleotides from nucleotides 1-1093 as set forth in SEQ ID NO: 6 (arbitrarily designated herein as the 3' flanking sequence), or the complements thereof. In one embodiment of this aspect the flanking sequence primers are selected from the group consisting of SEQ ID NO: 69 through SEQ ID NO: 72, and complements thereof.

According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 5, or SEQ ID NO: 6) and a second primer comprising a nucleotide sequence of at least 10-15 contiguous nucleotides of heterologous DNA inserted into the event 5307 genome. The second primer preferably comprises a nucleotide sequence which is or is complementary to the insert sequence adjacent to the plant genomic flanking DNA sequence as set forth in SEQ ID NO: 7. In one embodiment of this aspect the insert sequence primers are selected from the group consisting of SEQ ID NO: 15 through SEQ ID NO: 68, and complements thereof.

According to another aspect of the invention, methods of detecting the presence of DNA corresponding to event 5307 in a biological sample are provided. Such methods comprise: (a) contacting the sample comprising DNA with a pair of primers that, when used in a nucleic acid amplification reaction with genomic DNA from corn event 5307; produces an amplicon that is diagnostic for corn event 5307; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, and complements thereof.

According to another aspect, the invention provides methods of detecting the presence of a DNA corresponding to the 5307 event in a biological sample. Such methods comprise: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. The detected hybridized DNA sequence includes at least one ploynucleotide sequence comprising SEQ ID NO: 1, SEQ ID NO: 2, SEQ ID NO: 3, SEQ ID NO: 4, SEQ ID NO: 5, SEQ ID NO: 6, and complements thereof.

According to another aspect of the invention, a kit is provided for the detection of event 5307 nucleic acids in a biological sample. The kit includes at least one DNA sequence comprising a sufficient length of polynucleotides which is or is complementary to SEQ ID NO: 1, SEQ ID NO: 2, SEQ ID NO: 3, SEQ ID NO: 4, SEQ ID NO: 5 or SEQ ID NO: 6, wherein the DNA sequences are useful as primers or probes that hybridize to isolated DNA from event 5307, and which, upon amplification of or hybridization to a nucleic acid sequence in a sample followed by detection of the amplicon or hybridization to the target sequence, are diagnostic for the presence of nucleic acid sequences from event 5307 in the sample. The kit further includes other materials necessary to enable nucleic acid hybridization or amplification methods.

In another aspect, the invention provides a method of detecting corn event 5307 protein in a biological sample comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

In another aspect, the invention provides a biological sample derived from a event 5307 corn plant, tissue, or seed, wherein the sample comprises a nucleic acid comprising a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the invention provides an extract derived from a event 5307 corn plant, tissue, or seed comprising a nucleotide sequence which is or is complementary to a nucleotide sequence selected from the group consisting of SEQ ID NO: 1 and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided. In one embodiment of the invention, a deposit of event 5307 corn seed was made to the American Type Culture Collection (ATCC) in accordance with the Budapest Treaty on 15 Oct. 2008. An example of said seed being deposited as ATCC Accession No: PTA-9561.

According to another aspect, the invention provides a method for producing a corn plant resistant to at least corn rootworm infestation comprising: (a) sexually crossing a first parent corn plant with a second parent corn plant, wherein first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO: 3 and SEQ ID NO: 4.

According to yet another aspect, the invention provides a method for producing corn seed comprising crossing a first parent corn plant with a second parent corn plant and harvesting the resultant first generation corn seed, wherein the first or second parent corn plant is an inbred corn plant of the invention.

According to another aspect, the invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

According to another aspect of the invention, the invention provides a method of selecting corn plants and seeds comprising the nucleic acid molecules of event 5307 on chromosome 5. In one embodiment of the invention, polymorphic markers are used to select or track the sequences specific to the 5307 corn event. The invention provides a method of selecting sequences specific to the 5307 corn event comprising the steps of: (a) detecting a polymorphic marker sequence; (b) designing an assay for the purposes of detecting the marker; (c) running the assay on corn nucleic acid sequences from many corn lines, and (d) selecting corn lines based upon the sequences with nucleotides specific to corn event 5307.

According to another aspect of the invention, the invention provides a site on chromosome 5 for targeted integration of a heterologous nucleic acid. The invention provides a method of selecting sequences specific to the 5307 corn event for targeted integration comprising the steps of: (a) designing homologous sequences based on the insertion site or vector sequence; (b) using these homologous sequences at a target locus; (c) using zinc finger nucleases to create a break in the target locus, and (d) inserting a heterologous donor molecule within nucleotides specific to corn event 5307 or the vector sequence of pSYN12274. An example of this technique is demonstrated in Shukla et al. (Nature vol. 459, 21 May 2009).

The foregoing and other aspects of the invention will become more apparent from the following detailed description.

DESCRIPTION OF THE SEQUENCES IN THE SEQUENCE LISTING

SEQ ID NO: 1 is the 5' genome–insert junction.
SEQ ID NO: 2 is the 3' insert–genome junction.
SEQ ID NO: 3 is the 5' genome+insert sequence.
SEQ ID NO: 4 is the 3' insert+genome sequence.
SEQ ID NO: 5 is the 5' genome+insert sequence.
SEQ ID NO: 6 is the 3' corn genome flanking sequence.
SEQ ID NO: 7 is the event 5307 full length insert.
SEQ ID Nos: 8-14 are 5' flanking sequence primers useful in the invention.
SEQ ID Nos: 15-68 are 5307 transgene insert primers useful in the invention.
SEQ ID Nos: 69-72 are 3' flanking sequence primers useful in the invention.
SEQ ID Nos: 73-75 are FR8a TAQMAN primers and probe.
SEQ ID Nos: 76-78 are PMI TAQMAN primers and probe.
SEQ ID Nos: 79-81 are ZmAdh TAQMAN primers and probe.
SEQ ID Nos: 82-90 are 5307 event specific primers and probes useful in the invention.
SEQ ID Nos: 91-102 are corn genomic primers and probes useful in the invention.
SEQ ID NO: 103 is the AC202955 Chromosome 5 Sequence, where N is any base "A", "T", "G" or "C".
SEQ ID NO: 104 is the umc1475 marker region.
SEQ ID Nos: 105-106 are umc1475 primers.
SEQ ID NO: 107 is the uaz190 marker region.
SEQ ID NOs: 108-109 are uaz190 primers
SEQ ID NO: 110 is the reverse complement of SEQ ID NO: 103, AC202955 Chromosome 5 Sequence, where N is any base "A", "T", "G" or "C".
SEQ ID NO: 111 is the 5' corn genome flanking sequence.

DEFINITIONS

Figure 1:
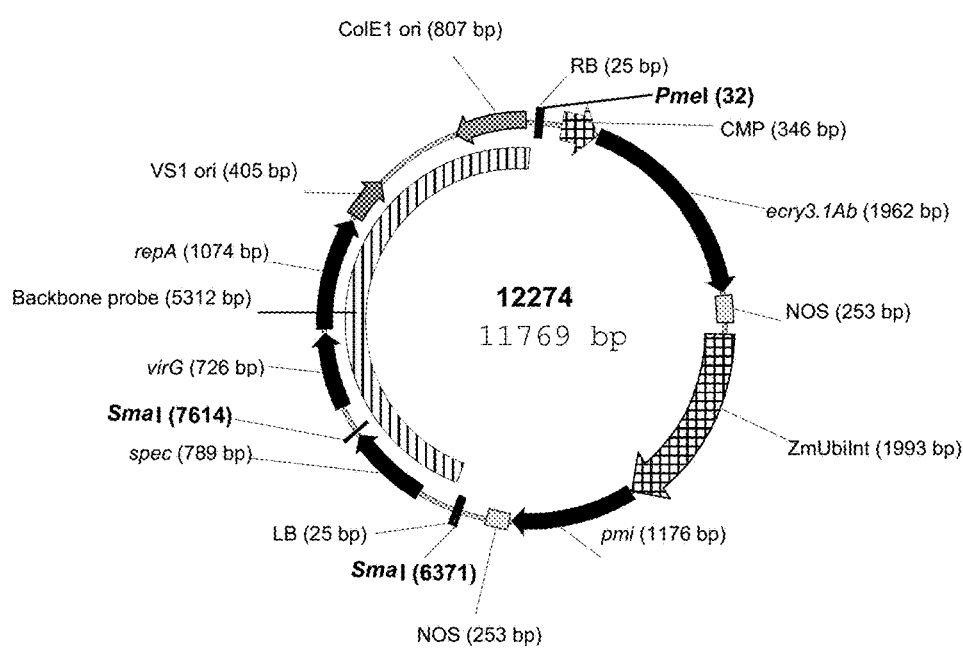
FIG. 1 illustrates a plant expression vector designated pSYN12274. The plasmid map identifies the SmaI and PmeI restriction sites used for Southern analysis.
Figure 2:
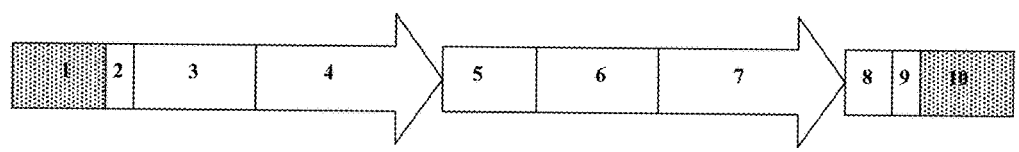
FIG. 2 is a graphical map illustrating the organization of the elements comprising the heterologous nucleic acid sequences inserted into the genome of corn to create event 5307 and sets forth the relative positions at which the inserted nucleic acid sequences are linked to corn genomic DNA sequences which flank the ends of the inserted heterologous DNA sequences. 1=5' flanking plant genome (SEQ ID NO: 5); 2=right border region; 3=CMP promoter; 4=FR8a gene; 5=NOS terminator; 6=ZmUbINT promoter; 7=PMI gene; 8=NOS terminator; 9=left border region (sections 2 through 9 are contained within SEQ ID NO: 7); and 10=3' flanking plant genome (SEQ ID NO: 6).

The following definitions and methods are provided to better define the invention and to guide those of ordinary skill in the art in the practice of the invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

A "biological sample" is a plant, plant material or products comprising plant material. The term "plant" is intended to encompass corn (*Zea mays*) plant tissues, at any stage of maturity, as well as cells, tissues, organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the invention, such biological sample are tested for the presence of nucleic acids specific to corn event 5307, implying the presence of nucleic acids in the samples. Thus, the methods referred to herein for identifying corn event 5307 in biological samples, relate to the identification in biological samples of nucleic acids which from an event 5307 corn plant and are diagnostic for event 5307.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Detection kit" as used herein refers to a kit used to detect the presence or absence of DNA from event 5307 cornplants in a sample comprising nucleic acid probes and primers of the invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event 5307", "5307 event" or "5307" as used herein, means the original 5307 transformant and/or progeny of the 5307 transformant, including any plant derived therefrom.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent corn plants not all of which is necessarily expressed in the descendant corn plants. The 5307 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

The term "isolated" when used in relation to a nucleic acid refers to a nucleic acid sequence that is identified and separated from at least one contaminant nucleic acid with which it is ordinarily associated in its natural source. An isolated nucleic acid is present in a form or setting that is different from that in which it is found in nature. In contrast, a non-isolated nucleic acids such as DNA and RNA found in the state they exist in nature. An isolated nucleic acid may be in a transgenic plant and still be considered "isolated".

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the invention, to a strand of genomic DNA from corn event, M5307. The genomic DNA of event 5307 can be from a corn plant or from a sample that includes DNA from the event. Probes according to the invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length, Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* ($5^{th}$ Ed. Cold Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. The sequences of the invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. § 1.822 is used herein.

DETAILED DESCRIPTION

This invention relates to a genetically improved line of corn that produces the insect control protein, FR8a, and a phosphomannose isomerase enzyme (PMI) that allows the plant to utilize mannose as a carbon source. The invention is particularly drawn to a transgenic corn event designated event 5307 comprising a novel genotype, as well as to compositions and methods for detecting nucleic acids from this event in a biological sample. The invention is further drawn to corn plants comprising the event 5307 genotype, to transgenic seed from the corn plants, and to methods for producing a corn plant comprising the event 5307 genotype by crossing a corn inbred comprising the event 5307 genotype with itself or another corn line. Corn plants comprising the event 5307 genotype of the invention are useful in controlling coleopteran insect pests including *Diabrotica virgifera virgifera*, the western corn rootworm, *D. virgifera zeae*, the Mexican corn rootworm, and *D. longicornis barberi*, the northern corn rootworm. Corn plants comprising the event 5307 genotype of the invention are also able to utilize mannose as a carbon source.

In one embodiment, the invention encompasses a transgenic corn seed of an event 5307 corn plant. An example of said seed being deposited as ATCC Accession No: PTA-9561. The transgenic seed of event 5307 comprises SEQ ID NO: 1, SEQ ID NO: 2, SEQ ID NO: 3, SEQ ID NO: 4, SEQ ID NO: 5, or SEQ ID NO: 6, and complements thereof. These sequences define a point of insertion of a heterologous DNA sequence inserted into the corn plant genome of corn event 5307. In another embodiment, the invention encompasses a preferably isolated nucleic acid molecule comprising SEQ ID NO: 1, SEQ ID NO: 2, SEQ ID NO: 3 or SEQ ID NO: 4. In another embodiment, the invention encompasses a preferably isolated nucleic acid molecule, wherein the nucleic acid molecule is comprised in a corn seed deposited as ATCC Accession No. PTA-9561

In one embodiment, the invention encompasses a nucleic acid molecule, preferably isolated, comprising at least 10 or more (for example 15, 20, 25, or 50) contiguous nucleotides of a heterologous DNA sequence inserted into the corn plant genome of corn event 5307 and at least 10 or more (for example 15, 20, 25, or 50) contiguous nucleotides of a corn plant genome DNA flanking the point of insertion of a heterologous DNA sequence inserted into the corn plant genome of corn event 5307. Also included are nucleotide sequences that comprise 10 or more nucleotides of contiguous insert sequence from event 5307 and at lease one nucleotide of flanking DNA from event 5307 adjacent to the insert sequence. Such nucleotide sequences are diagnostic for event 5307. Nucleic acid amplification of genomic DNA from the 5307 event produces an amplicon comprising such diagnostic nucleotide sequences.

In another embodiment, the invention encompasses a nucleic acid molecule, preferably isolated, comprising a nucleotide sequence which comprises at least one junction sequence of event 5307 selected from the group consisting of SEQ ID NO: 1, SEQ ID NO: 2, SEQ ID NO: 3, SEQ ID NO: 4, and complements thereof, wherein a junction sequence spans the junction between a heterologous expression cassette inserted into the corn genome and DNA from the corn genome flanking the insertion site and is diagnostic for the event.

In another embodiment, the invention encompasses a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and the complements thereof.

In another embodiment, the invention encompasses an nucleic acid molecule, preferably isolated, comprising a nucleotide sequence selected from the group consisting of SEQ ID NO: 1, SEQ ID NO: 2, SEQ ID NO: 3, SEQ ID NO: 4, and complements thereof.

In one embodiment of the invention, an amplicon comprising a nucleotide sequence selected from the group consisting of SEQ ID NO: 1, SEQ ID NO: 2, SEQ ID NO: 3, SEQ ID NO: 4, and the complements thereof is provided.

In another embodiment, the invention encompasses flanking sequence primers for detecting event 5307. Such flanking sequence primers comprise an isolated nucleic acid sequence comprising at least 10-15 contiguous nucleotides from nucleotides 1-1348 of SEQ ID NO: 5 (arbitrarily designated herein as the 5' flanking sequence), or the complements thereof, also disclosed as SEQ ID NO: 111. In one aspect of this embodiment the flanking sequence primers are selected from the group consisting of SEQ ID NO: 8 through SEQ ID NO: 14, and complements thereof. The flanking sequences can be extended to include chromosome 5 sequences, with specific emphasis on nucleotide comprised with SEQ ID NO: 103, useful in detecting sequences associated with the 5307 corn event. In the context of SEQ ID NO: 103, an "N" is defined as any base "A", "T", "G", or "C". SEQ ID NO: 110 is the reverse complement of this sequence. In the context of SEQ ID NO: 110, an "N" is defined as any base "A", "T", "G", or "C".

In another embodiment, the invention encompasses flanking sequence primers that comprise at least 10-15 contiguous nucleotides from nucleotides 1-1093 of SEQ ID NO: 6 (arbitrarily designated herein as the 3' flanking sequence), or the complements thereof. In one aspect of this embodiment the flanking sequence primers are selected from the group consisting of SEQ ID NO: 69 through SEQ ID NO: 72, and complements thereof.

In still another embodiment, the invention encompasses a pair of polynucleotide primers comprising a first polynucleotide primer and a second polynucleotide primer which function together in the presence of a corn event 5307 DNA template in a sample to produce an amplicon diagnostic for the corn event 5307, wherein the first primer sequence is or is complementary to a corn plant genome flanking the point of insertion of a heterologous DNA sequence inserted into the corn plant genome of corn event 5307, and the second polynucleotide primer sequence is or is complementary to the heterologous DNA sequence inserted into the corn plant genome of the corn event 5307.

In one aspect of this embodiment the first polynucleotide primer comprises at least 10 contiguous nucleotides from position 1-1348 of SEQ ID NO: 5 or complements thereof. In a further aspect of this embodiment, the first polynucleotide primer comprises the nucleotide sequence set forth in SEQ ID NO: 8 through SEQ ID NO: 14, or the complements thereof. In another aspect of this embodiment the first polynucleotide primer least 10 contiguous nucleotides from position 1-1093 of SEQ ID NO: 6 or complements thereof. In another aspect of this embodiment, the first polynucleotide primer comprises the nucleotide sequence set forth in SEQ ID NO: 69 through SEQ ID NO: 72, or the complements thereof. In yet another aspect of this embodiment, the second polynucleotide primer comprises at least 10 contiguous nucleotides of SEQ ID NO: 7, or the complements thereof. In still a further aspect of this embodiment, the second polynucleotide primer comprises the nucleotide sequence set forth in SEQ ID NO: 15 to SEQ ID NO: 68, or the complements thereof.

In another aspect of this embodiment, the first polynucleotide primer, which is set forth in SEQ ID NO: 8, and the second polynucleotide primer which is set forth in SEQ ID NO: 41, function together in the presence of a corn event 5307 DNA template in a sample to produce an amplicon diagnostic for the corn event 5307 as described in Example 4. In another aspect of this embodiment, the first polynucleotide primer, which is set forth in SEQ ID NO: 69, and the second polynucleotide primer which is set forth in SEQ ID NO: 72, function together in the presence of a corn event 5307 DNA template in a sample to produce an amplicon diagnostic for the corn event 5307 as described in Example 4.

It is well within the skill in the art to obtain additional sequence further out into the genome sequence flanking either end of the inserted heterologous DNA sequences for use as a primer sequence that can be used in such primer pairs for amplifying the sequences that are diagnostic for the 5307 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 3 or SEQ ID NO: 4 depending upon the nature of the product desired to be obtained through the use of the nested set of primers intended for use in amplifying a particular flanking sequence containing the junction between the genomic DNA sequence and the inserted heterologous DNA sequence. Further more, one skilled in the art would be able to design primers for a multitude of native corn genes for the purposes of designing a positive control. One such example is the corn Adh1 gene, where examples of suitable primers for producing an amplicon by nucleic acid amplification are set forth as SEQ ID NO: 79 and SEQ ID NO: 80.

In another embodiment, the invention encompasses a method of detecting the presence of DNA corresponding to the event 5307 in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. In one aspect of this embodiment the amplicon comprises a nucleotide sequence selected from the group consisting of SEQ ID NO: 1, SEQ ID NO: 2, SEQ ID NO: 3, SEQ ID NO: 4, and complements thereof.

In another embodiment, the invention encompasses a method of detecting the presence of a DNA corresponding to the 5307 event in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the 5307 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the invention encompasses a kit for detecting the presence of event 5307 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for event 5307, and other materials necessary to enable nucleic acid hybridization or amplification. A variety of detection methods can be used including TAQMAN (Perkin Elmer), thermal amplification, ligase chain reaction, southern hybridization, ELISA methods, and colorimetric and fluorescent detection methods. In particular the invention provides for kits for detecting the presence of the target sequence, i.e., at least one of the junctions of the insert DNA with the genomic DNA of the corn plant in event 5307, in a sample containing genomic nucleic acid from event 5307. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in event 5307, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the invention encompasses a method for detecting event 5307 protein in a biological sample, the method comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

Another embodiment of the invention encompasses a corn plant, or parts thereof, comprising the genotype of the transgenic event 5307, wherein the genotype comprises the nucleotide sequence set forth in SEQ ID NO: 1, SEQ ID NO: 2, SEQ ID NO: 3, SEQ ID NO: 4, or the complements thereof. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the event 5307 genotype can be introgressed into any plant variety that can be bred with corn, including wild maize species, and thus the preferred inbred lines of this embodiment are not meant to be limiting.

In another embodiment, the invention encompasses a corn plant comprising at least a first and a second DNA sequence linked together to form a contiguous nucleotide sequence, wherein the first DNA sequence is within a junction sequence and comprises at least about 10-15 contiguous nucleotides selected from the group consisting of nucleotides SEQ ID NO: 5, SEQ ID NO: 6, and complements thereof, wherein the second DNA sequence is within the heterologous insert DNA sequence selected from the group consisting of SEQ ID NO: 15 through SEQ ID NO: 68, and complements thereof; and wherein the first and the second DNA sequences are useful as nucleotide primers or probes for detecting the presence of corn event 5307 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2

Corn plants of the invention can be further characterized in that digesting the plant's genomic DNA with the restriction endonucleases SmaI and PmeI results in a single hybridizing band using a full length probe under high stringency conditions. Exemplified herein is a full length probe comprising a nucleotide sequence set forth in SEQ ID NO: 7.

In one embodiment, the invention provides a corn plant, wherein the event 5307 genotype confers upon the corn plant resistance to insects or the ability to utilize mannose. In one aspect of this embodiment, the genotype conferring resistance to insects upon the corn plant comprises a FR8a gene. In another aspect of this embodiment, the genotype conferring upon the corn plant the ability to utilize mannose comprises a PMI gene.

In one embodiment, the invention provides a biological sample derived from a event 5307 corn plant, tissue, or seed, wherein the sample comprises a nucleotide sequence which is or is complementary to a sequence selected from the group consisting of SEQ ID NO: 1, SEQ ID NO: 2, SEQ ID NO: 3 and SEQ ID NO: 4, and wherein the sequence is detectable in the sample using a nucleic acid amplification or nucleic acid hybridization method. Thus, the genetic sequence functions a means of detection. In one aspect of this embodiment, the sample is selected from corn flour, corn meal, corn syrup, corn oil, corn starch, and cereals manufactured in whole or in part to contain corn products.

In another embodiment, the invention provides an extract derived from a event 5307 corn plant, tissue, or seed comprising a nucleotide sequence which is or is complementary to a nucleotide sequence selected from the group consisting of SEQ ID NO: 1, SEQ ID NO: 2, SEQ ID NO: 3 and SEQ ID NO: 4. An example of such seed is deposited at the ATCC under Accession No. PTA-9561. In one aspect of this embodiment, the sequence is detected in the extract using a nucleic acid amplification or nucleic acid hybridization method. In another aspect of this embodiment, the sample is selected from corn flour, corn syrup, corn oil, cornstarch, and cereals manufactured in whole or in part to contain corn products.

In yet another embodiment, the invention provides a method for producing a corn plant resistant to at least corn rootworm infestation comprising: (a) sexually crossing a first parent corn plant with a second parent corn plant, wherein said first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; and (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO:3 and SEQ ID NO: 4.

In another embodiment, the invention provides a method of producing hybrid corn seeds comprising: (a) planting seeds of a first inbred corn line comprising a nucleotide sequence selected from the group consisting of SEQ ID NO: 1, SEQ ID NO: 2, SEQ ID NO: 3, and SEQ ID NO: 4, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The invention also encompasses the hybrid seed produced by the embodied method and hybrid plants grown from the seed.

In another embodiment, the invention provides a method of selecting markers associated with corn event 5307 comprising: (a) screening corn event 5307 chromosome 5 sequences, (b) comparing these with a non-transgenic NP2222 sequences, (c) comparing the sequences for the purpose of detecting sequence variations, (d) using these sequence variations as a means to develop markers associated with corn event 5307, (e) using the markers to screen lines, and (f) detecting marker confirming the presence of corn event 5307 sequences on chromosome 5.

One skilled in the art will recognize that the transgenic genotype of the invention can be introgressed by breeding into other corn lines comprising different transgenic genotypes. For example, a corn inbred comprising the transgenic genotype of the invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the invention include, the glyphosate herbicide tolerant events GA21 and NK603, the glyphosate tolerant/lepidopteran insect resistant MON802 event, the lepidopteran insect resistant event DBT418, the lepidopteran insect resistant event DAS-06275-8, the lepidopteran insect resistant event MIR162, the male sterile event MS3, the phosphinothricin tolerant event B 16, the lepidopteran insect resistant event MON 80100, the phosphinothricin herbicide tolerant events T14 and T25, the lepidopteran insect resistant event 176, the coleopteran insect resistant event MIR604 and the coleopteran insect resistant event MON863, all of which are known in the art. It will be further recognized that other combinations can be made with the transgenic genotype of the invention and thus these examples should not be viewed as limiting.

One skilled in the art will also recognize that transgenic corn seed comprising the transgenic genotype of the invention can be treated with various seed-treatment chemicals, including insecticides, to augment or syngergize the insecticidal activity of the FR8a protein. For example, the transgenic corn seed of the invention can be treated with the commercial insecticide Cruiser®. Such a combination may be used to increase the spectrum of activity and to increase the efficacy of the expressed protein and chemical.

Breeding

The transgenic genotype of the invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling.

Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, marker assisted selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

As is readily apparent to one skilled in the art, the foregoing are only some of the various ways by which the inbred of the invention can be obtained by those looking to introgress the transgenic genotype of the invention into other corn lines. Other means are available, and the above examples are illustrative only.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual, 3d Ed.*, Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1: Transformation and Selection of the 5307 Event

The 5307 event was produced by *Agrobacterium*-mediated transformation of the inbred corn (*Zea mays*) line NP2222. Immature embryos were transformed essentially as described in Negrotto et al. (Plant Cell Reports 19: 798-803, 2000), incorporated herein by reference, using a DNA fragment from plasmid pSYN12274 (FIG. 1). pSYN12274 contains a nucleotide sequence comprising tandem expression cassettes. The first expression cassette is comprised of a CMP promoter sequence (U.S. Pat. No. 7,166,770) operably linked to a FR8a coding sequence further operably linked to a nopaline synthase 3' end transcription termination and polyadenylation sequence. The second expression cassette is comprised of a maize ubiquitin promoter (ZmUbiInt) (Christensen et al. 1992 PMB 18: 675) operably linked to a PMI coding sequence further operably linked to a nopaline synthase 3' end transcription termination and polyadenylation sequence.

Immature embryos were excised from 8-12 day old ears and rinsed with fresh medium in preparation for transformation. Embryos were mixed with the suspension of *Agrobacterium* cells harboring the transformation vector pSYN12274, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the PMI and FR8a genes, as well as for the absence of the antibiotic resistance spectinomycin (spec) gene. Plants positive for both transgenes, and negative for the spec gene, were transferred to the greenhouse for further propagation. Positive events were identified and screened using insect bioassays against corn rootworm. Insecticidal events were characterized for copy number by TAQMAN analysis. Event 5307 was chosen for further analysis based on having a single copy of the transgenes, good protein expression as identified by ELISA, and better insecticidal activity against corn rootworm when compared to other events made with the same construct.

The $T_0$ 5307 event was backcrossed to inbred corn line NP2460, creating the $T_1$ population. The $T_1$ plants were self-pollinated to create the $T_2$ generation, and this process was repeated to create a $T_3$ generation. Progeny testing of the $T_3$ plants was employed to identify homozygous (converted) families. The event 5307-converted NP2460 inbred was crossed to other elite inbred lines to create hybrids used in further studies.

Example 2: Event 5307 Detection by TAQMAN PCR

TAQMAN analysis was essentially carried out as described in Ingham et al. Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (Adh) gene (Genbank accession no. AF044295). It will be recognized by the skilled person that other corn genes can be used as endogenous controls. Reactions were multiplexed to simultaneously amplify FR8a and Adh or PMI and Adh. For each sample, a master mixture was generated by combining 20 μL extracted genomic DNA with 35 μL 2×TAQMAN Universal PCR Master Mix (Applied Biosystems) supplemented with primers to a final concentration of 900 nM each, probes to a final concentration of 100 nM each, and water to a 70 μL final volume. This mixture was distributed into three replicates of 20 μL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event 5307 had one copy of the FR8a gene and one copy of the PMI gene.

Examples of suitable primer/probe sequence combinations which were used are:

| Primer Name | Primer Sequence | SEQ ID NO: |
|---|---|---|
| FR8a-forward | 5'-TACGAGAGCTGG GTGAACTTCA-3' | SEQ ID NO: 73 |
| FR8a-reverse | 5'-CGATCAGGTCCA GCACGG-3' | SEQ ID NO: 74 |
| FR8a-probe | 5'-CCGCTACCGCCG CGAGATGA-3' (5' label = FAM, 3' label = TAMRA) | SEQ ID NO: 75 |
| PMI-forward | 5'-CCGGGTGAATCA GCGTTT-3' | SEQ ID NO: 76 |
| PMI-reverse | 5'-GCCGTGGCCTTT GACAGT-3' | SEQ ID NO: 77 |
| PMI-probe | 5'-TGCCGCCAACGA ATCACCGG-3' (5' label = FAM, 3' label = TAMRA) | SEQ ID NO: 78 |
| ZmADH-267 forward | 5'-GAACGTGTGTTG GGTTTGCAT-3' | SEQ ID NO: 79 |
| ZmADH-337 reverse | 5'-TCCAGCAATCCT TGCACCTT-3' | SEQ ID NO: 80 |
| ZmADH-316 probe | 5'-TGCAGCCTAACC ATGCGCAGGGTA-3' (5' label = TET, 3' label = TAMRA) | SEQ ID NO: 81 |

The PM1271, MIC5307a and MIC5307b TAQMAN assays are designed as an event specific assay, which covers the 3' junction sequence.

Examples of suitable primer/probe sequence combinations which were used are:

| Primer Name | Primer Sequence | SEQ ID NO: |
|---|---|---|
| PM1277-forward | 5'-GCCGTATCCGCA ATGTGTTA-3' | SEQ ID NO: 82 |
| PM1277-reverse | 5'-GGCCCAGGGAAG AGGGTATAT-3' | SEQ ID NO: 83 |
| PM1277-probe | 5'-AAGTTGTCTAAG CGTCAAT-3' (5' label = TET, 3' label = TAMRA) | SEQ ID NO: 84 |
| MIC5307a-forward | 5'-TGTCTAAGCGTC AATTTGTTTACACC-3' | SEQ ID NO: 82 |
| MIC5307a-reverse | 5'-TTTGCCAGTGGG CCCA-3' | SEQ ID NO: 83 |
| MIC5307a-probe | 5'-ACAATATACCCTC TTCCCTGGGCCAGG-3' (5' label = TET, 3' label = TAMRA) | SEQ ID NO: 84 |
| MIC5307b-forward | 5'-GCCGTATCCGCAA TGTGTTA-3' | SEQ ID NO: 82 |
| MIC5307b-reverse | 5'-AAGTTGTCTAAGC GTCAAT-3' | SEQ ID NO: 83 |
| MIC5307b-probe | 5'-GGCCCAGGGAAGA GGGTATAT-3' (5' label = TET, 3' label = TAMRA) | SEQ ID NO: 84 |

Example 3: Event 5307 Detection by Southern Blot

Genomic DNA used for southern analysis was isolated from pooled leaf tissue of ten plants representing the backcross six (BC6) generation of event 5307 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the FR8a gene and the PMI gene. For the negative segregant controls, DNA was isolated from pooled leaf tissue of five plants representing the BC4 generation of event 5307. These negative segregant plants were individually analyzed using TAQMAN PCR and the assays were negative for the presence of the FR8a gene and the PMI gene, but were, as expected, positive for the assay internal control, the endogenous maize Adh gene.

Southern analysis was carried out using conventional molecular biology techniques. Genomic DNA (7.5 µg) was doubly digested with SmaI and PmeI restriction enzymes, which have single recognition sites within the event 5307 T-DNA insert from plasmid pSYN12274 (FIG. 1). This approach allows for determination of the number of copies of the elements, corresponding to the specific probe used for each Southern, which have been incorporated into event 5307. This results in one hybridization band per copy of the element present in event 5307. This results in one hybridization band per copy of the element present in event 5307. Following agarose gel electrophoresis and alkaline transfer to a Nytran® membrane, hybridizations were carried out using element-specific full-length PCR-generated probes. The full length probe used in the Southern blots comprises the nucleotide sequences set forth in SEQ ID NO: 7. The probe was labeled with $^{32}$P via random priming using the Rediprime™ II system (Amersham Biosciences, Cat. No. RPN1633).

The following high stringency hybridization conditions were used: 1-2 million cpm/ml are added to PerfectHyb (Sigma) supplemented with 100 µg/ml Calf Thymus DNA (Invitrogen) pre-warmed to 65° C. Pre-hybridization takes place in the same solution as above, at the same temp overnight or for at least one hour. Hybridization was carried out at 65° C. for 3 hours followed by washing 2× in 2×SSC, 0.1% SDS for 20 minutes at 65° C. and 2× in 0.1×SSC, 0.1% SDS for 20 minutes at 65° C.

Included on each Southern were three control samples: (1) DNA from a negative (non-transformed) segregant used to identify any endogenous Zea mays sequences that may cross-hybridize with the element-specific probe; (2) DNA from a negative segregant into which is introduced an amount of SmaI-PmeI digested pSYN12274 that is equal to one copy number based on probe length, to demonstrate the sensitivity of the experiment in detecting a single gene copy within the Zea mays genome; and (3) SmaI-PmeI digested pSYN12274 plasmid that is equal to one copy number based on probe length, as a positive control for hybridization as well as to demonstrate the sensitivity of the experiment.

The hybridization data provide confirmatory evidence to support the TAQMAN PCR analysis that event 5307 contains a single copy of the FR8a and PMI genes, and that 5307 event does not contain any of the vector backbone sequences present in pSYN12274. As expected for both the FR8a and PMI probes, the SmaI-PmeI digest resulted in a single hybridization band of the correct size, demonstrating that a single copy of each gene is present in the 5307 event. Additionally, for the backbone probe lack of hybridization demonstrates the absence of any pSYN12274 vector backbone sequences being incorporated into event 5307 during the transformation process.

Example 4: T-DNA Insert Sequencing

The nucleotide sequence of the entire transgene DNA insert present in event 5307 was determined to demonstrate overall integrity of the insert, contiguousness of the functional elements and to detect any individual basepair changes. The event 5307 insert was PCR amplified from DNA derived from the BC5 generation as two individual overlapping fragments. Each fragment was amplified using one polynucleotide primer homologous to plant genomic sequences flanking the event 5307 insert and one polynucleotide primer homologous to the FR8a gene. To generate the 5' fragment, a first polynucleotide primer homologous to the 5' flanking sequence, SEQ ID NO: 8 through SEQ ID NO: 15, was combined with a second polynucleotide primer homologous to the inserted DNA the FR8a gene, SEQ ID NO: 33 through SEQ ID NO: 41, the Ubiquitin promoter, SEQ ID NO: 42 through SEQ ID NO: 53 or the PMI gene, SEQ ID NO: 54 through SEQ ID NO: 60. To generate the 3' fragment, a first polynucleotide primer homologous to the 3' flanking sequence, SEQ ID NO: 69 through SEQ ID NO: 72, was combined with a second polynucleotide primer homologous to the inserted DNA within the FR8a gene, SEQ ID NO: 9 through SEQ ID NO: 17, the Ubiquitin promoter, SEQ ID NO: 18 through SEQ ID NO: 26 or the PMI gene, SEQ ID NO: 27 through SEQ ID NO: 32.

PCR amplification was carried out using the Expand High Fidelity PCR system (Roche, Cat. No. 1732650) and the following amplification parameters: 2 min at 94° C. for 1 cycle, followed by 10 cycles of 15 s at 94° C., 30 s at 55-65° C. and 5 min at 68° C., followed by 20 cycles of 15 s 94° C., 30 s at 55-65° C., and 5 min+5 s/cyc of 72° C., followed by 1 cycle of 7 min at 72° C.

The amplicon resulting from the PCR amplification using SEQ ID NO: 8 and SEQ ID NO: 41 comprised the 5' junction sequence (SEQ ID NO: 1). The amplicon resulting from the PCR amplification using SEQ ID NO: 69 and SEQ ID NO: 72 comprised the 3' junction sequence (SEQ ID NO: 2). Each sequencing fragment was individually cloned into the pCR®-XL-TOPO vector (Invitrogen, Cat. No. K4700-20) and three separate clones for each fragment were identified and sequenced. Sequencing was carried out using the ABI3730XL analyzer using ABI BigDye® 1.1 or Big Dye 3.1 dGTP (for GC rich templates) chemistry. The sequence analysis was done using the Phred, Phrap, and Consed package from the University of Washington and was carried out to an error rate of less than 1 in 10,000 bases (Ewing and Green, 1998). The final consensus sequence was determined by combining the sequence data from the six individual clones (three for each sequencing fragment) to generate one consensus sequence of the event 5307 insert. To further validate any individual basepair discrepancies between the event 5307 insert and the pSYN12274 plasmid, small (approximately 300-500 bp) PCR products specific to any regions where a basepair discrepancy was seen in the initial consensus sequence were amplified using the same methodology above. For all putative basepair discrepancies in the event 5307 insert, direct PCR product sequencing resulted in single clear peaks at all basepairs in question, indicating these discrepancies are likely present in the event 5307 insert. Alignment was performed using the ClustalW program with the following parameters: scoring matrix blosum55, gap opening penalty 15, gap extension penalty 6.66 (Thompson et al, 1994, Nucleic Acids Research, 22, 4673-4680).

The consensus sequence data for the event 5307 T-DNA insert demonstrates that the overall integrity of the insert and contiguousness of the functional elements within the insert as intended in pSYN12274 have been maintained.

Example 5: Analysis of Flanking DNA Sequence

Corn genome DNA sequence flanking the heterologous DNA inserted into the corn plant genome of event 5307 was obtained using OmniPlex™ Technology essentially as described in Kamberov et at (Proceedings of SPIE, *Tools for Molecular Analysis and High-Throughput Screening*, 4626: 1-12, 2002), incorporated herein by reference.

The 5' and 3' flanking sequences and junction sequences were confirmed using standard PCR procedures. The 5' flanking and junction sequences were confirmed using a first polynucleotide primer set forth in SEQ ID NO: 8 through SEQ ID NO: 14 combined with a second polynucleotide primer set forth in SEQ ID NO: 33 through SEQ ID NO: 41. The 3' flanking and junction sequences were confirmed using a first polynucleotide primer set forth in SEQ ID NO: 69 through SEQ ID NO: 72 combined with a second polynucleotide primer set forth in SEQ ID NO: 27 through SEQ ID NO: 32. It will be recognized by the skilled person that other primer sequences can be used to confirm the flanking and junction sequences.

The event 5307 insert was found to be flanked on the right border (5' flanking sequence) by the corn genomic sequence shown in SEQ ID NO: 5 and flanked on the left border (3' flanking sequence) by the corn genomic sequence shown in SEQ ID NO: 6. The 5' junction sequence is set forth in SEQ ID NO: 1. The 3' junction sequence is set forth in SEQ ID NO: 2. The integration site of the pSYN12274 vector insertion is comprised within SEQ ID NO: 103 or its reverse complement SEQ ID NO: 110, depending on the orientation of the nucleic acid used.

Example 6: Detection of Event 5307 Protein Via ELISA

To characterize the range of expression of FR8a (the active insecticidal principle) and phosphomannose isomerase (PMI) (the selectable marker) proteins in event 5307 plants, the concentrations of FR8a protein and PMI were determined by ELISA in several plant tissues. The hybrids were hemizygous for the transgenes in event 5307, whereas the inbred was homozygous for the transgenes.

Whole plants and individual parts (except pollen) were reduced to a fine powder by processing using either a coffee grinder, blender, Grindomix™ grinder (Brinkmann Instruments; Westbury, N.Y., USA), mortar with a pestle or mill, or a combination of these devices. All processing was done in the presence of either dry ice or liquid nitrogen. Samples were mixed well to ensure homogeneity. The entire plant tissue sample, or a representative sub-sample, was retained for analysis, allowing sufficient sample size for archival storage of reserve plant tissue samples. The percent dry weight of each sample was determined and the processed samples were stored at ca. −80° C. until lyophilization.

Fresh tissue (except pollen and silage) and whole-plant samples were extracted. For each sample analyzed, a 1.0 g aliquot of the powdered fresh material was weighed into a 15-ml polypropylene tube, suspended in 3 ml extraction buffer [50 mM CAPS, 0.1 M NaCl, 2 mM EDTA, 1 mM dithiothreitol, 1 mM 4-(1-aminoethyl)benzenesulfonyl fluoride HCl, 1 mM leupeptin, pH 10], and extracted using an Autogizer® homogenizer (Tomtek; Hamden, Conn., USA). After centrifugation for 15 min at 10,000×g at 4° C., the supernatant was used for FR8a and PMI analysis by ELISA. After treatment with iodoacetamide as described by Hill and Straka (1988), total protein in the extracts was quantitated using the BCA™ Protein Assay Reagent (Pierce; Rockford, Ill., USA).

Pollen extracts were prepared by suspending pollen 1:30 (w/v) in extraction buffer. After 30 min on ice, the pollen suspensions were disrupted by three passages through a French pressure cell at ca. 15,000 psi, followed by centrifugation at 14,000×g for 5 min at 4° C. Cry3A055 and PMI analyses by ELISA were performed on the supernatants as described below. Total protein was quantitated as described above.

Silage extracts were prepared by suspending silage 1:25 (w/v) in 2×extraction buffer. After 30 min on ice, the silage suspensions were extracted using a Brinkmann Polytron® Homogenizer (Brinkmann; Westbury, N.Y., USA). After centrifugation for 15 min at 10,000×g at 4° C., the supernatant was used for FR8a and PMI analysis by ELISA. Total protein was quantitated as described above.

FR8a Quantification

The extracts prepared as described above were quantitatively analyzed for FR8a by ELISA (Tijssen, 1985) using immuno-affinity purified monoclonal, anti-mCry3A antibody and immuno-affinity purified polyclonal anti-Cry1Ab antibody. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

Quantifiable levels of FR8a protein were detected in all event 5307-derived plant tissues. In most cases, results are presented as means of the five replicate tissue samples. Control sample levels were below the limit of quantification for all tissues.

Across all growth stages, mean FR8a levels measured in leaves, roots and pollen ranged from ca. 18-29 µg/g fresh wt. (77-113 µg/g dry wt.), ca. 1.8-4.1 µg/g fresh wt. (22-41 µg/g dry wt.) and ca. <LOD-0.15 µg/g fresh wt. (<LOD-0.15 µg/g dry wt.) respectively. [limit of detection (LOD)=0.08 µg/g fresh wt., 0.08 µg/g dry wt.].

The levels of FR8a were generally similar among the inbred and hybrid genotypes for each tissue type at each time point PMI Quantification The extracts prepared as described above were quantitatively analyzed for PMI by ELISA (Tjissen, 1985) using Protein A-purified polyclonal rabbit and immunoaffinity-purified polyclonal goat antibodies specific for PMI. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

PMI protein was detected in most of the event 5307-derived plant tissues analyzed. In most cases, results are presented as means of the five replicate tissue samples. Control sample levels were below the limit of quantification for all stages and tissues.

Across all plant stages, mean PMI levels measured in leaves, roots and pollen ranged from ca. 0.4 to ca. 0.6 µg/g fresh wt. (1.5-2.3 µg/g dry wt.), ca. 0.1-0.2 µg/g fresh wt. (0.9-1.5 µg/g dry wt.) and ca. 16.7-30.6 µg/g fresh wt. (17.1-31.1 µg/g dry wt.) respectively. [limit of detection (LOD)=0.08 µg/g fresh wt., 0.08 µg/g dry wt.].

The levels of PMI were generally similar among the inbred and hybrid genotypes for each tissue type at each time point.

Example 7: Field Efficacy of Event 5307

Western and Northern Corn Rootworm

Event 5307 plants were tested for efficacy against western and northern corn rootworm at 12 locations in the United States. Event 5307 was tested with and without the addition of the insecticidal seed treatment Cruiser®. Control groups consisted of seed treated with two different rates of Cruiser® and an untreated check. Treatments consisted of four replications of two 17.5-20 foot rows spaced 30" on center designed in a randomized complete block. Ten plants per treatment were chosen at random and evaluated for efficacy using a 0-3 scale wherein 0=No feeding damage (lowest rating that can be given); 1=One node (circle of roots), or the equivalent of an entire node, eaten back within approximately two inches of the stalk (soil line on the 7$^{th}$ node); 2=Two complete nodes eaten; 3=Three or more nodes eaten (highest rating that can be given). Damage in between complete nodes eaten was noted as the percentage of the node missing, i.e. 1.50=1½ nodes eaten, 0.25=¼ of one node eaten.

Event 5307 efficacy was compared with commercial granular insecticide standards applied in-furrow. The experimental design was as described above. Results in Table 2 demonstrate that the efficacy of event 5307 was comparable to the commercial standards in protecting plants against corn rootworm feeding damage.

TABLE 2

Comparison of efficacy of event 5307 with commercial insecticides applied in-furrow.

| Treatment | Root Damage Rating (0-3 CRW Scale) |
|---|---|
| 5307 | 0.06 |
| Force ® 3G | 0.23 |
| MIR604 | 0.13 |
| Untreated Check | 2.05 |

Mexican Corn Rootworm

Event 5307 plants were evaluated for resistance to the Mexican corn rootworm at two locations in Texas. Experimental design was essentially the same as described above.

A clear rate response was evident. Results shown in Table 3 demonstrate that the efficacy of event 5307 was comparable to the commercial standards in protecting plants against Mexican corn rootworm feeding damage.

TABLE 3

Efficacy of event 5307 compared with commercial insecticides applied in-furrow against Mexican corn rootworm.

| Treatment | Root Damage Rating (0-3 CRW Scale) |
|---|---|
| Event 5307 | 0.025 |
| Force ® 3G | 0.084 |
| MIR604 with Cruiser ® | 0.104 |
| Untreated Check | 0.710 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the invention.

Example 8: Use of Event 5307 Insertion Site for Targeted Integration in Maize

The event 5307 flanking sequences disclosed in SEQ ID NO: 5 and SEQ ID NO: 6 were used to search maize genome databases. Identical matches to both flanking sequences where found on a BAC clone, ZMMBBc0077H14, of chromosome 5 (NCBI Accession No. AC202955). More specifically, the event 5307 insert lies between a 5' marker, designated herein as the public molecular marker umc1475 (SEQ ID No: 104), and a 3' marker, designated herein as the public molecular marker uaz190 (SEQ ID No: 107). Using this information, it was determined that the heterologous DNA inserted into event 5307 displaced 38 nucleotides of maize genomic DNA, which lies between the 5' flanking sequence (upstream of the deleted sequence) and the 3' flanking sequence (down stream of the deleted sequence). Primers useful for identifying molecular marker uaz190 are set forth as SEQ ID NO: 108 and 109. Primers useful for identifying molecular marker umc1475 are set forth as SEQ ID NO: 105 and 106. Further markers were developed for the purposes of fine mapping the insertion site. These markers are designated as SM1108C, SM0584B, SM0377D and SM0501D. Primers and probes useful for detecting these markers are as follows: SM1108C, SEQ ID NO: 91 through SEQ ID NO: 93; SM0584B, SEQ ID NO: 94 through SEQ ID: 96; SM0377D, SEQ ID NO: 97 through SEQ ID NO: 99; and SM0501D, SEQ ID NO: 100 through SEQ ID NO: 102.

Consistent agronomic performance of the transgene of event 5307 over several generations under field conditions suggests that these identified regions around the event 5307 insertion site provide good genomic locations for the targeted integration of other transgenic genes of interest. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods know in the art to target transgenes to the same insertion site as that in event 5307 or to a site in close proximity to the insertion site in 5307. One such method is disclosed in US Patent Application Publication No. 20060253918, herein incorporated by reference in its entirety. Briefly, up to 20 Kb of the genomic sequence flanking 5' to the insertion site (SEQ ID NO: 5) and up to 20 Kb of the genomic sequence flanking 3' to the insertion site (SEQ ID NO: 6) are used to flank the gene or genes of interest that are intended to be inserted into a genomic location on Chromosome 5 via homologous recombination. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the event 5307 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the event 5307 insertion site and its flanking regions can be enhanced by expression of natural or designed sequence-specific endonucleases for cleaving these sequences.

An example of this technique is demonstrated in Shukla et al. (Nature vol. 459, 21 May 2009). This method uses zinc finger nucleases for the purposes of targeting heterlogous sequences to a specific locus based upon the use of homologous sequences within the target plant. One skilled in the art could use the event 5307 insert between a 5' marker, designated herein as the public molecular marker umc1475 (SEQ ID No: 104), and a 3' marker, designated herein as the public molecular marker uaz190 (SEQ ID No: 107) to create a locus for targeted insertion.

Example 9: Use of Event 5307 Insertion Site and Flanking Sequences for Stabilization of Gene Expression The genomic sequences flanking the event 5307 insertion site may also be used to stabilize expression of other gene(s) of interest when inserted as a transgene in other genomic locations in maize and other crops. Specifically, up to 20 Kb of the genomic sequence flanking 5' to the insertion site (SEQ ID NO: 5) and up to 20 Kb of the genomic sequence flanking 3' to the insertion site (SEQ OD NO: 6) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression. The DNA vectors containing the gene or genes of interest and event 5307 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the event 5307 insertion site flanking sequences can be delivered into plant cells. Thus, by surrounding a gene or genes of interest with the genomic sequence flanking the event 5307 insertion site, the expression of such genes are stabilized in a transgenic host plant such as a dicot plant or a monocot plant like corn.

DEPOSIT

Applicants have made a deposit of corn seed of event 5307 disclosed above on 15 Oct. 2008 in accordance with the Budapest Treaty at the American Type Culture Collection (ATCC), 10801 University Boulevard, Manassas, Va. 20110-2209 under ATCC Accession No. PTA-9561. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, applicants have no authority to waive any restrictions imposed by law on the transfer of biological material or its transportation in commerce.

All publications and published patent documents cited in this specification are incorporated herein by reference to the same extent as if each individual publication or patent document was specifically and individually indicated to be incorporated by reference.

What is claimed is:

1. A biological sample derived from event 5307 corn plant, tissue, seed or cell, wherein the sample comprises a nucleotide sequence which is or is complementary to SEQ ID NO: 1 or SEQ ID NO: 2.

2. The biological sample of claim 1, wherein the sequence is detectable in the extract using a nucleic acid amplification or nucleic acid hybridization method.

3. The biological sample of claim 1, wherein the sample is selected from the group consisting of corn flour, corn meal, corn syrup, corn oil, corn starch, and cereals manufactured in whole or in part to contain corn by-products.

4. An extract derived from a biological sample of event 5307 corn plant, seed, tissue, or cell, said extract comprising a nucleotide sequence which is complementary to SEQ ID NO: 1 or SEQ ID NO: 2.

5. The extract in claim 4, wherein the sequence is detectable in the extract using a nucleic acid amplification or nucleic acid hybridization method.

6. The extract of claim 4, wherein the sample is selected from the group consisting of corn flour, corn flour, corn meal, corn syrup, corn oil, corn starch, and cereals manufactured in whole or in part to contain corn by-products.

* * * * *

SEQUENCE LISTING

<160> NUMBER OF SEQ ID NOS: 111

<210> SEQ ID NO 1
<211> LENGTH: 20
<212> TYPE: DNA
<213> ORGANISM: Artificial
<220> FEATURE:
<223> OTHER INFORMATION: 5' genome-insert juction

<400> SEQUENCE: 1
caactcacga actgatagtt                                                     20

<210> SEQ ID NO 2
<211> LENGTH: 20
<212> TYPE: DNA
<213> ORGANISM: Artificial
<220> FEATURE:
<223> OTHER INFORMATION: 3' insert-genome junction

<400> SEQUENCE: 2
ccacaatata ccctcttccc                                                     20

<210> SEQ ID NO 3
<211> LENGTH: 200
<212> TYPE: DNA
<213> ORGANISM: Artificial
<220> FEATURE:
<223> OTHER INFORMATION: 5' genome + insert sequence

<400> SEQUENCE: 3
gtcgactcaa acggctagtt ctgacagcta gccgttggac agatggcata ccggacagtc         60
cgatacgctg tccggtgtgc ctctaaaatt caactcacga actgatagtt taaactgaag         120
gcgggaaacg acaatctgat catgagcgga gaattaaggg agtcacgtta tgaccccgc          180 cgatgacgcg ggacaagccg                                                     200

<210> SEQ ID NO 4
<211> LENGTH: 200
<212> TYPE: DNA
<213> ORGANISM: Artificial
<220> FEATURE:
<223> OTHER INFORMATION: 3' insert + genome sequence

<400> SEQUENCE: 4
gccctgcagg aaatttaccg gtgcccgggc ggccagcatg gccgtatccg caatgtgtta         60
ttaagttgtc taagcgtcaa tttgtttaca ccacaatata ccctcttccc tgggccaggc         120
tgggcccact ggcaaagggt gcaccggaca gtccggtgcc ccaaagccag aaaccctagc         180
ttctgttttg tgctgttttt                                                     200

<210> SEQ ID NO 5
<211> LENGTH: 1548
<212> TYPE: DNA
<213> ORGANISM: Artificial
<220> FEATURE:
<223> OTHER INFORMATION: 5' genome + insert sequence

<400> SEQUENCE: 5
tacaagaata ttgagacgtg agtacatagc attggcattt tcattagcaa gcatttcaaa         60
agaatttaat tttctcatag caatgtgata tctctcctca cgctcaattc tagttccttc        120
atgtagagca catatgtcca tccacaaatc atgacaattt ttatggtttc taactctatt       180
aaacacatct tgcaaaggc ctctaaaaag ggtgttttg gccttagcat tccatttctc         240

```
atagttcaac tcttcaccta caagatttgt gggatctcta ggttcgggga atctttgtgt      300
ggcggctttg tagacaccaa tgtctatagc ctctaaatat gcttccatac gaattttcca      360
atatggaaaa tcgtcaccat aaaaaacggg agaaggtcca tccccaccgg acatcgttac      420
tctagcggtt aagctaatct aagagcaaca aggctcttat accaattgaa aggatcacga      480
tgcccaagag ggggggttga attgggcttt tctaaaaatc aacactaact aaaatctaag      540
caagagccca acttcacccc gacaactagc actaagagaa taatactaga aatacaacaa      600
tgctaagata atacttcaaa tacttgctaa acaaatacac aatgtaaaat acttgaatta      660
agtgcggaat gtaaagcaag gtttagaaga ctcctccaat ttttctagag gtatcaagaa      720
gtcggcactc tccctagtc ctcgttggag cacctgcgta agggtatcgc tctcccttgg       780
tcatcgcaag aaccaagtgc tcacaacgag atgatccttt gccactccgg cgcggtggat      840
ccctcacgac cgcttacaaa cttgagtcgg gtcaccaaca agatctccac ggtgatcacc      900
gagctcccaa cgccaccaag ccgtctaggt gatgccgatc accaagagta ataagccata      960
gactttcact tgaccaagag aagcctaatg catgcggtgt gtgctctagg tggctctcgc     1020
tagcgttaat gaggtccaaa tgcgggatta agattctcaa gtcacctcac taggcttttgt    1080 ggtgcttgca atgctctacc aatgtgtagg agtaaatgtg ggcagcaaga ccatcaatat     1140
ggtaggtgga tggggtataa atagccctca cccaccaact agccattacc aggaatctgc     1200
tgcgcatggg cgcaccggac agtccggtgt gccaccggtg cgccaacggt cgactcaaac     1260
ggctagttct gacagctagc cgttggacag atggcatacc ggacagtccg atacgctgtc     1320
cggtgtgcct ctaaaattca actcacgaac tgatagttta aactgaaggc gggaaacgac     1380
aatctgatca tgagcggaga attaagggag tcacgttatg accccgccg atgacgcggg      1440 acaagccgtt ttacgtttgg aactgacaga accgcaacgc tgcaggaatt ggccgcagct     1500
gccatttaaa tcaattgggc gcgccgaatt cgagctcggt acaagctt                  1548
```

```
<210> SEQ ID NO 6
<211> LENGTH: 1093
<212> TYPE: DNA
<213> ORGANISM: Zea mays

<400> SEQUENCE: 6
```

```
ccctcttccc tgggccaggc tgggcccact ggcaaagggt gcaccggaca gtccggtgcc       60
ccaaagccag aaaccctagc ttctgttttg tgctgttttt tcaatttggt ttttgttcta      120
acttgtgagt atgttctaga gttacaccta gcactatatg tgagtgtgaa tatgcaccaa      180
cactacacta gaactctttt ggtcaaacta cttatcgaca acccctcttt atagtacggc      240
taaaacaaaa taaagacct aactatatca cgagtgtccg caactccttg acactcggaa      300
tacgaagacc ttcactttt gtttcgtcgc tttagccgtt gcttcaagtt tttatctccg       360
ggattgtttt caccattgta gtacatctac ctgtaatgcg acctaactta ccatttgcct      420
ctgcaaaaca catgttagtc acatataaaa ttacgttgtc attaatcact aaaaccaacc      480
aggggcctag atgctttcta gtttaaatcc ccaacaagtc aaaattcttt ctatttttt      540 ttgcaagttc caattgacat ctgaaaggtt gtaaggtaca cgtttggctc tcattgataa      600
cgggggaaag atacagtgca aaccaccata taatgaccca cttctaatcg aatggacctg      660
taacgacgaa atccctgtg agaactatgg ttcactcatg ttaattcatt gaaattgttg       720
tagtgaattg acatggttgg gagcctgctt agagagtata gattgtcact ttttttttgga    780
```

```
ccgcaactta tttttaaaag atattgcgat cgcttgttta gtagctgttt caggcccaa      840 tgcagtttct atcgtgatcc atttaagtca ctcaacattc tcatacttct cattttgcat     900
taattcattc caatctccac tactataaaa tactagcttc gatggtcgtc atacgccatg     960
cacgaagcat gtagatcaat ccgcatacca gtgggcatct atagataggc tgtgaaaacc    1020
acccaaatcc ctactagtgg acattttatc tatagatgga ccgtgagaaa ccacacaagt    1080
ctaacacgac agg                                                        1093
```

<210> SEQ ID NO 7
<211> LENGTH: 6206
<212> TYPE: DNA
<213> ORGANISM: Artificial
<220> FEATURE:
<223> OTHER INFORMATION: Vector insert

<400> SEQUENCE: 7

```
ctggcagaca aagtggcaga catactgtcc cacaaatgaa gatggaatct gtaaaagaaa       60
acgcgtgaaa taatgcgtct gacaaaggtt aggtcggctg cctttaatca ataccaaagt      120
ggtccctacc acgatggaaa aactgtgcag tcggtttggc ttttttctgac gaacaaataa     180 gattcgtggc cgacaggtgg gggtccacca tgtgaaggca tcttcagact ccaataatgg     240
agcaatgacg taagggctta cgaaataagt aagggtagtt tgggaaatgt ccactcaccc     300
gtcagtctat aaatacttag cccctccctc attgttaagg gagcaaggat ccaccatgac     360
tagtaacggc cgccagtgtg ctggtattcg cccttatgac ggccgacaac aacaccgagg     420
cctggacagc agcaccacca aggacgtgat ccagaagggc atcagcgtgg tgggcgacct    480
gctgggcgtg gtgggcttcc ccttcggcgg cgccctggtg agcttctaca ccaacttcct    540
gaacaccatc tggcccagcg aggaccctg gaaggccttc atggagcagg tggaggccct    600
gatggaccag aagatcgccg actacgccaa gaacaaggca ctggccgagc tacagggcct    660
ccagaacaac gtggaggact atgtgagcgc cctgagcagc tggcagaaga ccccgctgc    720 accgttccgc aaccccaca gccagggccg catccgcgag ctgttcagcc aggccgagag    780
ccacttccgc aacagcatgc ccagcttcgc catcagcggc tacgaggtgc tgttcctgac    840
cacctacgcc caggccgcca cacccacct gttcctgctg aaggacgccc aaatctacgg    900
agaggagtgg ggctacgaga aggaggacat cgccgagttc tacaagcgcc agctgaagct    960
gacccaggag tacaccgacc actgcgtgaa gtggtacaac gtgggtctag acaagctccg   1020
cggcagcagc tacgagagct gggtgaactt caaccgctac cgccgcgaga tgaccctgac   1080
cgtgctggac ctgatcgccc tgttccccct gtacgacgtg cgcctgtacc caaggaggt    1140 gaagaccgag ctgacccgcg acgtgctgac cgacccatcc gtgggcgtga caacctgcg    1200 cggctacggc accaccttca gcaacatcga gaactacatc gcaagcccc acctgttcga    1260 ctacctgcac cgcatccagt ccacacgcg tttccagccc ggctactacg gcaacgacag    1320
cttcaactac tggagcggca actacgtgag cacccgcccc agcatcggca gcaacgacat    1380
catcaccagc cccttctacg gcaacaagag cagcgagccc gtgcagaacc ttgagttcaa    1440
cggcgagaag gtgtaccgcg ccgtggctaa caccaacctg gccgtgtggc cctctgcagt    1500
gtacagcggc gtgaccaagg tggagttcag ccagtacaac gaccagaccg acgaggccag    1560
cacccagacc tacgacagca agcgcaacgt gggcgccgtg agctgggaca gcatcgacca    1620
gctgcccccc gagaccaccg acgagcccct ggagaagggc tacagccacc agctgaacta    1680
cgtgatgtgc ttcctgatgc agggcagccg cggcaccatc ccgtgctga cctggaccca    1740
```

```
caagagcgtc gacttcttca acatgatcga cagcaagaag atcacccagc tgcccctgac    1800
caagagcacc aacctgggca gcggcaccag cgtggtgaag ggccccggct tcaccggcgg    1860
cgacatcctg cgccgcacca gccccggcca gatcagcacc ctgcgcgtga acatcaccgc    1920 cccccctgagc cagcgctacc gcgtccgcat ccgctacgcc agcaccacca acctgcagtt    1980
ccacaccagc atcgacggcc gccccatcaa ccagggcaac ttcagcgcca ccatgagcag    2040
cggcagcaac ctgcagagcg gcagcttccg caccgtgggc ttcaccaccc ccttcaactt    2100
cagcaacggc agcagcgtgt tcaccctgag cgcccacgtg ttcaacagcg caacgaggt    2160 gtacatcgac cgcatcgagt tcgtgcccgc cgaggtgacc ttcgaggccg agtacgacct    2220
ggagagggct cagaaggccg tgaacgagct gttcaccagc agcaaccaga tcggcctgaa    2280
gaccgacgtg accgactacc acatcgatca ggtgtaggag ctgagctcta gatccccgaa    2340 tttcccccgat cgttcaaaca tttggcaata agtttcttta agattgaatc ctgttgccgg    2400
tcttgcgatg attatcatat aatttctgtt gaattacgtt aagcatgtaa taattaacat    2460
gtaatgcatg acgttatttta tgagatgggt ttttatgatt agagtcccgc aattatacat    2520
ttaatacgcg atagaaaaca aaatatagcg cgcaaactag gataaattat cgcgcgcggt    2580
gtcatctatg ttactagatc gggaattggg taccagcttg catgcctgca gtgcagcgtg    2640
acccggtcgt gccctctct agatataatg agcattgcat gtctaagtta taaaaaatta    2700
ccacatattt tttttgtcac acttgtttga agtgcagttt atctatcttt atacatatat    2760
ttaaacttta ctctacgaat aatataatct atagtactac aataatatca gtgtttaga    2820 gaatcatata aatgaacagt tagacatggt ctaaaggaca attgagtatt ttgacaacag    2880
gactctacag tttatccttt ttagtgtgca tgtgttctcc ttttttttg caaatagctt    2940 cacctatata atacttcatc cattttatta gtacatccat ttagggttta gggttaatgg    3000
tttttataga ctaattttttt tagtacatct atttttattct atttttagcct ctaaattaag    3060 aaaactaaaa ctctatttta gttttttttat ttaataattt agatataaaa tagaataaaa    3120
taaagtgact aaaaattaaa caaatacccct ttaagaaatt aaaaaaacta aggaaacatt    3180
tttcttgttt cgagtagata atgccagcct gttaaacgcc gtcgacgagt ctaacggaca    3240
ccaaccagcg aaccagcagc gtcgcgtcgg gccaagcgaa gcagacggca cggcatctct    3300
gtcgctgcct ctggacccct ctcgagagtt ccgctccacc gttggacttg ctccgctgtc    3360
ggcatccaga aattgcgtgg cggagcggca gacgtgagcc ggcacggcag gcggcctcct    3420
cctcctctca cggcaccggc agctacgggg gattcctttc ccaccgctcc ttcgctttcc    3480
cttcctcgcc cgccgtaata aatagacacc ccctccacac cctctttccc caacctcgtg    3540
ttgttcggag cgcacacaca cacaaccaga tctcccccaa atccaccccgt cggcacctcc    3600 gcttcaaggt acgccgctcg tcctccccccc ccccccctct ctaccttctc tagatcggcg    3660
ttccggtcca tggttagggc ccggtagttc tacttctgtt catgtttgtg ttagatccgt    3720
gtttgtgtta gatccgtgct gctagcgttc gtacacggat gcgacctgta cgtcagacac    3780
gttctgattg ctaacttgcc agtgtttctc tttggggaat cctgggatgg ctctagccgt    3840
tccgcagacg ggatcgattt catgattttt tttgtttcgt tgcatagggt ttggtttgcc    3900
cttttccttt atttcaatat atgccgtgca cttgtttgtc gggtcatctt ttcatgcttt    3960 ttttttgtctt ggttgtgatg atgtggtctg gttgggcggt cgttctagat cggagtagaa    4020
ttctgtttca aactacctgg tggatttatt aattttggat ctgtatgtgt gtgccataca    4080
```

```
tattcatagt tacgaattga agatgatgga tggaaatatc gatctaggat aggtatacat    4140
gttgatgcgg gttttactga tgcatataca gagatgcttt ttgttcgctt ggttgtgatg    4200
atgtggtgtg gttgggcggt cgttcattcg ttctagatcg gagtagaata ctgtttcaaa    4260
ctacctggtg tatttattaa ttttggaact gtatgtgtgt gtcatacatc ttcatagtta    4320
cgagtttaag atggatggaa atatcgatct aggataggta tacatgttga tgtgggtttt    4380
actgatgcat atacatgatg gcatatgcag catctattca tatgctctaa ccttgagtac    4440
ctatctatta taataaacaa gtatgtttta taattatttt gatcttgata tacttggatg    4500
atggcatatg cagcagctat atgtggattt ttttagccct gccttcatac gctatttatt    4560
tgcttggtac tgtttctttt gtcgatgctc accctgttgt ttggtgttac ttctgcaggg    4620
atccccgatc atgcaaaaac tcattaactc agtgcaaaac tatgcctggg gcagcaaaac    4680
ggcgttgact gaactttatg gtatggaaaa tccgtccagc cagccgatgg ccgagctgtg    4740
gatgggcgca catccgaaaa gcagttcacg agtgcagaat gccgccggag atatcgtttc    4800
actgcgtgat gtgattgaga gtgataaatc gactctgctc ggagaggccg ttgccaaacg    4860
ctttggcgaa ctgcctttcc tgttcaaagt attatgcgca gcacagccac tctccattca    4920
ggttcatcca aacaaacaca attctgaaat cggttttgcc aaagaaaatg ccgcaggtat    4980
cccgatggat gccgccgagc gtaactataa agatcctaac cacaagccgg agctggtttt    5040
tgcgctgacg cctttccttg cgatgaacgc gtttcgtgaa ttttccgaga ttgtctccct    5100
actccagccg gtcgcaggtg cacatccggc gattgctcac tttttacaac agcctgatgc    5160
cgaacgttta agcgaactgt tcgccagcct gttgaatatg caggtgaag aaaaatcccg    5220
cgcgctggcg attttaaaat cggccctcga tagccagcag ggtgaaccgt ggcaaacgat    5280
tcgtttaatt tctgaatttt acccggaaga cagcggtctg ttctcccgc tattgctgaa    5340
tgtggtgaaa ttgaaccctg cgaagcgat gttcctgttc gctgaaacac cgcacgctta    5400
cctgcaaggc gtggcgctgg aagtgatggc aaactccgat aacgtgctgc gtgcgggtct    5460
gacgcctaaa tacattgata ttccggaact ggttgccaat gtgaaattcg aagccaaacc    5520
ggctaaccag ttgttgaccc agccggtgaa acaaggtgca gaactggact cccgattcc    5580
agtggatgat tttgccttct cgctgcatga ccttagtgat aaagaaacca ccattagcca    5640
gcagagtgcc gccattttgt tctgcgtcga aggcgatgca acgttgtgga aaggttctca    5700
gcagttacag cttaaaccgg gtgaatcagc gtttattgcc gccaacgaat caccggtgac    5760
tgtcaaaggc cacggccgtt tagcgcgtgt ttacaacaag ctgtaagagc ttactgaaaa    5820
aattaacatc tcttgctaag ctgggagctc gatccgtcga cctgcagatc gttcaaacat    5880
ttggcaataa agtttcttaa gattgaatcc tgttgccggt cttgcgatga ttatcatata    5940
atttctgttg aattacgtta agcatgtaat aattaacatg taatgcatga cgttatttat    6000
gagatgggtt tttatgatta gagtcccgca attatacatt taatacgcga tagaaaacaa    6060
aatatagcgc gcaaactagg ataaattatc gcgcgcggtg tcatctatgt tactagatct    6120
gctagccctg caggaaattt accggtgccc gggcggccag catggccgta ccgcaatgt    6180
gttattaagt tgtctaagcg tcaatt                                          6206
```

<210> SEQ ID NO 8
<211> LENGTH: 28
<212> TYPE: DNA
<213> ORGANISM: Artificial
<220> FEATURE:
<223> OTHER INFORMATION: Primer

<400> SEQUENCE: 8
cacgaccgct tacaaacttg agttgggt                                          28

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ctcccaacgc caccaagccg t                                                 21

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
cctcactagg ctttgtggtg cttgc                                             25

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
gagtaaatgt gggcagcaag acca                                              24

<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12
cccaccaact agccattacc agga                                              24

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
aaacggctag ttctgacagc tag                                               23

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
atacgctgtc cggtgtgcct c                                                 21

<210> SEQ ID NO 15

<211> LENGTH: 18
<212> TYPE: DNA
<213> ORGANISM: Artificial
<220> FEATURE:
<223> OTHER INFORMATION: Primer

<400> SEQUENCE: 15
ggtagtttgg gaaatgtc                                                18

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
atacttagcc cctccctc                                                18

<210> SEQ ID NO 17
<211> LENGTH: 17
<212> TYPE: DNA
<213> ORGANISM: Artificial
<220> FEATURE:
<223> OTHER INFORMATION: Primer

<400> SEQUENCE: 17
atgactagta acggccg                                                 17

<210> SEQ ID NO 18
<211> LENGTH: 18
<212> TYPE: DNA
<213> ORGANISM: Artificial
<220> FEATURE:
<223> OTHER INFORMATION: Primer

<400> SEQUENCE: 18
gccgacaaca acaccgag                                                18

<210> SEQ ID NO 19
<211> LENGTH: 17
<212> TYPE: DNA
<213> ORGANISM: Artificial
<220> FEATURE:
<223> OTHER INFORMATION: Primer

<400> SEQUENCE: 19
ctacgccaag aacaagg                                                 17

<210> SEQ ID NO 20
<211> LENGTH: 17
<212> TYPE: DNA
<213> ORGANISM: Artificial
<220> FEATURE:
<223> OTHER INFORMATION: Primer

<400> SEQUENCE: 20
gagaggagtg gggctac                                                 17

<210> SEQ ID NO 21
<211> LENGTH: 17
<212> TYPE: DNA
<213> ORGANISM: Artificial
<220> FEATURE:
<223> OTHER INFORMATION: Primer

<400> SEQUENCE: 21
ccaccttcag caacatc        17

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
agttcagcca gtacaacg        18

<210> SEQ ID NO 23
<211> LENGTH: 17
<212> TYPE: DNA
<213> ORGANISM: Artificial
<220> FEATURE:
<223> OTHER INFORMATION: Primer

<400> SEQUENCE: 23
agaagatcac ccagctg        17

<210> SEQ ID NO 24
<211> LENGTH: 17
<212> TYPE: DNA
<213> ORGANISM: Artificial
<220> FEATURE:
<223> OTHER INFORMATION: Primer

<400> SEQUENCE: 24
ccttcaactt cagcaac        17

<210> SEQ ID NO 25
<211> LENGTH: 17
<212> TYPE: DNA
<213> ORGANISM: Artificial
<220> FEATURE:
<223> OTHER INFORMATION: Primer

<400> SEQUENCE: 25
aggtgtagga gctgagc        17

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
tctagatccc cgaatttc        18

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
cccctctcta gagataatg        19

<210> SEQ ID NO 28
<211> LENGTH: 18
<212> TYPE: DNA

<213> ORGANISM: Artificial
<220> FEATURE:
<223> OTHER INFORMATION: Primer

<400> SEQUENCE: 28
tttgcaaata gcttcacc                                              18

<210> SEQ ID NO 29
<211> LENGTH: 17
<212> TYPE: DNA
<213> ORGANISM: Artificial
<220> FEATURE:
<223> OTHER INFORMATION: Primer

<400> SEQUENCE: 29
atgccagcct gttaaac                                               17

<210> SEQ ID NO 30
<211> LENGTH: 17
<212> TYPE: DNA
<213> ORGANISM: Artificial
<220> FEATURE:
<223> OTHER INFORMATION: Primer

<400> SEQUENCE: 30
cctcctcctc ctctcac                                               17

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
tctgttcatg tttgtgttag                                            20

<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
gatgatgtgg tctggttg                                              18

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
tgtttcaaac tacctggtgt                                            20

<210> SEQ ID NO 34
<211> LENGTH: 17
<212> TYPE: DNA
<213> ORGANISM: Artificial
<220> FEATURE:
<223> OTHER INFORMATION: Primer

<400> SEQUENCE: 34
tagccctgcc ttcatac                                               17

```
<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
tcattaactc agtgcaaaac                                                 20

<210> SEQ ID NO 36
<211> LENGTH: 18
<212> TYPE: DNA
<213> ORGANISM: Artificial
<220> FEATURE:
<223> OTHER INFORMATION: Primer

<400> SEQUENCE: 36
tccgaaaagc agttcacg                                                   18

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
aaacacaatt ctgaaatcgg                                                 20

<210> SEQ ID NO 38
<211> LENGTH: 17
<212> TYPE: DNA
<213> ORGANISM: Artificial
<220> FEATURE:
<223> OTHER INFORMATION: Primer

<400> SEQUENCE: 38
aatcggccct cgatagc                                                    17

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
tggttgccaa tgtgaaattc                                                 20

<210> SEQ ID NO 40
<211> LENGTH: 19
<212> TYPE: DNA
<213> ORGANISM: Artificial
<220> FEATURE:
<223> OTHER INFORMATION: Primer

<400> SEQUENCE: 40
aacgaatcac cggtgactg                                                  19

<210> SEQ ID NO 41
<211> LENGTH: 17
<212> TYPE: DNA
<213> ORGANISM: Artificial
<220> FEATURE:
```

```
<223> OTHER INFORMATION: Primer

<400> SEQUENCE: 41
gtcataaggg cgaatac                                                  17

<210> SEQ ID NO 42
<211> LENGTH: 19
<212> TYPE: DNA
<213> ORGANISM: Artificial
<220> FEATURE:
<223> OTHER INFORMATION: Primer

<400> SEQUENCE: 42
acgctgatgc ccttctgga                                                19

<210> SEQ ID NO 43
<211> LENGTH: 17
<212> TYPE: DNA
<213> ORGANISM: Artificial
<220> FEATURE:
<223> OTHER INFORMATION: Primer

<400> SEQUENCE: 43
ccttgttctt ggcgtag                                                  17

<210> SEQ ID NO 44
<211> LENGTH: 17
<212> TYPE: DNA
<213> ORGANISM: Artificial
<220> FEATURE:
<223> OTHER INFORMATION: Primer

<400> SEQUENCE: 44
tagaactcgg cgatgtc                                                  17

<210> SEQ ID NO 45
<211> LENGTH: 17
<212> TYPE: DNA
<213> ORGANISM: Artificial
<220> FEATURE:
<223> OTHER INFORMATION: Primer

<400> SEQUENCE: 45
gatgttgctg aaggtgg                                                  17

<210> SEQ ID NO 46
<211> LENGTH: 17
<212> TYPE: DNA
<213> ORGANISM: Artificial
<220> FEATURE:
<223> OTHER INFORMATION: Primer

<400> SEQUENCE: 46
ctgtacactg cagaggg                                                  17

<210> SEQ ID NO 47
<211> LENGTH: 17
<212> TYPE: DNA
<213> ORGANISM: Artificial
<220> FEATURE:
<223> OTHER INFORMATION: Primer

<400> SEQUENCE: 47
gctgggtgat cttcttg                                                  17
```

<210> SEQ ID NO 48
<211> LENGTH: 17
<212> TYPE: DNA
<213> ORGANISM: Artificial
<220> FEATURE:
<223> OTHER INFORMATION: Primer

<400> SEQUENCE: 48
ttgctgaagt tgaaggg                                                17

<210> SEQ ID NO 49
<211> LENGTH: 17
<212> TYPE: DNA
<213> ORGANISM: Artificial
<220> FEATURE:
<223> OTHER INFORMATION: Primer

<400> SEQUENCE: 49
gtcacgtcgg tcttcag                                                17

<210> SEQ ID NO 50
<211> LENGTH: 20
<212> TYPE: DNA
<213> ORGANISM: Artificial
<220> FEATURE:
<223> OTHER INFORMATION: Primer

<400> SEQUENCE: 50
gccaaatgtt tgaacgatcg                                             20

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
caatgctcat tatctctaga g                                           21

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
gtgacaaaaa aaatatgtgg                                             20

<210> SEQ ID NO 53
<211> LENGTH: 18
<212> TYPE: DNA
<213> ORGANISM: Artificial
<220> FEATURE:
<223> OTHER INFORMATION: Primer

<400> SEQUENCE: 53
ctgcacttca aacaagtg                                               18

<210> SEQ ID NO 54
<211> LENGTH: 22
<212> TYPE: DNA
<213> ORGANISM: Artificial
<220> FEATURE:
<223> OTHER INFORMATION: Primer

<400> SEQUENCE: 54
tgaagtatta tataggtgaa gc                                    22

<210> SEQ ID NO 55
<211> LENGTH: 19
<212> TYPE: DNA
<213> ORGANISM: Artificial
<220> FEATURE:
<223> OTHER INFORMATION: Primer

<400> SEQUENCE: 55
acaggctggc attatctac                                        19

<210> SEQ ID NO 56
<211> LENGTH: 17
<212> TYPE: DNA
<213> ORGANISM: Artificial
<220> FEATURE:
<223> OTHER INFORMATION: Primer

<400> SEQUENCE: 56
gttagactcg tcgacgg                                          17

<210> SEQ ID NO 57
<211> LENGTH: 17
<212> TYPE: DNA
<213> ORGANISM: Artificial
<220> FEATURE:
<223> OTHER INFORMATION: Primer

<400> SEQUENCE: 57
ctatttatta cggcggg                                          17

<210> SEQ ID NO 58
<211> LENGTH: 17
<212> TYPE: DNA
<213> ORGANISM: Artificial
<220> FEATURE:
<223> OTHER INFORMATION: Primer

<400> SEQUENCE: 58
gacgtacagg tcgcatc                                          17

<210> SEQ ID NO 59
<211> LENGTH: 20
<212> TYPE: DNA
<213> ORGANISM: Artificial
<220> FEATURE:
<223> OTHER INFORMATION: Primer

<400> SEQUENCE: 59
ggtagtttga aacagaattc                                       20

<210> SEQ ID NO 60
<211> LENGTH: 23
<212> TYPE: DNA
<213> ORGANISM: Artificial
<220> FEATURE:
<223> OTHER INFORMATION: Primer

<400> SEQUENCE: 60
gtaactatga agatgtatga cac                                   23

<210> SEQ ID NO 61
<211> LENGTH: 17

```
<212> TYPE: DNA
<213> ORGANISM: Artificial
<220> FEATURE:
<223> OTHER INFORMATION: Primer

<400> SEQUENCE: 61
acaacagggt gagcatc                                                    17

<210> SEQ ID NO 62
<211> LENGTH: 17
<212> TYPE: DNA
<213> ORGANISM: Artificial
<220> FEATURE:
<223> OTHER INFORMATION: Primer

<400> SEQUENCE: 62
agtcaacgcc gttttgc                                                    17

<210> SEQ ID NO 63
<211> LENGTH: 17
<212> TYPE: DNA
<213> ORGANISM: Artificial
<220> FEATURE:
<223> OTHER INFORMATION: Primer

<400> SEQUENCE: 63
aggaaaggca gttcgcc                                                    17

<210> SEQ ID NO 64
<211> LENGTH: 17
<212> TYPE: DNA
<213> ORGANISM: Artificial
<220> FEATURE:
<223> OTHER INFORMATION: Primer

<400> SEQUENCE: 64
aggctggcga acagttc                                                    17

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
gcaaccagtt ccggaatatc                                                 20

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
agcttgttgt aaacacgcg                                                  19

<210> SEQ ID NO 67
<211> LENGTH: 18
<212> TYPE: DNA
<213> ORGANISM: Artificial
<220> FEATURE:
<223> OTHER INFORMATION: Primer

<400> SEQUENCE: 67
```
ccagcttagc aagagatg                                                18

<210> SEQ ID NO 68
<211> LENGTH: 17
<212> TYPE: DNA
<213> ORGANISM: Artificial
<220> FEATURE:
<223> OTHER INFORMATION: Primer

<400> SEQUENCE: 68
taacacattg cggatac                                                 17

<210> SEQ ID NO 69
<211> LENGTH: 21
<212> TYPE: DNA
<213> ORGANISM: Artificial
<220> FEATURE:
<223> OTHER INFORMATION: Primer

<400> SEQUENCE: 69
gcctggccca gggaagaggg t                                            21

<210> SEQ ID NO 70
<211> LENGTH: 25
<212> TYPE: DNA
<213> ORGANISM: Artificial
<220> FEATURE:
<223> OTHER INFORMATION: Primer

<400> SEQUENCE: 70
cagcacaaaa cagaagctag ggttt                                        25

<210> SEQ ID NO 71
<211> LENGTH: 26
<212> TYPE: DNA
<213> ORGANISM: Artificial
<220> FEATURE:
<223> OTHER INFORMATION: Primer

<400> SEQUENCE: 71
ccgagtgtca aggagttgcg gacact                                       26

<210> SEQ ID NO 72
<211> LENGTH: 26
<212> TYPE: DNA
<213> ORGANISM: Artificial
<220> FEATURE:
<223> OTHER INFORMATION: Primer

<400> SEQUENCE: 72
cttgaagcaa cggctaaagc gacgaa                                       26

<210> SEQ ID NO 73
<211> LENGTH: 22
<212> TYPE: DNA
<213> ORGANISM: Artificial
<220> FEATURE:
<223> OTHER INFORMATION: Primer

<400> SEQUENCE: 73
tacgagagct gggtgaactt ca                                           22

<210> SEQ ID NO 74
<211> LENGTH: 18
<212> TYPE: DNA
<213> ORGANISM: Artificial

-continued

```
<220> FEATURE:
<223> OTHER INFORMATION: Primer

<400> SEQUENCE: 74
cgatcaggtc cagcacgg                                                      18

<210> SEQ ID NO 75
<211> LENGTH: 20
<212> TYPE: DNA
<213> ORGANISM: Artificial
<220> FEATURE:
<223> OTHER INFORMATION: Probe

<400> SEQUENCE: 75
ccgctaccgc cgcgagatga                                                    20

<210> SEQ ID NO 76
<211> LENGTH: 18
<212> TYPE: DNA
<213> ORGANISM: Artificial
<220> FEATURE:
<223> OTHER INFORMATION: Primer

<400> SEQUENCE: 76
ccgggtgaat cagcgttt                                                      18

<210> SEQ ID NO 77
<211> LENGTH: 18
<212> TYPE: DNA
<213> ORGANISM: Artificial
<220> FEATURE:
<223> OTHER INFORMATION: Primer

<400> SEQUENCE: 77
gccgtggcct ttgacagt                                                      18

<210> SEQ ID NO 78
<211> LENGTH: 20
<212> TYPE: DNA
<213> ORGANISM: Artificial
<220> FEATURE:
<223> OTHER INFORMATION: Probe

<400> SEQUENCE: 78
tgccgccaac gaatcaccgg                                                    20

<210> SEQ ID NO 79
<211> LENGTH: 21
<212> TYPE: DNA
<213> ORGANISM: Artificial
<220> FEATURE:
<223> OTHER INFORMATION: Primer

<400> SEQUENCE: 79
gaacgtgtgt tgggtttgca t                                                  21

<210> SEQ ID NO 80
<211> LENGTH: 24
<212> TYPE: DNA
<213> ORGANISM: Artificial
<220> FEATURE:
<223> OTHER INFORMATION: Primer

<400> SEQUENCE: 80
tgcagcctaa ccatgcgcag ggta                                               24
```

<210> SEQ ID NO 81
<211> LENGTH: 20
<212> TYPE: DNA
<213> ORGANISM: Artificial
<220> FEATURE:
<223> OTHER INFORMATION: Probe

<400> SEQUENCE: 81
tccagcaatc cttgcacctt                                               20

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
gccgtatccg caatgtgtta                                               20

<210> SEQ ID NO 83
<211> LENGTH: 21
<212> TYPE: DNA
<213> ORGANISM: Artificial
<220> FEATURE:
<223> OTHER INFORMATION: Primer

<400> SEQUENCE: 83
ggcccaggga agagggtata t                                             21

<210> SEQ ID NO 84
<211> LENGTH: 19
<212> TYPE: DNA
<213> ORGANISM: Artificial
<220> FEATURE:
<223> OTHER INFORMATION: Probe

<400> SEQUENCE: 84
aagttgtcta agcgtcaat                                                19

<210> SEQ ID NO 85
<211> LENGTH: 26
<212> TYPE: DNA
<213> ORGANISM: Artificial
<220> FEATURE:
<223> OTHER INFORMATION: Primer

<400> SEQUENCE: 85
tgtctaagcg tcaatttgtt tacacc                                        26

<210> SEQ ID NO 86
<211> LENGTH: 16
<212> TYPE: DNA
<213> ORGANISM: Artificial
<220> FEATURE:
<223> OTHER INFORMATION: Primer

<400> SEQUENCE: 86
tttgccagtg ggccca                                                   16

<210> SEQ ID NO 87
<211> LENGTH: 27
<212> TYPE: DNA
<213> ORGANISM: Artificial
<220> FEATURE:
<223> OTHER INFORMATION: Probe

```
<400> SEQUENCE: 87
acaatatacc ctcttccctg ggccagg                                            27

<210> SEQ ID NO 88
<211> LENGTH: 20
<212> TYPE: DNA
<213> ORGANISM: Artificial
<220> FEATURE:
<223> OTHER INFORMATION: Primer

<400> SEQUENCE: 88
gccgtatccg caatgtgtta                                                    20

<210> SEQ ID NO 89
<211> LENGTH: 19
<212> TYPE: DNA
<213> ORGANISM: Artificial
<220> FEATURE:
<223> OTHER INFORMATION: Primer

<400> SEQUENCE: 89
aagttgtcta agcgtcaat                                                     19

<210> SEQ ID NO 90
<211> LENGTH: 21
<212> TYPE: DNA
<213> ORGANISM: Artificial
<220> FEATURE:
<223> OTHER INFORMATION: Probe

<400> SEQUENCE: 90
ggcccaggga agagggtata t                                                  21

<210> SEQ ID NO 91
<211> LENGTH: 25
<212> TYPE: DNA
<213> ORGANISM: Artificial
<220> FEATURE:
<223> OTHER INFORMATION: Primer

<400> SEQUENCE: 91
ccccacgatt aaatgtcaaa ctgat                                              25

<210> SEQ ID NO 92
<211> LENGTH: 25
<212> TYPE: DNA
<213> ORGANISM: Artificial
<220> FEATURE:
<223> OTHER INFORMATION: Primer

<400> SEQUENCE: 92
gctcagcctt gtttttgtac attca                                              25

<210> SEQ ID NO 93
<211> LENGTH: 20
<212> TYPE: DNA
<213> ORGANISM: Artificial
<220> FEATURE:
<223> OTHER INFORMATION: Probe

<400> SEQUENCE: 93
aattttcata gcttttgtg                                                     20

<210> SEQ ID NO 94
```

```
<211> LENGTH: 27
<212> TYPE: DNA
<213> ORGANISM: Artificial
<220> FEATURE:
<223> OTHER INFORMATION: Primer

<400> SEQUENCE: 94
cgctcttaag tctgctgttt gtttact                                              27

<210> SEQ ID NO 95
<211> LENGTH: 24
<212> TYPE: DNA
<213> ORGANISM: Artificial
<220> FEATURE:
<223> OTHER INFORMATION: Primer

<400> SEQUENCE: 95
cacacgccac ttcttgtctt ctat                                                 24

<210> SEQ ID NO 96
<211> LENGTH: 13
<212> TYPE: DNA
<213> ORGANISM: Artificial
<220> FEATURE:
<223> OTHER INFORMATION: Probe

<400> SEQUENCE: 96
cgcgagctca tgc                                                             13

<210> SEQ ID NO 97
<211> LENGTH: 25
<212> TYPE: DNA
<213> ORGANISM: Artificial
<220> FEATURE:
<223> OTHER INFORMATION: Primer

<400> SEQUENCE: 97
gctgcagctc acttgaaggt ataat                                                25

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
ggcaccaccc tgtaaaagca                                                      20

<210> SEQ ID NO 99
<211> LENGTH: 17
<212> TYPE: DNA
<213> ORGANISM: Artificial
<220> FEATURE:
<223> OTHER INFORMATION: Probe

<400> SEQUENCE: 99
aaccattaga tgcttcc                                                         17

<210> SEQ ID NO 100
<211> LENGTH: 16
<212> TYPE: DNA
<213> ORGANISM: Artificial
<220> FEATURE:
<223> OTHER INFORMATION: Primer

<400> SEQUENCE: 100
```

```
ccgtcgacga ggcgaa                                                   16

<210> SEQ ID NO 101
<211> LENGTH: 16
<212> TYPE: DNA
<213> ORGANISM: Artificial
<220> FEATURE:
<223> OTHER INFORMATION: Primer

<400> SEQUENCE: 101
gcggcgagct gttcag                                                   16

<210> SEQ ID NO 102
<211> LENGTH: 16
<212> TYPE: DNA
<213> ORGANISM: Artificial
<220> FEATURE:
<223> OTHER INFORMATION: Probe

<400> SEQUENCE: 102
tctgagcttc ggatac                                                   16

<210> SEQ ID NO 103
<211> LENGTH: 161748
<212> TYPE: DNA
<213> ORGANISM: Zea mays
<220> FEATURE:
<221> NAME/KEY: misc_feature
<222> LOCATION: (2151)..(2250)
<223> OTHER INFORMATION: n is a, c, g, or t
<220> FEATURE:
<221> NAME/KEY: misc_feature
<222> LOCATION: (6108)..(6207)
<223> OTHER INFORMATION: n is a, c, g, or t
<220> FEATURE:
<221> NAME/KEY: misc_feature
<222> LOCATION: (9770)..(9869)
<223> OTHER INFORMATION: n is a, c, g, or t
<220> FEATURE:
<221> NAME/KEY: misc_feature
<222> LOCATION: (18125)..(18224)
<223> OTHER INFORMATION: n is a, c, g, or t
<220> FEATURE:
<221> NAME/KEY: misc_feature
<222> LOCATION: (33520)..(33619)
<223> OTHER INFORMATION: n is a, c, g, or t
<220> FEATURE:
<221> NAME/KEY: misc_feature
<222> LOCATION: (44173)..(44272)
<223> OTHER INFORMATION: n is a, c, g, or t
<220> FEATURE:
<221> NAME/KEY: misc_feature
<222> LOCATION: (67063)..(67162)
<223> OTHER INFORMATION: n is a, c, g, or t
<220> FEATURE:
<221> NAME/KEY: misc_feature
<222> LOCATION: (91565)..(91664)
<223> OTHER INFORMATION: n is a, c, g, or t
<220> FEATURE:
<221> NAME/KEY: misc_feature
<222> LOCATION: (136173)..(136272)
<223> OTHER INFORMATION: n is a, c, g, or t
<220> FEATURE:
<221> NAME/KEY: misc_feature
<222> LOCATION: (148532)..(148631)
<223> OTHER INFORMATION: n is a, c, g, or t
<220> FEATURE:
<221> NAME/KEY: misc_feature
<222> LOCATION: (154026)..(154125)
<223> OTHER INFORMATION: n is a, c, g, or t
<220> FEATURE:
<221> NAME/KEY: misc_feature
<222> LOCATION: (158039)..(158138)
```

<223> OTHER INFORMATION: n is a, c, g, or t

<400> SEQUENCE: 103

| | | | | | |
|---|---|---|---|---|---|
| cccggccgct | gatgaatcag | cttgattcgt | tctgttatca | cgggtggtca | ctcaacgagc | 60 |
| aggtccaaag | gaaaggtact | caggaaaata | gcctgagtct | cctaaagtgc | cataagaaca | 120 |
| tcatcgtaat | cataataaca | acatcatatc | ataaatattc | gcatcatgtt | tgttgattaa | 180 |
| agtggagcaa | tagcttgaag | cttaccataa | taacccaaaa | ggtaaacaag | gacaagataa | 240 |
| atacagacta | gtcaaacctt | aggtttcaat | taagtaaagg | gggacagtga | attatgaagt | 300 |
| aagtaggaca | taataggtca | gaggacactt | gccttcacca | ggttgttgcc | caggaagatc | 360 |
| ttcggcaaca | cactcaggaa | ccatagactg | cttgttgtct | acgcaaagcg | atcatgcatt | 420 |
| caacacattt | cgataatgat | aaagaaacaa | tacaccaaaa | atatacaatc | aagtgaacac | 480 |
| taattcaaaa | gaaagtaaca | aactcaagcg | aagcctaggg | tctagggtgg | accaatacac | 540 |
| ataggttt | gtggttctct | aagtattact | tatctcaata | gattacataa | cttaatttca | 600 |
| tttatcttaa | tgagacaaaa | gaattatacc | agggataggt | tcatatatta | catattatta | 660 |
| acccacaaag | ttaaacatct | aactaccatt | atggttttcc | ttttatcctt | cttattaata | 720 |
| aataagccat | cagttacact | aacctatagt | ctaggcataa | aattagcaca | tgcagacagt | 780 |
| aaaaggttat | aatttaaaca | ggtagagaat | aaccttacaa | acattttgca | atttgaatca | 840 |
| ctcaatttgg | agttcatatg | caaaagatat | gaaataaaca | agttttggaa | ttcaaaatac | 900 |
| aaaactaggt | ctaattatgt | gataacctaa | aagattaggg | gcctttctgc | aaaagtacag | 960 |
| gggcatgcgt | gcgaaaacca | gggacgatgg | gttgattctc | agaaagccga | gggcctttt | 1020 |
| aacaaaacta | ccacgcaaag | gggtatcagc | tgatctcgac | tgcatgatca | cagatcaacg | 1080 |
| gccaggatta | gatttgagcg | cgagcacgag | cacgagctaa | caggtgggcc | aggatagtca | 1140 |
| gcgacctagg | ggcgaggcgg | actgtctggc | cgggcctagc | tgcagggcgc | gggtgaggtg | 1200 |
| gcggatccga | gtggccagat | ctccatcgga | cagctgggat | cagatcgagt | ttaattgaag | 1260 |
| ccaggtcgtt | agatctcaga | tggatgcctg | aaatctgatg | gcaagctcgg | gcggggttgc | 1320 |
| taggctgctc | atggcgccgc | cgcccaattt | cgcggcgtgg | cgcggccatg | gtgagggtct | 1380 |
| gggcgctggg | aaaaggctca | ggcgagctca | gggtgacacg | gcgggctcag | ccatgggcac | 1440 |
| gacaccggcg | tagaggcacc | agagagcacg | gtccgaggca | aagcagcccc | acggcggcgc | 1500 |
| agcttaactc | tggcgagcga | ttgcatggac | aacagggcag | taaatgggaa | attaagggca | 1560 |
| tgggtgggtt | ggttacgtcg | agagatgact | ctagagcgct | tgagcaacgg | cgaggacacc | 1620 |
| gcgagggccc | tggtggacgg | tggcggagac | tcggctgcat | ggtgataggt | ccggtgagcg | 1680 |
| aaccaaggga | aatagagggg | ctggggaaaa | ccagagggtg | tctcgtgttg | ctggcgagga | 1740 |
| ggcgaagatc | agtagggcaa | tggacgcgac | aggaactcga | cgacggccac | ggaacggacg | 1800 |
| gtggactacg | gcagtgctcc | acggctgtgc | gctcggtgcg | agagagaggt | gcgagggggt | 1860 |
| cggctgtggg | acgctactga | gcgaggggag | tgagcgagtg | agtgtgggct | ccaaaaaagt | 1920 |
| caggcgcgtg | gggggagtgg | ccgaaaaaca | cgcgacatgt | gtgcatccac | ggcggggtgc | 1980 |
| gcgagcgggt | ggttagggaa | aggggaggtg | gctgacaggt | ggggtccgct | tgccagcgag | 2040 |
| ggtgaatacg | cgaacgagcg | gttctgcgct | gacaggccga | cccaccgagg | caaaaaggag | 2100 |
| cgggcgtgtt | gcgtgaaaga | aaccggcacc | gacaaaccgg | cctccgcgcg | nnnnnnnnnn | 2160 |
| nnnnnnnnnn | nnnnnnnnnn | nnnnnnnnnn | nnnnnnnnnn | nnnnnnnnnn | nnnnnnnnnn | 2220 |
| nnnnnnnnnn | nnnnnnnnnn | nnnnnnnnnn | ctgcgggtac | cacgttctac | aaggtttgat | 2280 |

```
gatagtgagg aaggaagaat ttctggcact gaagcaaggg cccctgtctg tcagtgagta   2340
catggacaaa ttcctgcaac tatctcacaa tgcacccgag gatgtcaaca ttgatgctaa   2400
gaggtactac aggtttccga gagggttggt tgacccctgc actactagtt gatgaaccac   2460
acattcccta ccttccaaca tctgattgat agggcaataa tgactgagag gaagcgccag   2520
gagatggaag accaaaagcg caagattggt ggaccctagg ccaggagcag cagtcgtctc   2580
ccgtttctgg caatccaccc tagcagttca agtagatcca ccctcaggga taccaacacc   2640
agaaccaatg ttcgcaccag tagcaattcc agaggcagtt ccctcaacag cagcatgtca   2700
cacccgggtt ttaggggtcc aaaacccagg cgcgaaattc accaagtgct gggatcgagt   2760
ctcacacata tgatgactca tggtatagaa acaaatgtca catctttact atataataga   2820
agttctgcac aaaataacta aataattaca tcatacgatg acgacgatcc atcaacccaa   2880
agtttactgt gagacgacgg cctagacctc tcatgaactc atcgcgacat ccttcatgct   2940
cctcatcttg cggtacctgt tcttgaccag ggggatttga gtacagcaag ggtgagctca   3000
catacgttca tcgctcaaca agttgtgggg aataatgtgt atgaactcac caaaggtggg   3060
agctcatgtg aagtgtaagg cttaccaaag gagatgggta aagatgagca tgactttaa    3120 agttggtcaa aattttatta gcagttacta agtataagta gataccgacc caaataaata   3180
agagattaaa ttaataacaa cacccacaat gcaatgcata tgacaattta agtttagttc   3240
cataatttac tcatgtgagg gtccgagctg ctcatgaccg tgagcacggc tgatataaca   3300
gttttacagt ctgcacaggt tgcacatctt tacccacaag tcatgttacc tatttgccaa   3360
gggatcgcga cttctcattc atctctaccg agaagacaag gtaggttacc actacgaggc   3420
ctttacaaac ttccactagc ttccgaaaac ccgctacggt ttctaagaag gaaaatatag   3480
gaatccctcg tccaaaaagc catcgcagca tgatcgactc gagaacctcc ctatacgcat   3540
gctcctctac cgcccttgcc cctttcgggt aaggtagtct tccactagct ttcttaatta   3600
gtcagccaag ggcgtcccat accacccttg tggtagcact gttttcctgg gtggttgctc   3660
catgttccaa ttaacatagc aatcttatca tgaacaataa ttaaaataac aaaagaattg   3720
taacatgatc ataatgtaac attaatttcc caaaaccagg tagagcaata gcaatactac   3780
ccaatagtgc ttttgtttgc aaggtagggg ataaacaata ctaggaaaac ctattgggtc   3840
ccatcaaatt aacctgagca tgtcacagtg attaatagga acattattag gtaaagaaaa   3900
gtgatcaagg gcacaacttg gctgagactc aagattccta ggtaccagct tggtcttcaa   3960
gattctcgta acctcgctgc taatcatagc aatacaaaca aacatggtat aggcaaaatt   4020
aacatcacac caaacataaa gaacaaactg cataataatg atctacgcac cacaacgaga   4080
tcctaggttc gagaaccact aaaattcgga gttacggttaa caagatgtgg ttttcggaag   4140
acctatgtga ttaaatatga gactaggtct ttatgttgat tttataaatt atgtgataaa   4200
gatattaaag aaataacttt aatctacatc atactagagt agacataata ttttagttac   4260
cttataatca tagacaaact aactttgatt agtaggaata atctactaag catatattaa   4320
atgaatattt attttttgga aacatgctat ttgctaaaat aattttacag aagcgtaggc   4380
aaaattatta cgaagctaac gcaacatgaa tacattaaat cagagttaaa atgaaagaga   4440 tatgtatttta ttaagtttta ggatttaatt ctataattat taaatatttc tggattgggg   4500
acactattct ataaaagatc aggggctcc atataatatt taggacttat ccgcaatgat    4560
ttctacctat acccggactg cgggctgatt tgcaagaagt ctggggtctc ttttataagt   4620
```

```
tagtcacggt gaaggggtac acgtgactaa ttccttggat catcagccaa gcgcccagag    4680
tagaagattt gcccgccgaa ccggtacgca tcctagatcg tcggatctac gataaacggc    4740
ccacgcttaa aataatagag atcgatcctc atatgcaaga tccagatcag acgacccgga    4800
tcgattcgga tgaaacgtta cgtgtgatct aatcacagcc gatacctccc agatccacgg    4860
ttcacgcgag gcccagccat gccctgatcg tgatcgctca cccatgatct aacggctgct    4920
gcatttcctt ccacctcacg acggaaagca gagcactggt gcgggcacgc cgcggccatg    4980
ccccaccaca ccaccagtga tatcccgccc ggctccccat ttcctagtat cgagcgtggg    5040
tacgtgaatc acggagagga ggaggctcca agtatgctag gctgttctt accaaggatc     5100 acggtgtttc aagtgttgac cccaccacgc agttgctccg tggcgccgcg ggtcaccagc    5160
gaagcatgca ctggtcgttg ttctcgcacg aggtgccttc tagaatcctg cacgcgtccc    5220
acggatgacc caacccgacg ccgagaccgc aataccggcg tgcccgggaa ccccgtcgg     5280 tggcaattca cccctgtgt tctccttctc ccttacgacg atggtgatgg cgccttctct     5340
cccgatcggc agaccgagcg tagcccacga tgctgaagga gaggaaacta gagctgcacc    5400
catggccgag gttggagcgt ccgttatata tggccagggg tacggctagc agtgggcggg    5460
tgcaccatgg cacgaaggtc gttgcacagt ttacaggagg cgagcttgca gcggacgagc    5520
aggatcgcca tggggaggat agacttgacg gccatggccc acatgccaga cgcggctgca    5580
ggcgcgagag tgggcaggag cgggctgcgc cggagcaggg aaatagagtt gggcccgcta    5640
acgaaggaaa gaaactgggc cgagaagcca gagatccggc ccatagcgca gaaagcttcc    5700 ccttttctt tattctttaa tgattttctg ttttatcttc cctttcatat ttctttccct     5760
tattttaaac tctaatctaa atgctcaatc caaaactccg gcatgatatg caataattac    5820
atatatctgt ttagttttgt ttattttatc caaatatttt aagtatgcaa tgcacacaca    5880
tagagtaaaa attacttctt tgaatgtata gtccatttaa aattatgttc ataatttta    5940 agatagagga ttttttgtg tgtatagtat ttattaaggt ttttaagct taattctttt      6000 ggagaatatc tctaatcatg ttattcaaca agggttggtt taaattatat gagggtcttt    6060
tatttaatct ctcattataa aagacttcta tttaaatctt ggaattcnnn nnnnnnnnn     6120 nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnggg ggttttctt tatctcgtgc gtggttatcc     6240
atctaatcac gtgggagttt gttggctatc tcttaggaaa aggtccagac ctcctcccct    6300
ataaatataa aggggtacgg ccgattgaga accccgaac acattccaat cgaaccaatt     6360
accttattta cttttcctgc cctaggagta gatgtagcat agttctagtt gtagtcttcc    6420
acatatccac ctccacccct attcaactct acgtcgtcta gatccgtctt gggtggcctg    6480
ccgatcccaa gacgaccta ggatctcacc cctcccgggg ggcaagatct agttgtccat    6540
ccaagacttc ttcctcgatt tgatctctta attcctaggc gactccacgt cgtctgggga    6600
cgccccgggt gacctgtcga cccggagcac cttaagatct ttccccccag gggacgagat    6660
ctagattcca gcaaggagta ggaagacgac cctgtcgcca ggtcgcggac cgtccggccc    6720
agagctgcgg accgtccggt gtgacgcagg gaagacaccg ctcctgcgcc caggtcgcgg    6780
accgtccggc ccaaggctgc ggaccgtccg gcccaaggct gcggaccgtc cgcgcctgac    6840
cagagggcac cgccacggtt cttgttgagt gtttggcgct ccaaaaaggc gtcaacatac    6900 tttttgcga ctccgctggg gaagaagttg cagatctaca aaatcaggct tacatggccg     6960
attctaaaga tctcaacagt gcttctccaa acagcaacac aaggctgact aatttatcgg    7020
```

```
ccgctgagca taaaaaatta gaagatgaca tgaagaaaat agacgaggag gcccaccgac   7080
aaaaggatca ggtgctcaag gtggcggaca agtggtacct ctcgcacttc aaggtagact   7140
gccaccagaa gaccgtccaa gagagggaga taaacgccga gtatatgtta gccgtgctgc   7200
aacagctccc cacaataggt gatgccaggt cagccgatga tattccatct attaaaattt   7260
cttttgataa tcggattaaa agtatcacgg aggatataga gaggatgaca catgcattag   7320
gaaaaactca catgcctaat tttttatcac ataaattagg cgatgaaaca attgcgccaa   7380
acacatcggc ggcaaatggg tttccccagc catattctgg tatgccgatg gactcatatc   7440
taggacgacc gtcatcacca tctttgctaa atggtgagtc aaccctgggc acagccggac   7500
cgtccgcaca caattgcgga ccgtccggcc ctctgtcgga ccgtccggca ccctacgccg   7560
gacagtctgg agttacacag agcccaccac aagggtcaca ggtgttgcct gacgtgaccg   7620
gactgtccga ggatagtacc ggaccgtccg atccacccgc agaccgtccg actgtgcaag   7680
tcggaccgtc cggggcacca gaagtcacct gtgatccacc tagtgcggaa ggccgacata   7740
aatataatcg gccacccaag ccccaagaac taaaaaagtc acatgtccct gagcttgttt   7800
ggcccactaa ggccaaacct tctgttcgct cttacccgca ctcgaaacaa aaggaaaagg   7860
ttaagttcac atttaatatt actaaatgtg ataaatatt tgatgagttg cttaaacatg    7920
gtaatattaa attgtcacat gtaattcctc cggttgaaca attaaaaggg cgtgtttatt   7980
gcaaatggca tggctccttt ctccataaca ccaatgattg tgccgtcttc cgtcggcaaa   8040
tacaatcggc tataaacgaa ggccggttga ggtttcaaaa agaggtgaaa attgacaggc   8100
cacctgttcc tgtcaccaca ttagagccca tgagcaaaaa ggccataatt cggccttgtg   8160
cggccgataa aagtaaaaat aaaaatatcg tcattggtga tcctcgcaca ccaaatatgt   8220
cacgcagaat ggttactctg aaggctccgg acaaaagaaa gaccggaggc accgggggc    8280 aagcacgatc ggacacccga tcacggtcgc ctgtcatgcg tacgccggac gatccgggta   8340
ctaaggccga acagtccgag acaggcgcgg acagtccggc tatgatggcc ggacggtccg   8400
cagatggtca gaagcagcaa cctcagacca tcggaccaca acgttccaac acaagtgtta   8460
ggaaacaaaa cactactaag acgtctggac gactcagtag agtcggccct acttttggtc   8520
agttgcttgc caaatatatg aagaaggccg ttccacacaa ccggccaata aaacaaacaa   8580
agtcaatagg gcgatctgtg cgaaagcaaa agccgactaa acggacccaa agggtagcac   8640
aaccaatatc gccttatcat cctcctccag ggatagcatg gtgcgtccca ttctatccat   8700
cgccgatgtg ttgtcctact catgtgtggg gtggtacggc gatgaatttg tattactggc   8760
ccaatccgtt tgcttatttg ggctgggggg caccacaagt ttttgcctat tgacaggttg   8820
atcagataga catggctgaa gaggatgcga tccgaaacgg cctctgtgca ttaaagtccc   8880
atcaagtatt tatattatct gatcgcaaga gccgatgact tgcatcgagc tgagtcctta   8940
cttcggaaaa aaaaacctca tgaggtcaat tgtttccgaa gttttcgcta atgcttttgg   9000
ttcgccatgc tccaccaaaa ggcaggggg catatgttgg acaccaaaat gagcggacgg    9060
tccggcccat gggcccggac ggtccgcgtg tcccgagatt agattaactc ggatgtttat   9120
ccttatctcg tgcgtggtta tccatctaat cacgtgggag tttgttggct atctcttagg   9180
aaaaggtcca gacctcctcc cctataaata taagggggta cggccgattg agaaccccg    9240 aacacattcc aatcgaacca attaccttat ttacttttcc tgcccctagga gtagatgtag   9300 catagttcta gttgtagtct tccacatatc cacctccacc cctattcaac tctacgtcgt   9360
```

```
ctagatccgt cttgggtggc ctgccgatcc caagacgacc ctaggatctc acccctccgg    9420
ggggcaagat ctagttgtcc atccaagact tcttcctcga tttgatctct taattcctag    9480
gcgactccac gtcgtctggg gacgccccgg gtgacctgtc gacccggagc accttaagat    9540
cttccccca ggggacgaga tctagattcc agcaaggagt aggaagacga ccctgtcgcc     9600
aggtcgcgga cgtccggccc agagctgcgg acgtccggtg tgacgcaggg aagacaccgc    9660
tcctcgccca ggtcgcggac cgtccgaccc aaggctcgga cgtccgccca aggctgggac    9720
cgtccgcgcc tgaccagagc acgccacggt ctgtgaggtt gcaagatgcn nnnnnnnnn    9780
nnnnnnnnnn nnnnnnnnnn nnnnnnnnnn nnnnnnnnnn nnnnnnnnnn nnnnnnnnnn    9840
nnnnnnnnnn nnnnnnnnnn nnnnnnnnnt aatctataca gacgatctga gattcgtctc    9900
attttgagcc cgtctcaaga atcccttta tgtctcttgg gttagagatt tttcctgtaa     9960
aaagaatacc caagtgaagc gagaataatc atccacaata actagacagt acttactccc   10020
gccgatactt atgtaagcga tcgggccgaa taaatccatg tggaggagct ccagtggcct   10080
gtcacttgtc attatgttct tgtgtggatg atgagtgcca acttgcttcc cggcttggca   10140
tgcgctacaa atcctgtctt tctcaaaatg aacatttgtt aatcctaaaa tgtgttctcc   10200
ctttagaagc ttatgaagat tcttcatccc aacatgggct agtcggcggt gccagagcca   10260
acccatgtta gtcttggcaa ttaagcatgt gtcgagttca gctctatcaa aatctactaa   10320
gtatagctga ccctctaaca caccttaaa tgctattgaa tcgtcacttc ttctaaagac     10380
agtgacacct acatcagtaa aaagacagtt gtagcccatt tgacacaatt gggaaacaga   10440
aagcaagttg taatctaatg aatcaacaag aaaaacattg gaaatagtat ggtcaggtga   10500
tatagcaatt ttacccaatc ctttgaccaa acctcgattt ccatccccga atgtgatagc   10560
tcgttgggga tcttggtttt tctcatatga ggagaacatc cttttctccc cggtcatgtg   10620
ggtttgtgca cccgctgtcg agtatccaac ttgagccccc ggatgcataa acctacaaaa   10680
acaaatttag ttcttgactt taggtaccca aatggttttg ggtcctttgg cattagacac   10740
aataactttg ggtacccaaa cacaagtctt tgaccccttg tgcttgcccc caacatattt   10800
ggcaactact ttgccggatt tgtttgtaag cacataagaa gcatcaaaag tttaaatga     10860
aatagcatga tcatttgatg caataggagt tttctttcta ggcaacttgg cacgggttgg   10920
ttgcctagag ctagatgtct cacccttata cataaaagca tgattagggc cagagtgaga   10980
cttcctagaa tgaattttcc taattttgct ctcgggataa ccggcagggt acaaaatgta   11040
accctcgtta tcctgaggca tgggagcctt gcccttaaca aagttagaca gttttttaag   11100
agggcatta agtttgacat tgtctcccct ttggaagcca atgccatcct taatgtcagg    11160
gcgtctccca ttataaagca tgctacgagc aaatttaaat ttctcattct ctaggttgtg   11220
ctcggcaatt ttagcatcta attttgctat atgatcattt tgttgtttaa ttaaagccat   11280
atgatcaaga atagcattaa catcaacatc tctacatcta gtacaaatag atacatgctc   11340
atcaatagat gtagagggtt tgcaagaatt aagttcaaca atcttagcat gaagaatatc   11400
attcttatct ctaagatcgg aaattgtaac tttgcaaaca tcaaaatctt tagccttagc   11460
aatcaaattt tcattctcta atctaaggct agcaagagaa atgtttaatt cttcaatcct   11520
agcaagcaac tcatcattat tatctctagg attgggaatt gaaacattac aaatatgaga   11580
atcaacctta gcatttaaac tagcattttc atttctaagg ttgtcaatca tctcacggca   11640
agtgcttagc tcactagaca ttttttcaca tttctcaact tctagagcat aagcctttct   11700
aaccttaaca tgtttcttgt tttctttaat tagacaatcc tcttgggaat ccaaaaggtc   11760
```

```
atccttttca tgaatagcac tgactaattc atttaattt tccttttgag ctatgttaag    11820
gttggcaaag aggatacgca aattttcctc ctcatcacta gcattatcat cactagacga    11880
ttcatattta gtggaggagt tggatttaac cttcttcttt ttgccgtcct ttgccatgag    11940
gcacttgtgg ccgacgttgg ggaagagaag tcccttggtg acggcgatgt tggcggcatc    12000
ctcgtcgtcg gaggagtcgc ttgagctctc gtcggagtcc catttgcgac aaacatgggc    12060
atcgccgccc ttcttcttgt aatacctctt cttctccttt cttctcccct tcttgtcgtc    12120
gcctcggtca ctgtcactag atattggaca tttagcaata aaatgaccgg gcttaccaca    12180
tttgtagcaa accttcttgg agcgggactt gtagtctttc cccctccttt gtttgaggat    12240
ttggcggaag ctcttaatga cgagcgccat ctcctcattg tcaagcttgg aggcgtctat    12300
tggttgtcga cttggtgtag actcctcctt cttctcctcc gttgccttga atgcaacggg    12360
ttgggcttcg gatgagtcgc caagctcgtt gattttcctc gagccttcta tcatgcactc    12420
aaaacttaca aaatgcccga taacttcctc ggggtcatt ttagtatatc taggattacc    12480
acgaatcaat tgaacttgag tgggattaag aaaaatgaga gatcttaaaa taacatttac    12540
cacttcgtga tcgtcccact tcttgctccc gaggttgcgc acttggttca ccaaagtctt    12600
gagccggttg tacatgtgtt gtggctcctc tcctttgtga agccggaacc gaccgagctc    12660
cccctcgatc gtttcccgct tggtgatctt ggtgagctcg tctccctcgt gcgcggtttt    12720
gagtacatcc caaatctcct tggcgctctt caacccttgt actttgttat actcctctct    12780
acttagagag gcgaggagta ttgttgttgc ttgagagttg aagtgctcga tttgggccac    12840
ctcatcctca tcatagtcct catcccctac ggatggtacc tgcgcgccaa actcaacaac    12900
atcccatatg cttttgtgga gcgaggttag atgaaatcgc attaaatcgc tccacctagc    12960
gtaatcttca ccatcaaaag ttggtggttt gcctaatggg acggaaagta aggtgtatg    13020
tttggaaatg cgagggtagc gtaggggat cttactatac ttcttgcgct cttggcgctt    13080
agaagtgacg gagggcgcat cggagtcgga ggtcgatgtt gatgaagtgt cggtctcgta    13140
gtagaccacc ttcctcatcc ttttgtgctt gtcgcctttc cgatgcggct tgtgggaaga    13200
agattttcc ttcttctctt tgtggtgaga agaagatttc ttctccttcc ctttgttgga    13260
ggagctcttc ttcttctccc tccttttggt gcgagactct tccgatgaag tgctcccgtg    13320
gcttgtagtg ggcctttcgc cggtctccat ctccttcttg gcgtgatctc ccgacatcac    13380
ttcgagcggt taggctctaa tgaagcaccg ggctccgata ccaattgata gtcgcctaga    13440
gggggtgaa tagggcgaaa ctgaaatttg caaatataaa cacaactaca agccggggtt    13500
agcgttagta ataaggaatg agtccgcaag agagggcgca aaacaaatcc caagcgaatg    13560
agcaagtgag acacggagat ttgttttacc gaggttcggt tcttgcaaac ctactccccg    13620
ttgaggaggc cacaaaggcc gggtctcttt caacccttcc ctctctcaaa cgatccacgg    13680
atcgagtgag cttctcttct caaatcaaag ccgggaacaa aacttcccg caagggccac    13740
cacacaattg gtgcctcttg ccttgattac aatggagttt tgatctcaag aacaagtgag    13800
aaagaaaaga agcaatccaa gcgcaagagc tcaaatgaac acgacaaatc actctcacta    13860
gtcactaggg ctttgtgatg aattggagag gatttgatct ctttgtatgt gtctagaatt    13920
gaatgcctag ctcttgtagt agttgggaag tggaaaactt ggatgctatg aatggtgggg    13980
tggttggggt atttatagcc ccaaccacca aacttgaccg ttggctggag gcgtctgctc    14040
gatggcgcac cggacagtcc ggtgcacacc ggacagtccg gtgcccctgc cacgtcatca    14100
```

```
ctgccgttgg attctagccg ttgaagcttc cgacttgtgg gcccgcctgg gtgtccggtg    14160
cacaccggac atgtactgtt tgatgtccgg tgcaccggta tgggcgtgcc tggcgtctgc    14220
gcgcgctgcg cgcgcattaa atgcaccgca gggagccgtt ggcgccgcag ggagccgttg    14280
ctccgctggc acaccggaca gtccggtgca caccggacag tccggtgaat tttagcggag    14340
cggctgccgc gcgaacccga ggctagcgag ttcctgaggc cgacctccct tggcgcaccg    14400
gacactgtcc ggtgtacacc ggacagtccg gtgaattata gccgagtcgc cttagaaatt    14460
cccgaaggtg gcgagtttga gtctgagtcc cctggtgcac cggacaggta ctgttcactg    14520
tccggtggca caccggacag tccggtgcgc cagaccaggg gtgccttcgg ttgcccctttt   14580 gctcttttgt tgaatccaaa acttggtctt tttattggct gagtgtgaac cttttactcc    14640
tgtatacact atacacttgg gcaaacaagt tagtccaaaa gatttgtgtt gggcaattca    14700
accaccaaaa ttatttagga actaggtgta agcctaattc cctttcaatc tcccccttt     14760 tggtgattga tgccaacaca aaccaaagca aatatagaag tgcataattg aactagtttg    14820
cataatgtaa gtgtaaaggt tgcttggaat tgagccaata taactactta caagatatgc    14880
atggaatgtt tctttctttta tttagcattt tggaccacgt ttgcaccaca tgttttgttt    14940
ttgcaaattc ttttgtaagt ccatttcaaa gatcttttgc aaatagtcaa aggtgaatga    15000
ataagatttt tgcaaagcat tttcaagatt ttgaagtttt ctcccctgt ttcaaatgct     15060 tttcctttga ctaaacaaaa ctcccccctaa attaaatcct cctcttagtg ttcaagaggg    15120
ttttgatata tcatttttga aatactactt tctccccctt ttgaacacga taggatgcca    15180
attgataaat atttcttgga aaacactaag tttttgaaat tggtggtggt gcggtccttt    15240
tgctttgggc tcctttctcc cccttttttgg catgaatcgc caaaaacgga atcattagag    15300
ccctcgaagt aatttcttct cctttggtca taagtaaatg agttaagatt ataccaaaga    15360
cgaagtcctt ttctttgatg ctcatttctc ccccaaagaa tagagagatg gttggagtga    15420
tggcgaagga tgagttacgg agtggaagcc tttgtcttcg ccgaagactc caattccctt    15480
ccaatatacc tatgacttgg tttgaaatag acttgaaaac acattagtca tagcatataa    15540
aagagatatg atcaagggta ttcaaatgag ctatgtgtgc aagctagcaa agaaaatttc    15600
tagaatcaag aatattgagc tcatgcctaa gtctggtaaa agattgttca tcaagtggct    15660
tggtaaagat atcggctaat tgatctttag tattaatgta agaaatctcg atatcccccct   15720 tttgttggtg atccctaaga aaatgatacc gaatggctat gtgcttagtg cggctatgct    15780
cgacgggatt gtcggccatt ttgattgcac tctcattatc acatagcaaa gggactttgg    15840
ttaatttgta accatagtcc cgcagggttt gcctcatcca gagcaattgc gcgcaacaat    15900
gtcctgcggc aatgtactcg gcttcggcgg tggaaagagc gaccgagttt tgcttctttg    15960
aagcccaaga caccaaggat cttcccaaga actggcaagt cccgatgtg ctcttcctat     16020 taatttgca cccgcccaa tcggcatccg aataaccaat caaatcaaac gtggatcccc      16080
gagggtacca aagcccaaac ttaggtgtat aagccaaata tctcaagatt cgttttacgg    16140
ccgtaaggtg ggattcctta gggtcggatt ggaatcttgc acacatgcaa acggagagca    16200
taatgtccgg tcgagatgca cataaataaa gcaatgaacc aatcatcgac cggtatacct    16260
tttgatccac ggacttacct cccgtgtcga ggtcgagatg cccattggtt cccatgggtg    16320
ttttgatggg cttggcatcc ttcattccaa acttgcttag gatgtcttga gtgtactttg    16380
tttggctaat gaaagtgccc tcttggagtt gctttacttg aaatcttaag aaatacttca    16440
actcccccat catagacatc tcgaatttct gtgtcataat cctactaaac tcttcacatg    16500
```

```
tagactcgtt agtagaccca aatataatat catcaacata aatttggcat acaaacaagt   16560
cattttcaag agttttagta aagagtgtag gatcggcctt gccgactttg aagctattag   16620
aaataaggaa atctcttagg cattcatacc atgctcttgg ggcttgcttg agcccataaa   16680
gcgccttaga gagcctatag acatggttag ggtactcact gtcttcaaag ccgggaggtt   16740
gctcaacata gacctcttcc ttgattggtc cattgaggaa ggcacttttc acgtccattt   16800
gataaagctt aaagccatgg taagtagcat atgccaataa aatgcgaatt gactcaagcc   16860
tagctacggg tgcataggtt tcaccgaaat ccaaaccttc gacttgggag tatcccttgg   16920
ccacaagtcg agctttgttc cttgtcacca caccatgctc atcttgcttg ttgcggaaga   16980
cccatttggt tcctacaaca ttttggttag gacgtggaac caaatgccat acctcattcc   17040
ttgtgaagtt gttgagctcc tcttgcattg ccaccaccca atccgaatct tgtagtgctt   17100
cctctaccct gtgtggctca atagaggaaa caaacgagta atgttcacaa aaatgtgcaa   17160
tacgagatct agttgttacc cccttatgaa tgtcgccgag gatggtgtcg acggggtgat   17220
ctcgttgtat tgcttggtgg actcttgggt gtggcgccct tggttcttgc tcatcctcct   17280
tttcttgatt atttgcatct cccccttgat cattgccatc atcttgaggt ggctcatttg   17340
attgatcttc ttcttcatcg acttgagctt cttcctcatc ttgagttggt ggagatgctt   17400
gcatggagga ggatggttga tcttgtgcat ttggaggctc ttcggattcc ttaggacaca   17460
catccccaat ggacatgttc cttaatgcga tgcatggagc ctcttcatca cctatctcat   17520
caagatcaac ttgctctact tgagagccgt tagtttcatc aaacacaacg tcacatgaga   17580
cttcaactag tccagtggac ttgttaaaga ccctatatgc ccttgtgttt gagtcataac   17640
caagtaaaaa accttctaca gttttaggag caaatttaga ttttctacct cttttaacaa   17700
gaataaagca tttgctacca aaaactctaa agtatgaaat gttgggcttt ttaccggtta   17760
ggagttcata tgatgtcttc ttgaggattc ggtgtagata caatcggttg atggcgtagc   17820
aggcggtgtt gaccgcctcg gcccaaaacc gatccgaagt tttgtactca tcgagcatgg   17880
tccttgccat gtccaataga gttcgattct tcctctccac tacaccattt tgttgagggg   17940
tgtagggaga agagaactca tgcttgattc cctcttcctc aagaaagctt tcaatttgag   18000
agttcttgaa ctccgttccg ttgtcgcttc ttatttcttt gacccttaag ccgaactcat   18060
tttgagcccg tctcaagaat ccctttaatg tctcttgggt ttgaggacga attttctaag   18120
aattnnnnnn nnnnnnnnnn nnnnnnnnnn nnnnnnnnnn nnnnnnnnnn nnnnnnnnnn   18180
nnnnnnnnnn nnnnnnnnnn nnnnnnnnnn nnnnnnnnnn nnnntttca actctgagaa   18240 tcagcttgat tcgttcttct ggcatggctt ctactggcca actgctctct aggagggagc   18300
cgagttggtg aagtcctgcg aagcatgtca gtttcatgca aagcagacac acacacacac   18360
cagctcaggc tctgcaaatg attccaccct cttggccatt cgccgtatgg ggggtggata   18420
tcctgggacc atttcctagg gctgtcggcg ggtaccgttt tctctttgtc gccatctaca   18480
aattcataaa gtggtcggag gccaccccta tggtcagtat cacccaaggt gctgctgttg   18540
ccttcctcaa ttcgattgta tgcagatttg gggtcccaag ccatatcatt acggacaatg   18600
ggacccagtt caaaagtcga ctcttccaag agtattgcga gggcattggc acccagctct   18660
gctttacatc tgtgtctcat cccaggagca acgaccaggc tgagagggca aacacagaaa   18720
tccttagggg actcaaggca cacacctacg actgcttaaa aaagcatggt gccaattggg   18780
ccaatgagct tccgtccgta ctatggggga accggaccac acccagccga gctaccgggg   18840
```

```
agacccgtt cttcttggtc tacggggccg aagcctgcct tctcccggaa atcattatgg   18900
gctccccatg agtccagtct ttcgatgagt ctatgcagga atagctacga cgtgaggaca   18960
tggacttcat cgacgaacgc agatggcaag cggtgatccg aaatgcacgg tacaaccaag   19020
cgctcaggcg ctaccaccaa cggtttgtgc atagtaggga gctcagggtc ggggacctag   19080
tcctaaggcg agtactgaac cgagaagggc tccacaaact ctcccccagt tgggaaggac   19140
ccttcaaggt gacagaaata tgccgaccat ggtgtgtccg ccttgccaca acagaaggag   19200
tgcctcttcc caatccctgg aatatagagc atctctgtaa gttctatcca aatagcaaa    19260
actgggggt tgagttttct tcctttgtaa ctaggttacg catatgtgta tgtcaattcg    19320
gtgaggcccg ccctcgtaag cccatctgtt ggtctacacc catgtatatc gagttataag   19380
gaaaggattt acccctaga tgtgattttg tgatggtttt attctacttc ggtttacatg    19440
cattattttt tatctaaccc acccatatag tttcccaccc ttgttggtat gatgacatcc   19500
gaattgagta gacaggcttg cagttcaaga ccccttact gctacagggg gtccggcaaa    19560
ctgcggacca gttctagaga atgggcgcta gcctcctgga ggggtccgga gttgtgtagc   19620
cgcttagcat ggttccgtac cctaagcctg catgctccac cactctataa cgggtgccct   19680
agtatttgga actgtgatcc tatgggtcca ggcatacggc ttggcttccc aggctaaatc   19740
ctgcaggtcc tgttgcataa atcaaaggat ggcagatacc agacgatgga tcctatggtg   19800
tgctcctaac actttaaagc cgaagctgtg tacaagtcca ggtcccagtc cagtagtagg   19860
tagtctcaaa ctgtagagac tacctcctag gggccggacc accaattta tctttggtat    19920
actggtatcc agcctcgaca cgtcgagcct acctcccagg gggccaagta ccaaggggaa   19980
gttgatgaca ctacacataa caaggacaaa taacatacaa ataagtttaa gttccaatgc   20040
tacctcatta gcggttctta taatatctta caaaatcaaa agttattaca accgcttccc   20100
agtggaaccc ttgctttgtc tctataggtc gtcagcagga tcgtgctgga agcgctcggc   20160
caccagctcc acgcgtcctt gtacactctc ccaggcggcg tcttctatgg cggctaccgg   20220
accagcgatc actagcgcca aggatatggt ggggtcgtga ctccggaagc atgttaggac   20280
ttattcaacc actgcccgac agagcttgct gccctctgcc tctaggcggg ccccgaggat   20340
ctgatccagg cgacggaggc gatcggcggt agagtccagc accgggagcg catcagagat   20400
cgacgctggt agctccgaca ttgggatggg gctcatccct agtggcacta gtgccgtgct   20460
tgcctcgccg gcccacgcga caatacactg gacctcgacg cggtgctccg cttggagatc   20520
ttcaagggcc ttcctggtgg cctccatcgc ttggggaccc ggtgccgcct gcgctgcatt   20580
gaactagcgg atctgctcct ccagcttcct ctctttctcc tctgcctcga gcttgtgctt   20640
ggccagcaac tcgcctcgcc gggtgagcat ttcttccctg aagctgagat ccgtctcttg   20700
cctggcgagg tccgtctccc accggtccaa ggactgctcc ttcgccttaa gattttcctc   20760
ggcgagggtg gcattgctag ccttgccctc gagctcctgc taccacttt gcagcctctc    20820
cacgaccctg acctgctggg cccgctgggc ttccagagtc tggtccaggg cactcagctt   20880
ggcctggtac tctgttgtga gggtctcccg ctgggtcacg acctcctcct tcctggtcac   20940
cttcttctcc ctccgggacg cctccagctc cctggcgcac accctctgga ggtccctctt   21000
gtactcctta tggtcctgct cgagttggga ccgctcggag atgaattgtt gggacgccgt   21060
tctggtgcgc cctccagtt gggtgcgcca gtcacttagg cgctggtgct cagcctcaag   21120
cgcctcccac tcccgcaaga ttgctgcccc agtgtcacta aggacctagt gggcacgaga   21180
cattatgcga gggaggggga ctggcgccgc ttcttgctcg gcacccgacc ggagtcgccg   21240
```

```
cccaaacacc acctccatct cctccggagc aggcgggggg ttggagctgg acatgcctac   21300
tgcgtcaccc ccagtgtcga gagcgggcgc ggatccccca gctgggacct ccttcgccac   21360
tgcgacgccg cctgacgctg ccaccggacc cccggctggg gcatgagaag ccgctggtgc   21420
tgtcttggca gcagctgggg gtgggccgcc ggcaccactc tcagcaggtt cctgctgttg   21480
agagccagac ccgtcggtgg gcctggtatc tggtggagga ggcatgacct tgggagcggc   21540
gaaggaagaa gccctagcga acagatgatg ggttaaaact ggtcggcatg atgattagac   21600
tcatggaaaa ggggctacgc ttacttgggg ccctagactt tctagtgacc ctggaagcgg   21660
ggcgatcacc gctcctgctg ttgctatcgc tgttgctgtt gctgttgctg ctgctggtgc   21720
ccctgggggt gaggactgac gcgcctctgc gcgccgtggg cctgggagct agcttcctcg   21780
gccccacctg cagccctctg acgcttctgg gggggctcc gaaatgagcg acccatcagc   21840
gcgacatggc ctgcgttgcc tctcctcctc cgaccccctc ggagctacct ggggcggagg   21900
cactgctcgc agcccctttg cctttgtcca aggggctagg ggccacggcg gggttggtgc   21960
tgggagccgc accagtgggc tgggaacctc caatcggtgc attagaaatc tggatcccac   22020 ggaggggggtc ccggccaccg gtctagcgaa ccgccatgcc gctctcgtcg agggtcggca   22080
acgtggccaa gatcaccatc ctcaggcctg gatcgtcgca gagcgcaggg atgttctggg   22140
ggagtatcag ggactcaggg acaaaagttt ccccaataat ccctcccatc aggactgcta   22200
gctcgtccca ggacagaacg gtgcccggcc tgcgttggat cctatcgatg tcgtttgggc   22260
cggtgaacca acagcacata cgcggtctcc tctgcagcgg cgcgatccgg tgcttcagga   22320
gatcgccgac cacgtgcatt gatggcaggc cgcccgtagc caagcccttg attctgtcca   22380
atacaggcag gaactctagc aagagggacg gcttagtcct ccactgcttg cggtcgagcg   22440
ctggcccatc gctcggcagg acgaggcggt cgttggcctc ggcgctggca atcacccaat   22500
cgttgcgcca gttttcccac ctcgcaccgc caaaggtggg gatgtatacg acggctggat   22560
ctggcctcgt ctggaagtag taggcaccga tgtggtccct agtcttcccg aacttgacca   22620
gcacgaagaa gcagcggaag agggaagtac agggggccac acctacgaac atctcacaga   22680
ggtggacgaa gatggctgcc tggaggacgg agtgggggtgt gaggtgttga agctgaagcc   22740
caaactcctc cagcagcagc aagaagaagg gcgagaatcg gcaacgccaa cccgtagaag   22800
atgtaggagg tgaacagcac gaactccccg gcggtgagat cgccatgagg gacggcgccg   22860
gcgcggaact tccggcgagc cctggcgcgc tccatccaag caggccgcgc accaggttga   22920
gcgcctcctt agactgaaag cagtcaggat gaccaagcga ggccatggcg tgtgcggcgg   22980
cgcgagcgtg gaacagagga gcacgaaggc aaaggggtgc aggcgattgg gagagaatgc   23040
gaaaaggtaa ctgctgcacg cggggtgaat ccttttcaa ggaaacctga gtccttgttc   23100
agggaaaccc ttccgtgcgc ccttgaattg ccacaggaaa tctcgcccga tgcgcacata   23160
ggacccaggc agcccactct atgacacggt ggcccgggtc acaagtcat acagattgtg   23220 tgctggattt cgagtgcgga aagagcgaat cgccatgcga actccgcgc acgatagcgc   23280 acctcctcgg ggccgctgca gaagacaaaa ggttatgcag cggcaacgag gcgtcccacg   23340
cgtggcccga cgaaaccacc aggcatgggg ccatgggtca gtcagctgca gagacagata   23400
tggcagttga cgtgactgaa ggcggattga cagcgggcgt gtctgcagac gcgctaaaac   23460
ggcatgccaa tcaccgatca ggtcacgttg aagcaaagta caagctttgg ccccacatgc   23520
aggctcgcat cctcccctaa ggtgggtccg ggggccactt tcggcaccct gaaacaaggg   23580
```

```
taccccttac tactgtataa atacgcagta cccacgcgac tatctttagt cgcgtggtaa    23640
aagagctgta tgtgggacca aaccatgact cgccctagcc tcgggcgact actctaggcc    23700
agcaacagca cctgacccca ccacatgggc gggtccgggg ccgccatgtg tccagagaaa    23760
gtgatgtact ccaaggcatc aatagtgagt ccggaccccc ataggagagt gccgaaccca    23820
tgccagaccc ctgtatatac ggtccaggcc tccaagtttg gtcatgcgtt actctgtcag    23880
cattagttat ttacataatc tatttcttcc attatgctcc taggcccgca tgtcgaggct    23940
cagcatcctt gtatgtgcct cctgtgacac cccagtgtca cctagggttt ctcttaaaaa    24000
gccaaaccaa ggaccattat tttatgtgaa ccaaagtaag catgagcatc aaaataactt    24060
aagtaagaaa gaattcacca agtatatgct taaaagtgtc atgatcaaga caattgagtc    24120
tcttaaagga taagaatgtg caaccctaat taagaaccct aagtgaaccc catgaacaaa    24180
attcaagaaa ataagcaaaa gggaatgaaa agtttaaaat tttgagttga gccaattata    24240
taagttaaag tatatttgat aagcaacaag atagattgag aaagcttagc caaaataatt    24300
caagaaaacc cccaaatcaa gcttcttttg ttgggactca ttgggaattc tgaatttcag    24360
aattctgaaa ttcagacctt gagccaaaga tcagggatgt tcaccttgat ccctaactcg    24420
aatcctaatg gccccattga caaaattgtg tctaactaac ccctctgtct tgtgccagaa    24480
gatggcattg ggacgcgagc cctagacacg acaaaacttg ggatttgcct cgggtttggg    24540
cagggagaca gaccagattt cctggctcca tatctctgca accagtaggc aaaatcctat    24600
gacctccaca caagaatggt agcttgtagg gaggagaaga ggttttgtgc actgaccaag    24660
gcgagagcag gctcggatga cgaccacac gcgccagagc ttgggcagaa cgcacgggca    24720
cacgtgttcg accctggtcg gcacgccaga gctcgcccaa cccgcgcgcg cgctcgcccc    24780
ggcgtccggt caagtccgcc gcgcgcccac gccctcggcc gtgcccgccc gcgcctataa    24840
agcctccccg ggcgcacctc tcttcgcccc gcactcaccc tcaccggcca gccactgttc    24900
cttagctccg gcgagctcat ttccgcccgc cattgccgcc agaactacgg ccgccgtggc    24960
cagcccactc cagccaccct ccagcccaac cagtgctcgg ctagctccgc cagtagcccg    25020
tgaagcttgc caagccctcg gacccgaccg gaacttcacc gggaggcccg aagaatcaac    25080
ctcaccggac ttcggtcttc cgccgccgcg cgtggaccaa gctatccagt gagtctcccg    25140
cccgattcct ttcgctcatg tcttctctgg catcccgtgg acctccatga cctatttgat    25200
tgaactatct cgccgcgacc aggccggtct cctcgccgcc gacgagcatc cccgcctgcg    25260
cgcgtggacc gaccgactcc ggccatctcc gacggtgttc cgcacaccgt tgtgatcccc    25320
gcgacctccc cttcaccctc ggccacttca ccggaacagt ctcgccgccg gtaagcccct    25380 ccgcccttt cttcgccgcg gctactgttt aaggtagaag aaggacctcg ggttaggttc    25440
tgtagaaccc gagggttttt tcgtaatgtc agcgactcat gagaatagta acctaaggac    25500
tgaattgcga ggaaaactta gaaaccgcc agggaccca gtgcaaagtg gatttccatt    25560
taatcaattt tgttatttct ttttaaaatg accagagaac ttagaaaatc cataacttga    25620
tgaaatctta atgaaaagct gtcaaaccaa ttttgctagc tctggaattt tatgacctat    25680
catttaaaaa tagtgaacca tatgctttct gttctaaatt ttagagttta aaattaaaaa    25740
cagaaacccc ctaaaccttg tttaattaag gaaaattagt ttttcttttg tgctgagctt    25800
aagaaaattt gtagatgctt ataccttaat tagacactgt ttaaaaatag taggagccct    25860
agcattagag attatgatgt agttattcat ttaaagccat tttgtccaaa acttagaaa    25920 aatcagaaag gccttagaga ttaatgaaca gtgattagta atattttcc tagattactt    25980
```

```
atgcagcaga gaacctagga aaaatgcaga gaccattaat ttggaccagt ttctaattaa   26040
gatgctttaa ttagcattat gtagactgaa aatcaattat tagaattgca aaactataac   26100
caaagtggtt aacaaaaatc cagtgaactt ataaccacca gagccccact acaaaaatac   26160
agagcacccc agcctaactt tttaagtagg gaaaataaat acagaatgat aataaggcat   26220
tttcccacta aatcatgagc aaccccaaat aatgtgataa tgggcaacca aaattttgct   26280
aagtccatga tgagataaac caccagagaa aaatacaaac ccatgaaaaa gaagtgaacc   26340
catgcctttt gctagtaatt tgtgaggaag gccatttagc tcaaataatg caaccaccc    26400 cttcccttag gcaaaaggaa gccaaactcc agaatgattg ctcttgcaca aaatactagc   26460
taagaaaaat aagaactctg ttgtttgatg tttttcaagt atagtggtag tagaaagcac   26520 cccctttggct agaaaccttta agaaaatctt agggaaagaa ttaaagggta ttaatgacta   26580
gaaatttgta tcaagtcatg ttataacacc taaaagccag caaaaataag ttttttgagaa   26640 ttacccacta ttaaataata gttgtagttc aaagtaccc ttctgccctaaaatttggta   26700 attttgtcca gagaaaacca ttcactttct gaaccccaaa ttttgagaca gagaaccata   26760
caccagtaac aagccactgt aattttttgca gaattttttgg aattttataa aagcaacttg   26820
tagttcaaac ctactccaaa acattaaaga gaataaaaga aaagagaaga agaaataaac   26880
ctcatcccaa taagactaac ccaatttacc aagtatacca ctaaagggtt ttacataagt   26940
aaagttaact ggttttaaat caaaagatca tacatcttta aagttataaa ttctaaagca   27000
catatcatat catgcatata tcttacgcat tgcattcatt agattgtaat cttgccgacg   27060
gagagtacgt gctcatccct gagcaaggac ctatccaaga ggaggaccag gagcaggctt   27120
cagaggctgc tattgaggat ctccccgcag ccccagcaat tgaaggcaag ccccggtttt   27180
atgcataacc atgttattat atgctacttt actacactta atgcttgtag gattgcaatg   27240
tgcacttaag tgtaggagtt gcttgaaacc tctagttgca tgaacttagg attccttttt   27300
gagatgaata ctagtatgct aggtcgagta gctgcttgct aatcaggatc tcggtagaag   27360
tcgagtgatt tttctagcac tcgcgcgagg tcaggaattg attgtattca tcttgataat   27420
ggggtatatg ttagtccgtg gacttgggtc cagggaggat gccatgtcca tgagacggga   27480
aaaatgaatt aaggattaat gtgtggatac ctgagtcaag cttttgaacg tactaagcac   27540
atgccgggaa aaatggtaac cggtaaacct agtacctgag tgaagccggg cgcggacttt   27600
atccctcatg cgacctgaga cagggtctcc catgctagct atggtgggta caagtgcggc   27660
cactgcatga cggcagtcgg ggtcagtgga gcattgtatg ccaaggcggt gaggcctgga   27720
cgcgaacggg gaatcgatgg ggacggttgt catgtgtggg gtcggagtac cctgacatgc   27780
cgtgtgttta ggtttacctt gcaaggttta aaaactcgat tcgaatcgtc tgcttctcgc   27840
agctaatgag actgcttgat tccttgtact gcatcgagta agaagtgaaa tgtggattat   27900
atgagataac ttgttgactg aactaattga ttgttaccat gtatgcttag aaggagcaaa   27960
tctagctaag ttaatgatgg tagaatttga aaagctaaaa gttgatttta gaaacagcta   28020
gtgcttttgg caaaccaaac ccctcagcca aacagctgca tagtctagag gtagaggagt   28080
agactcctca caccggttaa gtctagctga gtattagtat actcagcctt gcttgtggca   28140
ccatttttgc aggtaccatg caggatgtag ttgatggtgt gacttggcct accacccigc   28200 caccgggttg gacggtcgag tgggatgttg ctccggcagg agaggagcat gaggagtagt   28260
gggctaggcc ttgcccattt cctcattacc gacgacatcg attatccgct gcactttaat   28320
```

```
ttatgaactt tattcgctac tcaaaaactc cgatttatgt aataactcag tacttaattt   28380
gaggtttcct gttttattgt atttcttctg tgactcacct tcgagtgaga ttgtgggatt   28440
tgatcctggt taagtggctt catcagacta gatctgaggg actgacgggt tattccgatt   28500
taagtgtgtt acggcccctg aggcgtgact taggcactta agctggaata attcgggcgg   28560
ttctgccaca gctggtatca gagcaaattc caccacagag aagggcaata aaccatgaat   28620
accaattttc aaaatctaaa acctgcctag aagctactac ggatcgtcag gactagaccg   28680
ctagacctag gacgaaaggc cttaggcata gagggagaaa taggtggcta actaattagg   28740
ccctgtgggc caatacttat attttaggat gccctaaaaa ggcaccctat tttccttttg   28800
agaggcaacg tttctttccg catgcatgca ttataaaaca taaagaggaa ttaaaattga   28860
gctaaccccc ttttcttcga aatcatccgg gctctctttt tcttttttcct tccaccataa   28920
tctttatctt tgattcccct ccgcagatga attcacccac ccccgccagt ggaggagact   28980
ctcgtttcag ttctgacttc ctttctcgcg atggcttccc ttccattttg tgggaagtgc   29040
ttaattccgc cggttaccct acgccccctt tgtacacggt gcagttgtat gaggagcatc   29100
gggtacctcg ttgtcgggtc tggctaactt tggaggctca tccccttcag ccgggttggc   29160
gttctcttga ctctgagacg attggactca ggacggacga caccgttgag gcagcagcca   29220
tgaagactct gacgactttt tgtggctacc atccccctgga gatggtgatg caccccttgg   29280
gactcttccc cgctgagaag aaggatgatc ccatgtggtg taaccgcgtg agccatgtga   29340
aggatgtgtg ggcaatgtat cctgacttgg ttgggagggt cactgttcag tgcatgagtg   29400
cgctgtaccg ccttcaggcc cttcagagcg atgctatgac acttcttgcc aataccgctc   29460
aggcagccaa gctcacccctc gacagtcggg aagattttgt ggtcgaccta tccacagagt   29520
tggtggaaaa ggatctgcag gtggagaggc tgaaccagcg tattaccacc ctggagcagc   29580
aagtggagat ccgagataac actattgatg tcttggagaa ccagcttcac gacgtgcaga   29640
gggaactcga ggaagcaaat gaccacttgg acatgcacca cctggagatg gaggccaatg   29700
aagcaggaag cgagggagaa gaggctcccg aggagctagg accagcccct ggtgccaatg   29760
ggactacctc cgcgatacct ccttcacccg tatccagtgt cgcttccacc gctcagggtt   29820
aagcagtcgc tttgacattt ttaggcggat agaaacctat gcgagcttag tggtatcaca   29880
ttttggacta ggcttgtggg taccttcccc tgattaatgt aaccctgtaa acttttgata   29940
tctgtgggat ccttgtcacc atgttatctt cattcgaacc taatattatg attatggcat   30000
tttccttcca tatgagatga tatccttgtcg ttcggaaatg tgaattggga taacaatggc   30060
gacaatctct gttttcagat ggcagcgagg cagcgtcgcg ggcaaaatga gcaagctccc   30120
ccgccacctc ctccagctcc cacagtgcag gagctgatgg cccagcagaa tgagattctg   30180
cgacagctct tgcagcgcca gccccaccct cagcatcctg gtggaggcca gcatcagcga   30240
cctccggcta tggcaacata ccaggagttt ctgagcacgc agccgccctt gttcaccaag   30300
gcagaggatc cattggacgc cgacgtgtgg cttcgcgtcg tcgagtccaa gtttcccctc   30360
ctcacaggag actgccctga tgaggccaag gctcgcttcg ccgcacagca gcttcgcggc   30420
cctgctcgga cttggtggga tcacttccgt gctatgctcc ccggtgatcg tgaagtatct   30480
tgggaggaat tcaagactgc cttcagaggg caccacattc cagctggcat tcttgatcgg   30540
aagttgaacg aattcctggc cctcaatcaa ggaacccgca cggtactgca gtatgcgcaa   30600
gccttcaacg acttatgcca gtatgcaggg tatcatgctg attctgatga aaagaagagg   30660
gatcgcttcc gcaggggtct caataccaag ctgcgggaac gactcaacac tgtccgggcc   30720
```

```
gatagcttca atgagttggt caacatggcc atctctcagg aggattgcat tgttgctcac   30780
cgggcagaga agaagagaaa ggcaccaatg gcagcaccat ccgctcaggc tcagaggttc   30840
cggattgttt ctcacaatca gagcaggggt tttcagcagc aggcaggcag atgggtgatc   30900
aggccacctc agcagcagca gcagccggca cccaaccgct atccagctcc cgccccaaga   30960
aacaatcagc ctccgcagca gcagcagttc cgccagggca tgggaacaa gtgtttcact    31020 tgtggcaatg tgggccacta tgccaagaat tgtcccagga accagcagag gcagatgcca   31080
gcaccaaatc aagacaaggg aagaaagcag aaggtacaag tcaggcaagg gaagctcaac   31140
ttcactgctc tagaggaagt gccagaagga gctcccatca tgaccggtac cttttcagtt   31200
tataatcaac ctgctttaat tctgtttgat tctggtgcat ctcatagttt cattagccaa   31260
aagttcagtg ctaattgcaa acttccattc tctcactcaa aagggtcatt catgatagtc   31320
acacctgggg gtaaaattgc aactaatcaa ttaaaccaaa gtgtgcctat tcaactggga   31380
agccacatta tcaaaaccac tcttcttgtg ttgggattgg aaaatgtgga cattattcta   31440
ggagcaaatt ggatgacctt gcaccaagtt gtgctcgacg tagccagtcg taccgtggaa   31500
gttaattctc ccttctgcgg gaatttcact ttgattctgc ctagtcaggg ttcttctcag   31560
tcatgtgctt tctctatgac ggaattaccc ctgaagaaga tcccagtggt ctgtgagtat   31620
gcagatgtct ttcctgatga attgccaaga atgccactgg accgggatat tgagttcgcc   31680
atcgagttgc aaccgggaac ggccccaatt tccaagaggc cctaccgaat gccacccgct   31740
gagttggcag agttgaagaa gcagttcaa gagttgctgg ataagggatt tattcgccca    31800
agcacttcgc cttggggctg tccagcactg tttgtgaaga agaaggatga aagcttgagg   31860
ttgtgtatag attaccgccc tcttaatgcg gtaactatca agaacaagta tcctttgcct   31920
cgtattgatg ttctctttga ccagttggtc ggggccaagg tgttttccaa gatagacctt   31980
cgctctggct accatcagat caaaatacga gcaagtgata ttccgaagac ggcattctca   32040
accagatatg ggctatatga attcttggtg atgtcattcg ggctgacgaa tgcaccagca   32100
tatttcatgt atctgatgaa ttctgttttc atgccagaat tggacaagtt cgtggtggtt   32160
ttcatcgatg atattctggt gtactcaagg aacgaagaag aacatgccgg gcatttgcat   32220
gtagtacttc aacgtctgcg agatcaccac ctttatgcca agttatccaa atgtgatttt   32280
tggctaaagg aaatcaaatt cttgggtcac actatctctc aggctggaat agctgttgat   32340
cctgataaag tgcaagaggt gatgaactgg aggccaccaa cgactgttcg ccagattcgg   32400
agttttctgg gattggctgg ttattaccga agatttattc cggacttctc tcgaattgcg   32460
aagcctatta ctgagttgct gaagaaagaa gtcaaatttg tgtggagtca gaagtgcgaa   32520
gatgccttcc atgcattaag gcagcatctg accacagcac cagtattggc gcaacccgac   32580
agcagcaagc ttttgatgt atattgtgat gcctctggca ccgggctagg ttgtgtcttg    32640
atgcaagaca accgagtcat tgcttatgcc tcaagagcac tcaggcctca tgagcaaaat   32700
tatcctactc atgaccttga gttagcagca gtggttcatg cattgaagat gtggaggcac   32760
tatctaatgg gaacccactg caacatcttc actgatcata gagccttaa gtacatttttt    32820 actcaggctg atctcaacat gaggcagaga agatggctag agctgatcaa ggattatgac   32880
ctggaggtac attatcaccc agggaaagct aatgtggtag cagatgcctt gagtcggaag   32940
ttgcagtgca actgtattct gatggattct cgtgttaaca ccttgtgtga tgagttgagc   33000
aagatgcaaa ttgaagtgat tccttctggt tctttgtctc acattgctgt tgagccagcc   33060
```

```
ttgcaagacc agattatcat ggcccagctc agtgacaagg gagtgcaaat tatcaagaag    33120
aatctccatc agaaggttga gaagtataat tgtttccgcc aggatgagaa gggtgtgtta    33180
tggttcaaaa gcagattggt aattcctaag gaccaggatc tcaagaagaa aattttggat    33240
gaggctcatc tctccaaatt ctctatgcat ccgggaagca ccaagatgta ccatgatttg    33300
aagcataaca atccccaccc ttttcctata agtctcaccc ttcgcttcac cctgggagga    33360
ctctggcccg aatctcggga cgagattcct ttaagggggg aaggctgtga caccctagtg    33420
tcacctacgg tttctcttaa aaatgccaaa ccaagaacca ttattttatg tgaaccaaag    33480
taagcatgag gatcaaatta acttaggaat aaagaattcn nnnnnnnnnn nnnnnnnnnn    33540
nnnnnnnnnn nnnnnnnnnn nnnnnnnnnn nnnnnnnnnn nnnnnnnnnn nnnnnnnnnn    33600
nnnnnnnnnn nnnnnnnnng ggtgctaatc atgaaccagt ccagagcaac actatccgat    33660
ggccattgcg tccggtcgca cgagagacgc gtgcggaacg tcccgtagga gcggccaacc    33720
ccccattttg cagctagcag ccgtccagta gggacagccg ccgagctccc cgacatgtct    33780
ccttcgggac cgggcttcta tttcaagctg cgggacggtg cggtcaatcc atgtggacac    33840
catgcgagtt cgcgcttcac tatctgggct ggggacccac ctccatcaat ggtctgcatg    33900
acgcaggata ttccatcagc catggtgcag tggaatccgt tccagaggat ggcctctgca    33960
ccaaacgctc gccaaggtaa cagaagcaat ccaggcccat cgggcgtgat ctcccatcga    34020
tccgtatcga tccttttgaca tgaaaaggca atcacgggct cacgcttttc ggagtgtaat    34080
tcaggctccc gggtgcagct ttttgcgcgc ttgcggcagg gggcatctgg tggacatcaa    34140
atgatatggg cttgcttggt ccagggaacc ggcagcacct gctgtcccga atcagttgt    34200
gatgctatgt catccgtcga tagtcggagc ttatccagct cggatcaggt gatacgcttc    34260
cctttcggag aggtttgagt ttcagacctg gtgctcagtt atgataaaaa gggtcggcag    34320
tgagagaaac cccgaaaact tgtcaatcga accaattacc ttatttactt ttcctgccct    34380
aggagtagat gtagcatagt tctagttgta gtcttccaca tatccacctc cacccctatt    34440
cgactctacg tcgtctagat ccgtcttggg tggcctgccg atcccaagac gaccctagga    34500
tctcacccct cccgggggc aagatctagt tgtccatcca agacttcttc ctcgatttga    34560
tctcttaatt cctaggcgac tccacgtcgt ctggggacgc cccgggtgac ctgtcgaccc    34620
ggagcacctt aagatctttc cccccagggg acgagatcta gattccagca aggagtagga    34680
agacgaccct gtcgccaggt cgcggaccgt ccggcccaga gctgcggacc gtccggtgtg    34740
acgcagggaa gacaccgctc ctgcgcccag gtcgcggacc gtccgaccca aggctgcgga    34800
ccgtccggcc caaggctgcg gaccgtccgc gcctgaccag agggcaccgc cacggttctt    34860
gttgagtgtt tggcgctcca aaaaggcgtc aacagtagcc gtcacatcat ctattgtgtg    34920
gctatgctta agtgtgcctt gatataattt agaataagtc gagtctctag aacgcggcaa    34980
tttttaaaag taaacagaag ctgaatttat tgattgctgt tttgggctgc acgcactgtt    35040
ttagttgtgc tgtttgtttg ataaaccaaa tcatgttttc tgtagaaaag tcatatagaa    35100
gagttgtaga tgacatgatt atcttgcttg tactaaaatt tgacagccat aaacctgatt    35160
gtttaggagt tgtgcttttc acaagcccag cacctgaatc tgtcaaattt ctgaacatat    35220
ttcagaaatt gcaatggttg cttaagttaa tgttgaaatt agttattggt ggtcacaaga    35280
aagttgtaga taactttatt atcgtacttg tgttaaaatt tgacaggcat aagtctaatt    35340
gtttaggagt tatgtttttt acaaattcag taactgaatc tgtccacttt ctgtacagat    35400
ttcagaagct gcattgtttg cttaagttaa tgttagaatc agcccttgta gattataaga    35460
```

```
aaagttgtag aggctttct tatcttgctt gtgttaaaat ttcataacta taggcctgac    35520
ggtttaagag ttatgaattt tacaaactgg ttgctgtgtt ctgtccaccg tcagaacaga    35580
tttcgaaaac tgtaatattt gatttagtta aacctggaat cacttcttgg tgattatgaa    35640
agttgtgtag tacttttgct aagatttca aaaagtctta gatcactctt tttggtggtc    35700
tgaagattaa gttacatgtg tttgaagtgt gaagactgaa tctgtccagt tttggacagc    35760
acagccttca tagtatattt taaccttgat acatgctaaa ccagcctggg atgtttataa    35820
ataatttgta gaacatttaa ttagcttttcc agaaagtcta ggatcaattt gtttggatgt    35880
ctgaatcttc agttatgaat ttttaaaatc acaagtctga atctgtccaa atctggacag    35940
agctgttgtg attgcacttt tgaccttgc taagtgttta atcatgctgt gatgaaaata    36000
ccaaaattgt agagcacttt ctaaacttc cagaaagttt tagtttgcta tttttggatt    36060
aatatttgaa aagttattat taaaacaagt aactgctgtg ctgctgtcca aaaaatctgc    36120
acgtgctcaa atgaatattt agttcaccat tttggctaaa aacgcttagt tagcacttaa    36180
cggacataga cttgtgatgg ctaaacttag gttaacatgt gttccatgat taatgtgctt    36240
gcttgctata gttgattgtg atagaggagt ccatcgacat tgatgcatcg gtcctttatt    36300
aaacttgtgt ttgtgatgct tttgtgtgat caatagaaga actaatgaaa agccgtagca    36360
actaaataaa tgcttgtaca tatgatatcg tgttgcgttg gttaattgta ggtagtgatc    36420
attgtctttc cagtggtagt gtttacgtgt gcccaatgac acataaataa ctagtgtttg    36480
cgtatagttg ttgcagtgtc ttactaatta atgtttagtt cgccactgtg tcttggtata    36540
tcttatgtta cttttattat attcatacat atgcatcttg cacctcatat aggaccgaga    36600
gatgatgatc gagccagtga tgtggtgcca accacaagat gccgttgatg gacgacctaa    36660
agaatggact taaccagtgg atgctcgcca agcgagtacc tcccccagca aacactacct    36720
aagtgttaaa ttaaaggcaa gccccggttt tatgcataac tgttatatat atgctatttt    36780
actgcactta atgtttgtag gcttgtacca tgcacttaag tgtaggagtt gaatgaaacc    36840
ctagttgcat gaactcagga ttccctttga gatggatact agtatgctag gttgagtagc    36900
tgctttgcta attagggatc tcggtagaag tcgagtgatt tttctagcac tcgcgcgagg    36960
tcaggaattg gttgtatcca cttttgataac ataatggtga tggtctgtgg acacgggtcc    37020
atggggacgc gtggtctacg agatgaaatt ggaataagga ttaacgtgcg gatacctgtg    37080
tcaagcgttt gaacgtacta aacacatgcc gagaaatatg gtaaatcggt aagcctagta    37140
cctgagtgaa cctgcccgca gattgccctc ctcaggcgac ctgagacgtg gtctcccatt    37200
ccggttatgg tgggtacaag tgcggtcact gcacgacggc agtcggggtc agtgaggcat    37260
tgtacgccaa ggcggtgagc ccctttctgt tgccagggaa tcgatgggga cggttgatgt    37320
gtgtggggac ggagtgcccc tacatgtcgt gtgtttaggt ttaccttgca aggtttaaaa    37380
acttgattcg aatcgtctgc ttctcgcagc taatgagact tcttgatcca ttgtactgca    37440
ttgagtaata agtggaaatg aggtgattgg caaaagatgt tgtttgataa aaattcttga    37500
tatcatgtat gattagctag gtacacatct agtcaaaaag gatcatacta aaacttgaaa    37560
agctaaaact tgatttaga ctcagctagt gcttttggca aaccaaaccc ctcagccaaa    37620
cagctgcatg tctagaggta gagaagtaga ctcctcacac cgggtaagtc tagttgagta    37680
atgtatactc agccttgctt gtggcataat ttttgcagat attcattagg atgattggtt    37740
gatggtgtga cttggcctcc atccctacca ccgggataga tggtcgagtg ggttactgct    37800
```

```
tccgcaagag aggaccagga ggagtagagt ggccaggctt cgccatgtta ctcggttctt   37860
ctccgttagt tatttctgct gcattaaaat ttatggttat tatttctgaa actccgataa   37920
tgtaatcact aatgatactt attaaatttg tggtattatg ttttattgta tttctctgtg   37980
tctcaccttc gagtgagcta gtggtattcg atcctggata agtggcttta tcggactaga   38040
tccgagggac tgacggttta ttcctattta agtgtggtct agcctctaag gcgggacttg   38100
ggcacttaag tttgaataat tcgggcggtt ccgccacagc tggtatcgga gcgaatacca   38160
tcacagagaa gtcaataagt catgattacc aaccttttct aaaagtaaaa cttgctagaa   38220
accaatgttg gatagatgtc aggacgataa ggatagactt aggacgtgaa gccttaggaa   38280
atagatgggt agctaggtgg ctatttatat aggccataaa ggctactact actattaata   38340
aggatgctgt agaagcaacc gaaaaagtag ttaggtctga gaagacgact agaatgagca   38400
tgcatcatga ttgtcgcatt ataattgtct tttgtgcacc aacatgcttc tctcaccttt   38460
attcaaataa taaaaaaaat tgtgaataat gtgctgtatt gctaggaact gcaaaaaaaa   38520
tgtcttatct tgtgtgtcat gatagtcttt actaggttat gttatgtgct tctcttgtct   38580
tgctatctag gtagtattgt aattgttcaa cccttttgc aaaacatttt gttgcttgtt   38640
ctgttcataa aaagactcct ccaaacaacc ttgagtttag caagtgaacc cgcttttaaa   38700
aaaatgcttg tgttggcgtt ttctagccct tgtgggtttt acccttgaag ttacacctgc   38760
acagcttgta gattcccata gcttgactcc tagatcgacc aaagcttcct tgtgcactgg   38820
ttacgtcaaa aaaaatttgt tgtttggtgt ctagttgcgc aaaccctatc aaggccatgt   38880
ttctttccat aaaattccttg cccctaaaac ttcatagcat tcctgttgat catccagctg   38940
atcttgttgc ctacctctcc tttcgcatgg atctagtgat cttttttcctt gtgaatcatg   39000 ttgtgacctt atcatccgaa tctctgatct ttcatgattc tgccctatta tcttgttatc   39060
tactataacc cgttctcaag tatcgaatgt tgatctacct aagtctctca attctggtca   39120
ttctcatact cgttctctga ggatcatgac gatgtttatc aactttatct ctaaacagtg   39180
tatccatttg gttcaaggga tgttgttgtc atcttgtggt tctctcatgt ctctacaagt   39240
tcatcaacat gatctctgga gtgcttcctt ctcatatcaa atctcgtact aatcgctggc   39300
ctgctaatcc ccgtgatgat cataaaataa ctctatgagt tgaagaaaat tctcatgtga   39360
tgatcttttg ccaataatct ctgcttcaac tctgatcaca ttcttatttt ctgagccata   39420
ctctcatggg ctccaactat cagtgctatg tgaatttctt attggttgcg tttggtaatg   39480
atgtcatgac taacgactga tggtgccgcg acgaaaccga gagcctacta tggtgcacac   39540
atggttgagc tgctcggcac gcgctagtat cgcggttaat agtcgtgatc cattacgaga   39600
ctatactgat gtgctatttt tttgtggaca ctctcagaat gatcgctgca ttttgtctcg   39660
atatgtcgcg atattctaac caaatctgtc tccagtatct tgtcagatac cctctcatga   39720
atttgcatct atcttcagtc tgggagttac atgcttctcc acccataaat atcctcattc   39780
gaatctcggg acgagattct ttttaagggg ggaaggctgt gacaccccag gtgtcagttt   39840
cgtgttacgt cgcgagattt atcctaatct cggatgctca gtaaaatttt ctatttctcg   39900
ctcgcgtatg tccctgatta tccagattat tcattcacgt ttcaccgaat tcggagttac   39960
tcagtctcac agaaggccaa ttttggagcc tgttaaaact tttatcgtcg gcacaaatgc   40020
gaactcaaaa atcattctcg aattataaac ctcatctgaa gctcattaaa tcaaactctc   40080
gacgactgtt atttgatctg tgtccgaatc caatttctcg atgttcgatc gatgtccaac   40140
tattttaatc cgagtccata ctcacaaacg aaataatcaa tatgtcgtcc tctaatcaaa   40200
```

```
tcttactcga ctcagcttag catctctgta tccaatccga tttcaaaatc aacatcggca   40260 acgatttta tatatcacga ttcgctttct ccgactaaaa atccaaaacc gatcaaatct    40320
caggacgatt tattttcgat ttacgcgtag ggaattattt tcaagcgaaa tctaaacaga   40380
ctctcggccg agtaatcgc gcaaccttcc gttcgtccga actcttttcg ctctgtttct    40440
cagtagcgac gaattccgca ggaacatttt tagtccggaa aatatttagc gcgacccaat   40500
ttagtgtttt gggccaaatc cagtccagcc cattcggccc ataagaaacc ctaccctaat   40560
ttctcctcta taaatatggg cttccctccc ttgcattctg aaaattttcc atttccaccc   40620
cagccgccaa caccettctc ttcctcctct accattttcc agccgtgggc tccttcaagc   40680
acgtagagct ggagctcctt ccccagcgcg caggggcttc catggccggg cgttccttcc   40740
ctccagcgcg ccgaagctct tcccgtggcg tcctctgcct ttcttcttcc ctgcttcaca   40800
gcagcaaggc caccagcagg ctccctgctc cccgcgcccc cagccatggc atccttcact   40860
cccctactgt ttttctccca gggcgcagca gcaaatccca tgcagcggct ccatggccga   40920
gcgccctgcc cggtgctcca gccggcctcc tctgcccctg ccattttcca caggagccga   40980
gctcctacct gcagcaggcg cccctgctc tttcctatcc gcgaccaggg agcttcagct    41040
ggcgtgaaac ttcacttgcg cacggcggcc agcaccctct ccttgggctc caacagcttg   41100
gatgccgaac ccctttcttc cttccctgg ccgagctcga gcttcccatg gcgccattcc    41160
tccctctctc tgttgtacat agcgccaagc agcaactcca ttttccctgc ccgcgcccaa   41220
ggtcggcgac cagcctcccc ttccctgttc ttgctgtggc cgagccacca cttccccagc   41280
cgtagccctc tcccctcca ttgtttcagc gcctgaaaca aacacctggc cgccatccac     41340
acttgtgctc gatgaaatgt gcagcagccc cgacggctcc gcgcgctgac ggcttgctgt   41400
tttgttgcgc agtgagcagc acgccgtgat gccgccgtgt gttcgctgtt tttgcgcagc   41460
cccaaacgtc gtcgtcgttc accccggtga gaccgcgacg ctccttgttc gattccgcat   41520
cgatgttatt ttcctatgat taattatgta tgtgtgttgc tttgtttta ttttgtggag    41580 gagagaaccc cgtgttttgc gaggagaaag caagtcgctt aacgctcgtc ggatgtttgg   41640
agcgatgcac gaatcggaat caccgtcatt cttgcaaaca tcgtttgggt ttgtttatgg   41700
tgagccgatg catgtcgctc tcgatcgact cgattaatca ttttgtatgg atgtgtgtaa   41760
aatgttcgat tatgcgcatt ggtaggatca tgtttgcgat tggagaacaa gaggttaatt   41820
gatgtgcgcg atttgtagtt gtctaattat gttttggtcg atgatgtgca tgtggttata   41880
tgtgtgtaaa agtataattt tataaatgga cgcgtgtagg gaagaaaatg aaatacaaaa   41940
gaactcgagt atttttattt tgataggaaa atatgcgatg cgttgtttga tgcgaaaact   42000
aagttacaaa atgtggattt tgttttggaa aatgcatcga tgtgtttatg tgaaaagtgt   42060
atttgtttta agcaatgtga tgggattcgt aatttagag gggatatatt tattgatgtg    42120
acgagtagtt tagagaatgc tagtttgcgt agaggatgta tcgttaagac atgagtgtcg   42180
gagtccattt atactagtgg tcgcgccaca tggattgaag tgtctcgagt gcacgccata   42240
atatggttgt atgcgagaca gggttatgcg tacgatgagt ttagtaaaaa ttccatcggt   42300
gtcagttgtg ttaagttgaa gtttatttgt gcgtataaag tagtaaggta tttaatgctt   42360
acgactctta atcgatggta gaaattgtct tgacttaaat agagaggtgg tgacatgcca   42420
gagtagtcat cgctttctct atattttatag gtcaagtcat gacgatgcgt attatgcgtt   42480
cgttaaaatt atgtttcgta tatagtgtat gattgtgctc acgatttcga gtagacactt   42540
```

```
caaataagtc aagtagcttt gtaatgcaag atgtgtgatg aagttagttt gttttaggat   42600
atgtgttgaa atgctccatt cctgtgatag acatgtaggg ttatttcaaa acgggtcgat   42660
gtgtgtgatg atgatattca tgatttaagt agatgtcctg aaattatgtg gcgaagctta   42720
ggttaagttg caagcgatgt ggaaatgttt tcgtaaagat atatgtggaa tgtgaacgag   42780
tcattcaatg tattcggtat gtcgtgtagt ggtggtatga aaaatgagtt aggaatcgat   42840
cggctaaatg ccaagttcgg ttagagttat tttgatagtt gggattgtgg ggtgaagtga   42900
tggcatgact acgtagctgt tggacaccaa aatgagcgga cggtccggcc catgggcccg   42960
gacggtccgc gtgtcccgag attagattaa ctcggatgtt tatccttatc tcgtgcgtgg   43020
ttatccatct aatcacgtgg gagtttgttg gctatctctt aggaaaaggt ccagacctcc   43080 tccctataa atataaaggg gtacggccga ttgagaaccc ccgaacacat tccaatcgaa    43140
ccaattacct tatttacttt tcctgcccta ggagtagatg tagcatagtt ctagttgtag   43200
tcttccacat atccacctcc acccctattc gactctacgt cgtctagatc cgtcttgggt   43260
ggcctgccga tcccaagacg accctaggat ctcaccccctc ccgggggca agatctagtt   43320 gtccatccaa gacttcttcc tcgatttgat ctcttaattc ctaggcgact ccacgtcgtc   43380
tggggacgcc ccgggtgacc tgtcgacccg gagcaccttta agatctttcc ccccagggga  43440
cgagatctag attccagcaa ggagtaggaa gacgaccctg tcgccaggtc gcggaccgtc   43500
cggcccagag ctgcggaccg tccggtgtga cgcagggaag acaccactcc tgcgcccagg   43560
tcgcggaccg tccggcccaa ggctgcggat cgtccggccc aaggctgcag accgtccgcg   43620
cctgaccaga gggcaccgcc acggttcttg ttgagtgttt ggcgctccaa aaaggcgtca   43680
acatactttt tggcgactcc gctggggaag aagttgcaga tctacaaaat caggcttaca   43740
tggccgattc taaagatctc aacagtgctt ctccaaacag caacacaagg ctgactaatt   43800
tatcggccgc tgagcataaa aaattagaag atgacatgaa gaaaatagac gaggaggccc   43860
accgacaaaa ggatcaggtg ctcaaggtgg cggacaagtg gtacctctcg cacttcaagg   43920
tagactgcca ccagaagacc gtccaagaga gggagataaa cgccgagtat atgttagccg   43980
tgctgcaaca gctcccccaca ataggtgatg ccaggtcagc cgatgatatt ccatctatta   44040
aaatttcttt tgataatcgg attaaaagta tcacggagga tatagagagg atgacacatg   44100
catttgttaa aactcacatg cctaattttt taaaacataa attaggcgat gagaacgatt   44160
actctagatt tcnnnnnnnn nnnnnnnnnn nnnnnnnnnn nnnnnnnnnn nnnnnnnnnn   44220
nnnnnnnnnn nnnnnnnnnn nnnnnnnnnn nnnnnnnnnn nnnnnnnnnn nngctgagca   44280
atattgccaa gagcggtagg accggtcgtc caaagagaat aaagtttatg actatgttca   44340
gaaataaaga aaggatcata taaacaagcg cgattaattc acgataggag tcctcatttg   44400
ttgcagagca tgggggcagt agacacgatg agggacgccg agtgataaga aaaaggaga    44460 taagccgctc aaattcgcca ccccaatcgg tttgcatagc aatgatttt ctattgagca    44520 agcgctcaac aaggctttga aattctttga agaactgaaa cacctcagac ttatggcgaa   44580
gaagatagat ccaagtaaat ttactataat catcaatgaa gctgacataa accctttttat  44640 tacaaaaaga atcaatggcg ggtccccaga catcgaaaaa caccagatct aaaggagcag   44700
cagactgact ggtcgactta ggataaggca actgatgggc cttagcacga aggcaggcat   44760
cacaaacata ctccgaggaa tctaagcctg aacacactaa attattattt ctaatgacac   44820
gagcgacaat atcacgcgat ggatgaccta atctgcaatg ccaacgctca taggatggct   44880
ttattgcggc aaggtcgtgc ttctgggtag gtgtgcaaga gatgtcaatg ggtagaggcc   44940
```

```
accccctacat ggtccgcgca ccagcacttg cctcgtggcc tgatccttaa tcaagaaaaa    45000
gaacggatgg aactcaataa aggtgttatt atcaagattg aaacgatgaa tggaaacaag    45060
atttttatgg gtatgaggga cacgaaggac atgatttagg tgcagagggc ggaaggaagt    45120
gggcaaaaca gaataaccaa tgtgagtaat ctccatacct gcaccattag ccgcccgaat    45180
ctgatcattg ccattgtaac gatcatgctg ttagcttttc cagctcgtcg gtgatgtgat    45240
cagtcacacc gaagtcaagg taccagtttg gatcagcagc agtggaggat gatgccatgg    45300
ccgcaacccg atcatcagga gtgaattctt cataaaagcg gtaccaacag atattagctc    45360
tgtgaccgac tttaaggtag acctagcagc gtggacaaga ctggccaccg gattgatctg    45420
tcggtggacc ggaactgcgc ctgaagtagt tgttgttgct gtagttgccg cgcgaagacg    45480
acgaaggata gccatggcca tttccgcgcg agcgtccgcg accgtgattt tggagaacca    45540
tcatgccagg agccaccacg gccacgagta gccgtattgg ctgatccatg agcagcgtac    45600
ctgccgccgg actgcttcgc aagccgaagc tcatagctga gcatctgcga gtataacttg    45660
gcagaggaga ttggctcgac gcaagtgacg atggacgaca caagcgggtt gtagatttct    45720
tcatcaaggt cggtgaggac ataggcgacg aactcctcat cgcccagagg ttggccggac    45780
gccgacatct catcggcata actcttcatc ttggattaga atccggccat tgtggtcgtg    45840
cctttcttcg tggtggcgag cgcaatgcgc gtgttgacag aacgcgcacg tgtgcaagat    45900
ccgtacatag ccgcgaggga gctccagacg tcggccgagg tcgtggctgt cgtgacaccc    45960
atcaagacct cacgcatcag agaggagagg atatatccca gcagcgcttg atcgtgagtc    46020
acccagttga tgtactcggg attgggcgtc tccatatagg cgtcgttagt catcacagag    46080
acagtcttaa ccagcatctt ttctttgccg atgagcagac cgtagagctg tgcagattgg    46140
atgggcggta ggatttgggc actccatagg cggtagttgg ttttggtgag tttttcggtg    46200
accgggatcg agaaggagga ggggatggtg gtggaatttg agaatctact cgccatgatg    46260
gatgtgttgt agaggacctg gctatggtac catgtagatt ggaatggttg atgtggcaga    46320
accgccggat ttattccagt ttaagtgccc aagtcacgcc ttaaaggccg caatgcactt    46380
aaatcggaat aagccatcag tccctcagat ctagtctaat aaagccactt atccaggatc    46440
aaataccaca agctcactcg aaggtgagtc acagaagaaa tacaataaaa caggaaaacc    46500
tcaaattaaa gtactggagt tattacataa atcagagttt ttcaagtagc tgagaaaagt    46560
tcacaaaata aactgcagcg gataatcgat gtcgtcaaaa gcgaggaata gggcaaggcc    46620
tggcccacta cttctcctgc tcctctcctg ccggagcagc atcccactcg accgtccaac    46680
ccggtgacag ggttgtaggc caagttacac cgtcaaccat atcctagagc gtacctgcaa    46740
aaattatgcc acaagcaagg ctaagtatac taatactcag ctagacttac ccggtgtgag    46800
gaatctactc ttctacctct agaccatgta gctgtttggt tgaggggttt ggtttgccaa    46860
aagcactagt tgtatctaag gtcaacttta tcttttccat ttctagtatc attattgtag    46920
ctaagtttgc tctttctaag catacatggt aacaatcatt taatacaatc aacaagttat    46980
ctcatgtaat cctcatttca cttcttactc aatgtagtac aagggggtcaa gcagtctcat    47040 tagctgcgag aagcagacga ttcaaatcga gtattaacct tgcaaggtaa acctaaacac    47100
acgacatgtc agggcactcc gtccccatcg attcccctttt cgcggccagg gctcaccgcc    47160
ttggcataca atgctccact gacccgggct gccgccgtgc agtgaccgca cttgtaccca    47220
ccaaagctag cataggagac ccagtctcag gacgagtgag gagaaaagtc cgcgcccagc    47280
```

```
ttcaatcagg tactaggttt accggttacc atatttcccg acatgtgttt agtacgttca    47340
aacgcttgac tcaggtatcc acacattaat ccttaattca tttcctgtc tcatggacaa     47400 ggcatccacc ctggatccaa gaccatagac catcatagat cccattatca agatgaatac    47460
aatcaattcc tgacctcgcg cgattgctag aaaaatcact cgacttctac cgagatccta    47520
attagtaaag cagctactcg acctagcata ctagtatcca tctcaaaaag gaatcctgag    47580
ttcatgcaac taagggtttc aagcaactcc tacacttaag tgcacattac aagcctacaa    47640
acactaagtg tagtaaagta gcatatataa attggttatg cataaaaccg gggcttgcct    47700
ccaaatgatg gggctgcggg gagatcctcg atggcagtct cgggagcttg ctcctggtct    47760
tcctcgtgga cagctccttg ctcagggatg agcacgtact ctccatcagc gaggttgcaa    47820
tctaatgaat gcaatgagta agatatatgc atggcatgat atttaattta gcaattaaaa    47880
tttgatggag gatgatcaat ttaatagggt agacctcatt ctcactactg gagattttg     47940 gtggtacact caccaactta gggtcaagtt gattactgaa tggttaaccc attttagtg     48000 ttctactgat tttcttcttt atatcttatg gatattttaa caagattctt agctgccatg    48060
ttggggtaat acttattaat ctttctaatt cctcccttct ttattccttt tatgctttta    48120
aggtgggttt gaactacaag atagcttaat aaatttccag aaattctgca acattacag     48180 tagcttctta ctggtgtata attttctgtc tcaaaatttg gggcttaaaa agtgaggggt    48240
tctctctgta caaaattagc aagtgttagg gcaaggggga tgttttgaac tacaactctc    48300
ttttaacagt gggttattct ttaagactta ttttgctgg catttagatg ttataacatg     48360
attttgtaca aattttcagc cactaatatt tattagttat tttattatga ttttctaaag    48420
tttctagcca aggggtgct ttctactacc actatacttg aaaaatatca aacaacagat     48480
ttccaatttt tcctatcttc ttctttgcgc aagagcaatc attctaaaat ttggtaacct    48540
ttttcttaag ggaagggtgg taggaatttc ttgaattaaa tggccttttt catgaagtag    48600
gggcaatggg tattactttg tagtttgaat aggttttgca ttttgctctg gtgatctatt    48660
ccattaataa tctagtaaaa atttattcgc ccattgttgc acacttttg gcttgcttat     48720 gatttaattg gaatatggct caatatcaag ttttatttgt tcaacccact taaaatgatg    48780
ggctaggtat ttatcatttt tgtagtggtg tcctagtggt tacaagtcta ctgaattttt    48840
cttaccaatt ttgaaattgt tctcatattt ctaataattg cccttctagc tttattagtg    48900
cctaataaaa catttcacct tgaatttgct ctggactagt gttccttta ttttttctag     48960 gttcttcatt acttaagtgg gctaggaaaa atatttgcat ccactgttca ttattttcta    49020
gtacctttct tattttccta agttttggac aattatggct tttaatagat aaccctgttt    49080
aaatcttcaa tactagggtg ctcaatattt ttaaacagtg tctaagtggg gtttgaactt    49140
ctacaaattt tcttaagttc agcacagaag cataactaat tttcttcatt ttaataaggt    49200
ttggtcagtt tctttaatta attctaaact ccaaaattta aaacagaaag cacagggttc    49260
aatattttta tgtgatagtt cataatattt tgaatctagt aaaattggtt tgactaaatt    49320
tggttgaata tttctcaaga tacaaatttc ctaagtcctt tactgaattt aaaaagaata    49380
aacagaaatg gataaaggaa aaagggtttt gcactgggt ccctggcgaa aggttttaag     49440
tgtattacag acaggtcctt ggttcactat ttatctgagt ctatgactct gcagaaaacc    49500
cctagggttt tgcgaaatcg aacccgcgat ccttccccta atggaatagt gaccgcagtg    49560
gaagaaaagg gcggagggc ttaccggcgg cgaggttgct ccggtgaggg gtcgggtgag     49620
gtccggggtc tctggcgatc acgtcgaggt gcggatcgtc ggcggtggtg gtcggagtag    49680
```

```
gttggtccac gtgcacaggc ggggagctcg tcggcggcga gggatccggc ctgctcacgg   49740
cgcgatagtc caattgaaca ggttaggag cttcaccaga ggtcaaggaa gacatgcgcg    49800
cgaggaattt gagaatgaat caccggattg ctcggtctac gcgcggctgc gggtgaccga   49860
agtccagcga ggtcgatcct gggtctctgg tgaaactctg ttgggtccga ggacttggaa   49920
agcttcacgg gccactggcg aagctaaccg agtgactggt gcagcttgga agtggctgga   49980
gggagctggc cgcggtggcc gaggctcggg cggtgatggc gggcggggga gagctcgcgg   50040
agttggagtt cttgctcgag gcgtgaggcg gagtgaaggg cagaccattg tgcatccagg   50100
gtacttatag gcgccctcag gcatggctga gtgcaggcgc gggggacaga agccgaccgt   50160
gcatggcgcg cgatcagagg gcagccagtg cgcggccaag cgcttgagca cgcgatcgaa   50220
cacgtggaag tgtgattctg cccgagttca aacgcctgtt ggccgaccaa aacgtgcata   50280
tcttgccaag gatcctgtgt agcgtctctt caccgtgcca aggtcttcct gtcgtgtgtg   50340
agtcccgagt gaagatatgg cctaggtgag aagatatgat ggcctgaaga tagctctgtt   50400
agcactgtcc aaaccgagac aaaacttatg tcaagtcgtg tcaaacgatt cgggtttgat   50460
ctcaaacttc tccaaagtgt tcctagggta ttttggcgcc actttgatat ttggactttg   50520
tggattcgag ttttggaaaa cagggaacac atctgaactt tgggaaaggg tttgaaattc   50580
agttttctga atttctgaat ttccccatag ggcattggtt catgggctga tttgggatt    50640
tggaaaattc aaatggcaaa actttcttac tatattttgt tggttattta gtgcactaaa   50700
actttgttat ttggttctta ccaaaatttt gtatttccc aagtcttttc ccaaattccc    50760
tttatgtgct taaatggtcc acttaggatt aattaggtt tgagagttct tcttaccttg    50820
aggtgcatgg catgattaag gagaatttct taagatgaaa aagactcact taaaccttgt   50880
tcttaatttt tttatgttca ttcctctttt tggttcacat gtgataatgg ttggagtcaa   50940
ctctaggaaa aaccctacgt gacactgggg tgtcacagtt gaagcgttct accacactag   51000
gtggccaagg attgcatgtt tatataggca caaggctggg tgcaacaact tatacaataa   51060
ggtaaccgaa tcaatctatt gttggagttt ctatctatgc acagcctaga atatatcctt   51120
tctatctata ggagattgat tcggttggct aaagattaca tgcacaagaa acttctagaa   51180
tatcgtaact tcatctaaca gttacaactc atgaacacaa tataatattc tgctatagaa   51240
atcatgattg tgtaattgtt tgttgcaata tgttatattt gatttatggt tgatctgttt   51300
tatatcagct aggggggttga gctagattat ggaaatgtca ccagcaggat cacaatcaac   51360
actgatcatg gtctctcaag ttacaacaag caatatgcaa gggactcttc aaaaaagtga   51420
tgccttaact accagcttca gaggctagcc atgcttcgag aataccaaca acaaaatgtt   51480
gatgaaaatc actgaaccaa cagtgacacc acaaagcagg aatgccagga ccacttctaa   51540
ggtatattct aactcacatt tgacagtaat ttgtgaaatc actcaaacaa cagaatacag   51600
ttcgcatgtt tgactaccaa tttgattttt tgtacactca tatttattc ttaaatctgt    51660
ggaagatgat atgaatctgc acatcatgag tgcagtttct gcaagttgct ttgcgaggtc   51720
aacagaaaca cagaaaactg atggtgatgc ccttatacct aaggtaaatt tttcttctaa   51780
ctgaagcctc ttttcgcctt ggaactcatt cctttagcta atactaagag atgatggaaa   51840
ttctctcatt ccaatgtcac cagcagtatg atgctaattt ctgtcaaatg ttcttgccat   51900
attaatctta gcatttcatt gaatttacat agtacttgaa aataaaataa catgagacac   51960
catgtctaaa atataatggt aatctatgtg cttgatcgcg ggttgctaca gatctttgat   52020
```

```
gctagtgtga acctggggtg gttctataac cgggacacag aagagtggta taaaaaaggt    52080
aacctttgta acgcaaaaat ctacttattt gtttccataa tacatatgag atcttatcct    52140
attgttgatt gcaatctact gataggactt acccacccct cccctgccaa aaagggcaa    52200 agaaactctt ccaagattgt gactttgaag atgttgatgg tgatgcctct gccaaagatg    52260
aggctgagct agggtactca gcctatctat ttctcaattt catcatattt ataattgtca    52320
atgcaattgg agatgataaa aatgctctat tttacataaa aacactgatc ttgatttgga    52380
ttgtttgcta aattgtctct ttatttgatg gtcttggcta tacttgtctc tggtagattt    52440
ttgcatcaca gggtgagcga tgcttagcca ccaagaaaga aaaaaatacc actacctctc    52500
tggtttcctt ttgtattgga tatttatgtc tcttgtcttt gttttgctc caaagtctta     52560 tacattatcg ttgactgcat tttagtcctt ctcccaaaaa ttcacttgtt agtggcgagg    52620
atatcataat aattgttggg gacttgttct caaatgctat gagttaagaa caaggcaaca    52680
caaaatgtta aatgttaatg tccttcgtcc ttcgaagcat tatttcccttt aggagataac   52740 gatcttcgga cgaaggttat gaaggacata ccttcataag tatgacatgt ataaacaaag    52800
gatgaagctt atgaaacata ggaagacaac ataaacaatt atataacatc ttaacataaa    52860
tatttattat taaataatca taagaacata agaataatat caaattacat ttataccttg    52920
agcttgatag aaggcaaaga taaagtaag atgcgaaagc gtgaacagta cgagggtact    52980
gttcacctat ttataggcac agggcgcagc ctgtgtaaat ttacattcat gtcctctaca    53040
aatgattaca atcataacat agattatcat gggcccaatt cgtcatttca tctttaagtc    53100
ggtgcatctg gaaatacgct acgaagctct ctgattggta gcttcggcat cattcctgtt    53160
ctggccttcc gaaggtgttt tttctcacag gaccttcggc gacgaaacag accccccaaca   53220 gtagccccctt cacggtgcca gatcatttt tgtaacgagc tcgacccgtg aaaaattctt    53280
ttaggcttcg gaatgccgaa ggtccgaaaa acaccttccc tgagctcgtt gtcgagaaac    53340
gatttaagta ttcctagtgc gaggtggtcc caccatagga cgggtacgca cgatctggtg    53400
attctccttc tcgcgccatg cggtccaccg ttcagtgaat gcgagcgact gttcggcggg    53460
tgcaggtggc ttgatgattc accttcccac ctgtagcact atataaacag acgggtaggt    53520
gtgaagttac cacagcattc attactatcg tattgttgtg ctgctgaaaa atttgaccat    53580
agccgaagct tattcttcgt attctcaatt agagcatcgt cttgttcttt agcttcgtca    53640
aaagagggag cttcggcaaa atcaaaaagt aatcaacttt gtcaaaaccg cgagaaattc    53700
agcatcaaat ggccagggtg cgttcaactg ctagagtcac acgcgacggg gaggaggccg    53760
aagctgccga gaccgcccca atctccgaag taatgagaca atcaggcttg gttgtgctag    53820
agggtgtttc tgacgaaggt gcacgtgctg ccgaaaccga gcaggctgac attgaagaag    53880
gtgaggctga tgaagaggag atagattatt tcgtcatgcc atctaaaccc agccacttgg    53940
aatttggaaa gtctaccgtc tctgaggccg atatgcccat gatgacgaag ctaggctact    54000
tcggggaagc cgagaagaag ctaattcgtt ttggcggaga taaatcact ccgaagctag     54060 aaaatgatga ggtggtagtt ttcagaagtt tctttaaagc aggactgagg tttcctctgc    54120
atgggatgat tgtggatgtt ttggaaaatt tcgaaattta ttttcatcag ctgactccta    54180
acgctatcgt taggcttagc gtctttatct gggctcttcg aagccaagga gtggagccgc    54240
ttgccgaagc cttctaccgg gtgcacgaac ttcactatca gacgaaggct agagaagatg    54300
gactgcacga gaacttcggc tgctataatt ttgcctaccg caaagacatg aagacaccgt    54360
tggttagcta ccgcaccaaa tggacaaccg gttggaaaac tgaatggttt tatgttaagg    54420
```

```
ttgatgagaa gaaggagaag ctagtttaga gcccactggg cctaaccttc gggttaacta   54480
ggccccagtg tcgcatgacg ctgggatcat catgcccaga tgttgtgggt gaatttagag   54540
ttgtgtccga gcatatcgga actagggatt tggttcagga atacttagcc aatagagtat   54600
tcccaacgtt aaaggaatgg agtatgccga agcttaaagg agagaagaaa aagaatgaac   54660
ttgttcgact gccctatcat tttaagttca agaaacactt caaagaaccc tgccaagaat   54720
ggttggatac gatcgaagtt atgtgcaatg aaatatttggg caattatacg aagaaagaag   54780
atcaattgat gacggcagcc ttcggcaccc gaccgaaacg aaggctaaac cgagtaatga   54840
acactctgaa atttgaatac ccagactatg aacggttaag taaaggtgcc gaagggccaa   54900
aacaaaaaag agctgtcagt gttatgcaaa gacaagctgc cagaatgata aagaagatg    54960 aaaatttagc aaaaaagaaa aaaatccag ccctgagccg aaggtggccg tttcgaagaa    55020
aagaaaagct acagctccga agccaaaagc tgatttagaa gaagttccct caacaccttc   55080
tgccactgac gcagaagaaa ttttaaaggt aatgaccgaa tctctaccta ataagctaag   55140
cccgctggga ccggaactga tgaagctttt acagaagaag aagaaggaac cttcggttgc   55200
cgagaagccc gctgaaccaa aaaagcgaag gattattact atcattgagg ctattgaaga   55260
aacaccatcg tcggcctcag tgctaaaaac agcagcagcc aaagctgctc cagccgaagc   55320
ttctacttcc gaagttgcag cagccgaagc cacaaatttg gaaaacacgc ttactgacat   55380
tgatgaaata attttgaata tggctgagga agaaactgct gcagctgctg aggaaacccc   55440
ggctacagtg cctgaaaagg agaaggagct tgccgaagat gcttcggaag aaagaaatat   55500
caactttcaa aacataattg gacaagagtt gtctaaggct aaaaaagaag agctgaggga   55560 cttttgctata tcttgcgggt accagccagg ggcactgctc ttcggtggta tagacgaaga   55620
gagcttaggt tgcctttgag accggactgg ggagaaagtt gtcaggactt tatcgaaaag   55680
tgttggtttt ccgaaactcg aagccgatct cagcagatac cgacgacagc atatcgtcgg   55740
tagcctattt tattctaact ttaaggtaaa attcttccct taacttttta ttgttttgat   55800
atgaagatgt tttctgatga aggttatttt gtcagagcct actactaagc aaaaccttga   55860
ggatgcaaca agacctcgag gacaagaaaa acgaagttat aattgaggc ttagagaaca    55920 agattaaaga tcatgaagct gccctagaaa agaaagactt cataattcaa acaatggaag   55980
gttcactggc agaagctcaa gccgagatcg ccagactgaa tagtgaactt tccatgaagt   56040
caaaaagcat tgagcaagag aagaaagatt tcgaaacaaa actcgaagct gaagttgaaa   56100
aaagttcaaa tctgcagaaa tcactcaaag atcttcaaga agcatggtct tgtacttgtt   56160
tggtgacttg tgcccgcttg atttctgctg agagccgagg caagggctga gcgcttggtc   56220
acgtacccga gccccctga caaggggggtt gcccatgccg tagtggttga cacagtactg   56280
agtatggcaa aaagtcccta agtaatatgt cagctctgca gtatatggtg acgttgggcg   56340
cctttccgtt gtggatattg aggctagagt cgggctcggg cgaggcagaa gtccgcccga   56400
ggtcacgacc gagcccgctc cagtattcgc ggggagcagg taaacgaggc cgggctcagg   56460
cgaggcgaag tttgtcccga ggccgaggtc gccttcagcg aggcagagtt cacgtccgag   56520
agccatcctg cactcttgtc gtattgtacg tcccatcagg ggttgacaga tggcatgtgg   56580
gaatagtggt cgcatgcgtc atcgtagttg gtgaagcttg acaggaccgc ggtcttgttg   56640
ctcctgttca cctgcaactc tacgtggggt aggtatgcat attgaatgct cctgcccct    56700 gcagactttg gttgagtctt gcattggggt tgtcttcctt acccgagatg tgctcgggcg   56760
```

```
aggcaaagac ttttgttctg ggagatggag cctcggccgg gacgagaatt ctccctagag    56820
cacaccatgt ccgagggcag gcttgagcga agcggaccta tggtgacccc tgagcggggc    56880
ctcgggcgaa gcgcggttta tgatcctttg atctcgggga atgtgtcttg aaggtggtct    56940
aagggttaag tgtgttttag gggcataatc tgggtacccc taattatgat acccgacaag    57000
tggtattgat tagaaatggc tcaacaaaag ataatggatg gttgaacaaa atgtgaatgg    57060
ctgacatcag ttttatagtg tatgtgtgta tatatgtgtg cacacataca atatctctcc    57120
tttatataac ataaacagac ataagttata gtggtagaag acgctcgctt gtatcgaaag    57180
agcatggttt gaatcccac gtcctatttt tgtgtggtt attccacgcg cctggctggc     57240
tggttcgtga ctaggtcgga cccatgcaac tggctagccc aaatttcccc aattatttca    57300
taaccaacct ctcatttgtt ctcctttatc tttatgttat taggatcaat catttgtagt    57360
tatcaaggtg aatcacttgt acttttatca aggtcaatca ttatagttac taggatcagt    57420
cgtgtattta tcagggtcat tcattgtaat tattagggtc atttttatttt ttaccagggc    57480 cagtcattgt attttatcag gatcagtcat tgtacttctt ctattagggt ctacatttta    57540
tcaaggtcag ttattgtagt tatcaggatc aatcattata ttttaatcag tgtcagtcaa    57600
tgtatttatt aaggtcaatc attgtattat taggatcagt cattgtattt atatcagagt    57660
cactcattat agttatcaag gtcggtcatt gtattttttt attagggtca gtcattgtat    57720
ttagcaggat atttttatca gggttagtta ttgtattatt aggttcaatc attgtatttt    57780
atcagggtca ctcattatag ctatcaagat aagtcattgt attttttatt agagccagtc    57840
atcgtattta ttaggaccaa tcattgtatt tattagggtc ggacattgcg attaaataaa    57900
aaattgaaaa agatatagca tgagtgtcta gttttgttcg aaaatctcat aaacacgaat    57960
ataacaaaaa aagggatttt ggttttttat gcctatatat gcgggttgca tgactgcata    58020
cacgcatact cgctgagcgt ggtgccaaat agtatccact gcgtgccctg cgctctaacc    58080
ggatgctcta tccatcacac ctcaataacc cattgagcat ccctccccc acacgcctgt     58140 gctccaatca gatgcttgtt tgactaatag caaggagatt ctccaatatc atgctaagaa    58200
tagctaggat ttccagaaga agatgtcatt cgtttgatga gaaataaaaa ggaatatcga    58260
gaattcgcgt ggctaaagct gaagcaacta cttttcgaagt aacagaaaga aaagcaacga    58320
ttggagtggg ggagtcagag tcaaaaagag aattcctcgc ttctttctct catgcaaaac    58380
cgtgcatgag actttcatct cgcacggctt ctaagtgata aagaaagaa gtccaatcgt     58440 gataaaaata attacatcaa tttaatagaa aggaatgact taaaaacata ttatgagtct    58500
ctggatgaat aaactattgg atgacttaaa atatttgtaa gaaagtcttg taacaactgt    58560
tgacaatatg aaatatttta aataagtcat aaaatgacta aatgcatgt gatgactaga     58620 attgtaacag aatgacttaa tttaacataa tatgtactga atgacctaac gagtgaatga    58680
ctgagaaaaa aatagaatgt tttaaataat catcaaaatg tcttaaatga ttaagaaata    58740
cttgattatc ttataaaata actagtacaa cacatgtgcg ctgcgacgac atacaatcat    58800
atttgatacc aataaaaaaa taatatcaaa tatcaaagtg aacatatggt ccatatatca    58860
gatactaaac tgataaaaac aaatattacg cttttatctt agctaaaata tcaggaaagg    58920
tatgagttga aagaagcctg actactttt taaagcttgc tcgatggctt gtcctccttt     58980
aggtagtgag gtggttctat gtgggagcgc tgcgctgcgt ttggcttccc tgtcgtgtta    59040
gacttgtgtg gtttctcacg gtccatctat agataaaatg tccactagta gggatttggg    59100
tggttttcac agcctatcta tagatgccca ctggtatgcg gattgatcta catgcttcgt    59160
```

```
gcatggcgta tgacgaccat cgaagctagt attttatagt agtggagatt ggaatgaatt    59220
aatgcaaaat gagaagtatg agaatgttga gtgacttaaa tggatcacga tagaaactgc    59280
attggggcct gaaacagcta ctaaacaagc gatcgcaata tcttttaaaa ataagttgcg    59340
gtccaaaaaa aagtgacaat ctatactctc taagcaggct cccaaccatg tcaattcact    59400
acaacaattt caatgaatta acatgagtga accatagttc tcacagggta tttcgtcgtt    59460
acaggtccat tcgattagaa gtgggtcatt atatggtggt ttgcactgta tctttccccc    59520
gttatcaatg agagccaaac gtgtacctta caacctttca gatgtcaatt ggaacttgca    59580
aaaaaaaata gaaagaattt tgacttgttg gggatttaaa ctagaaagca tctaggcccc    59640
tggttggttt tagtgattaa tgacaacgta attttatatg tgactaacat gtgttttgca    59700
gaggcaaatg gtaagttagg tcgcattaca ggtagatgta ctacaatggt gaaaacaatc    59760
ccggagataa aaacttgaag caacggctaa agcgacgaaa caaaaagtga aggtcttcgt    59820
attccgagtg tcaaggagtt gcggacactc gtgatatagt taggtctttt attttgtttt    59880
agccgtacta taaagagggg ttgtcgataa gtagtttgac caaaagagtt ctagtgtagt    59940
gttggtgcat attcacactc acatatagtg ctaggtgtaa ctctagaaca tactcacaag    60000
ttagaacaaa aaccaaattg aaaaaacagc acaaaacaga agctagggtt tctggctttg    60060
gggcaccgga ctgtccggtg caccctttgc cagtgggccc agcctggccc agggaagagg    60120
gttccctgcg cgcagaaacc cgagagcgcg ctgttcgtga gttgaatttt agaggcacac    60180
cggacagcgt atcggactgt ccggtatgcc atctgtccaa cggctagctg tcagaactag    60240
ccgtttgagt cgaccgttgg cgcaccggtg gcacaccgga ctgtccggtg cgcccatgcg    60300
cagcagattc ctggtaatgg ctagttggtg ggtgagggct atttataccc catccaccta    60360
ccatattgat ggtcttgctg cccacattta ctcctacaca ttggtagagc attgcaagca    60420
ccacaaagcc tagtgaggtg acttgagaat cttaatcccg catttggacc tcattaacgc    60480
tagcgagagc cacctagagc acacaccgca tgcattaggc ttctcttggt caagtgaaag    60540
tctatggctt attactcttg gtgatcggca tcacctagac ggcttggtgg cgttgggagc    60600
tcggtgatca ccgtggagat cttgttggtg acccgactca agtttgtaag cggtcgtgag    60660
ggatccaccg cgccggagtg gcaaaggatc atctcgttgt gagcacttgg ttcttgcgat    60720
gaccaaggga gagcgatacc cttacgcagg tgctccaacg aggactaggg gagagtgccg    60780
actctttgat acctctagaa aaattggagg agtcttctaa accttgcttt acattccgca    60840
cttaattcaa gtattttaca ttgtgtattt gtttagcaag tatttgaagt attatcttag    60900
cattgttgta tttctagtat tattctctta gtgctagttg tcggggtgaa gttgggctct    60960
tgcttagatt ttagttagtg ttgattttta gaaaagccca attcaccccc cctcttggg    61020 catcgtgatc ctttcaattg gtataagagc cttgttgctc ttagattagc ttaaccgcta    61080
gagtaacgat gtccggtggg gatggacctt ctcccgtttt ttatggtgac gattttccat    61140
attggaaaat tcgtatggaa gcatatttag aggctataga cattggtgtc tacaaagccg    61200
ccacacaaag attccccgaa cctagagatc ccacaaatct tgtaggtgaa gagttgaact    61260
atgagaaatg gaatgctaag gccaaaaaca ccctttttag aggcctttgc aaagatgtgt    61320
ttaatagagt tagaaaccat aaaaattgtc atgatttgtg gatggacata tgtgctctac    61380
atgaaggaac tagaattgag cgtgaggaga gatatcacat tgctatgaga aaattaaatt    61440
cttttgaaat gcttgctaat gaaaatgcca atgctatgta ctcacgtctc aatattcttg    61500
```

```
tagaggaagt aaatggcttg gggcttacac aaatttcaca accggatgtt gtgaggaaga    61560
ttctcagtgt cctcccaatt gataaatatg gacacattgt cactgtgctg catcagatgg    61620
atctttcagt tgtcactcct acacaaattt tgggaaagat caatgcacat gagatgtaca    61680
tgcacatcaa tgacaaggat gagtcatctt acaagagaaa ggatttggct ctcaaagaaa    61740
atcaagaaag agaaggaaaa gctaaagtac aagttgagga ggaatcctca agtgacgatg    61800
atcttaatgc taacattgcc ttgatggtga ggaagaccac caagatatta agaagctca    61860 acagagaagg catcaaattt gactcaagaa agaagaaatt ctttccagc aaaagaaagc    61920 ccatttctta aatggattgc tacaactgtg gagagcttgg tcatcttgct catcaatgta    61980
acaagtccaa gaagaacaag ttcaagggca agaaagaaga tgacagtgat gatgagaaaa    62040
atgaaaagag attcttcaag aggaaggatg gaaagcataa gaggttccac aaaaagaaaa    62100
atgtaaaggc atacattgtt ggtgattggc tcactgacat tgagtcgtca agtggatctt    62160
cttcaagtga agaagaaaat gatgaaaaag ttaccgccat cgctggggac ttctcttcac    62220
caccaccatc tccatcatcg acttctcacc tatgcctcat ggctagaggt gaacgaaaag    62280
tacaaaatga taatgatatt attgatgata gtgatagtga tagtgatgaa gaatttgctt    62340
caccttccta tgatgaacta gttgacttgc ttaatgaata cactcaactc attaggaagt    62400
caaaagctaa atgtgataag ttgaaagatg aaaatgaatt tttaaatgct aaatatgaca    62460
tagttatgaa agctagtaat gaaatgaaag aagaaaacaa aactatgtca tccactgtaa    62520
atgagcttac atcctcccta aaagatgcta aggataaatg tgacaagtta aatgaagcta    62580
atagggagtt gaaagataga ctagtaaaaa ataaggaaga ctatactaag attaaatttg    62640
atcatgataa tcttcttgtt gaaaatgaac ttttatcttg caatacacat gaggctatta    62700
accctgttgt taatattgat gtagcaacct catgtgatga tttgagtcaa ggtgatcaaa    62760
ctagtctaca tgatgaattg actgaaaaag ttgaagtctt gacattagac aaccaaaaat    62820
tgaagagata cttgactgat gcaactacta gaggaaaggt tgccattgag aacaatgact    62880
tcaacaatga gttggcagtg gataaagaaa ggcttaaaat gaggtcaaga aacttaagcg    62940
tgaaaatgaa catcttgcaa caagtgtgca aaagttcaac aagggccaat acctctaaaa    63000
tgaattgctc atgaacactg tcatgaaaaa caacaagagt ggtattggat ataactcctt    63060
tgtgcaaaag aaagctacaa ctcaatacaa gccaaatcag actcataagc atatcaaatg    63120
ctttgagtgt ggaaaagaag gtcattttc ccacaactgc aaagccaaac caccaactcc    63180
cctgccaaag cactcaagac catttgcctt caatgctcat tatgttttaa gaagtagcaa    63240
atggaaaagt cgaagttaca ttcctaggtc caccaagcaa gagtagacct agacaaattt    63300
gggttgcaaa gtccttgatt gagaaagtca ctggtcctat gcaatatagg gccctcaaaa    63360
cttaggcttg atttgtctgt ggatgtaggt gaactacaag accggtggga gccattgggt    63420
tattgatagt ggatgcacat aacatatgat aggcaaccca cggatgttca cctcacttga    63480
tgataatgtt gatggacaag acaaaatcac atttggggac aattcaaagg gaaaagttca    63540
aggacttggc aaggtggcaa tttcaaatga tctatcaatt tcaaatgttc tcttggttgc    63600
acctttaaga ttcaacttat tatcagtggg tcaactctgt gttcttggac ttcaatgctt    63660
attcactcca acagaggtta ttgtatcaaa aatggatgat gaataaatgg tgctcaaagg    63720
atttagatac aacaatctct acttagtgga tttcacctct gaagatgcag acttaagaac    63780
ttgcctcttt accaaagcat ctcttggatg actatgcat agaaggcttg cacatgttgg    63840
aatgagcaca ctgaagaaag tattaaagaa ggacatggtt agaggactaa aggatgttat    63900
```

```
atttgaaaag gacaagcctt gtagtgctta tcaagctgga aagcaagttg ctaacacaca   63960
tcctacaaaa gctttcatgt caacatcaag gccactggaa ctacttcaca tggatctatt   64020
tggaccaaca acttatgcaa gtgctggtgg caacctctac tgtctggtga tagttgatga   64080
tttctcaaga tacacttggg tgttttctc catgataaat ctgaagttgc atctatattc    64140
aagaagtttg ccaagaaagc tcaaaatgaa tttgattaca agatcaagaa gattagaagt   64200
gataatggaa aagaatttga caacaccaac attcatgaat actgtgatga gattgggatc   64260
aagcatgaag tatcagcaac atatacacct caacaaaatg gagttgttga aaggaaaaat   64320
aggaccttga tcacacttgc aaggacaatg attgatgagt ataacacacc ggagaggttt   64380
tgggccgaag ctatcaacac tgcatgttat gcatcaaaca ggctatttcc tcactggcta   64440
cttgcgaaga ctctctatga actgctaaat gggaaaaagc cagacgtctc attcttttgg   64500
gtgtttggat gcaaatgcta catttacaag aaacgccatc acctagggaa gtttcaaaga   64560
cgttgtgata ttggttttct tctgggttat tcattaaagt ccaaagcata tcgagtattc   64620
aatcatgcca ctggcgtggt agaataaaca tatgatgtgg agtttgatga gactaatggc   64680
tcccaaggag cacttgaaaa tcttgatgat gtaggtgatg agccacttaa ggaagccatg   64740
aagaacatgc caattggagc tatcaaacca aagaagatg aagaagaggt gcaaaacatt    64800
aataggcctt cttcatcaag tgtaccacaa gatgatgaaa aagatgagag gcatgcaaat   64860
gaagatacat ttgtctctca tgaacaagca aggatacaag ccgaagatgt tgatgctcca   64920
ggatcttctt cctaagtggt tgataggaga aactcatcac tgcttcaagc acacccacaa   64980
gatcaaatca ttggaagtcc ttcacaaggg gttattactc gatcacataa acatgcttct   65040
tttattgaac atcactcctt tgtttcttgt gttgagccta ctgtatagat gaggcgctac   65100
aggatccgga ctgggtgaat gccatgcatg aacaactaaa caacttcacc cgtaaccaag   65160 tttggacccct ggagaagcct ccacaagatg caaggatcat tggaacaaag tggttattca   65220
gaaacaaaca agatgatcaa ggcgtgattg tgaggaacaa ggcaagactt gttgcaaagg   65280
gcttctctca agttgaaggt ttagattttg gagagacctt tgcaccggtt gctcgacttg   65340
aagccatctg tatcctactc gcatatgcat catgctatga taaaaagctt tatcaaatgg   65400
atgtaaaaag tgcatttta aatggcttca taaatgaact tgtatatgtt gagcaaccac     65460
ccgggtttga agaccctaga tatcctaacc atgcttatag gttgtccaag cgctatatg     65520 ggttaaagca agctccaagg gcttggtatg agcgtcttcg cgacttcctc atcaaaaagg    65580
gcttcaagat caagaccgtc gacacaactc tattcacaaa gaaacataac ggtgatattt    65640
tcatttgtca agtatatgtt gatgacataa tctttggctc gataaatcgc tatcattgca    65700
aggaatttgg tgagttgatg tcgaaggagt tcgagatgtc aatgattggt gagctgatgt    65760
atttcctcgg cttttcaagtg aagcaaatga aagatggtaa cttcctctca caagagaagt    65820
ataccaaaga cttgttgaaa aggttcaaca tggagatcac ttgttgaaaa gatggtaact    65880
ctctaccgtt ctatgattgg tagtttattg tatcttattg catctaggcc cgatatcatg    65940
tttagtgtat gcatgtgtgc tagatttcaa tcaaatccta agaaagctca tatttgcgct    66000
cttaaaagaa ttcttaggta tctcaagcac acccccaagtt ttggcctttg gtatcccaaa    66060
ggagctactt ttgatttaat tggctattcc gattcggatt atgccggttg caaaattgat    66120
agaaaaagta cttctagggg tgtaatttgc ttgggagatc actactatta tggacatcca    66180 aaagaaaaa tagtgttgcc ttgtcaaccg ccgaagcgga atacattgcc gctggtgctt     66240
```

```
gttgcacaca gattttatat atgaaacaaa ctcttctaga ctatggtgta gttctagaaa   66300
aggtaccttt gttgtgtgac aatgagagtg ctgttaaaat tgctaataat cttgtacaac   66360
actctcgcac caagcacatt gatattcgtc atcacttcct tagagatcat attgctaaag   66420
gagacattat tttagaagaa gtgaggtcgg aagatcaatt agaggatatt ttcactaagc   66480
ctcttgataa aacccgcttt tgcatgttga gaaatgaatt aaacatactt gatctcagaa   66540
attttattta aagatctcaa aatagtgttg tcaagcctgc attgcatatt taaatttctt   66600
gtattgcatc tagggcttgt ctaacctagt taagataacc gccaacaaag cgagtgaaaa   66660
aagcttaact cgggctcaaa cttgacaagt cttagctttta agcttttagt acttaaattc   66720
ttatttacta tgccattgtt ggttcttgag atatgcatgt agtactacac ttaggggggg   66780
agtattcaaa actcaaatta ttcatgaaaa cccctagttc aaagctaaaa tgcaaatctc   66840
accatttgac tattttctct aaaaattgac tagcctatgg caaatatttt ttgaaaatta   66900
tgggaaaata tatgagggggg ccaataccta tcccaatagg tgttcttttg tatgattata   66960
agttgggatt tggtttggtt aaaatttaga tcgaaaaatt tgaaaatttt caaaatcacc   67020
tctgcctagg ctcaccggaa agtccggtgc actgtgcact gtnnnnnnnn nnnnnnnnnn   67080
nnnnnnnnnn nnnnnnnnnn nnnnnnnnnn nnnnnnnnnn nnnnnnnnnn nnnnnnnnnn   67140
nnnnnnnnnn nnnnnnnnnn nnagctactc gacctagcat actagtatcc atctcaaagg   67200
gaatcctgag ttcatgcaac tagggtttca ttcaactcct acacttaagt gcacggtaca   67260
agcctacaaa cattaagtgc agtaaaatag catatatata atggttatgc ataaaaccgg   67320
ggcttgcctt taatttaaca cttaggtagt gtttgctggg ggaggtactc gcttggtgag   67380
catccactgg ttaagtccat tcttcaggtc gtccatcaac ggcatcttgt ggttggcacc   67440
acatcactgg ctcgatcatc atctctcggt cctatatgag gtgcaagatg catatgtatg   67500
aatataataa aagtaacata agatatacca agacacagtg gcgaactaaa cattaattag   67560
taagacactg caacaactat acgcaaacac tagttattta tgtgtcattg ggcacacgta   67620
aacactacca ctggaaagac aatgatcact acctacaatt aaccaacgca acacgatatc   67680
atatgtacaa gcatttattt agttgctacg gcttttcatt aattcttata ttgatcacac   67740
aaaaacatca caaacacaag tttaataaaa ggaccgatgc atcaatgtcg atggactcct   67800
ctatcacaat caactacagc aagcaaacac attaattatg gaacacatgt taacctaagt   67860
ttagccatca caagtctatg tccgttaagt gcttactaaa gcgttttttag ccaaaatggt   67920 gaactaaata ttcatttgag cacgtgcaga ttttttaggac agcagcacag cagctacttg   67980
ttttaatcat aacttttaaa atattaatcc aaaaatagca aactaaaact ttctggaaag   68040
tttagaaagt gctctacaat tttggtattt tcatcacagc atgattaaac acttagcaag   68100
gtcaaaaagt gcaatcacag cagctctgtc cagatttgga cagattcaga cttgtgattt   68160
taaaaattca taactgaaga ttcagacatc caaacaaatt gatcctagac tttctggaaa   68220
gctaattaaa tgttctacaa attatttata aacatcccag gctggtttag catgtatcaa   68280
ggttaaaata tactatgaag gctgtgctgt ccaaaactgg acagattcag tcttcacact   68340
tcaaacacat gtaacttaat cttcagacca ccaaaaagag tgatctaaga cttttttgaaa   68400 agcttagcaa aagtactaca caactttttat aatcaccaag aagtgattcc aggtttaact   68460
aaatcaaata ttcagttttt cgaaatctgt tctgacggtg gacagaacac agcaaccagt   68520
ttgtaaaatt cataactctt aaaccgtcag gcctatagtt atgaaatttt aacacaagca   68580
agacaagaaa agcctctaca actttcttat aattgacaag ggctgattct aacattaact   68640
```

```
taagcaaaca atgcagcttt tgaaatctgt acagaaagtg gacagattca gttactgaat   68700
ttgtaaaaaa cataactcct aaacaatcag acttatgcct gtcaaatttt aacacaagta   68760
cgataataaa gttatctaca actttttgt gaccaccaat aactaatttc aacattaact    68820
taagcaatca ttgcaatttc tgaaatatgt tcagaaattt gacagattca ggtgctgggc   68880
ttgtgaaaag cacaactcct aaacaatcag gtttatggct gtcaaatttt agtacaagca   68940
agataatcat gtcatctaca actcttctat atgactttc tatagaaaac atgatttggt    69000
ttatcaaaca aacagcacaa ctaaaacagt gcgtgcagcc caaaacagca atcaataaat   69060
tcagcttcta tttactttta aaaattgccg cgttctagag actcgactta ttctaaatta   69120
tatcaaggca cgcttaagca tagccacgca atagatgacg tgacggctac gtagtcatgc   69180
catcacttca ccccacaatc ccaactatca aaataactgt cggagaccat aattaggggg   69240
accctcaaga ctcctaattc tcagctggta accccccacca gcataaagct gcaaaggcct   69300
gataggtgcg attaagtcag ggatcagtcc attcgagcga ctcgatcacg cctcgcccga   69360
gcctagcctc ggacaagggc agccgacccc agaggatttc cgtctcgccc gaggcccccc   69420
tctaacggcg gacacatctt cggctcgccc gaggccctgc cttcgctaag aagcaaccct   69480
gactaaatcg ccgcaccgac cgaccaagtc gcaggagcat ttaacgcaaa ggtggcctga   69540 caccttatc ctgacgcgcg ccctccggca gagccgaagt gaccgccgtc acttcgccgc    69600
tccactgacc ggtctgacag aaggacagcg ccgcctgcgc cacttcgact gcagtgccac   69660
ttgacagagt gatattgaca ggaagccagg ccctgccaaa ggcgccatag gaagctccgc   69720
ccgacccagg gctcggactc gggctcagcc ccggaagacg gcgaactccg ctccgcccga   69780
cccagggctc ggactcgggc tcagccccgg aagacggcga actccgctcc gcccaccca   69840 gggctcggac tcgggctaag acccggaaga cggcgaactc cgctctgccc gacccagggc   69900
tcggactcgg gctaagaccc ggaagacggc gaactccgct ccgccgacc cagggctcgg   69960 actcgggcta agacccggaa gacgacgaac tccgcttcgc ccgaccccag ggctcgggct   70020
cgagctcagc cccagaagac gacgaattcc gcttcacccg agcccagggc tcggacaccg   70080
ccctggactt ttgccgacga ccttccgcct tggcccgacc cagtgggctt cggactcgac   70140
cctcggccat ggaagatcca ctccacctcg gcttcggagg agcctccacg taccccccaga 70200 ctagggcgca ggccagccac gtcaacagga agcgccatca ttaccctacc ccgagctgac   70260
tcggaccgta gagaacaaga ccggtgtccc atctggctgt ctccaccaga taggcaatga   70320
tggcgccccg catgccctgt gacgacggca gctctcagct ctcttacgga agcaggagga   70380
cgtcggcaag gacacaaccg ctccgacagc tgtccctccg ccaggctccg ccgctcctcc   70440 gacgccacg acatcacact agctgggttc caagatctct ccggctgcca cattggcatg    70500
tactcagggc actagctctc cctcgctaga cacgtagcac tctgctacac ccccattgta   70560
cacatggatc ctctccttgc gtctataaaa ggaaggacca gggccctctt agagagggtt   70620
ggccgcgcgg gacgaggacg ggacaggcgc tctcttgggg ccgctcgctt ccctcacccg   70680
cgtggacact tgtaaccccc tactgcaagc gcacccgacc tgggcgcggg acgaacacga   70740
aggccgcgtg attcccacct ctctcacgcc ggtctccggc cgcctcgctc ctttcccccc   70800
ttcacgcttg cccacgcgct cgacccatct gggctggggc acgcggcact cactcgtcgg   70860
cctgagggac ccccggtct cgaaacgcct acagttggcg cgccaggtag gggcctgctg    70920
cgtgttgacg aacagcttcc cgtcgagctc cagatgggca gtctccaaca acctctccaa   70980
```

```
cccgggacgg tgctccgttt cgggagtctt gagttcatgt ccctcgacgg cagctacgac   71040
atgatactcc ttccaccgcc gcgcgacaac gacgatggcg gccgcagcc cgcccgccgg    71100 cggcggaatc gacgacgtct tccccgcgtg gcggaagaac aacattcgag ctcgcccgt    71160 cctctccccc gccaacggag gaggaggcgg ggcaacaaag gccaagcagg aggccgcgcc   71220
tcgtcggctg tcgagcgagt cgacgtccct agcaccccaa cgggggcgc gttgggcgtc    71280 gacctcgcgt ttgagacaaa ggcgagcgcc gtctccccgc gacacgccaa tcccgagcaa   71340
gtggacgacg ccagcgcgct tgcgaaaagc ttgcaggaca tcgccctcgt acctgaggcg   71400
acgatgcggt cagtcctcga cgtgacttca tcgccgctcg acgaccaaaa ggtaccaacc   71460
gattcccatc ctacgtcatt tgtactcagc ctcaacccgt ctagcaatct tgctttggcg   71520
ggcgcccttg tagaggcgag tacaaaccct ctggggtttc gcttgcggtc gccttgggac   71580
cggctgacgg acgtctcgac ctacgggccc tctgggtccg aggaagatga cgaccccaac   71640
atctgttggg atttctctgg atttggcaac cctagtgcca gcggaacttc atgaccgcat   71700
gtgactactg cctctccgac tgttccgacg gtagccgcag cctcgacgac gaggactgcg   71760
gcccaagccg cgaatgtttc cacgtcgatc taggggtcc ctccgaaggc aatcatctcg    71820
gcatgccgga ggacggtgct ccccctgggc cggtgcctcg cgctgacatc ccgcgggagc   71880
tagttgtggt ccctgttccg gcgggggggtt acgacccaca gctcgagcaa gtccgcgggg   71940
cgcaggccag gatcgacgag ggagcaggag cgcttgagcc gatccgccgg gacgtcgggc   72000
aggcatgggc gggccaaccc ccggccggag aaatacgtca cctgccccag ggtctccagc   72060
accgcgtcgc cgatgtcgtc agggtcaggc caccacctgc atccagtggg gtcggtcaga   72120
acctggtcgc agcagcgatg ctcctccgcg cgatgccgga gccatccacc accgagggtc   72180
ggcgaatcta gggagagctc aaaaatctcc tggaaggcgc cacggtccga cgggccgaga   72240
gcactgcctc ccgaaggcaa ggatacccct cggaacctca tgccgcgact tcccgattca   72300
tgcgggaagc ctcggtctac accgggcgca cgcgcaacac cgcgcctgcg gccccgggcc   72360
acctcggcaa cgagcgccat cactgcgacc gtcgagccca cctcgacgag agggtgcgct   72420
gaggctatca ccccaggcgt gggggacgct acgacagcgg ggaggatcgg agtccctcgc   72480
ccgaaccacc cggtccgcag gccttcagcc gggccatccg gcgggcaccg ttcccgaccc   72540
ggttccgacc cccgactact atcacaaagt actcggggga aacgaggccg gatttgtggc   72600
tcgcggacta ccgcctggcc tgccaactgg gtggaacaga cgacgacaac ctcatcatcc   72660
gcaacctccc cctgttcctc tccgacaccg ctcgcgcctg gttggagcac ctgcctccgg   72720
ggcagatctc caactgggat gacctggtcc aagccttcgc cggaaatttc cagggcacgt   72780
atgtgcgccc tgggaattcc tgggacctcc gaagctgctg acagcagccg ggagagtctc   72840
ttcgggacta catccggcga ttctcgaagc agcgcaccga gctgcccaac atcaccgact   72900
cagatgtcat cggcgcgttc cttgccggca ccacctgccg cgacctggtg agcaagttgg   72960
gtcgcaagac ccccaccagg gcgagcgagc tgatggacat cgccaccaag ttcgcctctg   73020
gccaggaggc ggtcgaggct atcttccgaa aggacaagca gccccagggc cgcccgtcgg   73080
aagatgctcc cgaggcgtct actccgtgcg gcgccaagaa gaaaggcaag aagaagtcgt   73140
aagcgaaacg cgacgccgcc gacgcggacc ttgtcgccgc cgccgagtac aagaaccctc   73200 gaaagcccc cggaggtgcc aacctctttg acaagatgct caaggagccg tgcccctatc    73260
atcagggggc cgtcaagcac acccttgagg agtgcgtcat gcttcggcgc cacttccaca   73320
gggccgggcc acccgcggag ggtggcaggg cccgcgacga cgacaagaag gaagatcacc   73380
```

```
aagtaggaga gttccacgag gtccgcgact gcttcatgat ctacggcggg catgtggcga   73440
atgcctcggc tcagcatcgc aagcaagagc gccgggaggg ctgctcggtg aaggtggcgg   73500
cgccagccta cctagactgg tccgacaagc ccatcacctt cgaccaagct gatcaccccg   73560
accacgtgcc gagcccgggg aaatacccac tcgtcgtcga ccctgtcatc ggtgacgtca   73620
ggctcaccaa ggtccttatg gacggggca gcagcctcaa catcatcaac gccgagaccc   73680
tcgggctcct gcgcgtcgat ctgtcctccg tccgagcagg cgctgcgccc ttccacggga   73740
tcattcccgg gaagcgcgtc cagcccctcg gacgactcga cctccctgtc tgtttcggaa   73800
caccctccaa cttcggaagg gagactctga cgttcgaggt ggtcgggttc cgaggaacct   73860
accacgcggt gctggggagg ccatgctacg cgaagttcat ggccgtcccc aactacacct   73920
acctgaagct caagatgccg ggccccaacg gggtcatcac cgtcggcccc acgtacaaac   73980
acgcgttcga atgcgacgtg gagtgcgtgg agtacgccga ggcctcgcc gagtccgagg   74040
ccctcatcgc cgacctggag agcctctcca aagaggtgcc agacgtgaag cgtcatgccg   74100
gcaacttcga gccagtggag acggctaagg ccgtccccct cgacccagt ggcgacgcct   74160
ccaagcagat ccggatcggt tccgggctcg agcccaaata ggaagcagtg ctcgtcgact   74220
ttctccgcgc gaacgccgac gtcttcgcgt ggagtccctc agacatgcct agcataccga   74280
gggatgtcgc cgagcactcg ctggatattc gggccggagc ccgaccggtc aagcagcctc   74340
tgcgccgatt cgacgaggag aagcgcagag cgataggcga ggagatccac aagctaatgg   74400
cagccgggtt catcaaagag gtattccatc ccgaatggct cgccaaccct gtgcttgtga   74460
gaaagaaagg ggggaaatgg cggatgtgtg tagactacac tggtctcaac aaagcatgtc   74520
cgaaggttcc ttaccctctg cctcgcatcg atcaaatcgt ggattccact gctgggtgcg   74580
aaaccctgtc tttcctcgat gcctactcag ggtatcatca aatcaggatg aaagagtccg   74640
accagctcgc gacttctttc atcacgcccct tcggcatgta ctgctatgtc accatgccgt   74700
tcggtttgag gaatgcgggt gcgacgtacc agcggtgcat gaaccatgtg ttcggcgaac   74760
acatcggtcg cacggtcgag gcctacgtcg atgacatcat agtcaagaca aggaaagctt   74820
ccgacctcct ctccgacctt gaagtgacat tccggtgtct caaggcaaaa ggcgtcaagc   74880
tcaatcccga gaagtgtgtc ttcggggtgc ccggggcat gctcttgggg ttcatcgtct   74940
ccgagcgggg catcgaagcc aacctggaga agatcgcagc catcaccagc atggggccca   75000
tcaaggactt aaaaggtgta cagagggtca tgggatgtct cgcggccctg agccgcttca   75060
tctcacgcct cggcgaaaga ggcctgcctc tgtaccgcct cttaaggaag gccgagtgct   75120
tcacttggac ccctgaggcc gaggaagctc tcgtagacct gaaggcgctc ctcaccaagg   75180
tgcctatctt ggtgccccca gctgatggag aaaaagccct cttggtctac gtcgccgcga   75240
ccactcaggt ggttagcgcc gcgattgtgg tcgagaggca agaagagggg catgcattgc   75300
ccattcagag gctagtttac ttcgtcagtg aggtactgtc cgaaaccaag atccgctacc   75360
cacaagttca gaagctgctg tatgcagtga tcctgacgag gcggaagttg cgacactact   75420
ttgagtctca cccggtaact gtggtgtcat ccttcccct gggggagatc atccagtgcc   75480
gagaggcctc gggcaggatt gcgaagtggg cggtggaaat catgggcgag accatctcgt   75540
tcgcgcctcg gaaggccatc aagtcccagg tcttggcgga cttcgtagcc gaatgggtcg   75600
acacccagct accgacggct ccgatccaac cggagctctg gaccatgttt ttcgacgggt   75660
cattgatgaa gacaggagcc ggcgcgggcc tactcttcgt ctcaccccctc gggaaacacc   75720
```

```
tacgctatgt gctacgcctc catttcccgg cgtcgaacaa tgtggctgag tacgaagctc    75780
tgaccaacgg attgcgaatc gccatcgagc taggggtccg acgcctcgac gctcgcggcg    75840
actcgcagct cgtcatcgac caagtcatga agaactccca ctatcgcgac tcgaagatgg    75900
aggcctattg cgatgaggtt cggcgcctgg aagacaagtt ctacgggctc gagcttaatc    75960
acatcgctcg gcgctacaac gagactgcag acgagctggc aaaaatagcc tcggggcgaa    76020
caacggttcc ccggacgtct tctcccggga tctgcattag ccctccgtca agatcgatga    76080
ccctcccgag cccgaggcgc cctcggacca gcccgaggta cgctcggcac ggcccgaggc    76140
accctcagct caacccgagg taccctcggt ctccgagggc gaggcatcgc gcatcgagga    76200
ggagcgaagt ggggccatgc ctgatcgaaa ttggcagacc ccgtacctgc aatatctccg    76260
ccaaggagag ctacccctcg accgagccga ggctcgacgg atagcgcgac gcgccaagtc    76320
gttcgtcttg ctgggcgatg agcaggagct ctaccaccgc aatccctcgg gcatcctcca    76380
gcgatgcatc tccatcgccg aaggtcagga actcctgcaa gagatacact cgggggcttg    76440
cggccatcac gcagcgcctc gagccctcgt tgggaatgct ttccggcaag gcttctactg    76500
gccaacggcg gtggctgacg ccactagaat tgtccgcacc tgcgaagggt gtcaattcta    76560
tgcaaagtag acccacctgc ccgctcaggc tctgcagaca atacccatca cctggcccTT    76620
cgctgtgtgg ggtctggacc tcgtcggccc tttgcagaag gcgcccgggg gctacacgca    76680
cctgctggtc gccatcgaca aattctccaa gtgggtcgag gtccgacctc tgaacagcat    76740
caggtccgag caggcggtga cgttcttcac caacatcatc catcgcttcg gggtcctgaa    76800
ctccatcatc accgacaacg gcacccagtt caccggcaga aaattcttgg acttctgcga    76860
ggatcaccac atccgggtgg actgggccgc cgtagctcat cccatgtcga atgggcaagt    76920
agagtgtgcc agcggcatga ttctacaagg gctcaagcct cggatttaca acgacctcaa    76980
caagttcggc aagcgatgga tgaaggaact cccctcggtg gtctggagcc tgaggacgac    77040
gccgagccgg gccacgggtt ttcacgcccgt tcttcctggt ctacggggct gaggccgtct    77100
tgcccactga cctagaatac ggctccccga ggacgagggc ctacgacgat caaagcaacc    77160
aagctagccg agaagactcg ctggaccagc tggaagaggc tcgggacaag gccttactac    77220
actcggcgcg gtatcagcag tccctgcggc gctaccacgc ccgaggggtc cgaccccgag    77280
acctccaggt gggcgacctg gtgcttcggc tgcggcaaga cgcccgaggg aggcacaagc    77340
tcacgccccc ctgggagggg ccattcgtca tcgccaaagt tctgaagccc ggaacgtaca    77400
agctggccaa cagtcaaggc gaggtctacg gcaacgcttg gaacatccaa cagctacgtc    77460
gcttctaccc ttaagatgtt ttcaggtcgt tcatatacct cgcacccacg caaagtttag    77520
tcatcaagga agggtcggcc tcgcctcggc aaagcccgac cctccctcgg gggctaaaag    77580 gggggaacc ccctctgcgt cgaaattttc ctcgaaaaaa ggtctcttct gccagaatat    77640
ctttcgtgct ttttgactac ttcgaaaagt ggatcctgaa aacgacggag tacacgtaag    77700
cagtcaaggc ggaccgagcc gagggactcc tacgcctccg ggatacggat acctcactca    77760
tcaccttctg cgataagtaa ctcgcgttcg gataaagtga ttccgcggac cgaacaagtc    77820
ttcatgttcg gaagttcttc tgccgaagca atccttcgag ccttctcgac tgagtcggtg    77880
gcagggcctc atggacgagt gaaagtacgt gtaagcggca aggccgaccg agccgaggga    77940
cttccacgcc tccgggatac ggatacctca ctcatcacct tccgcgagaa gcaactccca    78000
ctcacacaaa catccctgtt accgacaaaa aagtcaagat actcgaaaca agaggaaagg    78060
agacgcagct ttacaacaca gcgagggcgt gtattctggc ctcggcggct gcagaaggca    78120
```

```
cacgctacaa gacaatctga ccctacaggc tcgggtcttg acgctggaag ggggcagcaa    78180
caccctcggc atcgatgaca ccttcagcga ggcccgacct agcctcggac ggcgacgcgg    78240
tccgaggatc tccgctccga aggacgatgt catcaccacg cccgggcaat cgctgccagg    78300
gacttctccg ggaatccggc ccgagcaggc ggctcggccg gttaccoctg gggcctcggc    78360 cgaccatctc ccaagggcgc cagcccgacc tgaggcctcg gctgatcagc cccgacgtcg    78420
gtcccgccaa cggacaaccc ggctaggctc gaccaacca ggtttcattt tcgagccaac    78480
tccgcctctg ttcacactga tatcgctacc cctggcctcg gctcgtcgaa gagcggccga    78540
ggggtccctt taactaagct agaggagcct cggacagcaa ggccgaccga ccgagggac    78600 tcctacgcct ccgggatacg gatacctcac tcgtcacctt gacacggggc gactcatgct    78660
tggtgaagcg gttcagataa tcaacagacg agtcttagcg ctcaaaaatg aggaaaaaca    78720
cggctccgtg ccggaattac atacatgttc aggccccgaa agccgcaatg aacaaaaaca    78780
ccggcattcg aagtgccatt acaaacggaa ctccggttcc ccctccgca ggtacgaaca    78840 gccccactcg ataggggtgg gcctacggag caacagaaga ctgacgagcg gctcgccgcc    78900
gcccgctctg actacgacga catgcaagca actgcaccgc cacttgcgcc accaccgcgc    78960
ctcctcgatt gcggaaccaa taccgcgact cgaggcgacc cagcgtgcga cccagcagcg    79020
ccagcctgac gcggcggtca acacggccaa aagtgggccg gcagtaatga cggtggcagg    79080
cgcgtgggag cagcggtcac gtcgtcagcc aagctcacgt cccatccggg ggcagcaaga    79140
gaaccccctc tcacggcgtg aagacaacgc gcccgtgatc cgttcctcga acggctcgcg    79200
cacgcgcaac ggctgcccccg ccaactactc gcctcgtcgc attaactccg cggctggaca    79260
ggcggcgctt ctggcaggag cagcgggcga cacttcgcct tcgccgaaat aaccgcgcca    79320 aaaaggtac gccgcgtcgt tcggtttcgt atcctttcc ctttttcctc tttctctatc    79380
tcttgcgaca gggaccggga aaggggggata ccccgaaagg gatccttccc cgtgaaggaa    79440
ccaggctccg agcctcctta ctgatcagag gttcgaaggc tggccccccg aagggttcaa    79500
cagccgcctc agatcgcgtg ggccctacac ccactactgg tcagaggttc gaaggccggc    79560
cccccgaagg gttccacggt cgcctcaggc tactcgggct ccgtgcccat tactgatcag    79620
gggttcgaag gctggccccc gaagggttca cagccgcctc agacgccgag cgagggatga    79680
ccaggggtac gttcgataca taaccaaggc tcgggctgcg ctcctgaggt accctaggac    79740
atttccgaga ccagcgggag cgatcttgta atggaatccc atcggaggga ggcatcgagc    79800
cctcggaccc cgtcgccagg ggaccgggtc cggcagatca cccgcaggta ctttttgggcg    79860 tgcctctggg cccctagccg acccctaacg aacggggcac ggacgtccac tcggattacc    79920
tgcttgcagc tcaccggaga caccatgttc ggcgcccatc gagggtaaca tggcgccctc    79980
cccctagtcc tccttgcgga aaggcgacgc aggggcatat gtaaaaaagc cgagtctgtc    80040
cctgatcgcc ctcttgccct gtgcagaggc tcagggctg ctctcgcaaa cccggctccg    80100
gccaaaccgt tgacagcgtc aacataccag cccgagaact gggccccga ccgtacaccc    80160 gggctacggc cagctcgcat gagggaacaa ccagaccagc cgaagcatta cgcaaggcat    80220
taagacctcg aaggagtgaa accactcctc cgaggcctcg ggggctacac ccggcggtg    80280 cgctcgcgcg cacccaccgg aacaaaatgc aaccgagaaa ggctggtccc ttgcaaaaaa    80340
gtgcgacgaa agcctccaag cgagtgctaa cactcctttc gaggctcggg ggctactgtc    80400
ggggaccata attaggggta ccctcaagac tcctaattct cagctggtaa cccccatcag    80460
```

| | |
|---|---|
| cataaagctg caaaggcctg atgggtgcga ttaagtcagg gatcagtcca ttcgagcgac | 80520 |
| tcgatcacgc ctcgcccgag cctagcctcg gacaagggca gccgacccg gaggatttcc | 80580 |
| gtctcgcctg aggcccccct ctaacggcgg acacatcttc ggctcgcccg aggccctgcc | 80640 |
| ttcgctaaga agcaaccctg actaaatcgc cgcaccgacc gaccaagtcg caggagcatt | 80700 |
| taacgcaaac gtgacctgac acctttatcc tgacgcgcgc cctccggcag agccgaagtg | 80760 |
| accgccgtca cttcgccgct ccactgaccg gtctgacaga aggacagcgc cgcctgcgcc | 80820 |
| acttcgactg cagtgccact tgacagagag atactgacag gaagccaggc cctgccaaag | 80880 |
| gcgccatagg aagctccgcc cgacccaggg ctcggactcg ggctcagccc cggaagacgg | 80940 |
| cgaactccgc tccgcccgac ccagggctcg gactcgggct cagccccgga agacggcgaa | 81000 |
| ctccgctccg cccgacccag ggctcggact cgggctaaga cccggaagac ggcgaactcc | 81060 |
| gctccgtccg acccagggct cggactcggg ctaagacccg gaagacggcg aactccgctc | 81120 |
| caaccgaccc agggctcgga ctcgggctaa gacccggaag acgacgaact ccgcttcgcc | 81180 |
| cgaccccagg gctcgggctc gggctcagcc ccagaagacac acgaactccg cttcgcccga | 81240 |
| ccccagggct cggacaccgc cctggcctct gccgacgacc tccgcctcgc ccgacccagg | 81300 |
| ggctcggact cgtcctcggc catggaagac agactcgacc tcggcttcgg aggagcctcc | 81360 |
| acgtcgccca acctagggcg caggccagcc acgtcaacag gaagcgccat catcccta | 81420 |
| ccccgagctg actcgggccg tagagaacaa gaccggtgtc ccatctggct gtctccacca | 81480 |
| gataggcaat gatggcgccc cgcatgccct gtgacgacgg cagctctcag ctctcttacg | 81540 |
| gaagcaggag gacgtcagca aggacacaac cgctccgaca gctgtccctc cgccaggctc | 81600 |
| cgccgctcct ccgacggcca cgacatcaca ctagctgggt tccaagatct cttcggctgc | 81660 |
| cacattggca tgtactcagg gcactagctc tccctcgcta gacacgtagc actctgctac | 81720 |
| acccccattg tacacctgga tcctctcctt gcgtctataa aaggaaggac cagggtcctc | 81780 |
| ttagagaggg ttggccgcgc gggacgagga cgggacaggc gctctcttgg ggccgctcgc | 81840 |
| ttccctcacc cgtgtggacg cttgtaaccc cctactgcaa gcgcaccgga cctgggcgcg | 81900 |
| ggacgaacac gaaggccgcg ggattcccac ctctctcacg ccggtctccg gccgcctcgc | 81960 |
| tcctttcccc ccttcgcgct cgcccacgcg ctcgacccat ctgggctggc gcacgcggca | 82020 |
| ctcactcgtc gacctgaggg acccccggt tcgaaacgc cgacaataac tctaaccgaa | 82080 |
| cttggcattt agccgatcga ttcctaaccc atttttcata ccaccactac atgacatacc | 82140 |
| gaatacattg aatgactcgt tcacattcca catatatctt tacgaaaaca tttccacatc | 82200 |
| gcttgcaact taacctaagc ttcgccacat aatttcagga catctactta aatcatgaat | 82260 |
| atcatcatca cacacatcga cccgttttga aataaaccta catgtctatc acaggaatgg | 82320 |
| agcatttcaa cacatatcct aaaacaaact aacttcatca cacatcttgc attacaaagc | 82380 |
| tacttgactt atttgaagtg tctactcgaa atcgtgagca caatcataca ctatatacga | 82440 |
| aacataattt taacgaacgc ataatacgca tcgtcatgac ttgacctata aatatagaga | 82500 |
| aagcgatgac tactctggca tgtcaccacc tctctatta agtcaagaca atttctacca | 82560 |
| tcgattaaga gtcgtaagca ttaaatacct tactacttta tacgcacaaa taaacttcaa | 82620 |
| cttaacacaa ctgacaccga tggaattttt actaaactca tcgtacgcat aaccctgtct | 82680 |
| cgcatacaac catattatgg cgtgcactcg agacacttca atccatgtgg cgcgaccact | 82740 |
| agtataaatg gactctgaca ctcatgtctt aacgatacat cctctacgca aactagcatt | 82800 |
| ctctaaacta ctcgtcacat caataaatat atcccctcta aaattatgaa tcccatcaca | 82860 |

```
ttgcttaaaa caaatacact tttcacataa acacatcgat gcatttccca aaacaaaatc     82920
cacattttgt aacttagttt tcgcatcaaa caacgcatcg catattttcc tatcaaaata     82980
aaaatactcg agttctttc tatttcaatt tcttccctac acgcgtccat ttataaaatt     83040
atacagttac acacatataa ccacatgcac atcatcgacc aaaacataat tagacaacta     83100
caaatcgtgc acatcaatta acctcttgtt ctccaatcgc aaacgtgatc ctaccaatgc     83160
gcataatcga acattttaca cacatccata caaaatgatt aatcgagtcg atcgagagcg     83220
acatgcatcg gctcaccata aacaaaccca aatgatgttt gcaagaatga cggtgattcc     83280
gattcgtgca tcgctccaaa catccaacga gcgttaagcg acttgctttc tcctcgcaaa     83340
acacggggtt ctctcctcca caaaaataaa acaaagcaac acacatacat aattaatcat     83400
aggaaaataa catcgatgcg gaatcaaaca aggagcgtcg cggtctcacc ggggtgaacg     83460
acgacgacgt ttggggctgc gcaaaaacag cgaacacacg gcggcatcac ggcgtgctgc     83520
tcactacgca acaaaacagc aagccggcag cacgcgcgagc cgtcggggct gctgcacatt     83580
tcatcgagca caagtgtgga tggcggccag gtgtttgttt caggcgctga aacaatggag     83640
ggggagaggg ctacggctgg ggaagtggtg gctcggccac ggcaagaaca gggaagggga     83700
ggctggtcac cgaccttggg cgcggccagg gaaaatggag ttgctgcttg gcactatgta     83760
caacagagag agggaggaat ggctccatgg gaagctcgag ctcggccagg ggaaggaaga     83820
aaggggttcg gcatccaagc tgttggagcc caaggagagg gtgctggccg ccgtgcgcaa     83880
gtgaagtttc acgccagctg aagctccctg gtcgcggaca ggaaagagca gggggcgcct     83940
gctgcaggta ggagctcgac tcctatggaa aatggcaggg gcagaggagg ccggctggag     84000
caccgggcag ggtgctcggc catggagccg ctgcatggat ttgctgctgc gccctggag     84060 aaaaacagta gggagtgaa ggatgccatg gctgggggcg cggggagcag ggagcctgct     84120
ggtggccttg ctgccgtgaa gcggggaaga agaaaggcag aggacgctac gagaagagct     84180
tcgacgcgct ggagggaagg aacgcccggc catggaagcc cctgcgcgct ggggaaggag     84240
ctccagctct acgtgcttga aggagcccat ggctggaaaa tggtagagga ggaagagaag     84300
ggtgttggcg gctggggtgg aaatggaaaa ttttcagaat gcaaggtagg gaagcccata     84360
tttatagagg agaaattagg gtagggtttc ttatgggcca aacgggctgg actggatttg     84420
gcccaaaaca ctaaattggg tcgcgctaaa taatttccgg actaaaaatg ttcctgcgga     84480
attcgtcgct actgagaaac agagcgaaaa gagttcggac gaacggaagg ttgcgcgatt     84540
aactcagccg agagtctgtt tagattttgc ttgaaaataa ttccctacgc gtaaatcgaa     84600
aataaaccgt cctgagattt gatcggtttt ggattttag tcggagaaag cgaatcgtga     84660
tatataaaaa tcgttgccga tgttgatttt gaaatcggat tggatacaga gatgctaagc     84720
tgagtcgagt aagatttgat cagaggacga catattgatt atttcgtttg tgagtatgga     84780
ctcggattaa aatagttgga catcgatcga acatcgagaa attggattcg acacagatc     84840 aaataacagc cgtcgagagt ttgatttatt gagcttcaga tgaggtttat aattcgagaa     84900 tgattttga gttcgcattt gtgccaagga taaagttttt aacaggctcc aaaattggcc     84960
ttctatgaga ctgagtaact ccgaattcgg tgaaacatga atgaataatc tggataatca     85020
gggacatacg cgagcgagaa atagaaattt ttactgagca tccgagatta ggataaatct     85080
cgcgacgtaa cacgaaactg acacctgggg tgtcacaact ccagcactgc caccctgctg     85140
gcaggcggat ccgtcgaaga aaagcatcca gtggggctca gtgaagaccg aagcccttgg     85200
```

```
ctccgcaggt gtggtgtccg aatcgggatc tggaccccca ggagcgctcg gggaaggggt   85260
ccactccacg atgaagtcag ccaggacctg gctcttgaca gcgtggcggg gctggaactc   85320
cagttggaac tcagcaagct ccgtggccca cttggcgatg ttgcctgtgg cgtttgagtt   85380
gtggagaatg gcccttaacg ggaaggaggt caccaccaca actctgtgtg cctaaaaata   85440
gtggcgcaat ttcctggaca caacaagtat agcatagata agcttgtgcg tctcaaggta   85500
cctggctttt gcctcatgga ggacctcgct gacgtagtag accggcttct ggatggttcg   85560
gaccectgca ttcagtcccg agtcctcaaa ctcctggcct tctgtcaaca tcgtggtggt   85620
cagaccacca ccttctccta ggggaacttt atgactcccc tagggatgtt gtgtcgtact   85680
ttcgacgacc agcaccatgc tcaccgcctc tgtagccgct gcaatgtact agtataatgg   85740
ctctcctggc tctggagcta ccagtattga tagggacaca tggtgctgct tcaactcttg   85800
aaaggcttgt tctgtctctt tggtccaaga gaatgggtcg gacttccgca atagcttgaa   85860
gaagggtagt gccctctcaa ccagtcttga gatgaagcga ctaagggcgg ccagtgaccc   85920
cgtaagcttc tggacgtctt tgattcaggc cggaggcctc attgtctcta ttgctttgat   85980
cttctctggg tttgcttcaa tgccccggtg tgaaaccagg aatcctagca acttccctgc   86040
agagacacca aagacgcact tgtccgggtt cagcttcatg cgtgttgcct gcagcttgtc   86100
aaagactagg gttaagtctt ccactagggt cgaccctccc ttagtcttga ctacgatgtc   86160
atcgacgtat acctctaccc tgtccctaat caagtcacca aaagtattac tcatcgcccg   86220
tacaaatgtt ggcaaggcgt ttttcagact gtaaggcatt acaacataac agtaaagtcc   86280
atccacagtt acaaaagcgg tatgcttcct atcttgccta gacatctcga tctgatggaa   86340
actagagtaa gcatccagga aggataggag gttgcaccca gaggtagaat ccacgatttg   86400
atctattcgt ggaagtggat atgggtcctt ggacaggcc ttattgaggc tggtgtagtc   86460
gatgcacatc caaagcttcc cgttagcctt ggggacgatg actagattgg ccagccatac   86520
tgggtgatgg acctcttcga tgaaaccagc gtccagcagc ttccggacct ccttacggat   86580
gaaatcctgc cgctcgatgg actgtctttg aggcttctga ctcaccggtt tggcgtcagg   86640
gtggatcttc agatgttgct cgatcacctc cctagggatc ccaggcatct gcgatagttc   86700
ccatgcgaat acattggcat ttgcctggag gaaggcgatg agcgcgattt cctatttctc   86760
ctccagatcg cccgtgatgc gagtggtctg ggaggaatcc ccgttgagcc ggatggtctt   86820
gacagggacg ccgtctgccc cagatggttg caccttaggc accttagcag gcatcttggt   86880
acaggaagtc gagggtccc tcccctcgtc atccgggcga gcagcttctg ccgctagggc   86940
atgcaacttc tcgatagctg caagcgcagc gggacggtcg ccccgcatgg tgaggacccc   87000
agcagggat ggcatcttga ggaccaagta cctgtaatgg gcaatggaca tgaaccggta   87060
cagggccggc ctgccaatga tggcattgaa agggaggtta acctccgcaa catcgaacta   87120
gacattctta gtgtggaagt tatcctcagt cccgaatgta accaggagtg tgatgctccc   87180
aagggggatac accggtttag ggcccactcc agagaacgtg cgagagggtc ctagtcggga   87240
tcctgggatc tgcagctgct tgaacgcagc gtggctgatg acgttgagcc caaccccacc   87300
atcaatcagc acatgatgca acttcatgtt ggcgatgaca ggggcagtga tgagtggtag   87360
tataccagcc cctgccatgt tttcggggca gtcgggtgcc ccgaaggaga tagtggtgct   87420
ccgccaccgc tgatgtgggg ctgccttcgg gaccctggg gtcgccaaaa ggacctcgcg   87480
gcgcagggac ttcacgttcc tacgggaggt gagctcccag cttccaccat acattacgta   87540
cagcttcttg cggcggtcgt tgtcatcacc ggagtcggag tctccagtga ggatatcctt   87600
```

```
gaggacttgc tcgggggcct aattctcgag gtcccattct cccgtggcca ggtcaccttc    87660
gtcgaccttc tccttgccag gccggcgccg aggcggcgag ccatccctgg aggcatgctc    87720
gcgccgctca ctgatgcgct tcacgagctt caggatctct cgtcattctg aggcactgtg    87780
gcgactgttg gggtggacag ggcatgaccc aatgtcactt ccctgttgcc gtggatgctt    87840
gccgcgctcg tcccggtccc cagccgtagc tacagcaact ggagcaccag actacggcct    87900
atcgtgacac ggtgcttctt cttttcttg ccaccaccct gggtggcagc acctgagcca     87960
cccatttggg tgactctggt ttgcagcgtc gagtgccatg cacggccctc agtagctctg    88020
gcacatttgt cggccagagt gaagagcgta gtgacggttt ccacgtcatg cgtcgccaat    88080
ttctccaaca tcttcttatc acgcaccccc ctgttggaaa gcagtgataa tggaggcatc    88140
ggagatgcga ggtatagtcc cctgtacctt ggtgaagcgg gagatgaaag cccggagagt    88200
ctcctcgggt tcctgcctca ctgcatggag atgagcctcc acgccatgct actgataagc    88260
actggcgaag ttcattgtga accgtgcaca gagctcttcc caggagtaga tcgacccgg     88320
ggtgaggttc atgagccagg tctgtgccgg cacattcaag gctacatgga aatagcttac    88380
cattacagca gtgttcccac cagctgccgt aatggcggtg acatagacct acaggaattt    88440
cgacaggttc gatgtcccat cgtacttctc cggcaggtgt ggccggaaca tgggtggcca    88500
agtcgccgcg cggagatgat ctgctagtgc ggcgcagccc acgccgacca atgggacacc    88560
catctggatt cgggcgtccc ttgcagtgaa gtcttggtcg aggttgcgac cctcgaagtt    88620
ttgccggcgc tcacgcgccc tctccagaga gattcgagca tcctcgcctg cacgcctgtg    88680
gttgagttct gctcgcaggt cgttagtctg tgccccctca ctgagggtga atgcacagac    88740
gttgacgcct cgcgctgatg ccggaatgat cgaggcctgg acctggccga gctaggatgg    88800
gccatgccga ggagacggtc gacatcttca cgccactgcc tcatggcccc cggggaggcc    88860
gtggaacttg gtgggttacg cagcaactcc ctggctgcag acaatggccc accataggta    88920
gccctcgacg gagtcctaga ggtctgtgcg ggcgtgtgtt gctgcgcagc gtgcatagca    88980
gcagcaccag gcacagcgcg gttggagcct cgtggcatgg aagataatgc cccttcctcc    89040
atcaagaagt cctcgggaga caagccacgg tgctcgacga tctgaaccat cgtgtcgagc    89100
aagaaaacag gcaaaaacct aaagccaaag cccctacct ggagcaccaa atgtcgaagg      89160
gaaaatcctc cggccgggtg gcggaatgca cccgccctaa tcctaagatg aggaggggc     89220
ctaagcggtt gcctgtttgg tgaattcggg atgaacacaa gaggacacga gggattatag    89280
tggttcaggc cgccggagcg taatacacta cctccactgt gtgtatgttg tattgagtgt    89340
gtacagcgtg tcccttgtaa cgttgtgtgc cttccctttt atagtttaag ggaggcacat    89400
acaaggatgc tgagcccga catgtgggcc caggagcata atggaagaaa tacattatgt     89460
gaataactaa tgctgacaga gtaacacatg agtaatcagc gggagtcatg atggctgcag    89520
tccatgcagc attgatagac agtaacccctt ttcttggaaa catacgagta atggtgagtc   89580
attgccctcg atatggtaac gtgtgagtaa ctgcatggcc cacgtatcgt ggactgagca    89640
tgccgcctgt cagtggaatg gacaggcgca catcttctcc gtaatgaatg cgaaggcacg    89700
cgtagcccag aggcatcatg ccaggttcca cccgttggtt tatgccgcgc gcagtatgcc    89760
acgtggcagc atcgggtctc cgcctgagca gggagaagga gtgtatgcgg ataggtccgg    89820
atcccaccag accaggtcta gacacgtgtc ggctccggac ccccacctgg gtcctaatca    89880
aggcccgggt atgttctgtc ctagaaccct gggaccccac tatgggtggc ccagacccat    89940
```

```
acggggggtt cggatcccat cctagggtc cggtttgtac acgtggaggt cctggaccaa    90000
acttggaggc ctggaccgta tatacagggg tctggcactg gtccggcact ctcccatggg    90060
gtccggactc actgttgatg ccttggagta catcactttc tctggacaca tggcggcccc    90120
gaacccgccc atgtgtggg gtcaggtgct gttgctggcc cagagtagtc gcccgaggct    90180
agggcgagtc atggtctggt cccacataca gcttatttac cacgcgacta aagatagtcg    90240
tgtgggtact gcgtctttat acagtagtaa ggggtaccct agttttaggg tgccgacaca    90300
catcttcctc tagaacacca tgaagaaacg cgttctgcac atccagttgg cagaggctcc    90360
aaccctgaga gacagcaaga gacaaaataa ggcggacagt agcaaattta actactaggc    90420
taaaagtgtc atcatagtca atgtcgtagc gctgtttaaa acctttagcc accaatcgag    90480
ctttatgatg gtcaatagac tcatcagctt ttctcttgag tttataaacc cacttgcaat    90540
caatcaaatt tctgtcaggt gcgggaggaa ccaagtgcca tgttttattc cgcataaggg    90600
cagaaaattc taggtccatg gcagcttttc cagtttgggt caaacaatgc aacagacaag    90660
ctggagggtt cttcacaaat tgccaaattt ccatacctga tcgtgccatc tgtaaacttt    90720
ctgggcttca caataccact ctgtagccga gtgcgcctag caggaagcgg aataggacac    90780
gaggctgatg gcgagggcag atggctgtca gtgagagagg gaccagccgc gccagagtcg    90840
gcacgaggca atcccgaagt ggctgctgct attgatgcgg ccgtggtggt gggaagcacc    90900
gcgttgctgg gcgcacctgt agccgcgtcg gaggggtgtg gcgtggagcc tagcaacaga    90960
tcagcaccgg gattgaggcc accagccggg acagaatttg cagcagggat cattggtggc    91020
tgcaaaagct ggttaggcca caaaatcgga gcaagcatgc tggattcagc aggagaatta    91080
gtcacaagat catctgagtt ggcccgagaa ttattaggat cgggtagaag aagcacgtca    91140
gaggtatatc gagcaccgac tgtgggatgg agagcagcaa agggaaaagc gtctcatcaa    91200
aaacaacatc atgtgaaata taaacacggc ccgttgagat gtcaagacac ttgtaaccct    91260
tgtgaaggtt gctatagact agaaaagcac accaaatgga ccgaaactag agtttatggg    91320
tgttgtatgg ccgcaaattt ggctaacatg catagccaaa gacgcgtaga ttagagtaat    91380
ctggggtagc acctaagaga cggtggagcg atgtgtcata atcaagaagc ttagtaggag    91440
ttctattgat aagatgtgtt gaggtgagga acgcttggtc ccaaaacttg agcggtattg    91500
tccattagcg agtaaagaga ggcccatctc aacaatgtgc aacgaatcaa gctgatacat    91560
aagannnnnn nnnnnnnnnn nnnnnnnnnn nnnnnnnnnn nnnnnnnnnn nnnnnnnnnn    91620
nnnnnnnnnn nnnnnnnnnn nnnnnnnnnn nnnnnnnnnn nnnncaattc tagaagattt    91680
cgtcgatctt gatggtgtcg ttggccttga tgagcgggtc ggggtagcgg atggtgcggt    91740
cgtcgtaggt gtttaggcag gggatgcctt tctggccaaa ctgaacagac cttaccttgc    91800
agagcatgaa ctgcacacaa accaatagaa aagcagtgag aatttcacag gcgtactatg    91860
aaagggcatg ggaatttcca gcgatgtaaa tggatagata gacagagcaa catctattaa    91920
tagtcctaac gattgtagca catgacattt tcaatgcaag actttcatgc acacaacata    91980
tatggacagt atagcaagga taaggtacat agatctacag aaaaaaaaga acaacctgaa    92040
gcattagaca aatgggggaag tacagaagat tgtaggtacc aaagctagaa aatattgttt    92100
tgtcggcgtt tcgaccccgg ggggtccctg gaccgacgag taaattgtcg ctgcgtgtcc    92160
cagcccagat gggtcgacgc gagacagaac acaagggggg gaaaacagca aaggggaacc    92220
cgcggccttc gtgttgtcct gcgcccaggg cggatgcgct tgcagtaggg ggttacaagc    92280
gttcgtgtgg gagagagaga gagccttgtg cgtcagcccg ttctcccgcg cggccaaccc    92340
```

```
tctcgtacga gagccctgga ccttcctttt atagacgtaa ggagagggcc caggtgtaca    92400 atgggggtg tagcaatgtg ctaacatgtc tagcagagag gagacagagc cctaagtaca    92460
tgccgtcgtg gctgtcggag aggttttggc gccctgttca tgtgatgtcg tggccgtcgg    92520
aggagcgttt gagccctgtg gaagtacaac tatcggggct gtcggatcct tgctgacgtc    92580
tccttgcttc cgtaaggggc tgagagccgc cgtcgtcacg gagcacgcgg ggtgccatca    92640
ttacttgttt accggggcga gccagatggg acgccggtct tgttccccat agcctgagct    92700
agctaggggt agggtaatga tggctccccc tgcgacgtgt cggtccgagc ctgaggtcgg    92760
gcgaggcgga ggctcctccg aggtcgaggt tgagcccgag ccctaggatc gggcgaggca    92820
gagtccgtct tccgaggtcg aggctaagtc caagccctgg ggtcgggcga ggcggagtcc    92880
atcgtccgag gtcgaggctg agtccgagcc ctggggtcgg gcgagccgga gtccgtcttt    92940
cgaggtcgag gttgagtccg agccctgggg tcgggcgagg cggagtccgt cgtccgacgt    93000
ccaggttgag cccgagctct ggggtcgggc gaggcggagc ttcccatggc gcccgaggct    93060
ggacttagct gctgtcagcc tcactctgtc gagtggcata gcagtcggag cagggcaggc    93120
gatgctattt tcccgtcagg tcggtcagtg gagcggcgat gtgactgcag tcacttcggc    93180
cctgtcgact gaggagcacg cgtcaggata aggtgtcagt cgatccttgc attaaatgct    93240
cctgcgatac ggttggttgg cgtggcgatc tggccaaggt tccttctccg cgaagcttgg    93300
gcctcgggcg agccgaaggt gcgtccgttg cttgaggga ccctcgggca agacgtgaat    93360
cctcctgggt cggctgcctt tgcctgaggc taggctcggg cgaggcggga tcgtgtccct    93420
tgagtggaca gagccttgac ctgaattgcg cccatcaggc ctttgcagct tgtgctgat     93480 gggggttacc agctgagatt aggagtcttg ggggtacccc taattatggt ccccgacagt    93540
agcccccgag cctcgaaggg agtgttggta ctcacttgga ggcttttgtc gcactttttt    93600
gcaaggggac cggcctttct cggttgcgtt tcgttccggt gggtgcgcgc gagtgcaccc    93660
gccgggtgta gccctgagg cctcggagga gtggtttgac tccttcgagg tcttagcacg    93720
tttcgtgatg cttcggccgg tctggttgtt ccctcatgcg aactggccgt agcccgggtg    93780
catagtcagg ttccaagttc tcgggctggt ttggttgttc cctcatgcga gagcagcccc    93840
cgagcctccg cacagagcga gaggacggcc aaggactgac tcggctttt tcatacgccc     93900 ctgcgtcgcc tttccgcaag gaggaggggg gggaaagcgc catgttgccc tcagagggcg    93960
tcgaacatgg tgtctccagt gagttgctaa cggttgatcc gagtggacgc ccgtgccccg    94020
ttcgataagg gtcggctagt ggcccagagg cgcgctccaa aagtacctac aggtgatttg    94080
ccggacccgg tccgtttga tagggtccga gggctcgatg cctccctctg atgggattcc     94140
gttacagaat cgctcctgtt ggtctcggaa atgtcctagg gtacctcggg agcgtagccc    94200
gagcctcggc catgtatcgg acgtacccag agtcatccct cgctctgcgt gctctgaggc    94260
ggctggcgaa tccttcgggg gccagcctac aaaccctga tcagtagtgg gcgcagagct     94320
cgagtggctt gaggcggctg tcgaacccct ccgaggggct agccttcgaa cctctgacca    94380
gtagtgggca cggaacccga gtgctctgag gcggctgtcg aacccttccg aggggccagc    94440
cttcgaacct ctgatcagta ggagggcgcg gagcccgagt gctctaaggc gactgtcgaa    94500
cccttccgag gggccagcct tcgaacctct gattagtagg agggctcggg gcccgcttcc    94560
ttcgcggaga aggatccctt tcggagtatc ctctttcccg gtccctatag caagagagag    94620
aaagaggaag ggtaaaagga tacgaaatca aacgacgtgg cgcacctttt ttgacgcggt    94680
```

```
cattaaggcg gaggtgaagc gtcacctgct tcgcctgcca aaggtgccgc ctgtcctgcc   94740
gcagagttaa tgcgacggga tgagtggttc gcggggcagc cgttgtcgt gcgctagccg    94800
ttcgaggaac ggaacacggg cgtgtcgtct tcacgccgtg ggagggggct ctctcgctgt    94860
cccaggaggg gacgtgagcc tacagacgac ttgaccgctg cttccgcccg cctgccgccg   94920
ccattactgc cggcccactt ttggccatat caaccatcgc gccttctccc gcggctgact    94980
gacccgtgat cgatgtgctc ggttggcact gttgggccat cgcagggtt gcctcgagtc     95040
gcggcaccgg ttccgcagtc gagaaggcgc ggtactagca caagtggcgg tgcagtttct    95100
cgcgcgtagt aaccggcgcg ccggttacat gacgtgtggg cctgggcccc cgtgctggac    95160
gcgtcggagt cgaaagggtg caccccttg gtgcggttgc atgccgcctg catggcggtc     95220
cgcccttca cccgccggtc tgggcgaaag tggaggagtg cttgtaaccg ctgggcagtt     95280
acgcactctg cgcgcgacgg tttggcttct tctgccctgg gccagcttgc atgacgcgtg    95340
ggacccagcc cccatgtcgt aggggagga ccttggagcg tgttggtgaa gactcagtcc     95400
gcgacggctg aggacgcaag tggggagagt cgcctttaaa aggagggcga ccccttgga    95460
tggcaaccat gtcttcacac tcccttcatg catcgcgccc ttccaacttc cgagcccccg    95520
gatgggagc gcccgcgttg ctttcgtctt gtcgtcgttg gaggaacgca acttcgcgga     95580
agttggtacc tttcagccat cgctcggctt caaggatttt catcaggcgg cccggctgca    95640
tccctcgct ggtggtcacc caagacggtg accaccagtt tgatggtggg gacgtgggcg     95700
agggccttgt cgcagcagcg tctgcactga ggtcatcgct gctgctgttt ggctgtccgg    95760
agcggaggtc gttgtcgctg ctgccagagc gggcctcggc gagctgtcta gggttttgtt    95820
gctgaaagtt cccttgacc cgggaacagg atctggatgt cgcctagagg gggggtgaat    95880
aggcgaataa aacttttcac tttaaaactt aaattcttac tctactcgaa gacttagtat    95940
gcagtggagt gagaagactc ttcaagtagg ttgcagcgga atagaagatc ctgtctcaaa    96000
atgtcctgca cttcaaataa agcttatacc acagataagt attgaagtgc agatataaag    96060
gcgagtagaa agagagtcag gatacaatac agaacagagc acacagacgc aaggatttat    96120
cctgaggttc ggccaagcct gaaatgcttg cctagtcctc gttggagtta gccacacctg    96180
ggcttggagt ctatttcaac tccttcctcc gtttgctcag atctgtcagt atgacagata    96240
gagccttca ctattgagtg gggttacaac agaaccgcgg ctgcttacag acttcttggc     96300
agcaccccgg tagagtaacg atatgctcaa gaccttgctc tagctcttag cagcactact    96360
cctctctcta aggcttatag ttgtgccttc tacacaaact atagagttac acacaagagg    96420
gagagtgaga attgattcca gtggagtcta cacttgttgg ctgcacttct attttgctgg    96480
aggcacctag gggtcccttt tatagacaca aggggcctag gagccgttgg aagcaatcca    96540
ggaaggcaaa tcttgccttc tgtcgggtgg cgcaccggac agtccggtgc acaccggaca    96600
ctgtccggtg cccgatttct ttccttctac gtcgaagccg accgttggca gtcttggagc    96660
cgttcgcgca ccggacatgt ccggtgcaca ccggacagtc cggtgcctcc atctagccgt    96720
tggctcggcc acgtgtcccg cgcagatcgc gcggccaacc gttggcccgg ccgaccgttg    96780
gctcaccgga tagtccggtg cacaccggac agtccggtga attatagccg tacgtcgccg    96840
gtgaattccc gagagtggcc agttcgccag agttcagcct ggcgcaccgg acactgtccg    96900
gtgcaccacc ggacagtctg gtgtgccaga ctgaactaag tcttggctgt acacagccaa    96960
gcctttcaca cctcttccct tttcttcttc tttctgtttc taacacttag acaagatat    97020
tagtccccaa aaccaatgta ctaagtctag aaacatacct tctattaatc attacatcta    97080
```

```
tagcatttca caagcttgag ctttgatgtt ggactcataa attatcaagt cagcttgact   97140
tgatctagat tgacatcgct tggctccaac atcctgtaaa ggtcacatag aacatctcca   97200
aacataggaa caacccaaac taaagatcaa agtgaactta gctcttttgg gctgcttcca   97260
gttctggttt cgacacttgt tctccttcta gtgaccttga tctcctcctt agagcttgat   97320
cttgagcctt atgacttaca ccacataact atagctgtta cctcattggc tgtaagtcac   97380
gtccttatgt agtgatcctt gatgtgccgt agctgttctc aactcgatca cccttgactt   97440
tgcaagcctt cttcttcacc cttggctttg ggttcctcag cctccttgac cttctcccat   97500
gcatttggta cctcgaagct tttcttgcct ccgtccttgg cttgatcagt tgtcttcgag   97560
ctacgcaccc gagtctcact ttgtgcaatg tccatcttac ttgtgatgtc cattatgtat   97620
ccataatcca gttcttggac catcacattt gttcacttgt gttgaaccct gtaggcttta   97680
ccttaagcac atgttcaaca cttagtatac ttgttagtcc tttaattgag ttgtcatcca   97740
aacaccaaaa ctcacaagag agctttcaat ctcccccttt ttggtgattg gtggcaacac   97800
aattaaagct tacataagaa taagatttga agcacaaatt tgaattctaa gattatagaa   97860
tgctccccct aaataagtgc ttacttcaaa aacctaatttt tgaccacaaa cgtcaatttg   97920
cacatactta ggaaaattga aacatttcta caccttagca cttttttagga tgcattatgt   97980 caagaatcaa accatgatgc tataacacac aaatgcacat aatcagagtt aaacaccatt   98040
caaattagtg gatatatcac aggaatatca acctaccact attcaccatt aagataccaa   98100
cttaaactaa gatatcaatt taaagcaatc ttaaagcacc attaaccaca tgactatcta   98160
tttcactata gaagccaaat aattcatcgc agcggaaaca ctggtctagt ccatatgatc   98220
aacacgtata atactgcaag aaacatatga atataaaaca ctagtctagt ccatatgatc   98280
aacacgtata atactgcaag aaacatatga atatcacact tggcaaagct caaactaaca   98340
catcacccat taggataagc tttcctctca ggttgagata agctttaatg cacaacttct   98400
ccccctttga catcaaacac caaaaaccat actcaagcaa gaacatatga tgatgtcaag   98460
ggacagcagg gtgttaaggg gaaaaacgac tatcaaaact ccccttatt tattgaacat   98520 atgtcctatc aacatttagg taagatacat atatgcaaaa agattaatac ttccttttgt   98580
acctttacca tgatgtagtg tacttcccat cttgaaagta gttaatctct cgagagcttc   98640
tccacacttg tgcctgattc tctctcctaa cttttttcttg ttgctaagac accaaactta   98700
gaacaagtta tagtattggg cacaagaaga aacttctatt ctcatgatta tcaaaagatg   98760
tcaattgaag cgaactatta cggctaccaa ttgaaagata ccaattgcaa agttcattta   98820
ttatcatggc tccatgatat ttaagaataa gcatctatta tcaccagata ttatagagca   98880
tgagcaatct aaaaatatgc acttactcac aacttgagat accaattttc ttgacttaca   98940
gaggtaccca gtcctgatt gctccatttc ttgcttatct tctcttttcc acctagagac   99000
tatacaagat tgctcaagaa acagttagtc tcaaaagaca caagttatgt gtgctccccc   99060
tcaagttgtg catcaagtat ttgaatgact tgcactttgc acattctagc ttccttagaa   99120
ttagagggga tcacaacata ccttggtcaa ggcatactct accactttca tcacccaaag   99180
atgccaattt gaatatcaaa tgaaacgcca cataacacca attgaaggct aaatgaaagg   99240
ttgactaaat acaacaatgc acgcctcagt ggcacctaag ccaattgaat actcacagga   99300
agtctaacat ttcgcaact tgtacatgct tcatatttaa ctatcattgt atataccaat   99360
taaagataaa cacaatcgaa atatctaagc atgttataat taagaaggtt tcttaggtgc   99420
```

```
acaaaagaaa caacatttta aaggcataaa ttacctaagc caagatatta ccaattgaaa   99480
ggcaagaaca tagctatgat cacaatgaat ggaatttcaa gaatatttaa tgaaattgca   99540
tagctccatt ttccatacct ttgcctttat gagagcccct gttatcgcca atttagggct   99600
ccttttgctt acgcacctca tagctcaaaa gggcacgaca tggatttgaa attcacacag   99660
taccaaacta gggtaatcat gtgaacatgg actaaacaaa atgtcataat tgcacatagc   99720
atgacttaca aaagttacag gtttatccat atacatcaag agagttatcg ttgtggatat   99780
aacaaatgaa atagctaccc atgaatgatt caaaagatat atcctttata gcaccagtca   99840
tgattaagca accatcatta tgatcaattt aacacaggca atcataaagc ataactactc   99900
taaggacagg tagcacaaca agccaactta agagcaatac taaattgcaa ttatgtactt   99960
aaaatacacg ggtaccgtcc tttggagagc aggttgtaga ttctcatcaa gatcctttac  100020
ttgattcacc aataatgatt caggacctat acaccttatt tctcttgaga tgaacatggg  100080
attagtgttt cacaataatt caaccttggg tcaataaaca ctaaaacaat taacagctta  100140
agcatagagt tttagataac cgtcttaatc tttcccatgg tctccagtcc atctcgaggc  100200
acctgcatgg tctagttggc acagtttggt atccatctcg ggatgggtac ataatgatca  100260
tgtaaatgtg cctttggtac ccaaattgcc tttgtgctag ttctaggtga tctcgttata  100320
gatctagcac aagtgtatga tttgggtctc ctatgcgaat aagattgaca caaattcact  100380
tgtttaggaa tcttaccttt gtaacatacc ttggatagat gaccttgctc accacacttg  100440
tagcagaagc gtcgctcaac ttgacatgac gcttgttttg tgtcattttc cttggtgagg  100500
gtcactttgg aggatgcata tccttgattc ttcatgaccg gacatgaagt gatcatgtgg  100560
tccttattgt tgcatccaaa acaactcctt gttctttcat ccttgtcttt gtacggacaa  100620
gacgcgatga ggtggcctgt ctccttgcat ttgaagcacc tccttttttcc tcttcccttt  100680 ttgtgcttga atgacatgga gagatgatca gtgcaaacaa catgactaat tgaatttttta  100740 cctttttcct tgttcatgtt gatttcttca tttatagctt tgggaacatt cttcttattg  100800
agcttaacac ttgctgcagt ttttcctttc tcaagcttct tcaccacgcg cccgtggata  100860
tcttgagaga gttgagcaat gtgtcttctc cttagttgtc tttgcttctt gttcccacag  100920
aatttctttt gtgaccctaa aacttgttgc tcaatcaatg attggctttc ttttgagcaa  100980 cagggggttag cacatggtga tatacacttc aaatgcgcac acgtgcgaga atgaggttca  101040
catgaattta agtttgcaat tataacctca tgagcaacat taagcatgat atggtcatca  101100
actaatttat tatgagaatt tgacaacata tcatactttt tacctagagc acgttttct  101160 aagttcattg tttctacttg actcttaagc atagaatttt ccgttttaag ttgagcaata  101220
ttagataatg catcatgact atttctttgc tcaattaaaa catattcata cctttggacc  101280
aaatcatcat gagagcgcct tagcttctca tgttctttgg tcatcttctc caggctgttg  101340
ttggttttga tgagggactc ctctagcctg agaagcgtct cgccttgttc cttgttcctt  101400
ctcaacagct taaccaagag tgccttgtcc tctttgttga gatggatgta gaaacggtga  101460
atctcctctt cctccacatc atcggtctca ttttccctgt cattaatgtc agtggaagca  101520
atataggaaa atgtaccttg tgatgatgaa gattcatcct catatttctc cttatcatgg  101580
ctttcgtctc caccgtcatt gttagcaata aaacatttat cactagtgga gaacaaacct  101640
gtcgacgagg tggattcatc gtttggatgc catcgttctt gttcttctcc ctttgaatgg  101700
ttagtatcac aagtaatata gggagtagga gcatcacagt tgccacaaa atattttttct  101760 ttaatcctat tccataaatc atgagcatca acaaatagat cactatcact actcatgatg  101820
```

```
gcaaaatagg cacctctaga tagagaatca actaagatgt tgcaagcatg gtgatttaga   101880
gttagacatc ttagttcttc attggatggg tttttactaa tattggaggg aaaaatacta   101940
ctactaaaga cctgtctcaa atcaggatca acactcatga aagcactata aatagagaca   102000
gaccaagact tgtaattaga gccatcgtct aaaagaagtt ccacagttac ctcttgtgac   102060
gacatcgtca tctccggacg gctaagccca cactggagag gcctagctct gataccaatt   102120
gaaagttccc tttgacccgg gaacaggatc tggatgtcgc ctagggggg ggggtgaat    102180 aggcgaataa aacttttcac tttaaaactt aaattcttac tctactcgaa gacttagtat   102240 gcagtgggagt gagaagactc ttcaagtagg ttgcagccga atagaagatc ctgtctcaaa  102300
atgtcctgca cttcaaataa agcttatacc acagataagt attgaagtgc agatataaag   102360
gcgagtagaa agagagtcag gatacaatac agaacagagc acacagacgc aaggatttat   102420
cccgaggttc ggccaagcct gaaatgcttg cctagtcctc gttggagtta gccacacctg   102480
ggcttggagt ctatttcaac tccttcctcc gtttgctcag atctgtcagt atgacagata   102540
gagcctttca ctattgagtg gggttacaac agaaccgcgg ctgcttacag acttcttggc   102600
agcaccccgg tagagtaacg atatgctcaa gaccttgctc tagctcttag cagcactact   102660
cctctctcta aggcttatag ctgtgccttc tacacaaact atagagttac acacaagagg   102720
gagagtgaga attgattcca gtggagtcta cacttgttgg ctgcacttct attttgctgg   102780
aggcgcctag gggtcccttt tatagacaca aggggcctag aagccgttgg aagcaatcca   102840
ggaaggcaaa tcttgccttc tgtcgggtgg cgcaccggac agtccggtgc acaccggaca   102900
ctgtccggtg cacaccggac actgtccggt gcccgatttc tttccttcta cgtcgaagcc   102960
gaccgttggc agtcttggag ccgttggcgc accggacatg tccggtgcac accgacaat   103020 ccggtgcctc catctagccg ttggctcggc cacgtgtccc gcgcagatcg cgcggccaac   103080
cgttggcccg gccgaccgtt ggctcaccgg acagtccggt gcacaccgga cagtccggtg   103140
aattatagcc atacatcgcc ggtgaattcc cgagagcggc cagttcgcca gagttcagcc   103200
tggcgcaccg gacactgtcc ggtgcaccac cggacagtcc ggtgtgccag actgaactaa   103260
gtcttggctg tacacagcca agcctttcgc acctcttccc ttttcttctt ctttctgttt   103320
ctaacactta gacaagtata ttagtcccca aaaccaatgt actaagtcta gaaacatacc   103380
ttctattaat cattacatct atagcatttc acatgcttga gctttgatgt tggactcata   103440
aattatcaag tcagcttgac ttgatctaga ttgacatcgc ttggctccaa catcctgtaa   103500
aggtcacata gaacatctcc aaacatagga acaacccaaa ctaaagatca aagtgaactt   103560
agctcttttg ggctgcttcc agttctggtt tcgacacttg ttctccttct agtgaccttg   103620
atctcctcct tagagcttga tcttgagcct tatgacttac accacataac tatagctgtt   103680
acctcattgg ctgtaagtca cgtccttatg tagtgatcct tgatgtgccg tagctgttct   103740
caactcgatc acccttgact ttgcaagcct tcttcttcac ccttggcttt gggttcctca   103800
gcctccttga ccttctcccg tgcatttggt acctcgaagc ttttcttgcc tccgtccttg   103860
gcttgatcag ttgtctccga gctacgcacc cgagtctcac tttgtgcaat gtccatctta   103920
cttgtgatgt ccattatgta tccataatcc agttcttgga ccatcacatt tgttcacttg   103980
tgttgaaccc tgtaggcttt accttaagca cctgttcaac acttagtaca cttgttagtc   104040
ctttaattga gttgtcatcc aaacaccaaa actcacaaga gagctttcag ttgccccgca   104100
ggccctccaa tgtgggggt cgttcgtacc tgtgggggcg gaaccagagt tctgtttgta   104160
```

```
atggcaccctt gagtgccggt gtctgttcat tgcggctgtc ggggcctgaa gatgtgtatt    104220
ttggctaaag ccgtatttt tcctcatttc gagcactagg actcgcctgt cggctagctg    104280
aaccgcttaa ccaagtgtga gttgcctcgt gcggaaggtg acgagtgagg tatccgtatc    104340
ccggaggcgt aggagtccct cggatcggtc ggccttgccg cccgaggctt ctcttgctta    104400
gttaaagaaa ccctcggccg ctctgcgatg agccggagct agaggcagcg gtgtcagcgg    104460
tgtcagcgtg gacagaggcg gagttggctc aaaaagaagc ttcatcggcc ggagcctggt    104520
cgggccgtcc actggtggga ccgacgccgg agtcgggttg ccgaggccat gagccgggct    104580
gatgtcctcg ggggacagct ggctgaggct acagagcggt cggtcgagtc gtctactcgg    104640
gccgggttcc tggaggacac ctcggcgatg cccaggcgc ggtgctgaca ggttccttcg    104700
agatggagat cctccgaccg tgtcgccgtc cgaggctggg tcggactccg ccgaaggtgg    104760
agtcgacgcc gagggtgctg ctgctccccc actgatgtct gatcctgcag gaacaattta    104820
tctgtagtgt gcgtatgttt tttgcggccg ccgaggccca aacataccgt cgtcgtgttg    104880
taaagcggcg tttctttcc ccttgtttcg agtatcggga cttgttcgtc agtaacagaa    104940
ttgcttatcc gagcaagagt tacttttcac ggaaggtgat gagtgaggta tccgtatccc    105000
gaaggtgtag gagtccctcg gctcggtcgg ccttgccgct tacgtgtact cttactcgtc    105060
cgttggattc tgttatcgat atagtcgaga aggcacaaaa aatcgtttcg gcagaaaagc    105120
tttcgaacgt taagacttgt tcggccagc ggatcgctta tccgagcgtg agttacttat    105180
cgcagaaggt gatgagtgag gtatccgtat cccggaggcg taggagtccc tcggctcggt    105240
cgtccttgcc tgcttacgtg tactccgtcg ttttcaggat cccactttcg aagtagtcga    105300
aaagcacgaa agatgttctg gcagaaagac tttttcgag gaaaattttg acgtagaggg    105360 ggtgccccc ttctagcccc cgaggaggg tcggctttg ccgaggcaag gctgacccct    105420
ccttgatggt tagactttgt tggcgtatgt aaacgaggtg tatgaacgac ttgaaaacat    105480
cttaagggta gaagcgacgt agctgtcgga tgttccaagc gttgatgtag acctcgcctt    105540
gactgttggc cagcttgtat gttccgggct tcttagggag gcgtgagctt gtgacaccct    105600
cgggcgtctt gacgtagccg aagcaccaag tcgcccacct ggaggtctcg ggaccgaacc    105660
ccttgggcgt ggtagcgtcg cagggactgc tgataccgcg ccgagtgtag taaggccatg    105720
tcccgagcct cttccagctg gtccagtgag tcttctcggt tggttcgatt gcttcggtcg    105780
tcgtacgccc tcgtccccat agactagaaa aaacagcgtg aagatggccc agtgagtctg    105840
tgggcaagat ggcctcggcc ccatagacta gaaaaaacgg cgtgaagccc gtggctcagc    105900
ttggtgtcgt tctcagactc cagaccaccg aggggagttc cttcatccat cgcctgctga    105960
acttgttgag gtcgttgtag atccgtggct tgagtccttg tagaatcatg tcgttggcac    106020
gctctagctg cccattcgtc atggggtgag ctacggcggc ctagtccacc cggatgtggt    106080
aatcctcgca gtaggaactt tctaccggta aactgggtgc cgttgtcggt gatgatggag    106140
ttcgggaccc caaagcgatg gatgatgttg gtgaagaacg ccaccgcctg ttcggacctg    106200
atgctgttta ggggtctgac ctcgatccac ttggagaatt tgtcgatggc gaccagcagg    106260
tgcgtgtagc ccccgggtgc cttctgcaag gggctgacaa ggtccagacc ccacacagca    106320
aacggccagg tgatgggtat tgtttgcaga gcctgagcgg gcaggtgggt ctgctttgca    106380
tagaattgac acccttggca ggtgcgtaca atcctagtgg cgtcggccac cgcggttggc    106440
cagtagaaac cctgtcggaa ggcatttcca acgagggctc gaggtgctgc gtggtgaccg    106500
caagcccccg agtgtatttc ttgtaataac tcctgaccct cggcgatgga tatgcaacgt    106560
```

```
tgtaggacgc ctgaggggct gcggtggtag agctccttcc cgtcacccag caagacgaac    106620
gacttggcgc cccacgctag ttgccgagct tcggctctgt cgaggggtag ctctcctcgg    106680
tggagatatt gcaggtacag ggtctgccag tttcgattag gcgtgacccc ataccgctct    106740
tcctcgacgc gcagtgcctc accctcgggg gccgaggggtg cctcgggcag ggccaaggct   106800
ttctcgggct cgggcgtgtc gctggtcttg actgagggtt gatgtaggtc tcgggagaag    106860
acgtccgggg gaaccgttgt ccgcgccgag gctatcttag ccagctcatc cgtagtctcg    106920
ttgtatcgtc gggcgatgtg gttgagctcg agcccataga acttgtcctc caggcgccga    106980
acctcatcgc agtaggcttc catcttcggg tcgcgacagt gggagttctt catgacttgt    107040
cgatgacaag ttgcgagtcg ccgcgagcgt cgaggcgtcg acccctagc tcggtggcaa     107100 ttcgcaaccc gttaaccgag cctcgtactc ggccacgttg ttggacgccg ggaaatggag    107160
gtgcaacacg tagcggaggt gcttcccgag gggcgagatg aagagcaggc ccgcgcccgc    107220
tcctgttttc atcaacgacc cgtcgaaaaa catggtccag agttccagtt ggatcggagc    107280
tgctggaagc tgggtgtcga cccattcagc cacaaagtcc gccaagactt gggacttgat    107340
ggccttccga ggggcgaatg agattgtctc gcccataatc tccactgccc actttgcaat    107400
cctacccgag gcctctcggc actggatgat ctctcccagg gggaaggatg acaccacagt    107460
caccggatga gactcgaagt agtgtcgcaa ctttcgccgc gtcagaatta ccgcgtaaag    107520
tagcttctgg aatttgcggg tagcggattt tggtctcaga cagtacttca ctgatgaagt    107580
agaccggcct ctggacgggc aatgcgtgcc cctcttctcg tctctcgacc atgatcgcgg    107640
cgctgaccac ctgagtggta gcggcgacgt agaccaagag ggcttctccg gcaacagggg    107700
gcaccaagat gggcgcgctt gtgaggagca cctttaggtt cccgagggct tcctcggcct    107760 cggggggtcca agtgaagcgc tcggtcttcc tcaagaggcg gtacagaggt aggcctcttt   107820
cgccgaggcg tgagatgaaa cggctcagag ccgcaaggca tcccatgacc ctctgtactc    107880 cttcaagtc cttgatgggg cccatgttgg tgatggccgc gattttctcc gggttggcct     107940
cgatgccccg ctcggagacg atgaacccca agagcatgcc tcgggggact ccgaagacac    108000
acttctcggg attgagtttt acgcctttcg ccttgagaca cttgaatgtc gtttcaaggt    108060
cggagaggag gtcggaggct ttcctcgtct tgactatgat gtcatcgacg taagcctcaa    108120
ccgttcgacc aatgtgctct ccgaacacgt ggttcatgca tctttggtat gtcgcacccg    108180
cattcctcaa accgaatggc atagtaacgt agcagtacat gccaaagggt gtgatgaaag    108240
aagtcgcgag ctggtcggac tctttcatcc tgatttggtg ataccctgag taggcatcga    108300
ggaaagacag ggtttcgcac ccagcagtgg aatccatgat ttgatcgatg cgaggcagag    108360
ggagggaact ttcggacatg ctttgtttag accagtgtag tctacacaca tccgccattt    108420
ccctccttta tttctcacaa gcacagggtt gacaagccat tcgggatgga atacctcttt    108480
aatgaaccct gcagccatca gcttgtggat ctcctcgcct atggctctgc gcttttcttc    108540
gtcgaatcga tgtagaggct gcttcacggg tcgggctcca gctcggatat ccagcgagtg    108600
ctcggcgaca tccctcggta tgctaggcat gtccgaggga ctccatgcaa aaacctcggc    108660
gttcgcgcgg agaaagtcga cgagcactgc ttcctatttg gggtcgagct cggagccgat    108720
ccggatctgc ttggaggcgt cgttgctggg gccgagaggg acggacttaa tcgtctcagc    108780
tggctcgaag ttgccggcgt ggcgcttcgc atctggcgcc tccttggaga ggctcccag     108840 gtcggcgatg agggcctcgg attcggcgag ggcctcggcg tactccacgc actccacgtc    108900
```

```
gcattcgtac gtgtgtcggt acgtggagcc gatggtgatg accccgttgg ggcccgacat   108960
cttgagcttg aggtaggtgt agttggggac ggccatgaac ttggcgtagc atggtctccc   109020
cagcactgcg tggtaggttc ctcggaaccc gaccacctcg aacgtgaggg tttcctttcg   109080
gaagttggag ggagtcccga agcagactga cagattgagt tgcccaaggg gttggacgcg   109140
tttcccgggg atgatcccgt gaaaaggcgt cgcaccggcc cggatcgagg acagatcgat   109200
ctgcaggagc ccgagggtcg cggcgtagat gatgttgagg ctgctgcctc cgtccatgag   109260
gaccttggta agcctgacgt tgccgatgac ggggtcgaca atgagagggt actttcctag   109320
gctcggcacg cggtcgggt ggtcgccctg gtcgaaggtg atgggcttgt cggaccagtc   109380
taggtagact ggcgctgcca cctttactga gcagacctcc cgacgctctt gcttgcggtg   109440
ccgagtcgag gcgttcgcca cttgcccacc atagatcatg aagcagtcgt ggacctcggg   109500
gaactcctct gccttgtgat cctccttctt gtcgttgttg tgggctctgc cacctttcgc   109560
cggtggcccg gccttgtgga agtagcgtcg aagcatgacg cattcctcaa gggtgtgctt   109620
gatgggaccc tgatgatagg ggcacgactc cttgaccatc ctatcgaaca ggttggcgcc   109680
tccgggaggc ttccgagggt ttctgtgctc ggcggcggcg acaatgtctg tgtcggcgac   109740
gtcgcgtttt gcttgtgact tcttcttgcc cttcttcctc gcgccgcgct gagcggacgc   109800
cttggggacg tcttccggct gacgcccctg aggctgcttg tccttccgga agatggcctc   109860
gaccgcctcc tgaccagagg cgaacttggt ggcgatgtcc atcagctcgc tcgccctagt   109920
gggagtcttg cgacccagct tgctcaccag gtcgcgacaa gtggtaccgg tgaggaacgc   109980
gccgatgaca tccgagttgg tgatgttggg cagctcggtg ccctgcttcg aaaatcgccg   110040
gatgtagtcc cagagggatt ctctcggctg ctggcggcac cttcggagat cccaggagtt   110100
cccagggcgc acgtatgtgc cctggaagtt gccgacgaaa gctttgacca ggtcgtccca   110160
gttggagatc tgcacaggag atagatgctc cagccaggct cgggcggcgt cggagaggaa   110220
caggggaagg atgcagatga tgaggttgtc atcgtccgtc ccactcagct ggcaggccag   110280
ccggtagtcc gcgagccaca gttccggctt cgactccccc gagtacttgg tgatggtagt   110340
cggggttcag aaccaggtcg ggaacggtgc ccgttgtatg gccgggctga aagcttgcgg   110400
actgggtggt tcgggcgagg ggctccgatc ctccacgctg tcgtagcgtc ccccacgcct   110460
ggggtggtag cctcgacgca ccttctcgtc gaggtgggct tgacggtcgc ggcggtgctc   110520
gttgccgagg cgtcttgggg ccgcaggcgc tgtgtcccgc gtgcgccggg tgtggaccga   110580
ggcttcccgc atgaatcggg aagtcgcagc gcgatgctcc gggggtaccc ctgccttcgg   110640
gaggcagagc tctcggcccg tcggaccgcg acatcctcta ggagattttt gagctctcct   110700
tggatacgcc accctcggt ggtggatggt ttcggcatcg ctcggagtag tatcgctgct   110760
gcagccaggt tctggccgac cccactggaa gccggggca gcctcgccct ggcatcgtcg   110820
gtgatgcggt gctggacgtc ctgggccaga tgacgcgctt ctccagccgg tgctcggcct   110880
gcccactcct gcccgatatt ttgccgaagc tgcacaagtt gtcctgcttc ctcgtcgagc   110940
ctggcctgta cctcgcggat ttgctcaagc cgtgcgtctt gaccccccgc agggactggg   111000
accacagcta gctcccgaag gatgtcaacg cgaggcgcag gcctagggg atcaccatcc   111060 tccggcatac caagatggtt gccttcgtca agaccccta gatcgacgtg aagcattcg    111120 caccttgggc cacagtcctc gtcgccgagg ctgtggctgc tatcggagca atcggagagg   111180
cagtagtcac atgcggtcat gaagtcccgc atgcactgg ggttatcgag cccggagaaa   111240
tcccaaccag agtcaggctc gtcatcttcc tcggaaccgg ggggcccata ggtcgagacg   111300
```

```
gccgtcagtc ggtcccaggt tgaccgcata tgatacccg  gagggtttgg acatgccttt  111360
atgaaagcgt ccaccgaagc gggatcgctt ggtgggtcac aactgaatct aaaaggcatg  111420
ggatgggaaa cggacggtac ctcttgatcg acgggtggtg acgaagtcgc gtcagggacg  111480
gactgcaccg ttgtctcagg tacgaggtta acgcccagga agtccttcgc gagcgtgctg  111540
gcgtcatccg tctgcttggg gttggcgtgt tgcgggaaa  cgacgcttgt cttcgtctca  111600
gacgcgaggt caacgcccga cgtgtccccc gttgggcgt  cggcgccgtc gactcgctcg  111660
acagccgacg aggtgccgcc tcctgattgg ccatgcctac cccgcctcct cctccgtcag  111720
cggggaaggt gacgggacag acccggatat cgctcttccg ccacgtgggg aagacgtcgt  111780
cgattccgcc gccgacgggc gggctgacgg ccgccattgt cgttgtcgcg cggcggagga  111840
aggagtgtca tgtcgtagct gccgtcgagg gacatgaact caagactcct gaaatggagc  111900
accgtcccgg gttggagtgg ttgctggaga ctacccatct ggaacttgac gggaagctgt  111960
tcgtcaccat gcagtaggcc cctacctggc gtgccaactg tcagcgtttc gaccccgggg  112020
ggtccctgga ccgacgagta aactgtcgct gcgtgtccca ttccagatgg gtcggcacga  112080
gacgaaacac aaaggggga  aaacagcaaa ggggaacccg tggccttcgt gttgtcctgt  112140
gcccagggcg gatgcgcttg cagtaggggg ttacaagcgt tcgtgtggga gagagagaga  112200
gagagccttg tgcgtcagcc cgttctcccg cgcggccaac cctctcgtac gagagcccta  112260
gaccttcctt ttatagacgt aaggagaggg cccaggtgta caatgggggg tgtagcaatg  112320
tgctaacgtg tctagcagag aggagccaga gccctaagta catgctgtcg tggctgtcgg  112380
agaggttttg gcgccctgtt catgtgatgt cgtggccgtc ggaggagcgt ttgagccctg  112440
tggaagtaca gctgtcgggg ctgtcggatc cttgctgacg tctccttgct tccataaggg  112500
gctgagagcc gccgtcgtca cggagcacat ggggtgccat cattacttgt ttaccggggc  112560
gagccagatg ggacgtcggt cttgttcccc gtagcctgag ctagctaggg gtagggtaat  112620
gatggctccc cctgcgacgt ggtcggtccg agcccgaggt cgggcgaggc ggaggctcct  112680
ccgaggtcga ggttgagccc gagccctggg atcgggcgag gcggagtccg tcttccgagg  112740
tcgaggctga gtccgagccc tggggtcggg cgaggcggag tccgtcgtcc ggcgtcgagg  112800
ttgagcccga gctctggggt cgggcgaggc ggagcttctc atggcgcccg aggctggact  112860
tagctgctgt cagcctcact ctgtcgagtg gcacagcagt cggagcaggg caggcggcgc  112920
tattttcccg tcaggtcggt cagtggagcg gcgaagtgac tgcggtcact tcggccctat  112980
cgactgagga gcgcgcgtta ggataaggtg tcagtcgatc cttgcattaa atgctcctgc  113040
gatacggttg gttggcgtgg cgatctgtcc aaggttgctt ctccgcgaag cctgggcctc  113100
gggcgagccg aagtgcgtc  cgttgcttga ggggaccctc gggcgagacg tgaatcctcc  113160
tgggtcggct gcctttgccc gaggctgggc tcgggcgagg cgggatcgtg tcccttgagt  113220
ggacggagcc ttgacctgaa tcgcgcccat caggcctttg cagctttgtg ctgatggggg  113280
ttaccagctg agattaggag tcttgggggt accctaatt  atggtccccg acatgtttac  113340
ttacaaaagc tccaccaagc ttgtcgagca tccaatgctt gggcgcattg agcctcttca  113400
agtgcttctt caatcccta  gcctggattg caaaataata atgatcaaca aaagcgcaac  113460
agattccagt atggcattca taggtgactc atccagattg cattagctgt taaaagtaac  113520
agcaactaca cactacttga aaacaaaaga ccctttcat  acatgtctat ctctattact  113580
tatatatgag cagtgccatc gtcagcacct cctgtatgta tacctaggac gacatcagct  113640
```

```
ggcgaggggc acggggacgc acgggcgtct tggacgggct caccctaaaa acacactaga   113700
acgactctgt tatccaaccg cccagaagag ctccttcctc aatgcaaagc gtaagaagat   113760
cagttagagt tttaccttat tggcaaggat cccagtacca caccgctaca gtgagagcgg   113820
cagtagcact ttctgccttg aaaaaaaatt gaggcccagt cttaaaacaa ctcgcagaat   113880
aataaggcat ttgaacagca gaccaaacaa ctagcagaat aaaaagaag ctacgcaaat    113940 ttgaaggcga aggtatgctt agctgaccat cacgaatccc agtttcagcc catggagcgg   114000
gatttgttgc tcatgtctgc ctttctgtcc ttttagatag ctaatgccaa tagttcatgc   114060
aaaactatta tcaactgttc cattgtacat gtataatact tggaaataaa cacagccagt   114120
agccaccaat acccattcct tatgccaaat ttgtgacatg agatggaaat agtacatcaa   114180
taaccaaacg aggggtgagc atagaaattt aacatccaac atcaaaactt gcaaaacttg   114240
gatgtttgag tccacctctc gagcctaacg gacgtgaaat cgccatgacc tggcagcctt   114300
tgcatcaaaa aataactcca gttctatagt aaatgtaacc atgtgtgcat acgtaccttg   114360
cagttctgtg cggcctagta cttggtcacc tgcacaaggt acttgtaaca cccctggtgt   114420
tactgcaact aaaacttgag catagcatca taaacattgg cattgcatat gtttgacaca   114480
cctagagtgc attcactagg taaaaatttc aaacaagttg tattgtttta gtgttttgca   114540
aatagaaccc tagataggga atttaaccct aaataggat taagggta agatataacc      114600 caaattgaga aaacctaaaa gctctaggga atagtcatc aaatattctc aagaataaag    114660
ttgaaccaca tttataccccc tcggatacca aaaccctaa ttggaaccct agaaaaccct   114720
aaatccaaac cctaggggct tatgtgcaaa attcgaccac ttttggacta aagtgcaaaa   114780
accaagttaa ataagtatct taagtcattt gggtcactca tatgtgaatt tacaagccaa   114840
accctaagtt ttggcctcat ttgcaaaaag gaccctattt gaggttttat actaagtctg   114900
aaaacagtgt tatgggctca acttttgagc cttgtaactt ttaaatcata gggttttttgc  114960 cctaggtcac cacattaaaa ttatagccca atcataggag aacaactttg cttaagagtg   115020
tgagcatagt tttaagaaaa tattggagat aattgagcct gaagttggac tgtcagactg   115080
cttgaaatct gaaattcaga ttaacagtgg gatgacatga acttagggct taattttaag   115140
caagattcag tgacttttg tgggagcaca ttgtagcaaa gttatagctg gattgtagct    115200
ctacaacttt gctgtaggtc actggatgag ttgttatttg aaattgagag aaactgggc    115260 tccaaacttg actgtcaggc tgtctgaata taaatctcca tggtacagtg ctaccaggga   115320
gatcagacca ccagcgcggc agtctctcac cgccgatgac tgatcttcgc tgagattcac   115380
gccgccgccg ttgcgattca cgtcgccggt gaccagataa gatcgctcgg taaaggcatg   115440
cgctggacgg cactccggtg aaccccccagt acttcccctc taccgtgcgg cttgagcaga   115500
taagcccgct ggggatcccc gtcgctcggc cttacgccac gtatccgggc acctctgtcg   115560
catcgccgtg actccccact gttgtctcat cattgccggt gagcccgcca cggcggtgga   115620
cacgaaatcg cgaagccgat gatcttcctt atctccggcc gcccacactg tccactcaaa   115680
ttaagcgcca ccgcccctgg gatctataaa ttgaccctgc agagagcttc acaacatcat   115740
cacccaccca gccaccacgt attgctagca attgttcgcc caagctcgcg aattttgaat   115800
tcgccccaaa tcaattctcc gccacccgaa acccaacctc actgcggcca gccttattct   115860
ggtcagttcg tctccttctc tccctcattt aagctttccc ttaagtctac gatgcttgcc   115920
gacccacaca atcgagctag gagcccttttg gtcgccggga acgcgactgt cttgccgcga   115980
tgttcacggc caccgtggcc agagcaagcc attgggccat agatggaatt aggttagggg   116040
```

```
aaatgctcgg gctaggtcca atttgatgtc cgccgctcgg gaaccctagc cgttgccccg   116100
ttcggccggt gcaggcactc gccggagttc ggctgggcgt gaacgccgtc gaggacctcc   116160
ctctgcgaag agttagaact acagggctt ctctgcaatc tgtcagcgac acagtgtaat   116220
agtgatagaa gccagttctg attagccaaa ccccgaggac ctctgtgcaa gtcgccagg   116280 gcgcgagcgc gcgcgcgcgt tttcccctag tactgggccg gctgggctag aatcagccca   116340
acactattca atcttttttcc ttttcttttt ttgtagagct ttggaaattt gttaaaaatt   116400
gtagaaaaat cctaaaattg tgaaccaat tttcctaggc ttcttatttt ccatagaatt   116460
taataaaaat agttgtatga attttaggtt aactaaggaa ttttaaggta tttaaagtag   116520
tttaaggtag tggttctgga tttttagaaa ataaatggaa tttccaaaaa tgtccaaact   116580
ttttacataa gttctataca ttatttagag gccttgggta gaatttgggt tgatttggac   116640
cttgtttgat acttagaacc taaaaccccc ctgcccttg aactcctta ctgactccgg   116700 aaaccctaag ttctcggagt tccgtgaagg aaagttgtat tcaagactta gataataaat   116760
ctttattatc ttcgcactct catgagcatt acatggcatt cattcttata tatatacctr   116820
tatggttata tttagaaaat gaagaagaga ttgaagtgac caaagagaag acaccaccac   116880
ctacggattc tcaggccggc aattgtttct acttcgatat ctgcgggact gagcctgact   116940
cacctactaa cgaaggcaag ccccggtgca tttaccacct ccttgatgct tttaaaatct   117000
ttctcacttg attgctgcat taggtgatag gagttgaatg cttaaacaat tcctgcacta   117060
ccttccttga atttgattac cttccttgat cacccgtttt acaaaaggat tttgatgctt   117120
tgccttgctc tagaaaaaca aaaggatttg ttttacaaaa gatgtttggc aaaagtggga   117180
gggttatttt tgaaaataaa acttgatggt gaatctgtca aaggccttga tggattcaac   117240
atcggaaaag atgtacctct gccaggtacc aaactttggg tttgaaatga ttaagccgag   117300
accgggcggg tgacttgcac gagaaaggag tctcggtgta gtgtctccgt ctgagtcgat   117360
taaggaccgt ctcgatgtag gcctgctgac cggggaccct ttaactggtc acatgcctcg   117420
tcatgggtaa gccttgcctc gggcagacta aggccagaat aagataacac gaaatgggcg   117480
tggagcggtg gcgggagtag cgtgtaccct ccgtggcaag aggctggacg gtggtgtatc   117540
tgtgctctcg gtttgtgtga acctgatctg tcttaaaaa ccccagtggc gggttgacat   117600
atgcaagggt taagtgctac atatgtcgtg tgattggaga tcctcagctg agtataatcg   117660
attcggatcg ccgtaccttc gcggttatga agacttggtc actgacttac acgtagcatt   117720
ccactaaaga tgatggtttt gttaagaaat tggctagtgc aggacaagtg atttgaacta   117780
gggtagaaag aactctagtt acaggtaatt ctacttaatt tgacaaataa aactggattt   117840
ttaaggatcc actttagtaa gcatttctgc aaaacagagt ctttgattat tgaaaagcct   117900
taccttgact cccttaacca gcatacccct gagagtcttt tctttagtcg ggtaagactt   117960
gctgagtaat tccatactca gggtttatcc ctccgttgtt tttaggtgag gaagcgacaa   118020
atttttattg cttctgctcc aaggtggttc ccaaggaaga aaaacaagag tgaagccgcg   118080
ggaggacttg gtcctccata taggactttt gtttaaaaac tatcgggagg agttttgcc   118140 tcccttggta ttgtaataat attactctgc actcctagga taactctggt ctgtaataag   118200
taacttgatc ttactttta aataaatgta agttatgtaa tcgcttctgc atttctatat   118260
cttcgatgtt ctgtaatgtc tgcaagacgt gtgaaacgtt cctggaaagg taagaaagaa   118320
gataccgaac ttgtgaagta atttaggaac atctataggg tgtctgatgt ctgttggaca   118380
```

```
aggacaactg taggtgggct taattacttg ggaggttccg tcacagctgg tatcggagcg   118440
tagcccttct ttgcagatat tatgaggcat cttcaaaaag attttctaaa agtcttacct   118500
agaaactctc ttcctttctt acctaagtat tctgaagagt ctatcttaaa gaccaggtag   118560
taagagtgca acatatagaa ggtgtgaatc aactaaggtt gattctgtaa ttatacatgc   118620
atcatgctaa gaaccatact aatcaaattt tccccttag aaaatgccgc cgcgcacaag    118680
gagaacaacg cgcaaacata ctggaccgat tggtgtgccg agtcaccagc tgaccccaag   118740
gcatgataat agtagtagcg gaagcaatga tcctataggg gatcttgaag ctgaagtaag   118800
tcgactccaa gcgaaactcc gccgcagaac gactatctgg gtcatagatg gcgaccgcat   118860
aaatgagttg agaagagata tctgccatct gcgagatcag ctcgcggacc gggatttggc   118920
acttgactgg gttgttcaat cccgttcgct tgcatgggac aaggagcaaa agctcaagc    118980 tcgagtagcc gagctcaact tggctgttga tgaactgcag acatattgca ataccttaca   119040
tgaagagatt catgtattat attcgcaact gcatcccagt gagcctacga atcctggtga   119100
gtcggaagcc ggaccctcgc atgttgcggg acacgcgctt ggtggtgagt tagacctttt   119160 tcagcccct ccttctatga ggctagtcga cgaatggtct cccacacccg acgacgaggc    119220
cgccaaaagc aacggaaagc aggaataatg gggtagtaga agtagaagta gtgtattgta   119280
taacaggttg ctctaatgta taatattttg tactattgca ataggttg tgctattgta    119340 taataggtaa tgtatcctgt tgtaaaaatt cgagtctgta cattactctt tttggtaatg   119400
taaaatggat ggttttttcct tggcatatca tattgttttc caaatgttgt tgccacagat  119460
gccttccaag actcgagcac aggacggagc tagtacctcc tgtgggaggg agtctacccc   119520
aaatccacct cctgttcctc ccacactggc cgaggcgatt gtggccttgg taaatgcaac   119580
cgcggataat acccgttttc ttagagagat ggcgggtcaa caattgcaac aacaaggtgg   119640
gcggggttat caacagggcc cccgtgaaac ctcttacttg gacttctcag agacgcgacc   119700
accgctgttt gtcaaagccg aagacccgtt agaagcagat gaatggcttc gtgtgattga   119760
gcaaaagttt ggactgctgc gatgttcaga aacccagaag cctttattcg cagcccagca   119820
actgcgcgga cctgccagca cttggtgggg taattttgtg gccgttcaac cggccaatca   119880
ttagataact tgggaagaat tcaaggtggc cttccgcgag cactatatac cagaaggtgt   119940
tcttcacatg aagcaagaag agtttatgaa gctgaaacaa ggaggggata ctgttaacca   120000
gtatctcaat aagttcaatc atttgtcaca atatgcaatc gatcaagtga acactgatt   120060 gaagaagaag aattgctta tgagaggatt aaatgatcga ctgcaaagga agatggcaac   120120
ctgcatagat cttacttatg gaagagctgt cagtacagca ctggcagtag aagcgaagta   120180
tgcaggcgct ggtaaatcca aggtttgg aggtgacagg tctagtcagg gcccggtgaa    120240
caggcaacgg ttcgtcatcc ggccttctaa ccagaatcgt tctttcgctc gtccacctc    120300 ctttccttt aagcagccag tctttattcg tcccaataat gcccctacta catcaagtca    120360
gccgggtgcc ccaggcactc gattccctgc tttacccagc tcgtcgactg gatgtttcaa   120420
ttgtggcaaa tctgggcatt ttatcaagga ttgcccttat ccaaagcaga accagtcaaa   120480
taatcagcaa ggatctggga attcatctca agccaaggaa aataatatgg gcaaaaatac   120540
aaagaagacg ggacgcatat attatacgca agtggccact acaccggacg gtgagccggt   120600
aatgatgggt acgtttcttg tggccaatca tcccgcagtt attctctttg attctggtgc   120660
ttcgcataca ttcatcagca agaaatttgt ggagcaacat tgcatctcat gccatgaatc   120720
aaaagagggg tttaaaaatt cactcaccag ggggacaaat atttactaga gaagtggcct   120780
```

```
atcaagtgcc cgtaaccttg gccggatggg actttcctac taatatgatc attctgaaag   120840
gccaagatat atatgtcatt ttgggtatga attggttagc cagacataaa gcaactctca   120900
acactgatca gagaattatc aggttgagtc ataaccagga agaaattctt ttgcctatcc   120960
ccattccaac caaagctact ggcagagctt atgaagccat tataccggaa atcaaggata   121020
ttccggtggt atgcgagttt cccaatgtct ttcccgagga tttgcccgga ctgccacctg   121080
aacgggaggt agagtttgta attgagttga aacccggtac ggctccagta tctagaagat   121140
cgtaccgaat gcctcctaat gagttggcag aactgaagat ccaattacaa gatctacttg   121200
agaaaggatt tatccggcca agctcatcgc cgtgggttg tccagccata ttcgtcaaaa   121260
agaaggatca aactttacaa atgtgtgtgg attatcgacc cctgaatgag gtcaccatca   121320
aaaacaagta ccctcttcca aggattgaca ttttatttga tcaactgact ggagcaaggg   121380
tattttccaa gattgatctc agatcgggct atcaccagat ccgtattcgg cccgaagata   121440
taccaaagac cgccttcact acgcggtatg gattatttga ataccggta atgtctttcg   121500
gattgacaaa tgctcctgcc cacttcacgt atttgatgaa ctcggtattt atgcccgagt   121560
tggacaagtt tgtggtagtc ttcattgacg atatttgat atattccaag aatgaagagg   121620
agcacgccca acatttacgg atcgtgttaa cgcgcttgag agaacatcag ttatatgcca   121680
agtttagcaa atgcgtgttt tggctggacg aaattcagtt tctgggacat gtattgtctg   121740
ccagggggat tgcggtagat cccagcaaag tcaaggacat tttggagtgg aaaccccga   121800
ccactgttca tcaggtccga agtttccttg gactggctgg atattaccgc cgattcatac   121860
cagattttc taagcttgtg aagccaatca caagtttatt gaagaatgat attaagttca   121920
attggtcttc aaagtgtgat gaagcttttg aacaattgaa gacattagta accactactc   121980
cggtattggc tcaaccggac atcaccaagc cctttgatgt atattgtgat gcatcaggca   122040
gtggactcgg ttgtgtgcta atgcaagaag gccgagtaat tgcatatgct tcaaggcagt   122100
tgcgccgaca tgaggaacat tatcctactc atgatctgga gttagctgtg gtggttcatg   122160
ccctaaagat ctggcgtcat tatttgctgg gtaatgtctg tcatatttat acagaccata   122220
aaagcttgaa atacatcttc acccagtcag aattgaatat gagacagagg cgatggctcg   122280
agctaatcaa ggattatgaa ttagaaatcc attatcaccc aggaaaagca aatgtagtgg   122340
cagatgcgct caattgcaag gcttcctgcc attgtttaac agtgaggact tctgacatta   122400
cattatgcca ggagatggag aaattaaacc tgggaatgat tcaacatggg acttcaaatc   122460
atttgaagct ggagtcaatc atcatacgaa gaataattga cgcacaaaaa gatgatgagg   122520
gtatgaagca catacgtgag aagataatgg ctggaacagc caaatgtttc aaagaagatg   122580
atcaaggtgt gatatggttc aataaccgca tagtggtgcc gaagaatgaa gaactccgcc   122640
agcaaatctt agatgaagca catcttagtc gctattctat tcatctggga agcactaaga   122700
tgtatcatga tctaaagcag cactactggt ggacgaagat gaaaattgaa attgcacgct   122760
atgtggctaa gtgtgacact tgcagacttg tcaaggccat acacatgaag atagctggtc   122820
cattacaacc tttgccgatc ccaacataga aatgggaaga tattagtatg gacttcattg   122880
tgggattacc caggactaca aaagggtatg attctatctg ggttataatt gatcggctta   122940
cgaaaattgc tcactttcta ccggtcaaga cagatcaccc ggttactgtc tatgcccatt   123000
tgtacattgc tcgtattctt agtctgcatg gtgttccgaa gacccatagt gtcggatcgt   123060
ggacctcaat ttgtagccaa gttttgggaa gcacttcaca aatccttggg tactaagttg   123120
```

```
ctccatagtt cggcctacca tcctcaaacc agtggacaga ctgagagagt aaaccaaata   123180
cttgaagata tgctgcgggc atgtgttctg gaatttccac aaaaatggga tgaatgtttg   123240
ccgttagcgg aattttcata taataatagc tatcaagaaa gcatcaagat ggcacccttt   123300
gaagctttat atggacgacg atgtcgtact ccgctaaatt ggtctgaacc tggtgaaagg   123360
tacttcttca ggcctgatat ggtgaaagag actgaagaaa gagttcaaag gataattcat   123420
aatttgaaga aagctcaagc tcgtcaaaag agttacgtag acaaacggcg aatgccctta   123480
tatttccttg aaggatacta tgtctactta aaggtttcac caatgaaggg agtatcgcgt   123540
ttcggagtta aaggaaagct tgcaccataa tatattggtc cttttcttat cctggaaaga   123600
tatgggccag tggcataccg acttcagtta cccgaaacct tgtttgctgt gcataatgtg   123660
tttcacgtgt cccaattgaa gaagtgtctt cgggttcctg atcgaaccgt tgaagtgaca   123720
gatgttgtcc ttgaaccgga cttgacatat tctgagcacc ctattcgagt cttggatcaa   123780
aaggacaggg ttacccggag aaaactctca agtttataa gatacagtgg aaccaacatt   123840
ccgaagatga ggctacatgg gaaactcaag acttttaga taagaatttc ccaggctttt   123900
tagcttcttg taaattgtaa agcctgtata gctgttgtaa taaggagtg attccaaaac   123960 cacccctgcc ttgtaccaga aataaggaaa taaagtatg tcgtgtttcc ttttccatta   124020
cttaccctag gacttttaat ctcgggacga gattctttta tggggggaag gatgtaacac   124080
ccctggtgtt actgcaacta aaacttgagc atagcatcat aaacattggc attgcatatg   124140
tttgacacac ctagagtgca ttcactaggt aaaaatttca aacaagttgt attgttttag   124200
tgttttgcaa atagaaccta datagggaat ttaaccctaa atagggatta aaggggtaag   124260
atataaccca aattgagaaa acctaaaagc tctagggaaa tagtcatgaa atattcccaa   124320
gaataaagtt gaaccacatt tatacctctg ggataccaaa aaccctaatc ggaacccag   124380 aaaaccctaa atccaaaccc taggggctta tgtgcaaaat tagtccactt ttggactaaa   124440
gtgcaaaaac caagttaaat aagtatctta agtcatttgg gtcactcata tgtgaattta   124500
caagccaaac cctaagtttt ggcctcattt gcaaaaagga ccctatttga gattttatac   124560
taagtctgaa aaatagtgtt atgggctcaa cttttgagcc ttgtaacttt taaatcatag   124620
ggttttttcc ctaggtcacc acattaaaat tatagcccaa tcataggaga caaacttttc   124680
ttaagagtgt gagcatagtt gttaagaaaa tactggagat aattgagcct aaagttggac   124740
tgtcagactg cttgaaatct gaaattcaga ttaacagtgg gatgacatga acttagggct   124800
taattttaag caagatccag tgactttttg tgggagcaca ttgtagcaaa gttatagctg   124860
gattgtagct ctacaacttt gctgcaggtc actggatgag ttgttatttg aaattgagag   124920
aaaattgggc tccaaacttg actgtcaggc tgtctaaata taactctcca tggtacagtg   124980
ctaccaggga gatcagacag ccagcgcggt agtctctcac cgccgacgac tgatcttcgc   125040
tgagattcac gtcgccgccg ttgtgattca cgtcgccggt gaccagataa gatcgctcgg   125100
taaaggcatg cgctggacgg cactccggtg aaccccagt acttcccctc tgccgtgcgg   125160
cttgagcaga taagcccgcc ggggatcacc gtcgctcggc cttacaccat gtatccgagc   125220
acctctgtcg catcgccgtg actccccact gttgtctcat cattgccggt gagcccgcca   125280
cggcggtgga cacgaaatcg cgaagccgat gatcttcctt atctccggcc gcccacactg   125340
tcggctcaaa ttaagcgcca ccgcccctgg gatctataaa ttgacccgc agagagcttc   125400 acaacatcat cacccaccca gccaccacgt attgctagca attgttcgcc cgagctcacg   125460
aattttgaat tcgccccaaa tcaattctcc gccacccgaa accgaacctc acctcggcca   125520
```

```
gccttattcc ggtcagttcg tctccttctc tccctcgttt aagctttccc ttaagtctat   125580
gatgcttgcc gacccacaca atcgagctag gagcccttg gtcgccggga acgcgactgt    125640
cttgccgcga tgttcacggc caccgtggcc agagcaagcc attgggccat agatggaatt   125700
aggttagggg aaatgctcgg gctaggtcca atttgatgtc cgccgctcgg gaaccctagt   125760
cgttgccccg ttcggccggt gcaggcactc gccggagttc ggctgggcgt aacgccgtc    125820
gaggacctcc ctctgcgaag agttagaact gcagggct ctctgcaatc tgtcagcgac     125880
acagtgtaat agtgatagaa gccagttcta attagccaaa ccccgaggac ctctgtgcaa   125940
agtcgccagg gcgagggcgc gcgcgcgcgt tttcccctgg tactgggccg gctgggctag   126000
aatcagccca acactattca atcttttcc ttttcttttt ctatagagct ttggaaattt    126060
tttaaaaatt gtagaaaaat cctaaaattg tgaaaccaat tttcctaggc ttcttatttt   126120
ccatagaatt taataaaaat agttatatga attttaggtt aactaaggaa ttttaaggta   126180
tttaaagtag tttaaggtag tggttttgga tttttagaaa ataaatgaa tttccaaaaa    126240
tgtccaaact ttttacataa gttctatgca ttatttagag gccttgggta gaatttgggt   126300
tgatttggac cttgtttgat acttagaacc taaaaccccc ctgcccttg aactccttta    126360
ctgactccgg aaaccctaag ttctcggagt tccgtgaagg aaagttgtat tcaagactta   126420
gataataaat ctttattatc ttcgcactct catgagcatt acatggcatt cattcttata   126480
tatatatata cctatatggt tatatttaga aaacgaagaa gagattgaag tgaccgaaga   126540
gaagacaccc ccaccttcgg attctcaggc cggcaattgt ttctacttcg atatctgcgg   126600
gaccgagcct aactcaccta ctaacgaagg caagcccgg tgcatttgcc acctccttga    126660
tgcttttaaa atctttctca cttgattgct gcattaggtg ataggagttg aatgcttaaa   126720
caattcctgc attaccttcc ttgaatttga ttaccatcct tgatcacccg ttttacaaaa   126780
ggattttgat gcttagcctt gctctagaaa aacaaaagga tttgttttac aaagatgtt    126840
tggcaaaagt gggaggttg ttttcaaaaa taaaacttga tggtgaatct gtcaaaggcc    126900
ttgatggatt caacatcgga aaagatgtac ctctgccagg taccaaactt tgggtttgaa   126960
atgattaagc cgagaccggg cgggtgactt gcacgagaaa ggagtctcgg tgtagtgtct   127020
ccgtctgagt cgattaagga ccgtctcgat gtaggcctgc tgatcgggga cccttaact    127080
ggtcacatgc ctcgtcatgg gtaagccttg cctcgggcag actaaggcca gataagata    127140
acacaaaatg ggcgtggagc ggtggcggga gtagcgtgta ccctccgtgg caagaggctg   127200
gacggtggtg tatctgtgct ctcggttgc gtgaacctga tctggtctta agaaccccgg    127260
tggcgggttg acatatgcaa gggttaagtg ctacatatgt cgtgtgattg gagatcctca   127320
gctgagtata atcgattcgg atcgccgtac cttcgcggtt atgaagactt ggtcactgac   127380
ttacacgtag cattccacta aagatgatgg ttttgttaag aaattggcta gtgcaggaca   127440
agtgattgaa ctagggtaga aagaactcta gttacaggta attctactta atttgacaaa   127500
taaaactgga ttttttaagga tccactttag taagcatttc tgcaaaacag agtctttgat   127560
tattgaaaag ccttaccttg actcccttaa ccagcatacc cttgagagtc ttttctttag   127620
tcgggtaaga cttgctgagt aattccatac tcatggttta ttcctccgtt gttttaggt    127680
gaggaagcga caaatttttg ttgcttctgc tccaaggtgg ttcccaagga agaaaaacaa   127740
gagtgaagcc gcgggaagac ttggtcctcc atatagaact tttgtttaaa aaccatcggg   127800
aggagttttt gcctccttg gtattgtaat aatattactc tgcacttcta ggataactct    127860
```

```
ggtctgtaat aagtaacttg atcttacttt ttaaataaat gtaagttatg taatcgcttc    127920
tgcatttcta tatctccgat gttctgtaat gtctgcaaga tgggtgaaac gttcctggaa    127980
aggtaagaaa gaagataccg aacttgtgaa gtgatttagg aacatctata gggtgtctga    128040
tgtctgttgg acaaggacaa ctataggtgg gcctaattac ttgggaggtt ccgtcacagt    128100
actgatggta ctccggtggc gccatttaca tctcaagcaa tttttctcaa agttggattc    128160
ttgatccctg catatcgctg gtcgtgaccc gtgggcacgg cgctcggatc cggcagcagc    128220
agatcgaggc gaggccgcga gggaggagaa gagccatgat gggggggcatc agatcatcgc    128280
tcaacgacag cagtatgggc gtcctcttcc tgctggtgct cctgctggat gcgggcgtcg    128340
tcctcctagc cgtgctccta gcagtagagg ctccagtagc aggagaagag gcaggatgcg    128400
ggcgtcgtcc tcctggccgt gctcctactg ggcggcgtgt cgtgctcctg ctggtgctcg    128460
acgactggag cctgctgctt ggtggtgctc ggcggatgag caggggatcc gatcgggtag    128520
gggatgagga tgagatgact gatcggatca gatgggcagg ggatgaggat gagtggatga    128580
ccgaccggat gagttggttt gctcggaagc tgccggctgg gggatgggga ttagatcatt    128640
agtgttttgtc ggtttgggtg tttgccactt tgggtctttg gcggaatgat gccttagtgg    128700
gcaatgggct ggcgcttggc gcctgggcac aatggacaat ggtgggctgg cgatttgttc    128760
attggtgtcc atgtgtggat cgacagtaat ggactaatgg ttaatttcgg atatccaacg    128820
aattaccccgc gggtgaggtt taatatccaa atccatgtct gctttatctc ggatcgggta    128880
cgggtctaac ccgcaggtca aaaaacatat ccatatcctg atccgtcggg tcgaatatcc    128940
gacggatatc actatccacg cattaaattg ccatccctag atgtgagact taaggcatgt    129000
ttgttcgcta cctaagttat cacactttgc ctaacttttt cgtctaaggt tagttattca    129060
attcggacga ctaaacttag gcaaagtgtg gcacatttag ccacaaacca aacatgcctt    129120
taaccctctg gtttagatcc cgtttcgttt gagctgaata tacttattaa atgtctaaag    129180
catagcctag agcctgtcat gtcatgaatc atgaaatgac aataaaacat aaacaaaagc    129240
atagcctggg agtttggagc accgcgctgg gggcactgaa gacgacggat cttgcctctc    129300
agcctcggcg atgggcgtcg gacgcaggag atggcattaa ccaccgctat attaataaaa    129360
cgtattgtat atatgtgcaa tacgtatata aagagaaata ttcgtggcat taaccaccgc    129420
ttatcaggtt gcttataccg tacaaagaga cgatattata actataaaca tactgttgat    129480
gagaaaataa aaaataatca tatttcaaac gtataatttt atttgaagaa gattcttatt    129540
taagcaagat ttttttaccta tatgatatat agaaaccgta cgaacataca gtcagctaac    129600
tagttcattt taaattccaa aaaatgttta gttcaatcta atcagaattt actattgact    129660
atgttttttc acaatatgtc ctatcaaaaa tatcgtacga gacggtttta tgtttacaag    129720
tttctagtat actcactaac atctaagaca attttgtata gtctagatga ctctaataat    129780
atctttattt gagatggttt catatacaga agtgtctaat atactaacca aaataaaaga    129840
cacttcttgt aaacttaatg cctcaaaagg tatatttatt tgagacggtt ttcaacatca    129900
aactgtatta aatcaatata agacatttcc aaccatatat ctgcctcaaa accttcttc    129960
attaaagacg gatatccaac aaaccgtctt accgtactca gcaccatatg ataaaagacg    130020
cttctataaa atgcactgat atttgtctta agatgtatgt cttaaataag catatttcta    130080
gtagtggatg tccaagacat ccacagagtc attaacttag gtcataatca aaattttgaa    130140
cgaaacgcag tacgataagg ccttcacagg cagctaactg agggtttgcc actaatctag    130200
tctagaactc gtcgaagtcc tgaaactcct gaaagtcctc cacgttgcct tcatcttctc    130260
```

```
ctgagcacta gttgcaatgg ggacaacctg gggtttggtg tttttaagca atggtgagta    130320
cacctcaacg tactcaacaa atgtcctgtt tggctaaagt ggactagctg tatgtggggt    130380
taagcttaaa gcagttgctt ttagttggtt aggtatttat taccagtaga gagccatgtt    130440
ttagcaataa ccccaagtta taaacccaaa cattactccc tccaagagga aataccaaga    130500
attcataatc ataatcacca tcattaagca tcatcataaa agtatccaga gtaactctaa    130560
tcaaaggagc tcccaaggct gctcataact gtgagcatgg ctgatatact agcttctaac    130620
actctacaga ggttgcacac tttacccaca agtcgtgatc cctttttgcc tcaggtcgat    130680
caaaccctca aacactacca aggtgagtcg gcaaggtttc actacgtagc tgtaacaccc    130740
tgaattttgg ggtataaaaa tttccttgct ctatactcaa aatctaggtg ttaccctttc    130800
ctttattcac ttttctttc cctttatcaa aacagtagag agttattttg gttctatatt     130860
ggtgtgagct ctagaagtgt catgattgtt gcattcatgc tgctacatag tgtttccaag    130920
tgatgatccg aggtgaggac gagctgacca gtcgggccca cgctagggc acagatgact     130980 gacaagtggg gcccaggggc aagggcaccc acgtgaagcg atatccagcg atctagaccg    131040
ctagatcaag gctaaacggc taggattagg cgtcaggggg gttaacagca ctgcggccgg    131100
cgctgctcca tccgcagcgg tgaagtcgcc aaagacgaga caagcgcgga ccccaggggg    131160
tctggggtcg ctggagttgg ccagaccggt gaggggacc cgacgaactc gatggcaggg     131220
ttctggccat gagaacggga ctggaggtga gtgaatggcg gagggggcgc tctgggcggg    131280
acacttattg tgatatcctg gcccctggga tgggatgtcc tggcccaagg cttaatagaa    131340
ttaatagtgt aatcatacca acaaggtgca tcttctttt cggaagccta tctcgaaaga     131400
acctccaagt taagcgtgct tggcttggag caatttggga tgggtgaccg accgggaagt    131460
tttctcgggt gcgcatgagt gaggacaaag tgcgcacaaa agactcgtgt tggtctgtgg    131520
ggacaatata tgatcctaga cagctgccag gagtaagtac cgccggtcca gggattagac    131580
ggggtgttac aagtggtatc agagccgaca ctcgcggttt cacgggcgtg tgtgggctag    131640
ggggttcggg tatatggcgc atggcacatg tgggcccgga gtggtcacat ggcatggcat    131700
atgacggcac tagacacaca gacgtggcca agaggggagg ttcctggatt ggggttgacc    131760
gacgaggacg tcggtcttct aagggggtg gattgtgata tcctggcccc tgggatggga    131820
tgtcctggcc caaggcttaa tagaattaat agtgtaatca taccaacaag gtgcatcttc    131880
tttttcggaa gcctatctcg aaagaacctc caagttaagc gtgcttggct tggagcaatt    131940
tgggatgggt gaccgaccgg gaagttttct cgggtgcgca tgagtgagga caaagtgcgc    132000
acaaaagact cgtgttggtc tgtggggaca atatatgatc ctagacagct gccaggagta    132060
agtaccgccg gtccagggat tggacggggt gtgtaacacc ccaggtgttt attttccgct    132120
caacaacgag ttcggattta agcacgcaat atcagtggat aaaacgaatt ttaaatttta    132180
atcattgtcg cttatcgcta ttttaatatc gcatcggtgt cgtttgtcgc gagtgcgaca    132240
tcgtttttat ttttttatct gtccgggctc ttcctaaatt ttcgtaatgt tcggaaccta    132300
gctgttccga aaatcggtgc gtccgatgag tatttaaaat ccatcgctcg cgcgaacaca    132360
aattcggaag cccgaactca ctcgaatgat cttatttcga gcaaattaat ttgaacttga    132420
cgactaaaat gttcagggta aaataatctg aatcgcgcat tgtctgagaa agatcgtgcg    132480
cggggatatg atctaatttg ttcttttagcc cgcaatgtag gataaccaaa tcaactgtgt    132540
tttggtgacg gataagtttt tatctgattt caattaaatg taacaccgat taaaacattg    132600
```

```
taactaaaat cattttaat ttagtcctc ttacatcttt ccaaattcta gtcccaatct   132660
ccagctgata attgtatttt tattcaaatt tttgagtaaa agaaaacgaa ggaagaaaat   132720
atctgcaacc gctcttctct ctgattttat ccaccgcttt tcccttccat atctgaagtc   132780
actagcctgg atattttctc cacgtagttc tcctcttcct cacgtctcct tctctcttat   132840
ccattggacg ctagctcgct ggaaaatctc acgcacgtct ctcctccagc cttacccagc   132900
gaccagcatt tcttccatcc atcagcatcc aaaggcagcc ggctgccggc tgtgctcgtc   132960
ggaccctccg agcacctctg tgcccgacga cctgaccaag ctcgtctcca gcttgcgtcc   133020
atcctgtgct cagtttccat ccactagcac cgtgtctctg gtcctgctcg tcgtggacat   133080
cgtcggctct agttccttgc tcgagctcgc cctttgcgca gaccgcgtct cccctcacct   133140
tgccgcggtc gggctggccg tcgtcgtcag cttgtgtcca tgccgacgaa tttgtcgaac   133200
tgctcactgc atctctttaa tctcgtcgcc tgatttttct gtaccgcgcc gcgcaacccc   133260
tagaaataaa aatcacgccg ccgagcgctc ctatccttat cccgccaccg cccttggtct   133320
cctacaaatc tccagcgcgc aggtttcttc tccacgcacg cccggcagca agccgcagcc   133380
gagcagctcc ttcccatctc ccctctgctc gctggctgaa tccccagccg ctcggctctg   133440
cttttctccc atggcgcggg gttccctgca ggctgctcgc ggtatccatc tcctctgctc   133500
ctgctcgtcc gtccctgagc tcctgtgccg cggcacctct gttcggccac gctgatcgg    133560
atttcttgtg ccgtggcttc ccctccgagc tcgcccagct ctattgccgc gcccatggcc   133620
ggcgctccct gcttggttcc gtctgtcgcg ccgtcgtctt actgctcgcc tttgcgtcgc   133680
gcgcatagcg ttctgttgtt cttgcacgcg cgaagctctt tgctcgtcaa cgcttcagcc   133740
tggatttcgc tttgtcgccc agctcggctc tacatgacta catctcccat gactgtctac   133800
tctagctcgc cgtagttcct gcgcgcgtcg agttttctct actctagctc gccgtagttc   133860
ctgcgcgcgt cgagttttcg tgtggagctc tctgctcacg cgtagctcgc tctttctttg   133920
ttgccgcgcg cacgaatttt atctgctcgt cacagcgtgt cgagttctca caccatcatc   133980
gcttctgtcg caagctcgtt ggtcacagtt gtcttgaccg cgttaactcg cgactgtggt   134040
cgtgttcatc gaattcgcca actctttgtt gccgatttga ctgtcgtcgc ttcgcgtgtt   134100
gtcgagccgt cgttttttcc tgtcttgtgc tcgcacggtt tcctgctcgc cagcgtgccc   134160
tctcggctcg ctcggcttta atttccaatc acgtcgtcga tctcgtcgtt tgccgtcgag   134220
ttgtcaaaca cgtcatctcc ggctcgatcc ccacctcacc agcttacccc agacttcaat   134280
cgaaggtcat cgtcgctcgt gcgtccccaa gaaaacccaa gaatcgggtg aagacgaagt   134340
tagcagcgcg atattcccta agcgctcgac aaattgcgtg gatcgaaaaa tcactgccga   134400
tctcatggat tcgtgtcaac tgttgaaacg gtaagctgat gaattgttta gaatagttcg   134460
atcgttgaat aagttaatgt gttagtgcga ggctcattag ggtgctcgat aaattgcgta   134520
agtcacgaaa ctctcgtcga cttcgcagtt cttgcgatta tcgagccagg ttcagttata   134580
gcgagttatt tcgctattcc ggtcacttag ctgaattagt ggaccgagta gaatttttagt  134640
aggcatatgt gttgataaaa tatttttaatc acttataaag atgtagtata atttataagg   134700
caagggatta gttcagaatt taattaatta actgataagt tgtgattagg ctaattatat   134760
ttcttgtgta tagtttgttg ttcgtgatgt ttgcgttagg ttcgagaagc gtaatcattg   134820
cgcgtagtcg catattaata actagtgttt ccgtacaaaa ttgtacaacg cctcgccact   134880
aggtgtttaa tacgctatcg tatagcacta tttagatttg tgctattctt gtttatatgc   134940
attcatgtgc atcgtgcatc tcaattaggt acgataattg atcgcgtgat gcggaagaca   135000
```

```
agccaagtcg accccaagcg cgggctaatc cgcaggatga tgctgatgga caaacctgaa   135060
aatggtcgcc aagtggacgt cgtctaacaa cactaaccta gtgttaccca ggcaagcccc   135120
ggtgcatttg ccacctccct tgatgttttt aaaatctttc tcacttgatt gctgcattag   135180
gtgacaggag ttgattgatt aaacaattcc tgcattacct tccttgatct tgattaccct   135240
ccttgaaaac ctgttttac aaaaggttt tactatgctt agtattgctt agaaaaacaa    135300
aaggatttgt tttagaaaag atgtttggca aagtgggagg ttgttttca aaataaaac    135360
ttgatggtga atccatcatg gctatgatgg attcaacatc ggaaaagatg tacctctgct   135420
aggtaccaag tttttggtta aaagattaag ctaaggccgg gcgggtgact tgcacgggaa   135480
aggagtctcg gtgtagtgtc tccgtctgag tcgattaagg accttgtcga tgtaggcttg   135540
atgatcgagg acccttttaac tggtcacatg cctcgtcatg ggtaagcctt gcctcggca    135600
gactaaggcc agaataagat aacacgaaat gggcgtggag cagtggcgag agtagcgtgt   135660
accctccgtg gcaagaggct ggacggtggt gtaactgtgc tctcggtttg cgtgaacctg   135720
atctggtctt aagaaccccg gtggcgggtt gacatatgca agggttaagt gctacatatg   135780
tcgtgtgatt ggagatcctc agctgagtat aatcgattcg gatcgccgta ccttcgtggt   135840
tatgaagact tggtcactgc cctacacgta gcattccact aaagatgatg ggtttttgtt   135900
aagaaattgg ctagtgcagg accagtgatt gaactagggt agaaagaact ctagttacag   135960
gtaattctac ttaacttgac aaataaaact ggattttaag gatccacatt agtaagcatt   136020
tctgcaaaac agagtctttg attattgaaa agccttacct tgactcccat atacccagca   136080
taccccttgag agtctttttct ttagtcgggt aagacttgct gagtaattcc atactcaggg  136140
ttttatccta acgaatcaag ctgatcatca acnnnnnnnn nnnnnnnnnn nnnnnnnnnn   136200
nnnnnnnnnn nnnnnnnnnn nnnnnnnnnn nnnnnnnnnn nnnnnnnnnn nnnnnnnnnn   136260
nnnnnnnnnn nnggtcagcc cagattgctt ctgcgagcgc accggctatt gggtcttcct   136320
gtgttctgct agccgctggt gcagactctg agatgcatct cacatatttg ctgggacttc   136380
tcactcttct gactaccagc ggcagatatg ttgaggagtg ggtccgtgtg ttcaatgcgt   136440
cagtatggat cgaccccgat caccagtgga tgaggttccg ctttgagcga gaggatgtta   136500
cacttcatgc tagctagatt cgccagctgt ttggattcaa tgagtcatcg acttgtcttc   136560
atagcttgtg ctatggtacc tctgatcctc ctcgtcgccc tcacgacgga gttgctccag   136620
ctacagctca catcgcggct ttgttccgac cgcccttctc agatgggtcg cgacgttctc   136680
cggcagattt cactacagta gccaagtact tatatcagct catgagacgg acgcttctgt   136740
cgtggatggg ttatagagag gctaccactc atattcagct ttggctcctc ggtgccctga   136800
tctttcattc agagtttgat gttgttgact tccttatttg tgagatcgag gacacggtat   136860
tggatggtct tcgtgctcgg cgacagctgc caaatgctca ttatctctgc cacatcttcg   136920
cacagctgat ccgaccacca tagttccagg gcacccttga ggcctcacgc tcctatttg    136980
gctcctacca tccagcccct gaggatccag taccagtacc tgatccagtg acagacattc   137040
aggcagagga tacaagtttc catcagtttg agacttaggg cgcagcagtt cctgacgatg   137100
atgatgatga tgatgatgat gattttggga ttccgcctct gcctcctgtg cctccacgct   137160
cacatgacca tgaggcccgg agttctcgtg ctgcccctgc tgttcctcct gccattgacc   137220
ctgctctggc tgcgatcctc cagactctta ctcagcagca ggctcatctg gcagcggtgc   137280
aacagcagat gtccgagaga atgctatcga tgttttagac tattcaggac agacaggaca   137340
```

```
ctctgcagca gcagcttttg gcagacaagg ctgagaaccg ggccttcatg actcacatac   137400
ttcagcatac cggtgctcag attcctcctg ttcagtctgc accccctcta gatcttcagg   137460
ccgctgttgt gctagccctt caggcaggac ccctctacc ttcatttggt ccttcttcct    137520
ctccgctcct gccggtcacc ctggttttct cgtcgccggt catcagctcc atcagcgctc   137580
agccgccagt gccaccagct cctgctgtta ccactgctgt tgtggcggtg tctgtgacct   137640
cttcagcttc ggtagctcct gcagcacagc ctccatccga gtcagtacta gctccagctt   137700
ctacggtaga tcctggatcc gaggctgact ctgaccctca gctggcgttt gctcttctgc   137760
cacgatcgtg atcggatgcg ccccagccac ctccttcctc ttctggtctg taggttcagg   137820
tttccttttg gtgtttgacg ccaaaggggg agagatatga gagttgtgag agctagggg    137880 agttagggag ttagtataga gtcatttga tgtaatatat gtgcttgata ctctctgtac    137940
tagatccact tttgtatgac gattttggct cacaaactct attatatgct ctcgatgctt   138000
atgttgactg tgtgtgtatt gtgttttcac cttatatgtt atcaccagtc tctagttctt   138060
gttcatcgat ttgatttcac ttttatatga acaagaaact tacaatgtgt atgcactcac   138120
tcttattatt atgttacaca ctcttttctgt caaaaatttt tgagtataac taaccatctt   138180
ctctattgac agaaatttca aaacaaacta ctctcacaat cttgtaggtt gtcatcaatc   138240
accaaaaagg gggagattga aagcatctag gcccctggtt ggttttagtg attaatgaca   138300 atgtaattt atatgtgact aacatgtgtt ttgcagaggc aaatggtaag ttaggtcgca    138360
ttacatgtag atgtactaca acggtgaaaa caatctcgga gataagaact tgaagcgacg   138420
gctaaagcga caaaacaaaa agtgaaggtc ttcgtattcc gagtgtcaag gagttgcgga   138480
cactcgtgat atagttaggt ctttttatttt gttttagtcg tactataaag aggggttgtc   138540
gatgagtagt ttgaccaaga gagttctagt gtagtgttgg tgcatattca cactcacata   138600
tagtgctagg tgccactcta gaacatactc acaagttaga acgaaaaccg aattgaaaaa   138660
acagcacaaa acagaaaacta gggtttctgg cttttggggca ccggactgtc cggtgtgcac   138720
cggactgtcc ggtgcaccct ctgccagtgg ggccagcctg gcccaaggaa gagggttccc   138780
tgcgcacaga aacctgagag cgcgttgttc gcgagttgaa ttttagtgga ctgtccggtg   138840
tgccatctgc ccaacggcta gctgtcagaa ctagccattg gagtcgaccg ttggcgcacc   138900
gttggcgcac cggactgtcc ggtgcgccca tgtgcagcag attcctggta atggctagtt   138960
ggtgggtgag ggctatttat accccctcca cccactatat tgatggtctt gctacccaca   139020
tttactccta cacattggta gagcattgca agcaccacaa agcctagtga ggttatttga   139080
gaatcttaat cccgcatttg gaccttatta gcgctagcga gagccaccta gagcatacac   139140
cgcatgcatt aggcttctct tggtcaagtg aaagtctatg gcttgttact cttggtgatc   139200
gtcatcacct agacggcttg gtggcgttgg gagctcggtg atcaccgtgg agatcttgtt   139260
ggtgacccga ctcaagtttg taagcggtcg tgagggatcc actgcgctgg agtggcaaag   139320
gatcatctcg ttgtgagcac ttggttcttg cgaggaccaa ggggagtga tacccttgcg    139380 agggtgctcc aacgaggact agaggagagt gccgactctt cgatacctcg agaaaaattg   139440
gagtcttcta aaccttgctt tacattccgc acttaattaa acatttttac attgtgtatt   139500
tgtttagcaa gtatttgaaa tattgtctta acattgttgt atttctatta ttattctctt   139560
agtgatagtt atcggggtga agttggactc ttgcttagat tttaattagt gttgattttt   139620
agaaaagtcc aattcacccct cctcttgggc atcgtgatcc tttcaaaact cactcaattc   139680
cgtctaatcc acgtggattc aaaataaaac gaacagaccc taatacatgc gatccgacgc   139740
```

```
tacaccggaa ctatcagtgg tcagcttcta ggcttcagca ttatacgtac tatgaaaata  139800
tgaatgcact tcaggtcatc atcaacaacc aaaatggata tagcaaatat tcaggctcat  139860
tatacttgaa aacaatagaa ttacattaaa aaaggccgaa accgtgaggc tggattaaca  139920
agagaaacgg taatggtaca gtaattcatg aagtgaagga ttttacatca ccaccagctg  139980
gtgctgaacc ttcccgttgg atccagctaa ctgcccttgg caggagcatc tacaaccaat  140040
acccaaagtg ggttatctta cttatctaga gccctggtat cgcaagccca atatgcctca  140100
gggtcagggc aggaccaaga aatgtggtga agttcacatt cccaaggcaa ccctacgtct  140160
caatgccacc tcgaagtatc atctagtaaa agcaaagttc aacagaaatg ctgtgccagc  140220
aagttgtctt ggaaccgacg tggtaaaatg agcatcgttt gatcactttg tttttcttct  140280
cgatgcaatc tccgctgccc atgcttttcc caagtctgtc tgaaatttgc ctgcatggga  140340
attaggtgcg gggatatggt tttgttacac aatgactcta atgctaatag cctaggctaa  140400
gtttaccatc cccatattca aattccactc tgcgaatagt gcaatctaag tgcaaaacag  140460
tgttttgggt gggtgaactg ctggacacgg tctaatacaa tgtaaaaatg agatcaaaca  140520
taagcacgtg ataaaagaaa accataaaag gcataggcat gtatcagttc atggtaaaga  140580 aaccattat aggtggtagt gtccagtttt caattagcaa taatcattca ggcactaata  140640
tgttctgaat tgctgatgaa tgtttatatt atctcaggaa aacatttta agtgtaagac  140700 caaaaaatg gcaacatcct tctcagctta aatgaactgt tcaaatttat gtacaggatg  140760
ctcatgaaaa ttgagaagag caagatttat gtactggatt gtcatgaaaa ttgagaagag  140820
caagatttat gtactggata ctcatgaaaa ttgagaagag cataacagaa agagaaaaat  140880
cacacctgct gttgattgga agaattcttc aaggtcccgt ccttgctctg aaaattttaa  140940
aatacatagg cgtaagtgtg atactgttaa ccccatctat caacaaggag ttcaccaggt  141000
gttaagtgat agtacattga tcatatgtat cacttctcac acccagaagg ccgtggagca  141060
aattaaataa tggtgtaagc acagatgggc agatctaggg cggaggctgc cacatgagtg  141120
gggtcttgag atgggataaa tcgagacaag cctcccctgc aaatgcagag aggctgtttc  141180
gaactggcaa catagtgact tagtgagact gccctcacca ctacaccagg cctacccaat  141240
ataagcacaa atgatgcaaa gaaaaagatg tgctgtattt gaaatgtgaa atgtgagctg  141300
attttactat atacatttat ttggttatta caacaagaat atttgatgaa tgcatttaaa  141360
tagttgtggt ttgtacttta tagctactgt gcatgggaaa tgttagttca aatattcaag  141420
caccagtatg aactcaccct tttcatactc cagagcttga agtatcatct caacctgaaa  141480
atataacagt gcaacaaagg attacagcat gcaaggaaa aggaagaagt ggagccatat  141540
gggttagggc cataaatcat aatgattgcc tacattagtt aaatatcctg ccagttatat  141600
gcattgccta ttgaatgatc acaagaacta ccatctgata gcttcagaca gacgttgcaa  141660
tcatgccacc aacttgatgg attgaaatat gaaactgtac cttgtcaaaa tctttgacaa  141720
ccttcgcttc caaagacgca ttctcctcat actccatcca aagttcacga atttcttgtg  141780
ctgcaagaca acagcatgca gataaaggca agtatttatt atatatacca tgtcaaagat  141840
cacatgaact ctttagtctc gcctgtacag agaacatcct tttatcctgc atgaaaaact  141900
gtttccaaaa ggctgctaag atactttatt tagttctaaa aggttcactt cacatgtaag  141960
ggatgctgga tctctccaat attttttaac gattaatgat atgaataatg agaacacaac  142020
cagaatacta gaattctatg ttgtgaaact cttagggaaa aaatgttgga tgctatgata  142080
```

```
gccatttgag cataaataat ttacgatcca taatgcttca aggtagaaaa tcattagaga  142140
tggaataata ttatcaccat caattacaat atcatgttca aattccaaaa ctcatagtca  142200
tcaacatttg ctgaatataa actcttcggt tttggcttct acaaaaacat cccttatctt  142260
ttcaacctcc atttcaaaat gtagggcgta aggattcaaa aaagtcaatg aaactagtca  142320
aaatatttgt atatttattg cacaaagata aatctataga ttcatatttc acatgcattt  142380
tagtgagaca ttgcttttgt agtaattgat aatatattga gttcatatat tgcaagggaa  142440
attattggat aaagcatatc tttgaatgaa attctcaaac actaatacac cttataaaaa  142500
gaaaaagaga agtataaata acagtttctc tggaaataat ctgagtgatt ttaagttacc  142560
aagagtttcc ttgacaccta actaagggat gtgaatactc taagaattat ccaatactta  142620
tttaaactat gtatcaaaaa ataagaacaa aagctgcccg ctggatttct acaaaataat  142680
tgccaggtta tgatctgctt ccctgatgga agtgaaaagt atcggatgga aaaatgacca  142740
tctaagaaat aataataaca gatgaatagc ttttcaaggg taaaataaaa tatgtatatg  142800
acctgcaagt actatagtat tgtattcaca aaattcattg gcatccacat attgttcttt  142860
tttccttgaa actatggtac tatgcacaca taatgggatc attaagtcta gactattgag  142920
taatctagaa agatgatgcc agtgtgcaat agcaccacat tcatttcata taaactaaa  142980 tcatgaaaag acaatttgag gcataagatg cctaattaac tacagcataa aatgctaatg  143040
tatcacaatt gcaagtttca gtattcacct cttgaaccac caccaagcag ctcgcacata  143100
tggtccaatg cttctttctc cctgcggttc ttctcttcct tgggtacatt atcagaaggg  143160
gtgatgtcac caacaattgc tggagtacca aagaaaaaa caattgaaat gagtcaactg  143220
aacccacatc ctcataggca gttagttcca gaaacaggca agctggctta ggaacagcag  143280
caagagtcca tatgagcgga gggcaaaatc atgtgttcat ttctaagctg agcatgcttc  143340
tgaatgaaaa taggaaaatg tgcacatagt ttaaagtttt acactttggc tagcagaggt  143400
caaagaacca actaattggc acaagtactt gaacacacat cctacattcc tactacaggt  143460
ctccagtcca gtggtctagt taccatctac caacatctca ggtagtaata ggctcgcata  143520
ttcacaaaat tgcatccctc atctcacaca aagcccaaa acttcagtga agccgtctag  143580
acggaagtct tttgagacca taccttctgc aatgtcgtgc acaatcgcca tcttgacaca  143640
cctgtaattg aagggataaa taaacagtgt atgaaaacgg aaccgtaaga aggctaaata  143700
ctgccgagct agacttgaga gcgaaactgt caggatcacc tgtcgcggtt gacgccgggt  143760
agatcggccg cgacgagcgc catgacgccc atccggtaca tgtggtcggc caccgactcg  143820
ggcgcctgca ccccgcgctt cacccacccc gccctcttgg tcgtctgcaa ttacatccac  143880
aatctcatcc atcgcgtcac atttccatcc atctcaacca agccggcccg tggaaatgcg  143940
aagcgactaa acagggcgc tcagtcgctc accttgaggc ggtagcagag cgtgaggaag  144000
tcgatggcgt tggacgccga aggggccggg gcaccggcgt ccaccgatgc ggcggggtc   144060 ggggaggaag aggaggacat ggcggcggcg aggcggtggg ggagcgcgcg gtgagccggg  144120
gcgaagggga cggggtgctg tggggcttg gcggcggcga gggtggtggc gcagagggag    144180
gagagggaaa gggctcggct cccaccaccc atcgttatta gctgaggccg gagtaggcgg  144240
aggagcggtg ggcagcgcag ggcaggctcc gcggatggcg gggtggtcgc tcgcggaacc  144300
ggcgcatgcc cgcccgcgag cccgtggccc agcttgcgcg gcgggcggac cgtggatcac  144360
gtggggtact gaggttctcc taatttgggc cccagcgcac ggggatcgat cgcgctagag  144420
ggtcgatcct ttcctttttc attttcggct gccgggccca ttcggccaat ccggattccg  144480
```

```
gagtctgcaa tgttgcggat agcccatggt tggccaagaa tgcggcccgg cccgtgaggg   144540
gtccaccccc acgtggaaat aacaccagcc catcaattta tatgtctttg agtctgaatt   144600
ttaacccagc taaatctgtc gagaacttac agcagggaa gagattaagc gctgtttgga   144660
tcaaaatatt agactcactt atccaataaa ataggtaaca cagaatttta gatgatatta   144720
tttacagagt tgcgtttaat ataggaataa aatagaggat acaatagggg atcagttgga   144780
gatggcctta tactatcaaa aaatcttatg tgggctaata tcaaacgaga agctctagtc   144840
gtctatataa caaggaaata gttttttgtg cttctgcctc gacaaaaaga gaataagccc   144900
tccattgctg aggagagggt tcaaggtctg aatttggaaa ttgcaccaca gcaagtcctc   144960
ccgccttgcc taattgtctt acatgatagg cttcgtttcc gttcgctgaa taagaagca    145020 cggtatgtcg ttttgaccg ctctagacaa ttgtttagta gattttgttc aaactagatt    145080
gttttctcgc ggtcagatac atattgtaga gtgatttctt actgtcagat acatattgta   145140
gattgattta tgtatacact agcatgttaa atcctgatga tttgacctgc ttaatatatc   145200
caatctatta cttttactta aaaagccatc gatgtcctac taaccgcggg tcgtacgaat   145260
caccccgatg gcgaggctcg tgcgccagtc gcgtgcacta cacacccacc ccaccggtgg   145320
cccacacgtt gcgttcatga atagatcggt catgccggct tctagtcgta cactatgtcg   145380
gcgcccccaa ctctgcgcct tgatgtcaca ctgaccacg cacccatgcc ctgctgctgt    145440
tcacgccatc tcgagctgag atggttcacg ctgcgtcagc ccacggcgcc accccgcact   145500
gggtcgcgct tgctcggcca gctggggcgc agctcgtcgg catatgcttc agccacgcct   145560
cgtcagcacg ccctggaccg gctcccgtgg gtcatgcaat ttatctattt aaatttctat   145620
tattgataat tagcacgcct aattaaccta aagttaattt tgtgtgacgg actatggttg   145680
aagacaacag aattgattcg tggagcttgt cctcaatggc aagaactaac cgacctagac   145740
taacgactgc aagtttcacc tagaggcgat atagctagga aaggagatct tctggtaggg   145800
cccgaatgac acttgcctga aacttcatga gaaagcaaaa attacgatct tcgtcgggca   145860
ccacatccat ccaggcctga agatggagta tccagaggtg aaagaccata tgatattgtg   145920
gacagagcta tgtgagtgtt tcagtgtgga gaagcatgtg atgctcccgc gggcgcaaca   145980
tgaatgggcc actctcgact tcaatgcagt tgaggcttac aacactgtca tccatcgcat   146040
tgtcgctcag ctacatttct gtggccagat agccatagac ttagagatga tcgagaaaac   146100
tctccaaacc ttctacccct ccaatatggt gctccaacag cagtactgta gcaacaagta   146160
cacaaataat gtgacctcgt caacatgttg cttggtgcta aggctcagaa tgagcttctg   146220
atgcagaact actagaagca tccattcggc acgcggtcat gcataaagca cacgccaact   146280
tctagtctta aaggaagaaa ggtccctcca gagaaagggg tcatgggcac tgtaataatc   146340
aggggatgag aggggaatt tttacgaagc caccacaaaa tggcagtaga gtagcaatgg    146400
ctatggcaaa ggcaaaggca aaggcaaaac ctcagaaggg ctatgcaagc tcctcaaagc   146460
atgccagtga aggttgtttc aaagaaacac ttgattggca tgtatcagga gtggaagaaa   146520
cgcatagctc ataggctcac cttatttatt catgcatcta tacacgctat gattatagag   146580
cctatgtaac accctgaatt tgggggtata aaatttcttc tctaatatct accaaattca   146640
ggtgttacca cttttctcat ctccgtagat ttcctatttt cttccttcct aatagagttt   146700
tggttatata tttgggagat gtattttttt tctttactat attcaaacct aggggagaca   146760
tgaattgttg catcatgctg agcttaaact ttgttttgg ttgatgcaca tgtttgaaat    146820
```

```
attcaaattt gaatttgtgg tttcgttgga tttgaattca atagagaaaa taaaaataaa    146880
aggaactaga aattcagaat aaaaagaaaa tagaaaagca gcccagccta cgcacctgcc    146940
ctctctctcc atctgccagg tgggcccgac ctattggtgc cgctcaccct cgcgcgcacg    147000
cccccgctct ccctctgtgc agtgggccca gcccatcagc gctgaatcat ttcctcctca    147060
cacgtgctcg tgcctctact ctgtgggccc gccttgtcag tctcatcttc cccgcaaccg    147120
ctgctgaccc gcacacgcac tcacgccgag gaagccgacc acgttgccta cccacgcccc    147180
cagctccctt ttgagccccg cctacacccg ctctccctcc ccttcctaat ttcacccact    147240
ctcaacctct ctcgcgctta gccgccgccg ctcaagctcg ccggagaagc gcgccaccgc    147300
gtcgtctgcc cggagctcct agcatcgtgt caagcatccc cgagcacact cctaaggtaa    147360
ggaaccatcc ccgtgccctt cctgccccga ttctttttccc tctacggtga atttgtgttc    147420
gctggagctc tatcgcgctg gtttgccgcg cccgctcggt gtccgaccga ttcagccccg    147480
ccccgtgccc gtgccttggc cctaggcgtc cctcacccct caccgaagct tgtgctggcc    147540
tcggtgcacc ggattccgcc tcctcacggt cgggattgct caccggagta accccgacct    147600
gtggcagaac ctcccaagtt attaggccca catgcaccta tccttgtccc aaagacctca    147660
gaccccaaaa aacgtgcacc agataactta acaggatctg taagatctac caaaggacat    147720
cggataaacc acttacaacc agaaccgcga gaaaacgaat cccaaatcac acacaccaat    147780
attgttgcag cgaacatctt actaccaaat tttacaggtt acaaaaattt tacattagtt    147840
tatcggagtg attacaaaag tataagtttg aaatatatat gctagctcaa gggatcatcc    147900
tcaataagaa gtatagaagg gttacttaga ctcataagaa ggccgagccc accggcactt    147960
aacaccatca acaacagcac aaagttagaa cctgaaaaac aacaaggaat aaaaccctga    148020
gtatggaatt actcagcaag tcttacccga ctaaagaaaa gactctcaag ggtatgctgg    148080
ttatatggga gtcaaggtaa ggcttttcaa taatcaaaga ctctgttttg cagaaatgct    148140
tactaaagtg gatccttaaa atccagttttt atttgtcaag ttaagtagaa ttacctgtaa    148200
ctagagttct ttctacccta gttcaatcac ttgtcctgca ctagccaatt tcttaacaaa    148260
aacccatcat ctttagtgga atgctacgtg tagggcagtg accaagtctt cataaccacg    148320
aaggtacggc gatccgaatc gattatactt agctgaggat ctccaatcac acgacatatg    148380
tagcacttaa cccttgcata tgtcaacccg ccaccggggt tcttaagacc agatcaggtt    148440
cacgcaaacc gagagcacag ttacaccacc gtccagcctc ttgccacgga ggtacacgct    148500
actctcgcca ccgctccacg cccatttcgt gnnnnnnnnn nnnnnnnnnn nnnnnnnnnn    148560
nnnnnnnnnn nnnnnnnnnn nnnnnnnnnn nnnnnnnnnn nnnnnnnnnn nnnnnnnnnn    148620
nnnnnnnnnn nttcagggat taaacaatgt cattttgaga aagactggat ttgtagagca    148680
taccagtcgg aagcaagtgg cactcatcat ccacacacga acaaaaagac aacgaccgcc    148740
cagtgaagat cctcccccaa agcaacagtc aagcatccct gacagaactc ttaacgtaag    148800
taagtacctt caggcccttc ctgccccgat tcttttccct ctacggtgaa tttgtgttcg    148860
ctggagctct atcgcggtgg tttgccgcgc ccgctcggtg tccgaccgat tcagcccgc     148920 cccgtgcccg tgccttggcc ctaggcgtcc ctcacccctc accgaagctt gtgctggcct    148980
cggtgcaccg gattccgcct cctcacggtc gggattgctc accggagtaa ccccgacctg    149040
tggcagaacc tcccaagtta ttaggcccac atgcacctat ccttgtccca aagacctcag    149100
acggctgtgc atgtgcacca gataacttaa caggatgtgt ccgattgccc caaggacatc    149160
ggataaacca atttcaacca gaaccgcgag attaagtctt gaaactcaca cacggataca    149220
```

```
aagtggtagc ggaaatatta ttgacaaatt tgacaggtta cacaaatttt tcatacctct  149280
atcggaggga atacaaaatt ctaagtctga aatataaatg ctagctcaag ggatcatcct  149340
caataagaag tatagaaggg ttacttagac tcataagaag gccgagccca ccggcactta  149400
acaccatcaa caacagcaca aagttagaac ctgaaaaaca acaaggaata aaaccctgag  149460
tatggaatta ctcagcaagt cttacccgac taaagaaaag actctcaagg gtatgctggt  149520
tatatgggag tcaaggtaag gcttttcaat aatcaaagac tctgttttgc agaaatgctt  149580
actaaagtgg atccttaaaa tccagtttta tttgtcaagt taagtagaat tacctgtaac  149640
tagagttctt tctaccctag ttcaatcact tgtcctgcac tagccaattt cttaacaaaa  149700
acccatcatc tttagtggaa tgctacgtgt agggcagtga ccaagtcttc ataaccacga  149760
aggtacggcg atccgaatcg attatactta gctgaggatc tccaatcaca cgacatatgt  149820
agcacttaac ccttgcatat gtcaacccgc caccgggggtt cttaagacca gatcaggttc  149880
acgcaaaccg agagcacagt tacaccaccg tccagcctct tgccacggag ggtacacgct  149940
actctcgcca ccgctccacg cccatttcgt gttatcttat tctggcctta gtctgcccga  150000
ggcaaggctt acccatgacg aggcatgtga ccagttaaag ggtcctcgat catcaagcct  150060
acatcgacaa ggtccttaat cgactcagac ggagacacta caccgagact ccttttcccgt  150120 gcaagtcacc cgcccggtct tagcttaatc ttttaaccca aaaacttggt acctggcaga  150180
ggtacatctt ttccgatgtt gaatccatca tagccatgat ggattcacca tcaagtttta  150240
tttttgaaaa caaccctccc actttgccaa acatctttc taaaacaaat cctttttgttt  150300 ttctaagcaa tactaagcat agtaaaacct ttttgtaaaa acgggttttc aaggagggta  150360
atcaagatca aggaaggtaa tgcaggaatt gtttaatcaa tcaactcctg tcacctaatg  150420
cagcaatcaa gtgagaaaga ttttaaaaac atcaagggag gtggcaaatg caccgggggct  150480 tgcctgggta acactaggtt agtgttgtta gacgatgtcc acttggcgac cattttcagg  150540
tttgtccatc agcatcatcc tgcggattag cccgcgcttg gggtcgactt ggcttgtctt  150600
ccgcatcacg cgatcaatta tcgtacctaa ttgagatgca cgatgcacat gaatgcatat  150660
aaacaagaat agcacaaatc taaatagtgc tatacgatag cgtattaaac acctagtggc  150720
gaggcgttgt acaatttttgt acagaaacac tagttattaa tatgcgacta cgcacaatga  150780
ttacgcttct cgaacctaac gcaaacatca cgaacaacaa actatacaca agaaatataa  150840
ttagcctaat cacaacttat cagttaatta attaaattct gaactaatcc cttgccttat  150900
aaattatact acatctttat aagtgattaa aatattttat caacacatat gcctactaaa  150960
attctactcg gtccactaat tcagctaagt gaccgaaata gcgaaataac tcgctataac  151020
tgaacctggc tcgataatcg caagaactgc gaagtcgacg agagtttcgt gacttacgca  151080
atttatcgag caccctaatg agcctcgcac taacacatta acttattcaa cgatcgaact  151140
attctaaaca attcattagc ttaccgaact attctaaaca attcatcagc ttaccgtttc  151200
aacagctgac acgaatccgt gagatcggca gtgatttttc gatccacgca atttgtcgag  151260
cgcttaggga atatcgcgct gctaacttcg tcttcacccg attcttgggt tttcttgggg  151320
acgcacgagc gacgatgacc ttcgattgaa gtctggggta agctggtgag gtggggatcg  151380
agccggagat gacgtgtttg acaactcgac ggcaaacgac gagatcgacg acgtgattgg  151440
aaattaaagc cgagcgagcc gagagggcac gctggcgagc aggaaaccgt gcgagcacaa  151500
gacaggaaaa acgacggctc gacaacacgc gaagcgacga cagtcaaatc ggcaacaaag  151560
```

```
cgttggcgaa ttcgatgaac acgaccacag tcgcgagtta acgcggtcaa gacaactgtg   151620
accaacgagc ttgcgacaga agtgatgatg gtgtgggaac tcgacacgct gtgacgagca   151680
gataaaattc gtgcgcgcgg caacaaagaa agagcgagct gcgcgtgagc agagagctcc   151740
acacgaaaac tcgacgcgcg caggaactac ggcgagctag agtagagaaa actcgacgcg   151800
cgcaggaact acggcgagct agagtagaca gtcatgggag atgtagtcat gtagagccga   151860
gctgggcgac aaagcgaaat ccaggctgaa gcgttgacga gcaaagagct tcgcgcgtgc   151920
aagaacaaca gaacgctatg cgcgcgacgc aaaggcgagc agtaagacga cggcgcgaca   151980
gacggaacca agcagggagc gccggccatg ggcgcggcaa tagagctggg cgagctcgga   152040
ggggaagcca cggcacaaga aatccgatca ggcgcggccg aacagaggtg ccgcggcaca   152100
ggagctcagg gacggacgag caggagcaga ggagatggat accgcgagca gcctgcaggg   152160
aaccccgcgc catgggagaa aagcagagcc gagcggctgg ggattcagcc agcgagcaga   152220
ggggagatgg gaaggagctg ctcggctgcg gcttgctgcc gggcgtgcgt ggagaagaaa   152280
cctgcgcgct ggagatttgt aggagaccaa gggcggtggc gggataagga taggagcgct   152340
cggcggcgtg attttttattt ctaggggttg cgcggcgcgg tacagaaaaa tcaggcgacg   152400
agattaaaga gatgcagtga gcagttcgac aaattcgtcg gcatggacac aagctgacga   152460
cgacggccag cccgaccgcg gcaaggtgag gggagacgcg gtctgcgcaa agggcgagct   152520
cgagcaagga actagagccg acgatgtcca cgacagcag gaccagagac acggtgctag   152580
tggatggaaa ctgagcacag gatggatgca agctggagac gagcttggtc aggtcgtcgg   152640
gcacagaggt gctcggaggg tccgacgagc acagccggct gccggctgcc tttggatgct   152700
gatggatgga agaaatgctg gtcgctgggt aaggctggag gagagacgtg cgtgagattt   152760
tccagcgagc tagcgtccaa tggataagag agaaggagc gtgaggaaga ggagaactac   152820
gtggagaaaa tatccaggct agtgacttca gatatggaag gggaaagcgg tggataaaat   152880
cagagagaag agcggttgca gatattttct tccttcgttt tcttttactc gaaaatttga   152940
ataaaaatac aattatcagc tggagattgg gactagaatt tggaaagatg taagaggact   153000
aaaattaaaa atgatttttag ttacaatgtt ttaatcggtg ttacatttaa ttgaaatcag   153060
ataaaaactt atccgtcacc aaaacacagt tgatttggtt atcctacatt gcgggctaaa   153120
gaacaaatta gatcatattg aaagggaatt aggcttacac ctagttccta ataattttg   153180 gtggttgaat tgcccaacac aaatcttttg gactaacttg tttgcccaag tgtatagtgt   153240
atacaggagt aaaaggttca cactcagcca ataaaaagac caagttttgg attcaacaaa   153300
agagcaaagg ggcaaccgaa ggcacccctg gtctggcgca ccggactgtc cggtgtgcca   153360
ccggacagtg aacagtacct gtccggtgca ccagggact cagactcaaa ctcgccacct   153420
tcgggaattt ctaaggcgac tcggctataa ttcaccggac tgtccggtgt acaccggaca   153480
gtgtccggtg cgccaaggga ggtcggcctc aggaactcgc tagcctcggg ttcgcgcggc   153540
agccgctccg ctaaaattca ccggactgtc cggtgtgcac cggactgtcc ggtgtgccag   153600
cggagcaacg gctccctgcg gcgccaacgg ctccctgcgg tgcatttaat gcgcgcgcag   153660
cgcgcgcaga cgccaggcac gcccataccg gtgcaccgga catcaaattc cagatgtccg   153720
cagtccgcta cacactggta ttgtgaagcc cataaaattt accgatggct cgatcccgta   153780
tggaaatttg acaatttgtg aagaaccctc cagcttgtct gttgcattgt ttgacccaaa   153840
ctggaaaagc tgccatggac ctagaatttt ctgcccttat gcggaataaa acatggcact   153900
tggttcctcc cgcacctgac agaaatttga ttgattgcaa gtgggtttat aaactcaaga   153960
```

```
gaaaagctga tgagtctatt gaccatcata aagctcgatg ggtggctaaa tgttttaaac   154020
agcttnnnnn nnnnnnnnnn nnnnnnnnnn nnnnnnnnnn nnnnnnnnnn nnnnnnnnnn   154080
nnnnnnnnnn nnnnnnnnnn nnnnnnnnnn nnnnnnnnnn nnnnntgaaa ctagagattc   154140
gtcctcagct ggtttaggcg tgagcagaag gattgtcccc tcatataagg accggtttgt   154200
catcttcact acctgtactc tttaatagta caaccactcg agactgtgtg ggcagtcact   154260
caatctgaac tcgtacggtc caaccccagg gttatgaagg ctggggagca ccggaggat    154320 aaggaggggg aaagttttgt ccggtttgga catggtggtg gcctgactcc ttcaggataa   154380
ccattaaggt taggacatgc ggggaaagaa agagagtcgg attcgggtct cattgatcat   154440
gggatcgcag agctggacta gtgggtaaag tgtacacctc tgcgcagagt ttgaaaacct   154500
attcgaatag tctgtgtcca caggaatgga cgagtctggt atggtatggc aattaatgtt   154560
ttgttttcca aaaaaagag atgcttttga aaagtggttt ttaaaaggtc cggcggttga    154620
gccgtgagct atggtggacg ggaagtccag tagctgtttt tgaaaatgaa aaccagtggg   154680
aaactgctga gatacctgga tggtttagtc caggggattt tgttataata ctgaaaaact   154740
tcctgctcct tttggagagg atgcactttg caaaatacaa aatgttttc aaaacaaccc    154800 tgcataaaat attgctgttt ctgcaaatat cctgagctct acatattcca tgcattatat   154860
ctgatttccc cattccgcgg gtgaaggtgg gctgctgagt acgtttgtac tcacccttgc   154920
ttatttgttg tttttcagaa aaaagagatc gggtaagagt tacgactgtt cccaaccttg   154980
cctgtggctg ttggaccgct gaattgcttc actgcgtata tcgggctgct tcagccccac   155040
tctgatgata tgtcccgagt tgtggaccaa ctcttaaagt tgatcgccac ctttataggt   155100
ttgtctcgtt taagcagatc tgaatcatct gatgtataaa tgtgtttact agcctcctgg   155160
gactagtaat tgtatcacat ttgagtccca gaggattggg gacgcttcaa gctgtggcag   155220
aacctcccaa gttattgggc ccacatgcac ctgtccttgt cccaaagacc tcagacggct   155280
gtgcatgtgc accagataac ttaacaggat ctgtccgatt gccccaagga catcggataa   155340
accacttaca accagaaccg caggattaag taacacaaat cacacacacc aatattgttg   155400
cagcggaaat cttactacca aattttacag gttacaaaaa ttttacatta gtttatcgga   155460
gtgattacaa aagtataagt ttgaaatata tatgctagct caagggatca tcctcaataa   155520
gaagtataga agggttactt agacttataa gaaggccgag cccaccggca cttaacacca   155580
tcaacaacag cacaaagtta gaacctgaaa acaacaggg ataaaaccc tgagtatgga     155640 attactcagc aagtcttacc cgactaaaga aaagactctc aagggtatgc tggttatatg   155700
ggagtcaagg taaggctttt caataatcaa agactctgtt ttgcagaaat gcttactaaa   155760
gtggatcctt aaaatccagt tttatttgtc aagttaagta gaattacctg taactagagt   155820
tctttctacc ctagttcaat cactggtcct gcactagcca atttcttaac aaaaacccat   155880
catctttagt ggaatgctac gtgtagggca atgaccaagt cttcataacc gcgaaggtac   155940
ggcgatccga atcgattata ctcagctgag gatctccaat cacacgacat atgtagcact   156000
taacccttgc atatgtcaac ccgccaccgg ggttcttaag accagatcag gttcacgcaa   156060
accgagagca cagttacacc accgtccagc ctcttgccac ggagggtaca cgctactctc   156120
gccaccgctc cacgcccatt tcgtgttatc ttattctggc cttagtctgc ccgaggcaag   156180
gcttacccat gacgaggcat gtgaccagtt aaagggtcct cgatcatcaa gcctacatcg   156240
acaaggtcct taatcgactc agacggagac actacactga gactcctttc ccgtgcaagt   156300
```

```
cacccgcccg gtcttagctt aatcttttaa cccaaaaact tggtacctgg cagaggtaca    156360
tcttttccga tgttgaatcc atcatatcca tgatggattc accatcaagt tttatttttg    156420
aaaacaaccc tcccactttg ccaaacatct tttctaaaac aaatcctttt gtttttctaa    156480
gcaatactaa gcatagtaaa accttttgt aaaaacgggt tttcaaggag ggtaatcaag     156540
atcaaggaag gtaatgcagg aattgtttaa tcaatcaact cctgtcacct aatgcagcaa    156600
tcaagtgaga aagattttaa aaacatcaag ggaggtggca aatgcaccgg ggcttgcctg    156660
ggtaacacta ggttagtgtt gttagacgac gtccacttgg cgaccatttt caggtttgtc    156720
catcagcatc atcctgcgga ttagcccgcg cttggggtcg acttggcttg tcttccgcat    156780
cacgcgatca attatcgtac ctaattgaga tgcacgatgc acatgaatgc atataaacaa    156840
gaatagcaca aatctaaata gtgctatacg atagcgtatt aaacacctag tggcgaggcg    156900
ttgtacaatt ttgtacggaa acactagtta ttaatatgcg actacgcgct atgattacgc    156960
ttctcgaacc taacgcaaac atcacgaaca acaaactata cacaagaaat ataattagcc    157020
taatcacaac ttatcagtta attaattaaa ttctgaacta atcccttgcc ttataaatta    157080
tactacatct ttataagtga ttaaaatatt ttatcaacac atatgcctac taaaattcta    157140
ctcggtccac taattcagct aagtgaccgg aatagcgaaa taactcgcta taactgaacc    157200
tggctcgata atcgcaagaa ctgcgaagtc gacgagagtt tcgtgactta cgcaatttat    157260
cgagcaccct aatgagcctc gcactaacac attaacttat tcaacgatcg aactattcta    157320
aacaattcat cagcttacta aactattcta aacaattcat cagcttaccg tttcaacagc    157380
tgacacgaat ccgtgagatc ggcagtgatt tttcgatcca cgcaatttgt cgagcgctta    157440
gggaatattg cgctgctaac ttcgtcttca cccgattctt gggttttctt ggggacgcac    157500
gagcgacgat gaccttcgat tgaagtctgg ggtaagctgg tgaggtgggg atcgagccgg    157560
agatgacgtg tttgacaact cgacggcaaa cgacgagatc gacgacgtga ttggaaatta    157620
aagccgagcg agccgagagg gcacgctggc gagcaggaaa ccgtgcgagc aagacagg     157680
aaaaacgacg actcgacaac acgcgaagcg acgacagtca aatcggcaac aaagcgttgg    157740
cgaattcgat gaacacgacc acagtcgcga gttaacgcgg tcaagacaac tgtgaccaac    157800
gagcttgcga cagaagcgat gatggcgtgg gaactcgaca cgctgtgacg agcagataaa    157860
ttcgtgtgcg cggcacaaga tagagcgagt gctcgtgagc agagagctcc acacgaaact    157920
cgacgcgcgc tgactacgcg agctagagta gagaaactcg acgcgcgcag actacgtgag    157980
ctaagtagac agtcatggag atgtagtcat gtaaagcgag ctggcgacaa cgaatcagnn    158040
nnnnnnnnnn nnnnnnnnnn nnnnnnnnnn nnnnnnnnnn nnnnnnnnnn nnnnnnnnnn    158100
nnnnnnnnnn nnnnnnnnnn nnnnnnnnnn nnnnnnnnat ttattctaac catttcatca    158160
gctttataaa ctattctaaa caattcatca gcttaccgtt tcaacagctg acacgaatcc    158220
gtgagatcgg gcagtgattt ttcgatccac gcatttgtcg agcgcttagg gaatattgcg    158280
ctgctaactt cgtcttcacc cgattcttgg gttttcttgg ggaacgcacg agcgacgatg    158340
accttcgatt gaagtctggg gtaagctggt gaggtgggga tcgagccgga gatgacgtgt    158400
ttgacaactc gacggcaaac gacgagatcg acgacgtgat tggaaattaa agccgagcga    158460
gccgagaggg cacgctggcg agcaggaaac cgtgcgagca agacagga aaaacgacga     158520
ctcgacaaca cgcgaagcga cgacagtcaa atcggcaaca aagcgttggc gaattcgatg    158580
aacacgacca cagtcgcgag ttaacgcggt caagacaact gtgaccaacg agcttgcgac    158640
agaagcgatg atggcgtggg aactcgacac gctgtgacga gcagataaaa ttcgtgtgcg    158700
```

```
cggcaacaaa gaaagagcga gttgcgcgtg agcagagagc tccacacgaa aactcgacgc  158760
gcgcaggaac tacggcgagc tagagtagag aaaactcgac gcgcgcagga acttcggtga  158820
gctagagtag acagtcatgg gagatgtagt catgtagagc cgagctgggc gacaaagcga  158880
aatccaggct gaagcgttga cgagcaaaga gcttcgcgcg tgcaagaaca acagaacgct  158940
atgcgcgcga cgcaaaggcg agcagtaaga cgacggcgcg acagacggaa ccaagcaggg  159000
agcgccggcc atgggagaaa agcagagccg agcggctggg gattcagcca gcgagcagag  159060
gggagatggg aaggagctgc tcggctgcgg cttgctgccg ggcgtgcgtg gagaagaaac  159120
ctgcgcgctg gagatttgta ggagaccaag ggcggtggcg ggataaggat aggagcgctc  159180
ggcggcgtga ttttattc taggggttgc gcggcgcggt acagaaaaat caggcgacga  159240
gattaaagag atgcagtgag cagttcgaca aattcgtcgg catggacaca agctgacgac  159300
gacggccagc ccgaccgcgg caaggtgagg ggagacgcgg tctgcgcaaa gggcgagctc  159360
gagcaaggaa ctagagccga cgatgtccac gacgagcagg accagagaca cggtgctagt  159420
ggatggaaac tgagcacagg atggacgcaa gctggagacg agcttggtca ggtcgtcggg  159480
cacagaggtg ctcggagggt ccgacgagca cagccggctg ccggctgcct ttggatgctg  159540
atggatggaa gaaatgctgg tcgctgggta aggctggagg agagacgtgc gtgagatttt  159600
ccagcgagct agcgtccaat ggataagaga aagggagacg tgaggaagag gagaactacg  159660
tggagaaaat atccaggcta gtgacttcag atatggaagg ggaaagcgat ggataaaatt  159720
agagagaaga gcggttgcag atattttctt ccttcgtttt cttttactcg aaaatttgaa  159780
taaaaataca attatcagct ggagattggg actagaattt ggaaagatgt aagaggacta  159840
aaattaaaaa tgattttagt tacaatgttt taatcggtgt tacatttaat tgaaatcaga  159900
taaaaactta tccgtcacca aaacacagtt gatttggtta tcctacattg cgggctaaag  159960
aacaaattag atcatatccc cgcgcacgat cttctcaga caatgcgcga ttcggattat  160020
tttaccctga acatttagt cgtcaagttc aaattatttt gctcggaata agatcattcg  160080
agtgagttcg ggcttccgaa ttcgtgttcg cgcgagcgat ggattttaaa tactcatcgg  160140
acgcaccgat tttcggaaca gctaggttcc gaacattacg aaaatttagg aagagcccgg  160200
acagataaaa aaataaaaac gatgtcgcac tcgcgacaaa cgacaccgat gcgatattaa  160260
aatcgcgata agcgacgatg attaaaattt aaaatccgtt ttatccactg atattgcgtg  160320
cttaaatccg aactcgttgt tgagcggaaa ataaacacct ggggtgttac agccctcccc  160380
ccttaaaaga atctcgtccc gagattcaaa acgaaagact tctaagagta gagaagcatg  160440
taacccatgt ccatatcagc gataatcatg agacaattcc aaacaaagtc gagtgtctca  160500
aaatgtcgtt cctctagtgg acataacatg tgtcgcctta ggctaattta gaaatgtcca  160560
ccaatagaga cgatgtctgc cagaagtaca cataaggttc catgtgtgca gtttacttt  160620 tctgatgaca ctgtaatatc tgagtctgtt gagcgagtgg tagatatgca actttacaca  160680
aacagaatca gatgcaacct cttgggtaaa acacacagaa agagatttac caacaagtgg  160740
tcacggtaag ttcatagcac acgagacgag tgtggatgtc gaataacatc acagttaact  160800
cgtgttagcc agagaatcca agtccaagaa aaatgataaa gacttgaaaa aaattaccag  160860
cagagggatc tgtaaatgct gccttcgcaa ccaatccatt ttatcaagca ctaatcatgg  160920
atctacttga tcacacatgc tggaaaagca cacgtgagac gatcgaggca tgactagagc  160980
gatgtttagg tggttactgg ccgacttaat ctcgattctt gaaagtactt ccttaggatg  161040
```

```
gtttggacca tagcgagttt agataactcg atgaaacgat ctctaaactc gaccttcgtt  161100
cacaaagcag ttacaagtta gtaaaaccaa cttgttaaac tacttttgac attgagcaag  161160
tcctctcagt accattggta atccaagggt tgagagttca catttgctaa caggaaatca  161220
tgcacttggg tagaaatcca tttggtcacg ttgttcatcc gtttcttcta tacaagatga  161280
accgacttgg ttagggaata catggattaa ataagagagc gaatgaacaa attcttgcat  161340
ttcagcagca ggggaaacaa atctccattt tgggaactaa ttggttgtct tgcaacacta  161400
aaaagctcca aggcttcacc tttacacaaa ggatgtaaag ggaacttgta tgtgtgaagt  161460
caccatcaaa gtcaagagat aagagatcac acatgaaagt ggtatgccct tttgatccac  161520
agagatgata gatgttgctt gatcacttga caaacaacat agaaattgtt tcaagggagg  161580
actccacgga agatcacaca tcagtgtact tccacaatgg atcatgacca cagaccttga  161640
taccagcatc cgatgagtgg cacagtccta tgtgcgcatt cacaggaggc tctcagtttt  161700
cgttgcggca ccataagtca ttaatcatga ccaccactac cgaagctg             161748
```

<210> SEQ ID NO 104
<211> LENGTH: 634
<212> TYPE: DNA
<213> ORGANISM: Zea mays

<400> SEQUENCE: 104

```
caatccaggg ccaggccagg ccaggccaac caaaccctag gcactgcgcc acgcctagcg      60
cgcgtggtat ccatgggctg accgcgtccc ggtggggagc ccggatccgg agctagggtt     120
ccgtcctagg cggcaccacc atggagtggg acagcgagtc cgacggcgcc ggcagcgtcg     180
acgccggcta tgaggagcag gaggaggagg aggaggagcg gggaggcgag ggtggaggtg     240
gcgacgccgg gggcggcggt gggatgttca cgttcgcgat tgaaggcatg ctgcgctcct     300
ccgggccctg cgggctagtc gtcaccgacg cgctcgagcc cgattgcccc atcatctacg     360
tcaaccgcgg cttcgaggag gccacgggct accgcgccga ggaggtcctc ggcaggaact     420
gccgatttct gcagtgcaga gggccattcg ctcgaaggag gcacccccta gttgatgctg     480
cactggtttc agagattcga agatgcatag acaatggcat tgagttccgt ggtgatttac     540
taaatttcag aaaagatgga tctccagtga tgaacagatt gcatctgacc cctatttatg     600
gagatgatga aaccataacc cattatatgg gcat                                  634
```

<210> SEQ ID NO 105
<211> LENGTH: 20
<212> TYPE: DNA
<213> ORGANISM: Artificial
<220> FEATURE:
<223> OTHER INFORMATION: Primer

<400> SEQUENCE: 105

```
accaccatgg agtgggacag                                                   20
```

<210> SEQ ID NO 106
<211> LENGTH: 21
<212> TYPE: DNA
<213> ORGANISM: Artificial
<220> FEATURE:
<223> OTHER INFORMATION: Primer

<400> SEQUENCE: 106

```
ttcaatcgcg aacgtgaaca t                                                 21
```

<210> SEQ ID NO 107
<211> LENGTH: 388
<212> TYPE: DNA
<213> ORGANISM: Zea mays
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 107

```
ctgaacaaga tcgaccaaac agttcattca ccagctagaa aatgtgttca aataggagtg      60
gcagaaaaat aacacggttt accagattat actgtcacaa actgttaccg aacacttaaa     120
acaaagacta gatgttcccc aaaactgatg acaaagcaca gctcctcagt acttgatagg     180
ggcaagantc tccaactgag accccaactt ctcctcggnt gccttctcgg ccttgacacg     240
cagcttggcc aattgcttct tcctctcgta ggcaaccttg ggccttctcc ttgctctttc     300
tcctcaagtt ccctgatggt gtcatggtag ttccacccgg cctccttaga gagctcgccg     360
aggaggcagt acttgtgtcc aggctgta                                        388
```

<210> SEQ ID NO 108
<211> LENGTH: 21
<212> TYPE: DNA
<213> ORGANISM: Artificial
<220> FEATURE:
<223> OTHER INFORMATION: Primer

<400> SEQUENCE: 108

```
cgaccaaaca gttcattcac c                                                21
```

<210> SEQ ID NO 109
<211> LENGTH: 19
<212> TYPE: DNA
<213> ORGANISM: Artificial
<220> FEATURE:
<223> OTHER INFORMATION: Primer

<400> SEQUENCE: 109

```
ctcctcggcg agctctcta                                                   19
```

<210> SEQ ID NO 110
<211> LENGTH: 161748
<212> TYPE: DNA
<213> ORGANISM: Zea mays
<220> FEATURE:
<221> NAME/KEY: misc_feature
<222> LOCATION: (3611)..(3710)
<223> OTHER INFORMATION: n is a, c, g, or t
<220> FEATURE:
<221> NAME/KEY: misc_feature
<222> LOCATION: (7624)..(7723)
<223> OTHER INFORMATION: n is a, c, g, or t
<220> FEATURE:
<221> NAME/KEY: misc_feature
<222> LOCATION: (13118)..(13217)
<223> OTHER INFORMATION: n is a, c, g, or t
<220> FEATURE:
<221> NAME/KEY: misc_feature
<222> LOCATION: (25477)..(25576)
<223> OTHER INFORMATION: n is a, c, g, or t
<220> FEATURE:
<221> NAME/KEY: misc_feature
<222> LOCATION: (70085)..(70184)
<223> OTHER INFORMATION: n is a, c, g, or t
<220> FEATURE:

```
<221> NAME/KEY: misc_feature
<222> LOCATION: (94587)..(94686)
<223> OTHER INFORMATION: n is a, c, g, or t
<220> FEATURE:
<221> NAME/KEY: misc_feature
<222> LOCATION: (117477)..(117576)
<223> OTHER INFORMATION: n is a, c, g, or t
<220> FEATURE:
<221> NAME/KEY: misc_feature
<222> LOCATION: (128130)..(128229)
<223> OTHER INFORMATION: n is a, c, g, or t
<220> FEATURE:
<221> NAME/KEY: misc_feature
<222> LOCATION: (143525)..(143624)
<223> OTHER INFORMATION: n is a, c, g, or t
<220> FEATURE:
<221> NAME/KEY: misc_feature
<222> LOCATION: (151880)..(151979)
<223> OTHER INFORMATION: n is a, c, g, or t
<220> FEATURE:
<221> NAME/KEY: misc_feature
<222> LOCATION: (155542)..(155641)
<223> OTHER INFORMATION: n is a, c, g, or t
<220> FEATURE:
<221> NAME/KEY: misc_feature
<222> LOCATION: (159499)..(159598)
<223> OTHER INFORMATION: n is a, c, g, or t

<400> SEQUENCE: 110
```

| | | | | | |
|---|---|---|---|---|---|
| cagcttcggt | agtggtggtc | atgattaatg | acttatggtg | ccgcaacgaa | aactgagagc       60 |
| ctcctgtgaa | tgcgcacata | ggactgtgcc | actcatcgga | tgctggtatc | aaggtctgtg      120 |
| gtcatgatcc | attgtggaag | tacactgatg | tgtgatcttc | cgtggagtcc | tcccttgaaa      180 |
| caatttctat | gttgtttgtc | aagtgatcaa | gcaacatcta | tcatctctgt | ggatcaaaag      240 |
| ggcataccac | tttcatgtgt | gatctcttat | ctcttgactt | tgatggtgac | ttcacacata      300 |
| caagttccct | ttacatcctt | tgtgtaaagg | tgaagccttg | gagctttta | gtgttgcaag       360 |
| acaaccaatt | agttcccaaa | atggagattt | gttccccctg | ctgctgaaat | gcaagaattt      420 |
| gttcattcgc | tctcttattt | aatccatgta | ttccctaacc | aagtcggttc | atcttgtata      480 |
| gaagaaacgg | atgaacaacg | tgaccaaatg | gatttctacc | caagtgcatg | atttcctgtt      540 |
| agcaaatgtg | aactctcaac | ccttggatta | ccaatggtac | tgagaggact | tgctcaatgt      600 |
| caaaagtagt | ttaacaagtt | ggttttacta | acttgtaact | gctttgtgaa | cgaaggtcga      660 |
| gtttagagat | cgtttcatcg | agttatctaa | actcgctatg | gtccaaacca | tcctaaggaa      720 |
| gtactttcaa | gaatcgagat | taagtcggcc | agtaaccacc | taaacatcgc | tctagtcatg      780 |
| cctcgatcgt | ctcacgtgtg | cttttccagc | atgtgtgatc | aagtagatcc | atgattagtg      840 |
| cttgataaaa | tggattggtt | gcgaaggcag | catttacaga | tccctctgct | ggtaattttt      900 |
| ttcaagtctt | tatcattttt | cttggacttg | gattctctgg | ctaacacgag | ttaactgtga      960 |
| tgttattcga | catccacact | cgtctcgtgt | gctatgaact | taccgtgacc | acttgttggt     1020 |
| aaatctcttt | ctgtgtgttt | tacccaagag | gttgcatctg | attctgtttg | tgtaaagttg     1080 |
| catatctacc | actcgctcaa | cagactcaga | tattacagtg | tcatcagaaa | aagtaaactg     1140 |
| cacacatgga | accttatgtg | tacttctggc | agacatcgtc | tctattggtg | gacatttcta     1200 |
| aattagccta | aggcgacaca | tgttatgtcc | actagaggaa | cgacatttg | agacactcga      1260 |
| ctttgtttgg | aattgtctca | tgattatcgc | tgatatggac | atgggttaca | tgcttctcta     1320 |
| ctcttagaag | tctttcgttt | tgaatctcgg | gacgagattc | ttttaagggg | ggagggctgt     1380 |
| aacaccccag | gtgtttattt | tccgctcaac | aacgagttcg | gatttaagca | cgcaatatca     1440 |
| gtggataaaa | cggatttaa | attttaatca | tcgtcgctta | tcgcgatttt | aatatcgcat     1500 |

-continued

```
cggtgtcgtt tgtcgcgagt gcgacatcgt ttttatttt ttatctgtcc gggctcttcc    1560
taaattttcg taatgttcgg aacctagctg ttccgaaaat cggtgcgtcc gatgagtatt    1620
taaaatccat cgctcgcgcg aacacgaatt cggaagcccg aactcactcg aatgatctta    1680
ttccgagcaa ataatttga acttgacgac taaaatgttc agggtaaaat aatccgaatc    1740
gcgcattgtc tgagaaagat cgtgcgcggg gatatgatct aatttgttct ttagcccgca    1800
atgtaggata accaaatcaa ctgtgttttg gtgacggata agttttttatc tgatttcaat    1860
taaatgtaac accgattaaa acattgtaac taaaatcatt tttaatttta gtcctcttac    1920
atctttccaa attctagtcc caatctccag ctgataattg tattttatt caaattttcg    1980
agtaaaagaa aacgaaggaa gaaaatatct gcaaccgctc ttctctctaa ttttatccat    2040
cgcttccc ttccatatct gaagtcacta gcctggatat tttctccacg tagttctcct    2100
cttcctcacg tctccttctc tcttatccat tggacgctag ctcgctggaa aatctcacgc    2160
acgtctctcc tccagcctta cccagcgacc agcatttctt ccatccatca gcatccaaag    2220
gcagccggca gccggctgtg ctcgtcggac cctccgagca cctctgtgcc cgacgacctg    2280
accaagctcg tctccagctt gcgtccatcc tgtgctcagt ttccatccac tagcaccgtg    2340
tctctggtcc tgctcgtcgt ggacatcgtc ggctctagtt ccttgctcga gctcgccctt    2400
tgcgcagacc gcgtctcccc tcaccttgcc gcggtcgggc tggccgtcgt cgtcagcttg    2460
tgtccatgcc gacgaatttg tcgaactgct cactgcatct ctttaatctc gtcgcctgat    2520
ttttctgtac cgcgccgcgc aacccctaga aataaaaatc acgccgccga gcgctccat    2580
ccttatcccg ccaccgccct tggtctccta caaatctcca gcgcgcaggt ttcttctcca    2640
cgcacgcccg gcagcaagcc gcagccgagc agctccttcc catctcccct ctgctcgctg    2700
gctgaatccc cagccgctcg gctctgcttt tctcccatgg ccggcgctcc ctgcttggtt    2760
ccgtctgtcg cgccgtcgtc ttactgctcg ccttttgcgtc gcgcgcatag cgttctgttg    2820
ttcttgcacg cgcgaagctc tttgctcgtc aacgcttcag cctggatttc gctttgtcgc    2880
ccagctcggc tctacatgac tacatctccc atgactgtct actctagctc accgaagttc    2940
ctgcgcgcgt cgagttttct ctactctagc tcgccgtagt tcctgcgcgc gtcgagtttt    3000
cgtgtggagc tctctgctca cgcgcaactc gctctttctt tgttgccgcg cacacgaatt    3060
ttatctgctc gtcacagcgt gtcgagttcc cacgccatca tcgcttctgt cgcaagctcg    3120
ttggtcacag ttgtcttgac cgcgttaact cgcgactgtg gtcgtgttca tcgaattcgc    3180
caacgctttg ttgccgattt gactgtcgtc gcttcgcgtg ttgtcgagtc gtcgtttttc    3240
ctgtcttgtg ctcgcacggt ttcctgctcg ccagcgtgcc ctctcggctc gctcggcttt    3300
aatttccaat cacgtcgtcg atctcgtcgt ttgccgtcga gttgtcaaac acgtcatctc    3360
cggctcgatc cccacctcac cagcttaccc cagacttcaa tcgaaggtca tcgtcgctcg    3420
tgcgttcccc aagaaaaccc aagaatcggg tgaagacgaa gttagcagcg caatattccc    3480
taagcgctcg acaaatgcgt ggatcgaaaa atcactgccc gatctcacgg attcgtgtca    3540
gctgttgaaa cggtaagctg atgaattgtt tagaatagtt tataaagctg atgaaatggt    3600
tagaataaat nnnnnnnnn nnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn ctgattcgtt    3720
gtcgccagct cgctttacat gactacatct ccatgactgt ctacttagct cacgtagtct    3780
gcgcgcgtcg agtttctcta ctctagctcg cgtagtcagc gcgcgtcgag tttcgtgtgg    3840
```

-continued

```
agctctctgc tcacgagcac tcgctctatc ttgtgccgcg cacacgaatt tatctgctcg      3900
tcacagcgtg tcgagttccc acgccatcat cgcttctgtc gcaagctcgt tggtcacagt      3960
tgtcttgacc gcgttaactc gcgactgtgg tcgtgttcat cgaattcgcc aacgctttgt      4020
tgccgatttg actgtcgtcg cttcgcgtgt tgtcgagtcg tcgttttttcc tgtcttgtgc     4080
tcgcacggtt tcctgctcgc cagcgtgccc tctcggctcg ctcggcttta atttccaatc      4140
acgtcgtcga tctcgtcgtt tgccgtcgag ttgtcaaaca cgtcatctcc ggctcgatcc      4200
ccacctcacc agcttacccc agacttcaat cgaaggtcat cgtcgctcgt gcgtccccaa      4260
gaaaacccaa gaatcgggtg aagacgaagt tagcagcgca atattcccta agcgctcgac      4320
aaattgcgtg gatcgaaaaa tcactgccga tctcacggat tcgtgtcagc tgttgaaacg      4380
gtaagctgat gaattgttta gaatagttta gtaagctgat gaattgttta gaatagttcg      4440
atcgttgaat aagttaatgt gttagtgcga ggctcattag ggtgctcgat aaattgcgta      4500
agtcacgaaa ctctcgtcga cttcgcagtt cttcgcgatta tcgagccagg ttcagttata      4560
gcgagttatt tcgctattcc ggtcacttag ctgaattagt ggaccgagta gaattttagt      4620
aggcatatgt gttgataaaa tattttaatc acttataaag atgtagtata atttataagg      4680
caagggatta gttcagaatt taattaatta actgataagt tgtgattagg ctaattatat      4740
ttcttgtgta tagtttgttg ttcgtgatgt ttgcgttagg ttcgagaagc gtaatcatag      4800
cgcgtagtcg catattaata actagtgttt ccgtacaaaa ttgtacaacg cctcgccact      4860
aggtgtttaa tacgctatcg tatagcacta tttagatttg tgctattctt gtttatatgc      4920
attcatgtgc atcgtgcatc tcaattaggt acgataattg atcgcgtgat gcggaagaca      4980
agccaagtcg accccaagcg cgggctaatc cgcaggatga tgctgatgga caaacctgaa      5040
aatggtcgcc aagtggacgt cgtctaacaa cactaaccta gtgttaccca ggcaagcccc      5100
ggtgcatttg ccacctccct tgatgttttt aaaatctttc tcacttgatt gctgcattag      5160
gtgacaggag ttgattgatt aaacaattcc tgcattacct tccttgatct tgattaccct      5220
ccttgaaaac ccgttttac aaaaaggttt tactatgctt agtattgctt agaaaaacaa      5280
aaggatttgt tttagaaaag atgtttggca aagtgggagg gttgttttca aaataaaac      5340
ttgatggtga atccatcatg gatatgatgg attcaacatc ggaaaagatg tacctctgcc      5400
aggtaccaag ttttgggtt aaaagattaa gctaagaccg ggcgggtgac ttgcacggga      5460
aaggagtctc agtgtagtgt ctccgtctga gtcgattaag gaccttgtcg atgtaggctt      5520
gatgatcgag gacccttaa ctggtcacat gcctcgtcat gggtaagcct tgcctcgggc       5580
agactaaggc cagaataaga taacacgaaa tgggcgtgga gcggtggcga gagtagcgtg      5640
taccctccgt ggcaagaggc tggacggtgg tgtaactgtg ctctcggttt gcgtgaacct      5700
gatctggtct taagaacccc ggtggcgggt tgacatatgc aagggttaag tgctacatat      5760
gtcgtgtgat tggagatcct cagctgagta taatcgattc ggatcgccgt accttcgcgg      5820
ttatgaagac ttggtcattg ccctacacgt agcattccac taaagatgat gggttttgt       5880
taagaaattg gctagtgcag gaccagtgat tgaactaggg tagaaagaac tctagttaca      5940
ggtaattcta cttaacttga caaataaaac tggattttaa ggatccactt tagtaagcat      6000
ttctgcaaaa cagagtcttt gattattgaa aagccttacc ttgactccca tataaccagc      6060
atacccttga gagtcttttc tttagtcggg taagacttgc tgagtaattc catactcagg      6120
gttttattcc ctgttgtttt tcaggttcta actttgtgct gttgttgatg gtgttaagtg      6180
ccggtgggct cggccttctt ataagtctaa gtaacccttc tatacttctt attgaggatg      6240
```

```
atcccttgag ctagcatata tatttcaaac ttatactttt gtaatcactc cgataaacta   6300
atgtaaaatt tttgtaacct gtaaaatttg gtagtaagat ttccgctgca acaatattgg   6360
tgtgtgtgat ttgtgttact taatcctgcg gttctggttg taagtggttt atccgatgtc   6420 cttgggcaa tcggacagat cctgttaagt tatctggtgc acatgcacag ccgtctgagg    6480
tctttgggac aaggacaggt gcatgtgggc caataactt gggaggttct gccacagctt    6540
gaagcgtccc caatcctctg ggactcaaat gtgatacaat tactagtccc aggaggctag   6600
taaacacatt tatacatcag atgattcaga tctgcttaaa cgagacaaac ctataaaggt   6660
ggcgatcaac tttaagagtt ggtccacaac tcgggacata tcatcagagt ggggctgaag   6720
cagcccgata tacgcagtga agcaattcag cggtccaaca gccacaggca aggttgggaa   6780
cagtcgtaac tcttacccga tctcttttt ctgaaaaaca caaataagc aagggtgagt    6840 acaaacgtac tcagcagccc accttcaccc gcggaatggg gaaatcagat ataatgcatg   6900
gaatatgtag agctcaggat attgcagaa acagcaatat tttatgcagg gttgttttga    6960
aaaacatttt gtattttgca aagtgcatcc tctccaaaag gagcaggaag ttttttcagta   7020 ttataacaaa atcccctgga ctaaaccatc caggtatctc agcagtttcc cactggtttt   7080
cattttcaaa aacagctact ggacttcccg tccaccatag ctcacggctc aaccgccgga   7140
ccttttaaaa accacttttc aaaagcatct cttttttttg gaaaacaaaa cattaattgc   7200
cataccatac cagactcgtc cattcctgtg gacacagact attcgaatag gttttcaaac   7260
tctgcgcaga ggtgtacact ttaccccacta gtccagctct gcgatcccat gatcaatgag   7320
acccgaatcc gactctcttt ctttccccgc atgtcctaac cttaatggtt atcctgaagg   7380
agtcaggcca ccaccatgtc caaaccggac aaaactttcc ccctccttat cctcccggtg   7440
ctccccagcc ttcataaccc tggggttgga ccgtacgagt tcagattgag tgactgccca   7500
cacagtctcg agtggttgta ctattaaaga gtacaggtag tgaagatgac aaaccggtcc   7560
ttatatgagg ggacaatcct tctgctcacg cctaaaccag ctgaggacga atctctagtt   7620
tcannnnnnn nnnnnnnnnn nnnnnnnnnn nnnnnnnnnn nnnnnnnnnn nnnnnnnnnn   7680
nnnnnnnnnn nnnnnnnnnn nnnnnnnnnn nnnnnnnnnn nnnaagctgt ttaaaacatt   7740
tagccaccca tcgagcttta tgatggtcaa tagactcatc agcttttctc ttgagtttat   7800
aaacccactt gcaatcaatc aaatttctgt caggtgcggg aggaaccaag tgccatgttt   7860
tattccgcat aagggcagaa aattctaggt ccatggcagc ttttccagtt tgggtcaaac   7920
aatgcaacag acaagctgga gggttcttca caaattgtca aatttccata cgggatcgag   7980
ccatcggtaa atttatggg cttcacaata ccagtgtgta gcggactgcg gacatctgga   8040
atttgatgtc cggtgcaccg gtatgggcgt gcctggcgtc tgcgcgcgct gcgcgcgcat   8100
taaatgcacc gcagggagcc gttggcgccg cagggagccg ttgctccgct ggcacaccgg   8160
acagtccggt gcacaccgga cagtccggtg aattttagcg gagcggctgc cgcgcgaacc   8220
cgaggctagc gagttcctga ggccgacctc ccttggcgca ccggacactg tccggtgtac   8280
accggacagt ccggtgaatt atagccgagt cgccttagaa attcccgaag gtggcgagtt   8340
tgagtctgag tcccctggtg caccggacag gtactgttca ctgtccggtg gcacaccgga   8400
cagtccggtg cgccagacca ggggtgcctt cggttgcccc tttgctcttt tgttgaatcc   8460
aaaacttggt cttttattg gctgagtgtg aaccttttac tcctgtatac actatacact   8520
tgggcaaaca agttagtcca aaagatttgt gttgggcaat tcaaccacca aaattattta   8580
```

```
ggaactaggt gtaagcctaa ttccctttca atatgatcta atttgttctt tagcccgcaa    8640
tgtaggataa ccaaatcaac tgtgttttgg tgacggataa gtttttatct gatttcaatt    8700
aaatgtaaca ccgattaaaa cattgtaact aaaatcattt ttaattttag tcctcttaca    8760
tctttccaaa ttctagtccc aatctccagc tgataattgt attttttattc aaattttcga   8820
gtaaaagaaa acgaaggaag aaaatatctg caaccgctct tctctctgat tttatccacc    8880
gctttcccct tccatatctg aagtcactag cctggatatt ttctccacgt agttctcctc    8940
ttcctcacgt ctccttctct cttatccatt ggacgctagc tcgctggaaa atctcacgca    9000
cgtctctcct ccagccttac ccagcgacca gcatttcttc catccatcag catccaaagg    9060
cagccggcag ccggctgtgc tcgtcggacc ctccgagcac ctctgtgccc gacgacctga    9120
ccaagctcgt ctccagcttg catccatcct gtgctcagtt ccatccact agcaccgtgt     9180
ctctggtcct gctcgtcgtg gacatcgtcg gctctagttc cttgctcgag ctcgcccttt    9240
gcgcagaccg cgtctcccct caccttgccg cggtcgggct ggccgtcgtc gtcagcttgt    9300
gtccatgccg acgaatttgt cgaactgctc actgcatctc tttaatctcg tcgcctgatt    9360
tttctgtacc gcgccgcgca accctagaa ataaaaatca cgccgccgag cgctcctatc      9420
cttatcccgc caccgccctt ggtctcctac aaatctccag cgcgcaggtt tcttctccac    9480
gcacgcccgg cagcaagccg cagccgagca gctccttccc atctcccctc tgctcgctgg    9540
ctgaatcccc agccgctcgg ctctgctttt ctcccatggc gcggggttcc ctgcaggctg    9600
ctcgcggtat ccatctcctc tgctcctgct cgtccgtccc tgagctcctg tgccgcggca    9660
cctctgttcg gccgcgcctg atcggatttc ttgtgccgtg gcttcccctc cgagctcgcc    9720
cagctctatt gccgcgccca tggccggcgc tccctgcttg gttccgtctg tcgcgccgtc    9780
gtcttactgc tcgcctttgc gtcgcgcgca tagcgttctg ttgttcttgc acgcgcgaag    9840
ctctttgctc gtcaacgctt cagcctggat ttcgctttgt cgcccagctc ggctctacat    9900
gactacatct cccatgactg tctactctag ctcgccgtag ttcctgcgcg cgtcgagttt    9960
tctctactct agctcgccgt agttcctgcg cgcgtcgagt tttcgtgtgg agctctctgc   10020
tcacgcgcag ctcgctcttt ctttgttgcc gcgcgcacga atttatctg ctcgtcacag    10080
cgtgtcgagt tcccacacca tcatcacttc tgtcgcaagc tcgttggtca cagttgtctt   10140
gaccgcgtta actcgcgact gtggtcgtgt tcatcgaatt cgccaacgct tgttgccga     10200
tttgactgtc gtcgcttcgc gtgttgtcga gccgtcgttt ttcctgtctt gtgctcgcac   10260
ggttcctgc tcgccagcgt gccctctcgg ctcgctcggc tttaatttcc aatcacgtcg    10320
tcgatctcgt cgtttgccgt cgagttgtca aacacgtcat ctccggctcg atccccacct   10380
caccagctta ccccagactt caatcgaagg tcatcgtcgc tcgtgcgtcc ccaagaaaac   10440
ccaagaatcg ggtgaagacg aagttagcag cgcgatattc cctaagcgct cgacaaattg   10500
cgtggatcga aaaatcactg ccgatctcac ggattcgtgt cagctgttga aacggtaagc   10560
tgatgaattg tttagaatag ttcggtaagc taatgaattg tttagaatag ttcgatcgtt   10620
gaataagtta atgtgttagt gcgaggctca ttagggtgct cgataaattg cgtaagtcac   10680
gaaactctcg tcgacttcgc agttcttgcg attatcgagc caggtcagt tatagcgagt      10740
tatttcgcta tttcggtcac ttagctgaat tagtggaccg agtagaattt tagtaggcat   10800
atgtgttgat aaaatatttt aatcacttat aaagatgtag tataatttat aaggcaaggg   10860
attagttcag aatttaatta attaactgat aagttgtgat taggctaatt atatttcttg   10920
tgtatagttt gttgttcgtg atgtttgcgt taggttcgag aagcgtaatc attgtgcgta   10980
```

-continued

```
gtcgcatatt aataactagt gtttctgtac aaaattgtac aacgcctcgc cactaggtgt    11040
ttaatacgct atcgtatagc actatttaga tttgtgctat tcttgtttat atgcattcat    11100
gtgcatcgtg catctcaatt aggtacgata attgatcgcg tgatgcggaa gacaagccaa    11160
gtcgacccca agcgcgggct aatccgcagg atgatgctga tggacaaacc tgaaaatggt    11220
cgccaagtgg acatcgtcta acaacactaa cctagtgtta cccaggcaag ccccggtgca    11280
tttgccacct cccttgatgt ttttaaaatc tttctcactt gattgctgca ttaggtgaca    11340
ggagttgatt gattaaacaa ttcctgcatt accttccttg atcttgatta ccctccttga    11400
aaacccgttt ttacaaaaag gttttactat gcttagtatt gcttagaaaa acaaaaggat    11460
ttgttttaga aaagatgttt ggcaaagtgg gagggttgtt ttcaaaaata aaacttgatg    11520
gtgaatccat catggctatg atggattcaa catcggaaaa gatgtacctc tgccaggtac    11580 caagttttg ggttaaaaga ttaagctaag accgggcggg tgacttgcac gggaaaggag    11640
tctcggtgta gtgtctccgt ctgagtcgat taaggacctt gtcgatgtag gcttgatgat    11700
cgaggaccct ttaactggtc acatgcctcg tcatgggtaa gccttgcctc gggcagacta    11760
aggccagaat aagataacac gaaatgggcg tggagcggtg gcgagagtag cgtgtaccct    11820
ccgtggcaag aggctggacg gtggtgtaac tgtgctctcg gtttgcgtga acctgatctg    11880
gtcttaagaa ccccggtggc gggttgacat atgcaagggt taagtgctac atatgtcgtg    11940
tgattggaga tcctcagcta agtataatcg attcggatcg ccgtaccttc gtggttatga    12000
agacttggtc actgccctac acgtagcatt ccactaaaga tgatgggttt ttgttaagaa    12060
attggctagt gcaggacaag tgattgaact agggtagaaa gaactctagt tacaggtaat    12120
tctacttaac ttgacaaata aaactggatt ttaaggatcc actttagtaa gcatttctgc    12180
aaaacagagt ctttgattat tgaaaagcct taccttgact cccatataac cagcataccc    12240
ttgagagtct tttctttagt cgggtaagac ttgctgagta attccatact cagggtttta    12300
ttccttgttg tttttcaggt tctaactttg tgctgttgtt gatggtgtta agtgccggtg    12360
ggctcggcct tcttatgagt ctaagtaacc cttctatact tcttattgag gatgatccct    12420
tgagctagca tttatatttc agacttagaa ttttgtattc cctccgatag aggtatgaaa    12480
aatttgtgta acctgtcaaa tttgtcaata atatttccgc taccactttg tatccgtgtg    12540
tgagtttcaa gacttaatct cgcggttctg gttgaaattg gttatccga tgtccttggg    12600 gcaatcggac acatcctgtt aagttatctg gtgcacatgc acagccgtct gaggtctttg    12660
ggacaaggat aggtgcatgt gggcctaata acttgggagg ttctgccaca ggtcggggtt    12720
actccggtga gcaatcccga ccgtgaggag gcggaatccg gtgcaccgag gccagcacaa    12780
gcttcggtga ggggtgaggg acgcctaggg ccaaggcacg ggcacggggc ggggctgaat    12840
cggtcggaca ccgagcgggc gcggcaaacc accgcgatag agctccagcg aacacaaatt    12900
caccgtagag ggaaaagaat cggggcagga agggcctgaa ggtacttact tacgttaaga    12960
gttctgtcag ggatgcttga ctgttgcttt gggggaggat cttcactggg cggtcgttgt    13020 cttttttgttc gtgtgtggat gatgagtgcc acttgcttcc gactggtatg ctctacaaat    13080
ccagtctttc tcaaaatgac attgtttaat ccctgaannn nnnnnnnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnncac gaaatgggcg tggagcggtg gcgagagtag cgtgtacctc    13260
cgtggcaaga ggctggacgg tggtgtaact gtgctctcgg tttgcgtgaa cctgatctgg    13320
```

```
tcttaagaac cccggtggcg ggttgacata tgcaagggtt aagtgctaca tatgtcgtgt    13380
gattggagat cctcagctaa gtataatcga ttcggatcgc cgtaccttcg tggttatgaa    13440
gacttggtca ctgccctaca cgtagcattc cactaaagat gatgggtttt tgttaagaaa    13500
ttggctagtg caggacaagt gattgaacta gggtagaaag aactctagtt acaggtaatt    13560
ctacttaact tgacaaataa aactggatttt taaggatcca ctttagtaag catttctgca    13620
aaacagagtc tttgattatt gaaaagcctt accttgactc ccatataacc agcatacccct   13680
tgagagtctt ttctttagtc gggtaagact tgctgagtaa ttccatactc agggttttat    13740
tccttgttgt ttttcaggtt ctaactttgt gctgttgttg atggtgttaa gtgccggtgg    13800
gctcggcctt cttatgagtc taagtaaccc ttctatactt cttattgagg atgatccctt    13860
gagctagcat atatatttca aacttatact tttgtaatca ctccgataaa ctaatgtaaa    13920
attttttgtaa cctgtaaaat ttggtagtaa gatgttcgct gcaacaatat tggtgtgtgt    13980
gatttgggat tcgttttctc gcggttctgg ttgtaagtgg tttatccgat gtcctttggt    14040
agatcttaca gatcctgtta agttatctgg tgcacgtttt ttggggtctg aggtcttgg     14100
gacaaggata ggtgcatgtg ggcctaataa cttgggaggt tctgccacag gtcgggtta     14160
ctccggtgag caatcccgac cgtgaggagg cggaatccgg tgcaccgagg ccagcacaag    14220
cttcggtgag gggtgaggga cgcctagggc caaggcacgg gcacggggcg gggctgaatc    14280
ggtcggacac cgagcgggcg cggcaaacca gcgcgataga gctccagcga acacaaattc    14340
accgtagagg gaaagaatc ggggcaggaa gggcacgggg atggttcctt accttaggag     14400
tgtgctcggg gatgcttgac acgatgctag gagctccggg cagacgacgc ggtggcgcgc    14460
ttctccggcg agcttgagcg gcggcggcta agcgcgagag aggttgagag tgggtgaaat    14520
taggaagggg agggagagcg ggtgtaggcg ggctcaaaa gggagctggg ggcgtgggta     14580
ggcaacgtgg tcggcttcct cggcgtgagt gcgtgtgcgg gtcagcagcg gttgcgggga    14640
agatgagact gacaaggcgg gcccacagag tagaggcacg agcacgtgtg aggaggaaat    14700
gattcagcgc tgatgggctg ggcccactgc acagagggag agcgggggcg tgcgcgcgag    14760
ggtgagcgga accaataggt cgggcccacc tggcagatgg agagagaggg caggtgcgta    14820
ggctgggctg cttttctatt ttctttttat tctgaatttc tagttccttt tatttttatt    14880
ttctctattg aattcaaatc caacgaaacc acaaattcaa atttgaatat ttcaaacatg    14940
tgcatcaacc aaaaacaaag tttaagctca gcatgatgca acaattcatg tctcccctag    15000
gtttgaatat agtaaagaaa aaaaatacat ctcccaaata tataaccaaa actctattag    15060
aaaggaagaa aataggaaat ctacggagat gagaaaagtg gtaacacctg aatttggtag    15120
atattagaga agaaattta tacccccaaa ttcagggtgt tacataggct ctataatcat    15180
agcgtgtata gatgcatgaa taaataaggt gagcctatga gctatgcgtt tcttccactc    15240
ctgatacatg ccaatcaagt gtttctttga aacaaccttc actggcatgc tttgaggagc    15300
ttgcatagcc cttctgaggt tttgcctttg cctttgcctt tgccatagcc attgctactc    15360
tactgccatt ttgtggtggc ttcgtaaaaa ttcccctct catcccctga ttattacagt    15420
gcccatgacc cctttctctg gagggaccctt tcttcctta agactagaag ttggcgtgtg     15480
ctttatgcat gaccgcgtgc cgaatggatg cttctagtag ttctgcatca gaagctcatt    15540
ctgagcctta gcaccaagca acatgttgac gaggtcacat tatttgtgta cttgttgcta    15600
cagtactgct gttggagcac catattggag gggtagaagg tttggagagt tttctcgatc    15660
atctctaagt ctatggctat ctggccacag aaatgtagct gagcgacaat gcgatggatg    15720
```

```
acagtgttgt aagcctcaac tgcattgaag tcgagagtgg cccattcatg ttgcgcccgc   15780
gggagcatca catgcttctc cacactgaaa cactcacata gctctgtcca caatatcata   15840
tggtctttca cctctggata ctccatcttc aggcctggat ggatgtggtg cccgacgaag   15900
atcgtaattt ttgctttctc atgaagtttc aggcaagtgt cattcgggcc ctaccagaag   15960
atctcctttc ctagctatat cgcctctagg tgaaacttgc agtcgttagt ctaggtcggt   16020
tagttcttgc cattgaggac aagctccacg aatcaattct gttgtcttca accatagtcc   16080
gtcacacaaa attaacttta ggttaattag gcgtgctaat tatcaataat agaaatttaa   16140
atagataaat tgcatgaccc acgggagccg gtccagggcg tgctgacgag gcgtggctga   16200
agcatatgcc gacgagctgc gccccagctg gccgagcaag cgcgacccag tgcggggtgg   16260
cgccgtgggc tgacgcagcg tgaaccatct cagctcgaga tggcgtgacc agcagcaggg   16320
catgggtgcg tgggtcagtg tgacatcaag gcgcagagtt gggggcgccg acatagtgta   16380
cgactagaag ccggcatgac cgatctattc atgaacgcaa cgtgtgggcc accggtgggg   16440
tgggtgtgta gtgcacgcga ctggcgcacg agcctcgcca tcggggtgat tcgtacgacc   16500
cgcggttagt aggacatcga tggcttttta agtaaaagta atagattgga tatattaagc   16560
aggtcaaatc atcaggattt aacatgctag tgtatacata aatcaatcta caatatgtat   16620
ctgacagtaa gaaatcactc tacaatatgt atctgaccgc gagaaaacaa tctagtttga   16680
acaaaatcta ctaaacaatt gtctagagcg gtcaaaaacg acataccgtg cttctttatt   16740
cagcgaacgg aaacgaagcc tatcatgtaa gacaattagg caaggcggga ggacttgctg   16800
tggtgcaatt tccaaattca gaccttgaac cctctcctca gcaatggagg gcttattctc   16860
tttttgtcga ggcagaagca caaaaaacta tttccttgtt atatagacga ctagagcttc   16920
tcgtttgata ttagcccaca taagattttt tgatagtata aggccatctc caactgatcc   16980
cctattgtat cctctatttt attcctatat taaacgcaac tctgtaaata atatcatcta   17040
aaattctgtg ttacctattt tattggataa gtgagtctaa tattttgatc caaacagcgc   17100
ttaatctctt cccttgctgt aagttctcga cagatttagc tgggttaaaa ttcagactca   17160
aagacatata aattgatggg ctggtgttat ttccacgtgg gggtggaccc ctcacgggcc   17220
gggccgcatt cttggccaac catgggctat ccgcaacatt gcagactccg gaatccggat   17280
tggccgaatg ggcccggcag ccgaaaatga aaaggaaag gatcgaccct ctagcgcgat   17340
cgatccccgt gcgctggggc ccaaattagg agaacctcag taccccacgt gatccacggt   17400
ccgcccgccg cgcaagctgg gccacgggct cgcgggcggg catgcgccgg ttccgcgagc   17460
gaccaccccg ccatccgcgg agcctgccct gcgctgccca ccgctcctcc gcctactccg   17520
gcctcagcta ataacgatgg gtggtgggag ccgagccctt tccctctcct ccctctgcgc   17580
caccaccctc gccgccgcca agccccaca gcaccccgtc cccttcgccc cggctcaccg   17640
cgcgctcccc caccgcctcg ccgccgccat gtcctcctct tcctcccga ccccgccgc   17700 atcggtggac gccggtgccc cggcccttc ggcgtccaac gccatcgact tcctcacgct   17760
ctgctaccgc ctcaaggtga gcgactgagc gccctgtttt agtcgcttcg catttccacg   17820
ggccggcttg gttgagatgg atggaaatgt gacgcgatgg atgagattgt ggatgtaatt   17880
gcagacgacc aagagggcgg ggtgggtgaa gcgcggggtg caggcgcccg agtcggtggc   17940
cgaccacatg taccggatgg gcgtcatggc gctcgtcgcg gccgatctac ccggcgtcaa   18000
ccgcgacagg tgatcctgac agtttcgctc tcaagtctag ctcggcagta tttagccttc   18060
```

```
ttacggttcc gttttcatac actgtttatt tatcccttca attacaggtg tgtcaagatg    18120
gcgattgtgc acgacattgc agaaggtatg gtctcaaaag acttccgtct agacggcttc    18180
actgaagttt tggggctttg tgtgagatga gggatgcaat tttgtgaata tgcgagccta    18240
ttactacctg agatgttggt agatggtaac tagaccactg gactggagac ctgtagtagg    18300
aatgtaggat gtgtgttcaa gtacttgtgc caattagttg gttctttgac ctctgctagc    18360
caaagtgtaa aactttaaac tatgtgcaca ttttcctatt ttcattcaga agcatgctca    18420
gcttagaaat gaacacatga ttttgccctc cgctcatatg gactcttgct gctgttccta    18480
agccagcttg cctgtttctg gaactaactg cctatgagga tgtgggttca gttgactcat    18540
ttcaattgtt ttttcttttg gtactccagc aattgttggt gacatcaccc cttctgataa    18600
tgtacccaag gaagagaaga accgcaggga gaaagaagca ttggaccata tgtgcgagct    18660
gcttggtggt ggttcaagag gtgaatactg aaacttgcaa ttgtgataca ttagcatttt    18720
atgctgtagt taattaggca tcttatgcct caaattgtct tttcatgatt tagttatata    18780
tgaaatgaat gtggtgctat tgcacactgg catcatcttt ctagattact caatagtcta    18840
gacttaatga tcccattatg tgtgcatagt accatagttt caaggaaaaa agaacaatat    18900
gtggatgcca atgaattttg tgaatacaat actatatgac ttgcaggtca tatacatatt    18960
ttattttacc cttgaaaagc tattcatctg ttattattat ttcttagatg gtcattttc     19020
catccgatac ttttcacttc catcagggaa gcagatcata acctggcaat tattttgtag    19080
aaatccagcg ggcagctttt gttcttattt tttgatacat agtttaaata agtattggat    19140
aattcttaga gtattcacat cccttagtta ggtgtcaagg aaactcttgg taacttaaaa    19200
tcactcagat tatttccaga gaaactgtta tttatacttc tctttttctt tttataaggt    19260
gtattagtgt ttgagaattt cattcaaaga tatgctttat ccataatttt cccttgcaat    19320
atatgaactc aatatattat caattactac aaaagcaatg tctcactaaa atgcatgtga    19380
aatatgaatc tatagattta tctttgtgca ataaatatac aaatattttg actagtttca    19440
ttgactttt tgaatcctta cgccctacat tttgaaatgg aggttgaaaa gataagggat     19500
gttttttgtag aagccaaaac cgaagagttt atattcagca aatgttgatg actatgagtt   19560
ttggaatttg aacatgatat tgtaattgat ggtgataata ttattccatc tctaatgatt    19620
ttctaccttg aagcattatg gatcgtaaat tatttatgct caaatggcta tcatagcatc    19680
caacatttt tcccctaagag tttcacaaca tagaattcta gtattctggt tgtgttctca    19740
ttattcatat cattaatcgt taaaaaatat tggagagatc cagcatccct tacatgtgaa    19800
gtgaaccttt tagaactaaa taaagtatct tagcagcctt ttggaaacag ttttcatgc     19860
aggataaaag gatgttctct gtacaggcga gactaaagag ttcatgtgat ctttgacatg    19920
gtatatataa taaatacttg cctttatctg catgctgttg tcttgcagca aagaaattc     19980
gtgaactttg gatggagtat gaggagaatg cgtctttgga agcgaaggtt gtcaaagatt    20040
ttgacaaggt acagtttcat atttcaatcc atcaagttgg tggcatgatt gcaacgtctg    20100
tctgaagcta tcagatggta gttcttgtga tcattcaata ggcaatgcat ataactggca    20160
ggatatttaa ctaatgtagg caatcattat gatttatggc cctaacccat atggctccac    20220
ttcttccttt tcctttgcat gctgtaatcc tttgttgcac tgttatattt ccaggttgag    20280
atgatacttc aagctctgga gtatgaaaag ggtgagttca tactggtgct tgaatatttg    20340
aactaacatt tcccatgcac agtagctata agtacaaaac cacaactatt taaatgcatt    20400
catcaaatat tcttgttgta ataaccaaat aaatgtatat agtaaaatca gctcacattt    20460
```

```
cacatttcaa atacagcaca tcttttttctt tgcatcattt gtgcttatat tgggtaggcc    20520
tggtgtagtg gtgagggcag tctcactaag tcactatgtt gccagttcga aacagcctct    20580
ctgcatttgc aggggaggct tgtctcgatt tatcccatct caagaccccca ctcatgtggc   20640
agcctccgcc ctagatctgc ccatctgtgc ttacaccatt atttaatttg ctccacggcc    20700
ttctgggtgt gagaagtgat acatatgatc aatgtactat cacttaacac ctggtgaact    20760
ccttgttgat agatggggtt aacagtatca cacttacgcc tatgtatttt aaaattttca    20820
gagcaaggac gggaccttga agaattcttc caatcaacag caggtgtgat ttttctcttt    20880
ctgttatgct cttctcaatt ttcatgagta tccagtacat aaatcttgct cttctcaatt    20940
ttcatgacaa tccagtacat aaatcttgct cttctcaatt ttcatgagca tcctgtacat    21000
aaatttgaac agttcattta agctgagaag gatgttgcca ttttttttggt cttacactta    21060
aaaatgtttt cctgagataa tataaacatt catcagcaat tcagaacata ttagtgcctg    21120
aatgattatt gctaattgaa aactggacac taccacctat aatggttttc tttaccatga    21180
actgatacat gcctatgcct tttatggttt tcttttatca cgtgcttatg tttgatctca    21240
tttttacatt gtattagacc gtgtccagca gttcacccac ccaaaacact gttttgcact    21300
tagattgcac tattcgcaga gtggaatttg aatatgggga tggtaaactt agcctaggct    21360
attagcatta gagtcattgt gtaacaaaac catatccccg cacctaattc ccatgcaggc    21420
aaatttcaga cagacttggg aaaagcatgg gcagcggaga ttgcatcgag aagaaaaaca    21480
aagtgatcaa acgatgctca ttttaccacg tcggttccaa gacaacttgc tggcacagca    21540
tttctgttga actttgcttt tactagatga tacttcgagg tggcattgag acgtagggtt    21600
gccttgggaa tgtgaacttc accacatttc ttggtcctgc cctgaccctg aggcatattg    21660
ggcttgcgat accagggctc tagataagta agataaccca ctttgggtat tggttgtaga    21720
tgctcctgcc aagggcagtt agctggatcc aacgggaagg ttcagcacca gctggtggtg    21780
atgtaaaatc cttcacttca tgaattactg taccattacc gtttctcttg ttaatccagc    21840
ctcacggttt cggcctttttt taatgtaatt ctattgtttt caagtataat gagcctgaat    21900
atttgctata tccattttgg ttgttgatga tgacctgaag tgcattcata ttttcatagt    21960
acgtataatg ctgaagccta gaagctgacc actgatagtt ccggtgtagc gtcggatcgc    22020
atgtattagg gtctgttcgt tttatttttga atccacgtgg attagacgga attgagtgag    22080
ttttgaaagg atcacgatgc ccaagaggag ggtgaattgg acttttctaa aaatcaacac    22140
taattaaaat ctaagcaaga gtccaacttc accccgataa ctatcactaa gagaataata    22200
atagaaatac aacaatgtta agacaatatt tcaaatactt gctaaacaaa tacacaatgt    22260
aaaatgttttt aattaagtgc ggaatgtaaa gcaaggttta gaagactcca attttttctcg   22320
aggtatcgaa gagtcggcac tctcctctag tcctcgttgg agcaccctcg caagggtatc    22380
actccccctt ggtcctcgca agaaccaagt gctcacaacg gatgatcct ttgccactcc    22440
agcgcagtgg atccctcacg accgcttaca aacttgagtc gggtcaccaa caagatctcc    22500
acggtgatca ccgagctccc aacgccacca agccgtctag gtgatgacga tcaccaagag    22560
taacaagcca tagactttca cttgaccaag agaagcctaa tgcatgcggt gtatgctcta    22620
ggtggctctc gctagcgcta ataaggtcca aatgcgggat taagattctc aaataacctc    22680
actaggcttt gtggtgcttg caatgctcta ccaatgtgta ggagtaaatg tgggtagcaa    22740
gaccatcaat atagtgggtg gaggggggtat aaatagcccct cacccaccaa ctagccatta    22800
```

```
ccaggaatct gctgcacatg ggcgcaccgg acagtccggt gcgccaacgg tgcgccaacg    22860
gtcgactcca atggctagtt ctgacagcta gccgttgggc agatggcaca ccggacagtc    22920
cactaaaatt caactcgcga acaacgcgct ctcaggtttc tgtgcgcagg aaccctctt     22980 ccttgggcca ggctggcccc actggcagag ggtgcaccgg acagtccggt gcacaccgga    23040
cagtccggtg ccccaaagcc agaaaccct agtttctgttt tgtgctgttt tttcaattcg    23100
gttttcgttc taacttgtga gtatgttcta gagtggcacc tagcactata tgtgagtgtg    23160
aatatgcacc aacactacac tagaactctc ttggtcaaac tactcatcga caaccctct     23220 ttatagtacg actaaaacaa aataaaagac ctaactatat cacgagtgtc cgcaactcct    23280
tgacactcgg aatacgaaga ccttcacttt ttgttttgtc gctttagccg tcgcttcaag    23340
ttcttatctc cgagattgtt ttcaccgttg tagtacatct acatgtaatg cgacctaact    23400
taccatttgc ctctgcaaaa cacatgttag tcacatataa aattacattg tcattaatca    23460
ctaaaaccaa ccaggggcct agatgctttc aatctccccc tttttggtga ttgatgacaa    23520
cctacaagat tgtgagagta gtttgttttg aaatttctgt caatagagaa gatggttagt    23580
tatactcaaa aattttgac agaaagagtg tgtaacataa taataagagt gagtgcatac     23640
acattgtaag tttcttgttc atataaaagt gaaatcaaat cgatgaacaa gaactagaga    23700
ctggtgataa catataaggt gaaaacacaa tacacacaca gtcaacataa gcatcgagag    23760
catataatag agtttgtgag ccaaaatcgt catacaaaag tggatctagt acagagagta    23820
tcaagcacat atattacatc aaaatgactc tatactaact ccctaactcc ccctagctct    23880
cacaactctc atatctctcc cccttttggcg tcaaacacca aaaggaaacc tgaacctaca    23940
gaccagaaga ggaaggaggt ggctggggcg catccgatca cgatcgtggc agaagagcaa    24000
acgccagctg agggtcagag tcagcctcgg atccaggatc taccgtagaa gctggagcta    24060
gtactgactc ggatggaggc tgtgctgcag gagctaccga agctgaagag gtcacagaca    24120
ccgccacaac agcagtggta acagcaggag ctggtgcac tggcggctga cgctgatgg      24180 agctgatgac cggcgacgag aaaaccaggg tgaccggcag gagcggagag gaagaaggac    24240
caaatgaagg tagagggggt cctgcctgaa gggctagcac aacagcggcc tgaagatcta    24300
gagggggtgc agactgaaca ggaggaatct gagcaccggt atgctgaagt atgtgagtca    24360
tgaaggcccg gttctcagcc ttgtctgcca aaagctgctg ctgcagagtg tcctgtctgt    24420
cctgaatagt ctaaaacatc gatagcattc tctcggacat ctgctgttgc accgctgcca    24480
gatgagcctg ctgctgagta agagtctgga ggatcgcagc cagagcaggg tcaatggcag    24540
gaggaacagc aggggcagca cgagaactcc gggcctcatg gtcatgtgag cgtggaggca    24600
caggaggcag aggcggaatc ccaaaatcat catcatcatc atcatcatca tcgtcaggaa    24660
ctgctgcgcc ctaagtctca aactgatgga aacttgtatc ctctgcctga atgtctgtca    24720
ctggatcagg tactggtact ggatcctcag gggctggatg gtaggagcca aataggaggc    24780
gtgaggcctc aagggtgccc tggaactatg gtggtcggat cagctgtgcg aagatgtggc    24840
agagataatg agcatttggc agctgtcgcc gagcacgaag accatccaat accgtgtcct    24900
cgatctcaca ataaggaag tcaacaacat caaactctga atgaaagatc agggcaccga    24960
ggagccaaag ctgaatatga gtggtagcct ctctataacc catccacgac agaagcgtcc    25020
gtctcatgag ctgatataag tacttggcta ctgtagtgaa atctgccgga gaacgtcgcg    25080
acccatctga gaagggcggt cggaacaaag ccgcgatgtg agctgtagct ggagcaactc    25140
cgtcgtgagg gcgacgagga ggatcagagg taccatagca caagctatga agacaagtcg    25200
```

```
atgactcatt gaatccaaac agctggcgaa tctagctagc atgaagtgta acatcctctc  25260
gctcaaagcg gaacctcatc cactggtgat cggggtcgat ccatactgac gcattgaaca  25320
cacggaccca ctcctcaaca tatctgccgc tggtagtcag aagagtgaga agtcccagca  25380
aatatgtgag atgcatctca gagtctgcac cagcggctag cagaacacag gaagacccaa  25440
tagccggtgc gctcgcagaa gcaatctggg ctgaccnnnn nnnnnnnnnn nnnnnnnnnn  25500
nnnnnnnnnn nnnnnnnnnn nnnnnnnnnn nnnnnnnnnn nnnnnnnnnn nnnnnnnnnn  25560
nnnnnnnnnn nnnnnngttg atgatcagct tgattcgtta ggataaaacc ctgagtatgg  25620
aattactcag caagtcttac ccgactaaag aaaagactct caagggtatg ctgggtatat  25680
gggagtcaag gtaaggcttt tcaataatca aagactctgt tttgcagaaa tgcttactaa  25740
tgtggatcct taaaatccag ttttatttgt caagttaagt agaattacct gtaactagag  25800
ttctttctac cctagttcaa tcactggtcc tgcactagcc aatttcttaa caaaaaccca  25860
tcatctttag tggaatgcta cgtgtagggc agtgaccaag tcttcataac cacgaaggta  25920
cggcgatccg aatcgattat actcagctga ggatctccaa tcacacgaca tatgtagcac  25980
ttaacccttg catatgtcaa cccgccaccg gggttcttaa daccagatca ggttcacgca  26040
aaccgagagc acagttacac caccgtccag cctcttgcca cggagggtac acgctactct  26100
cgccactgct ccacgcccat ttcgtgttat cttattctgg ccttagtctg cccgaggcaa  26160
ggcttaccca tgacgaggca tgtgaccagt taaagggtcc tcgatcatca agcctacatc  26220
gacaaggtcc ttaatcgact cagacggaga cactacaccg agactccttt cccgtgcaag  26280
tcacccgccc ggccttagct taatcttta accaaaaact tggtacctag cagaggtaca  26340
tcttttccga tgttgaatcc atcatagcca tgatggattc accatcaagt tttattttg  26400 aaaacaaccc tcccacttg ccaaacatct tttctaaaac aaatccttt gtttttctaa  26460 gcaatactaa gcatagtaaa acctttttgt aaaaacaggt tttcaaggag ggtaatcaag  26520
atcaaggaag gtaatgcagg aattgtttaa tcaatcaact cctgtcacct aatgcagcaa  26580
tcaagtgaga aagattttaa aaacatcaag ggaggtggca aatgcaccgg ggcttgcctg  26640
ggtaacacta ggttagtgtt gttagacgac gtccacttgg cgaccatttt caggtttgtc  26700
catcagcatc atcctgcgga ttagcccgcg cttggggtcg acttggcttg tcttccgcat  26760
cacgcgatca attatcgtac ctaattgaga tgcacgatgc acatgaatgc atataaacaa  26820
gaatagcaca aatctaaata gtgctatacg atagcgtatt aaacacctag tggcgaggcg  26880
ttgtacaatt ttgtacggaa acactagtta ttaatatgcg actacgcgca atgattacgc  26940
ttctcgaacc taacgcaaac atcacgaaca acaaactata cacaagaaat ataattagcc  27000
taatcacaac ttatcagtta attaattaaa ttctgaacta atcccttgcc ttataaatta  27060
tactacatct ttataagtga ttaaaatatt ttatcaacac atatgcctac taaaattcta  27120
ctcggtccac taattcagct aagtgaccgg aatagcgaaa taactcgcta taactgaacc  27180
tggctcgata atcgcaagaa ctgcgaagtc gacgagagtt tcgtgactta cgcaatttat  27240
cgagcaccct aatgagcctc gcactaacac attaacttat tcaacgatcg aactattcta  27300
aacaattcat cagcttaccg tttcaacagt tgacacgaat ccatgagatc ggcagtgatt  27360
tttcgatcca cgcaatttgt cgagcgctta gggaatatcg cgctgctaac ttcgtcttca  27420
cccgattctt gggttttctt ggggacgcac gagcgacgat gaccttcgat tgaagtctgg  27480
ggtaagctgg tgaggtgggg atcgagccgg agatgacgtg tttgacaact cgacggcaaa  27540
```

```
cgacgagatc gacgacgtga ttggaaatta aagccgagcg agccgagagg gcacgctggc  27600
gagcaggaaa ccgtgcgagc acaagacagg aaaaaacgac ggctcgacaa cacgcgaagc  27660
gacgacagtc aaatcggcaa caaagagttg gcgaattcga tgaacacgac cacagtcgcg  27720
agttaacgcg gtcaagacaa ctgtgaccaa cgagcttgcg acagaagcga tgatggtgtg  27780
agaactcgac acgctgtgac gagcagataa aattcgtgcg cgcggcaaca aagaaagagc  27840
gagctacgcg tgagcagaga gctccacacg aaaactcgac gcgcgcagga actacggcga  27900
gctagagtag agaaaactcg acgcgcgcag gaactacggc gagctagagt agacagtcat  27960
gggagatgta gtcatgtaga gccgagctgg gcgacaaagc gaaatccagg ctgaagcgtt  28020
gacgagcaaa gagcttcgcg cgtgcaagaa caacagaacg ctatgcgcgc gacgcaaagg  28080
cgagcagtaa gacgacggcg cgacagacgg aaccaagcag ggagcgccgg ccatgggcgc  28140
ggcaatagag ctgggcgagc tcggagggga agccacggca caagaaatcc gatcaggcgt  28200
ggccgaacag aggtgccgcg gcacaggagc tcagggacgg acgagcagga gcagaggaga  28260
tggataccgc gagcagcctg cagggaaccc cgcgccatgg gagaaaagca gagccgagcg  28320 gctgggggatt cagccagcga gcagagggga gatgggaagg agctgctcgg ctgcggcttg  28380
ctgccgggcg tgcgtggaga agaaacctgc gcgctggaga tttgtaggag accaaggcc  28440 gtggcgggat aaggatagga gcgctcggcg gcgtgattt tatttctagg ggttgcgcgg  28500
cgcggtacag aaaaatcagg cgacgagatt aagagatgc agtgagcagt tcgacaaatt  28560
cgtcggcatg gacacaagct gacgacgacg gccagcccga ccgcggcaag gtgaggggag  28620
acgcggtctg cgcaaagggc gagctcgagc aaggaactag agccgacgat gtccacgacg  28680
agcaggacca gagacacggt gctagtggat ggaaactgag cacaggatgg acgcaagctg  28740
gagacgagct tggtcaggtc gtcgggcaca gaggtgctcg gagggtccga cgagcacagc  28800
cggcagccgg ctgcctttgg atgctgatgg atggaagaaa tgctggtcgc tgggtaaggc  28860
tggaggagag acgtgcgtga gattttccag cgagctagcg tccaatggat aagagagaag  28920
gagacgtgag gaagaggaga actacgtgga gaaaatatcc aggctagtga cttcagatat  28980
ggaagggaaa agcggtggat aaaatcagag agaagagcgg ttgcagatat tttcttcctt  29040
cgttttcttt tactcaaaaa tttgaataaa aatacaatta tcagctggag attgggacta  29100
gaatttggaa agatgtaaga ggactaaaat taaaaatgat tttagttaca atgttttaat  29160
cggtgttaca tttaattgaa atcagataaa aacttatccg tcaccaaaac acagttgatt  29220
tggttatcct acattgcggg ctaaagaaca aattagatca tatccccgcg cacgatcttt  29280
ctcagacaat gcgcgattca gattatttta ccctgaacat tttagtcgtc aagttcaaat  29340
taatttgctc gaaataagat cattcgagtg agttcgggct tccgaatttg tgttcgcgcg  29400
agcgatggat tttaaatact catcggacgc accgattttc ggaacagcta ggttccgaac  29460
attacgaaaa tttaggaaga gcccggacag ataaaaaaat aaaaacgatg tcgcactcgc  29520
gacaaacgac accgatgcga tattaaaata gcgataagcg acaatgatta aaatttaaaa  29580
ttcgttttat ccactgatat tgcgtgctta aatccgaact cgttgttgag cggaaaataa  29640
acacctgggg tgttacacac cccgtccaat ccctggaccg gcgtactta ctcctggcag  29700 ctgtctagga tcatatattg tccccacaga ccaacacgag tcttttgtgc gcactttgtc  29760
ctcactcatg cgcacccgag aaaacttccc ggtcggtcac ccatcccaaa ttgctccaag  29820
ccaagcacgc ttaacttgga ggttcttccg agataggctt ccgaaaaaga agatgcacct  29880
tgttggtatg attacactat taattctatt aagccttggg ccaggacatc ccatcccagg  29940
```

```
ggccaggata tcacaatcca ccccccttag aagaccgacg tcctcgtcgg tcaaccccaa    30000
tccaggaacc tccccctcttg gccacgtctg tgtgtctagt gccgtcatat gccatgccat   30060
gtgaccactc cgggcccaca tgtgccatgc ccatatacc cgaacccct agcccacaca      30120 cgcccgtgaa accgcgagtg tcggctctga taccacttgt aacacccgt ctaatccctg     30180 gaccggcggt acttactcct ggcagctgtc taggatcata tattgtcccc acagaccaac    30240
acgagtcttt tgtgcgcact ttgtcctcac tcatgcgcac ccgagaaaac ttcccggtcg    30300
gtcacccatc ccaaattgct ccaagccaag cacgcttaac ttggaggttc tttcgagata    30360
ggcttccgaa aaagaagatg caccttgttg gtatgattac actattaatt ctattaagcc    30420
ttgggccagg acatcccatc ccaggggcca ggatatcaca ataagtgtcc cgcccagagc    30480
gccccctccg ccattcactc acctccagtc ccgttctcat ggccagaacc ctgccatcga    30540
gttcgtcggg tcccctcac cggtctggcc aactccagcg accccagacc ccctggggtc     30600
cgcgcttgtc tcgtctttgg cgacttcacc gctgcggatg gagcagcgcc ggccgcagtg    30660
ctgttaaccc ccctgacgcc taatcctagc cgtttagcct tgatctagcg gtctagatcg    30720
ctggatatcg cttcacgtgg gtgcccttgc ccctgggccc cacttgtcag tcatctgtgc    30780
cctagcgctg ggcccgactg gtcagctcgt cctcacctcg gatcatcact tggaaacact    30840
atgtagcagc atgaatgcaa caatcatgac acttctagag ctcacaccaa tatagaacca    30900
aaataactct ctactgtttt gataaaggga aagaaaagt gaataaagga aagggtaaca     30960
cctagatttt gagtatagag caaggaaatt tttataccc aaaattcagg gtgttacagc     31020
tacgtagtga aaccttgccg actcaccttg gtagtgtttg agggtttgat cgacctgagg    31080
caaaaaggga tcacgacttg tgggtaaagt gtgcaacctc tgtagagtgt tagaagctag    31140
tatatcagcc atgctcacag ttatgagcag ccttgggagc tcctttgatt agagttactc    31200
tggatacttt tatgatgatg cttaatgatg gtgattatga ttatgaattc ttggtatttc    31260
ctcttggagg gagtaatgtt tgggtttata acttggggtt attgctaaaa catggctctc    31320
tactggtaat aaatacctaa ccaactaaaa gcaactgctt taagcttaac cccacataca    31380
gctagtccac tttagccaaa caggacattt gttgagtacg ttgaggtgta ctcaccattg    31440
cttaaaaaca ccaaaccca ggttgtcccc attgcaacta gtgctcagga gaagatgaag     31500
gcaacgtgga ggacttttcag gagtttcagg acttcgacga gttctagact agattagtgg   31560
caaaccctca gttagctgcc tgtgaaggcc ttatcgtact gcgtttcgtt caaaattttg    31620
attatgacct aagttaatga ctctgtggat gtcttggaca tccactacta gaaatatgct    31680
tatttaagac atacatctta agacaaatat cagtgcattt tatagaagcg tcttttatca    31740
tatggtgcta agtacggtaa gacggtttgt tggatatccg tctttaatga agaaggtttt    31800
tgaggcagat atatggttgg aaatgtctta tattgattta atacagtttg atgttgaaaa    31860
ccgtctcaaa taaatatacc ttttgaggca ttaagtttac aagaagtgtc ttttattttg    31920
gttagtatat tagacacttc tgtatatgaa accatctcaa ataaagatat tattagagtc    31980
atctagacta tacaaaattg tcttagatgt tagtgagtat actagaaact tgtaaacata    32040
aaaccgtctc gtacgatatt tttgatagga catattgtga aaaaacatag tcaatagtaa    32100
attctgatta gattgaacta aacattttt ggaatttaaa atgaactagt tagctgactg      32160
tatgttcgta cggtttctat atatcatata ggtaaaaaat cttgcttaaa taagaatctt    32220
cttcaaataa aattatacgt ttgaaatatg attatttttt attttctcat caacagtatg    32280
```

```
tttatagtta aatatcgtc tctttgtacg gtataagcaa cctgataagc ggtggttaat    32340
gccacgaata tttctcttta tatacgtatt gcacatatat acaatacgtt ttattaatat    32400
agcggtggtt aatgccatct cctgcgtccg acgcccatcg ccgaggctga gaggcaagat    32460
ccgtcgtctt cagtgccccc agcgcggtgc tccaaactcc caggctatgc ttttgtttat    32520
gttttattgt catttcatga ttcatgacat gacaggctct aggctatgct ttagacattt    32580
aataagtata ttcagctcaa acgaaacggg atctaaacca gagggttaaa ggcatgtttg    32640
gtttgtggct aaatgtgcca cactttgcct aagtttagtc gtccgaattg aataactaac    32700
cttagacgaa aaagttaggc aaagtgtgat aacttaggta gcgaacaaac atgccttaag    32760
tctcacatct agggatggca atttaatgcg tggatagtga tatccgtcgg atattcgacc    32820
cgacggatca ggatatggat atgttttttg acctgcgggt tagacccgta cccgatccga    32880
gataaagcag acatggattt ggatattaaa cctcacccgc gggtaattcg ttggatatcc    32940
gaaattaacc attagtccat tactgtcgat ccacacatgg acaccaatga acaaatcgcc    33000
agcccaccat tgtccattgt gcccaggcgc caagcgccag cccattgccc actaaggcat    33060
cattccgcca aagacccaaa gtggcaaaca cccaaaccga caaacactaa tgatctaatc    33120
cccatccccc agcggcagc ttccgagcaa accaactcat ccggtcggtc atccactcat    33180
cctcatcccc tgcccatctg atccgatcag tcatctcatc ctcatcccct acccgatcgg    33240 atccctgct catccgccga gcaccaccaa gcagcaggct ccagtcgtcg agcaccagca    33300
ggagcacgac acgccgccca gtaggagcac ggccaggagg acgacgcccg catcctgcct    33360
cttctcctgc tactggagcc tctactgcta ggagcacggc taggaggacg acgcccgcat    33420
ccagcaggag caccagcagg aagaggacgc ccatactgct gtcgttgagc gatgatctga    33480 tgcccccat catggctctt ctcctccctc gcggcctcgc ctcgatctgc tgctgccgga    33540
tccgagcgcc gtgcccacgg gtcacgacca gcgatatgca gggatcaaga atccaacttt    33600
gagaaaaatt gcttgagatg taaatggcgc caccggagta ccatcagtac tgtgacggaa    33660
cctcccaagt aattaggccc acctatagtt gtccttgtcc aacagacatc agacaccta    33720 tagatgttcc taaatcactt cacaagttcg gtatcttctt tcttaccttt ccaggaacgt    33780
ttcacccatc ttgcagacat tacagaacat cggagatata gaaatgcaga agcgattaca    33840
taacttacat ttatttaaaa agtaagatca agttacttat tacagaccag agttatccta    33900
gaagtgcaga gtaatattat tacaatacca agggaggcaa aaactcctcc cgatggtttt    33960
taaacaaaag ttctatatgg aggaccaagt cttcccgcgg cttcactctt gttttcttc    34020 cttgggaacc accttggagc agaagcaaca aaaatttgtc gcttcctcac ctaaaaacaa    34080
cggaggaata aaccatgagt atggaattac tcagcaagtc ttacccgact aaagaaaaga    34140
ctctcaaggg tatgctggtt aagggagtca aggtaaggct tttcaataat caaagactct    34200
gttttgcaga aatgcttact aaagtggatc cttaaaaatc cagttttatt tgtcaaatta    34260
agtagaatta cctgtaacta gagttctttc tacccctagtt caatcacttg tcctgcacta    34320
gccaatttct taacaaaacc atcatcttta gtggaatgct acgtgtaagt cagtgaccaa    34380
gtcttcataa ccgcgaaggt acggcgatcc gaatcgatta tactcagctg aggatctcca    34440
atcacacgac atatgtagca cttaacccctt gcatatgtca acccgccacc ggggttctta    34500
agaccagatc aggttcacgc aaaccgagag cacagataca ccaccgtcca gcctcttgcc    34560
acggagggta cacgctactc ccgccaccgc tccacgccca ttttgtgtta tcttattctg    34620
gccttagtct gcccgaggca aggcttaccc atgacgaggc atgtgaccag ttaaagggtc    34680
```

```
cccgatcagc aggcctacat cgagacggtc cttaatcgac tcagacggag acactcacc    34740 gagactcctt tctcgtgcaa gtcacccgcc cggtctcggc ttaatcattt caaacccaaa    34800
gtttggtacc tggcagaggt acatcttttc cgatgttgaa tccatcaagg cctttgacag    34860
attcaccatc aagttttatt tttgaaaaca accctcccac ttttgccaaa catcttttgt    34920
aaaacaaatc cttttgtttt tctagagcaa ggctaagcat caaaatcctt ttgtaaaacg    34980
ggtgatcaag gatggtaatc aaattcaagg aaggtaatgc aggaattgtt taagcattca    35040
actcctatca cctaatgcag caatcaagtg agaaagattt taaaagcatc aaggaggtgg    35100
caaatgcacc ggggcttgcc ttcgttagta ggtgagttag gctcggtccc gcagatatcg    35160
aagtagaaac aattgccggc ctgagaatcc gaaggtgggg gtgtcttctc ttcggtcact    35220
tcaatctctt cttcgttttc taaatataac catataggta tatatatata taagaatgaa    35280
tgccatgtaa tgctcatgag agtgcgaaga taataaagat ttattatcta agtcttgaat    35340
acaactttcc ttcacggaac tccgagaact tagggttttcc ggagtcagta aaggagttca    35400
aagggcaggg gggttttagg ttctaagtat caaacaaggt ccaaatcaac ccaaattcta    35460
cccaaggcct ctaaataatg catagaactt atgtaaaaag tttggacatt tttggaaatt    35520
ccatttattt tctaaaaatc caaaaccact accttaaact actttaaata ccttaaaatt    35580
ccttagttaa cctaaaattc atataactat ttttattaaa ttctatggaa ataagaagc    35640 ctaggaaaat tggtttcaca atttttaggat ttttctacaa tttttaaaaa atttccaaag    35700
ctctatagaa aaagaaaagg aaaaagattg aatagtgttg ggctgattct agcccagccg    35760
gcccagtacc aggggaaaac gcgcgcgcgc gccctcgccc tggcgacttt gcacagaggt    35820
cctcggggtt tggctaatta gaactggctt ctatcactat tacactgtgt cgctgacaga    35880
ttgcagagaa gcccctgcag ttctaactct tcgcagaggg aggtcctcga cggcgttcac    35940
gcccagccga actccggcga gtgcctgcac cggccgaacg gggcaacgac tagggttccc    36000
gagcggcgga catcaaattg gacctagccc gagcatttcc cctaacctaa ttccatctat    36060
ggcccaatgg cttgctctgg ccacggtggc cgtgaacatc gcggcaagac agtcgcgttc    36120
ccggcgacca aagggctcct agctcgattg tgtgggtcgg caagcatcat agacttaagg    36180
gaaagcttaa acgagggaga gaaggagacg aactgaccgg aataaggctg gccgaggtga    36240
ggttcggttt cgggtggcgg agaattgatt tggggcgaat tcaaaattcg tgagctcggg    36300
cgaacaattg ctagcaatac gtggtggctg ggtgggtgat gatgttgtga agctctctgc    36360
ggggtcaatt tatagatccc aggggcggtg gcgcttaatt tgagccgaca gtgtgggcgg    36420
ccggagataa ggaagatcat cggcttcgcg atttcgtgtc caccgccgtg gcgggctcac    36480
cggcaatgat gagacaacag tggggagtca cggcgatgcg acagaggtgc tcggatacat    36540
ggtgtaaggc cgagcgacgg tgatccccgg cgggcttatc tgctcaagcc gcacggcaga    36600
ggggaagtac tggggggttca ccggagtgcc gtccagcgca tgcctttacc gagcgatctt    36660
atctggtcac cggcgacgtg aatcacaacg gcggcgacgt gaatctcagc gaagatcagt    36720
cgtcggcggt gagagactac cgcgctggct gtctgatctc cctggtagca ctgtaccatg    36780
gagagttata tttagacagc ctgacagtca agtttggagc ccaattttct ctcaatttca    36840
aataacaact catccagtga cctgcagcaa agttgtagag ctacaatcca gctataactt    36900
tgctacaatg tgctccccaca aaagtcact ggatcttgct taaaattaag ccctaagttc    36960
atgtcatccc actgttaatc tgaatttcag atttcaagca gtctgacagt ccaactttag    37020
```

```
gctcaattat ctccagtatt ttcttaacaa ctatgctcac actcttaaga aaagttgttc    37080
tcctatgatt gggctataat tttaatgtgg tgacctaggg aaaaaaccct atgatttaaa    37140
agttacaagg ctcaaaagtt gagcccataa cactatttt cagacttagt ataaaatctc    37200
aaatagggtc cttttgcaa atgaggccaa aacttagggt ttggcttgta aattcacata    37260
tgagtgaccc aaatgactta agatacttat ttaacttggt ttttgcactt tagtccaaaa    37320
gtggactaat tttgcacata agccctagg gtttggattt agggttttct agggttccga    37380
ttagggtttt tggtatccca gaggtataaa tgtggttcaa ctttattctt gggaatattt    37440
catgactatt tccctagagc ttttaggttt tctcaatttg ggttatatct tacccctta    37500 atccctattt agggttaaat tccctatcta ggttctattt gcaaacact aaaacaatac     37560 aacttgtttg aaattttac ctagtgaatg cactctaggt gtgtcaaaca tatgcaatgc     37620
caatgtttat gatgctatgc tcaagttta gttgcagtaa caccaggggt gttacatcct    37680
tccccccata aaagaatctc gtcccgagat taaagtcct agggtaagta atggaaaagg     37740
aaacacgaca tactttatt tccttatttc tggtacaagg caggggtggt tttggaatca    37800
ctcctttatt acaacagcta tacaggcttt acaatttaca agaagctaaa aagcctggga    37860
aattcttatc taaaaagtct tgagtttccc atgtagcctc atcttcggaa tgttggttcc    37920
actgtatctt ataaaacttg agagttttct ccgggtaacc ctgtccttt gatccaagac    37980 tcgaataggg tgctcagaat atgtcaagtc cggttcaagg acaacatctg tcacttcaac    38040
ggttcgatca ggaacccgaa gacacttctt caattgggac acgtgaaaca cattatgcac    38100
agcaaacaag gttcgggta actgaagtcg gtatgccact ggcccatatc tttccaggat    38160
aagaaaagga ccaatatatt atggtgcaag cttccttta actccgaaac gcgatactcc    38220
cttcattggt gaaccttta agtagacata gtatccttca aggaaatata agggcattcg    38280
ccgtttgtct acgtaactct tttgacgagc ttgagctttc ttcaaattat gaattatcct    38340
ttgaactctt tcttcagtct cttcaccat atcaggcctg aagaagtacc tttcaccagg    38400
ttcagaccaa tttagcggag tacgacatcg tcgtccatat aaagcttcaa agggtgccat    38460
cttgatgctt tcttgatagc tattattata tgaaaattcc gctaacggca acattcatc    38520 ccatttttgt ggaaattcca gaacacatgc ccgcagcata tcttcaagta tttggtttac    38580
tctctcagtc tgtccactgg tttgaggatg gtaggccgaa ctatggagca acttagtacc    38640
caaggatttg tgaagtgctt cccaaaactt ggctacaaat tgaggtccac gatccgacac    38700
tatgggtctt cggaacacca tgcagactaa gaatacgagc aatgtacaaa tgggcataga    38760
cagtaaccgg gtgatctgtc ttgaccggta gaaagtgagc aattttcgta agccgatcaa    38820
ttataaccca gatagaatca tacccttttg tagtcctggg taatcccaca atgaagtcca    38880
tactaatatc ttcccatttc tatgttggga tcggcaaagg ttgtaatgga ccagctatct    38940
tcatgtgtat ggccttgaca agtctgcaag tgtcacactt agccacatag cgtgcaattt    39000
caattttcat cttcgtccac cagtagtgct gctttagatc atgatacatc ttagtgcttc    39060
ccagatgaat agaatagcga ctaagatgtg cttcatctaa gatttgctgg cggagttctt    39120
cattcttcgg caccactatg cggttattga accatatcac accttgatca tcttctttga    39180
aacatttggc tgttccagcc attatcttct cacgtatgtg cttcatacc tcatcatctt     39240 tttgtgcgtc aattattctt cgtatgatga ttgactccag cttcaaatga tttgaagtcc    39300
catgttgaat cattcccagg tttaatttct ccatctcctg gcataatgta atgtcagaag    39360
tcctcactgt taaacaatgg caggaagcct tgcaattgag cgcatctgcc actacatttg    39420
```

```
cttttcctgg gtgataatgg atttctaatt cataatcctt gattagctcg agccatcgcc    39480
tctgtctcat attcaattct gactgggtga agatgtattt caagctttta tggtctgtat    39540
aaatatgaca gacattaccc agcaaataat gacgccagat ctttagggca tgaaccacca    39600
cagctaactc cagatcatga gtaggataat gttcctcatg tcggcgcaac tgccttgaag    39660
catatgcaat tactcggcct tcttgcatta gcacacaacc gagtccactg cctgatgcat    39720
cacaatatac atcaaagggc ttggtgatgt ccggttgagc caataccgga gtagtggtta    39780
ctaatgtctt caattgttca aaagcttcat cacactttga agaccaattg aacttaatat    39840
cattcttcaa taaacttgtg attggcttca caagcttaga aaaatctggt atgaatcggc    39900
ggtaatatcc agccagtcca aggaaacttc ggacctgatg aacagtggtc gggggtttcc    39960
actccaaaat gtccttgact ttgctgggat ctaccgcaat cccectggca gacaatacat    40020 gtcccagaaa ctgaatttcg tccagccaaa acacgcattt gctaaacttg gcatataact    40080
gatgttctct caagcgcgtt aacacgatcg gtaaatgttg ggcgtgctcc tcttcattct    40140
tggaatatat caaaatatcg tcaatgaaga ctaccacaaa cttgtccaac tcggcataa    40200 ataccgagtc catcaaatac gtgaagtggg caggagcatt tgtcaatccg aaagacatta    40260
ccaggtattc aaataatcca taccgcgtag tgaaggcggt cttggtata tcttcgggcc    40320 gaatacggat ctggtgatag cccgatctga gatcaatctt ggaaaatacc cttgctccag    40380
tcagttgatc aaataaaatg tcaatccttg aagagggta cttgtttttg atggtgacct    40440
cattcagggg tcgataatcc acacacattt gtaaagtttg atccttcttt ttgacgaata    40500
tggctggaca accccacggc gatgagcttg gccggataaa tccttctca agtagatctt    40560 gtaattggat cttcagttct gccaactcat taggaggcat tcggtacgat cttctagata    40620
ctggagccgt accgggtttc aactcaatta caaactctac ctcccgttca ggtggcagtc    40680
cgggcaaatc ctcgggaaag acattgggaa actcgcatac caccggaata tccttgattt    40740
ccggtataat ggcttcataa gctctgccag tagctttggt tggaatgggg ataggcaaaa    40800
gaatttcttc ctggttatga ctcaacctga taattctctg atcagtgttg agagttgctt    40860
tatgtctggc taaccaattc atacccaaaa tgacatatat atcttggcct ttcagaatga    40920
tcatattagt aggaaagtcc catccggcca aggttacggg cacttgatag gccacttctc    40980
tagtaaatat ttgtccccct ggtgagtgaa tttttaaacc cctcttttga ttcatggcat    41040
gagatgcaat gttgctccac aaatttcttg ctgatgaatg tatgcgaagc accagaatca    41100
aagagaataa ctgcgggatg attggccaca agaaacgtac ccatcattac cggctcaccg    41160
tccggtgtag tggccacttg cgtataatat atgcgtcccg tcttctttgt attttttgccc    41220 atattatttt cctggcttg agatgaattc ccagatcctt gctgattatt tgactggttc    41280
tgctttggat aagggcaatc cttgataaaa tgcccagatt tgccacaatt gaaacatcca    41340
gtcgacgagc tgggtaaagc agggaatcga gtgcctgggg cacccggctg acttgatgta    41400 gtagggcat tattgggacg aataaagact ggctgcttaa aaggaaagga gggtggacga    41460
gcgaaagaac gattctggtt agaaggccgg atgacgaacc gttgcctgtt caccgggccc    41520
tgactagacc tgtcacctcc aaaacccttg gatttaccag cgcctgcata cttcgcttct    41580
actgccagtg ctgtactgac agctcttcca taagtaagat ctatgcaggt tgccatcttc    41640
ctttgcagtc gatcatttaa tcctctcata aagcaattct tcttcttcaa atcagtgttc    41700
acttgatcga ttgcatattg tgacaaatga ttgaacttat tgagatactg gttaacagta    41760
```

```
tcccctcctt gtttcagctt cataaactct tcttgcttca tgtgaagaac accttctggt   41820
atatagtgct cgcggaaggc caccttgaat tcttcccaag ttatctaatg attggccggt   41880
tgaacggcca caaaattacc ccaccaagtg ctggcaggtc cgcgcagttg ctgggctgcg   41940
aataaaggct tctgggtttc tgaacatcgc agcagtccaa acttttgctc aatcacacga   42000
agccattcat ctgcttctaa cgggtcttcg gctttgacaa acagcggtgg tcgcgtctct   42060
gagaagtcca agtaagaggt ttcacggggg ccctgttgat aaccccgccc accttgttgt   42120
tgcaattgtt gacccgccat ctctctaaga aaacgggtat tatccgcggt tgcatttacc   42180
aaggccacaa tcgcctcggc cagtgtggga ggaacaggag gtggatttgg ggtagactcc   42240
ctcccacagg aggtactagc tccgtcctgt gctcgagtct tggaaggcat ctgtggcaac   42300
aacatttgga aaacaatatg atatgccaag gaaaaaccat ccattttaca ttaccaaaaa   42360
gagtaatgta cagactcgaa tttttacaac aggatacatt acctattata caatagcaca   42420
acctattatg caatagtaca aaatattata cattagagca acctgttata caatacacta   42480
cttctacttc tactacccca ttattcctgc tttccgttgc ttttggcggc ctcgtcgtcg   42540
ggtgtgggag accattcgtc gactagcctc atagaaggag ggggctgaaa aaggtctaac   42600
tcaccaccaa gcgcgtgtcc cgcaacatgc gagggtccgg cttccgactc accaggattc   42660
gtaggctcac tgggatgcag ttgcgaatat aatacatgaa tctcttcatg taaggtattg   42720
caatatgtct gcagttcatc aacagccaag ttgagctcgg ctactcgagc ttgagctttt   42780
tgctccttgt cccatgcaag cgaacgggat tgaacaaccc agtcaagtgc caaatcccgg   42840
tccgcgagct gatctcgcag atggcagata tctcttctca actcatttat gcggtcgcca   42900
tctatgaccc agatagtcgt tctgcggcgg agtttcgctt ggagtcgact tacttcagct   42960
tcaagatccc ctataggatc attgcttccg ctactactat tatcatgcct tggggtcagc   43020
tggtgactcg gcacaccaat cggtccagta tgtttgcgcg ttgttctcct tgtgcgcggc   43080
ggcattttct aaggggggaaa atttgattag tatggttctt agcatgatgc atgtataatt   43140
acagaatcaa ccttagttga ttcacacctt ctatatgttg cactcttact acctggtctt   43200
taagatagac tcttcagaat acttaggtaa gaaaggaaga gagtttctag gtaagacttt   43260
tagaaaatct ttttgaagat gcctcataat atctgcaaag aagggctacg ctccgatacc   43320
agctgtgacg gaacctccca agtaattaag cccacctaca gttgtccttg tccaacagac   43380
atcagacacc ctatagatgt tcctaaatta cttcacaagt tcggtatctt ctttcttacc   43440
tttccaggaa cgtttcaccc gtcttgcaga cattacagaa catcgaagat atagaaatgc   43500
agaagcgatt acataactta catttattta aaaagtaaga tcaagttact tattacagac   43560
cagagttatc ctaggagtgc agagtaatat tattacaata ccaagggagg caaaaactcc   43620
tcccgatagt ttttaaacaa aagtcctata tggaggacca agtcctcccg cggcttcact   43680
cttgtttttc ttccttggga accaccttgg agcagaagca ataaaaattt gtcgcttcct   43740
cacctaaaaa caacggaggg ataaaccctg agtatggaat tactcagcaa gtcttacccg   43800
actaaagaaa agactctcaa gggtatgctg gttaagggag tcaaggtaag gcttttcaat   43860
aatcaaagac tctgttttgc agaaatgctt actaaagtgg atccttaaaa atccagtttt   43920
atttgtcaaa ttaagtagaa ttacctgtaa ctagagttct ttctacccta gttcaaatca   43980
cttgtcctgc actagccaat ttcttaacaa aaccatcatc tttagtggaa tgctacgtgt   44040
aagtcagtga ccagtcttc ataaccgcga aggtacggcg atccgaatcg attatactca   44100
gctgaggatc tccaatcaca cgacatatgt agcacttaac ccttgcatat gtcaacccgc   44160
```

```
cactggggtt tttaagacca gatcaggttc acacaaaccg agagcacaga tacaccaccg    44220
tccagcctct tgccacggag ggtacacgct actcccgcca ccgctccacg cccatttcgt    44280
gttatcttat tctggcctta gtctgcccga ggcaaggctt acccatgacg aggcatgtga    44340
ccagttaaag ggtccccggt cagcaggcct acatcgagac ggtccttaat cgactcagac    44400
ggagacacta caccgagact cctttctcgt gcaagtcacc cgcccggtct cggcttaatc    44460
atttcaaacc caaagtttgg tacctggcag aggtacatct tttccgatgt tgaatccatc    44520
aaggcctttg acagattcac catcaagttt tattttcaaa ataaccctc ccacttttgc     44580 caaacatctt ttgtaaaaca aatccttttg tttttctaga gcaaggcaaa gcatcaaaat    44640 cctttttgtaa aacgggtgat caaggaaggt aatcaaattc aaggaaggta gtgcaggaat   44700
tgtttaagca ttcaactcct atcacctaat gcagcaatca agtgagaaag attttaaaag   44760
catcaaggag gtggtaaatg caccggggct tgccttcgtt agtaggtgag tcaggctcag   44820
tcccgcagat atcgaagtag aaacaattgc cggcctgaga atccgtaggt ggtggtgtct   44880
tctctttggt cacttcaatc tcttcttcat tttctaaata taaccatata ggtatatata    44940
taagaatgaa tgccatgtaa tgctcatgag agtgcgaaga taataaagat ttattatcta    45000
agtcttgaat acaactttcc ttcacggaac tccgagaact tagggtttcc ggagtcagta    45060
aaggagttca aagggcaggg gggttttagg ttctaagtat caaacaaggt ccaaatcaac    45120
ccaaattcta cccaaggcct ctaaataatg tatagaactt atgtaaaaag tttggacatt    45180
tttggaaatt ccatttattt tctaaaaatc cagaaccact accttaaact actttaaata    45240
ccttaaaatt ccttagttaa cctaaaattc atacaactat ttttattaaa ttctatggaa    45300
aataagaagc ctaggaaaat tggtttcaca attttaggat ttttctacaa tttttaacaa    45360
atttccaaag ctctacaaaa aaagaaaagg aaaaagattg aatagtgttg ggctgattct    45420
agcccagccg gcccagtact aggggaaaac gcgcgcgcgc gctcgcgccc tggcgacttt    45480
gcacagaggt cctcggggtt tggctaatca gaactggctt ctatcactat tacactgtgt    45540
cgctgacaga ttgcagagaa gcccctgtag ttctaactct tcgcagaggg aggtcctcga    45600
cggcgttcac gcccagccga actccggcga gtgcctgcac cggccgaacg gggcaacggc    45660
tagggttccc gagcggcgga catcaaattg gacctagccc gagcatttcc cctaacctaa    45720
ttccatctat ggcccaatgg cttgctctgg ccacggtggc cgtgaacatc gcggcaagac    45780
agtcgcgttc ccggcgacca aagggctcct agctcgattg tgtgggtcgg caagcatcgt    45840
agacttaagg gaaagcttaa atgagggaga gaaggagacg aactgaccag aataaggctg    45900
gccgcagtga ggttgggttt cgggtggcgg agaattgatt tggggcgaat tcaaaattcg    45960
cgagcttggg cgaacaattg ctagcaatac gtggtggctg ggtgggtgat gatgttgtga    46020
agctctctgc aggtcaatt tatagatccc aggggcggtg gcgcttaatt tgagtggaca    46080
gtgtgggcgg ccggagataa ggaagatcat cggcttcgcg atttcgtgtc caccgccgtg    46140
gcgggctcac cggcaatgat gagacaacag tggggagtca cggcgatgcg acagaggtgc    46200
ccggatacgt ggcgtaaggc cgagcgacgg ggatccccag cgggcttatc tgctcaagcc    46260
gcacggtaga ggggaagtac tgggggttca ccggagtgcc gtccagcgca tgcctttacc    46320
gagcgatctt atctggtcac cggcgacgtg aatcgcaacg gcgcggcgt gaatctcagc     46380 gaagatcagt catcggcggt gagagactgc cgcgctggtg gtctgatctc cctggtagca   46440
ctgtaccatg gagatttata ttcagacagc ctgacagtca agtttggagc ccagttttct    46500
```

```
ctcaatttca aataacaact catccagtga cctacagcaa agttgtagag ctacaatcca   46560
gctataactt tgctacaatg tgctcccaca aaaagtcact gaatcttgct taaaattaag   46620
ccctaagttc atgtcatccc actgttaatc tgaatttcag atttcaagca gtctgacagt   46680
ccaacttcag gctcaattat ctccaatatt ttcttaaaac tatgctcaca ctcttaagca   46740
aagttgttct cctatgattg ggctataatt ttaatgtggt gacctagggc aaaaacccta   46800
tgatttaaaa gttacaaggc tcaaaagttg agcccataac actgttttca gacttagtat   46860
aaaacctcaa atagggtcct ttttgcaaat gaggccaaaa cttagggttt ggcttgtaaa   46920
ttcacatatg agtgacccaa atgacttaag atacttattt aacttggttt ttgcacttta   46980
gtccaaaagt ggtcgaattt tgcacataag cccctagggt ttggatttag ggttttctag   47040
ggttccaatt agggttttg gtatccgagg ggtataaatg tggttcaact ttattcttga   47100
gaatatttga tgactatttc cctagagctt ttaggttttc tcaatttggg ttatatctta   47160
cccctttaat ccctatttag ggttaaattc cctatctagg gttctatttg caaaacacta   47220
aaacaataca acttgtttga aattttacc tagtgaatgc actctaggtg tgtcaaacat   47280
atgcaatgcc aatgtttatg atgctatgct caagttttag ttgcagtaac accaggggtg   47340
ttacaagtac cttgtgcagg tgaccaagta ctaggccgca cagaactgca aggtacgtat   47400
gcacacatgg ttacatttac tatagaactg gagttatttt ttgatgcaaa ggctgccagg   47460
tcatggcgat ttcacgtccg ttaggctcga gaggtggact caaacatcca agttttgcaa   47520
gttttgatgt tggatgttaa atttctatgc tcacccctcg tttggttatt gatgtactat   47580
ttccatctca tgtcacaaat ttggcataag gaatgggtat tggtggctac tggctgtgtt   47640
tatttccaag tattatacat gtacaatgga acagttgata atagttttgc atgaactatt   47700
ggcattagct atctaaaagg acagaaaggc agacatgagc aacaaatccc gctccatggg   47760
ctgaaactgg gattcgtgat ggtcagctaa gcataccttc gccttcaaat ttgcgtagct   47820
tcttttttat tctgctagtt gtttggtctg ctgttcaaat gccttattat tctgcgagtt   47880
gttttaagac tgggcctcaa tttttttca aggcagaaag tgctactgcc gctctcactg   47940
tagcggtgtg gtactgggat ccttgccaat aaggtaaaac tctaactgat cttcttacgc   48000
tttgcattga ggaaggagct cttctgggcg gttggataac agagtcgttc tagtgtgttt   48060
ttagggtgag cccgtccaag acgcccgtgc gtccccgtgc ccctcgccag ctgatgtcgt   48120
cctaggtata catacaggag gtgctgacga tggcactgct catatataag taatagagat   48180
agacatgtat gaaaagggtc ttttgttttc aagtagtgtg tagttgctgt tacttttaac   48240
agctaatgca atctggatga gtcacctatg aatgccatac tggaatctgt tgcgcttttg   48300
ttgatcatta ttattttgca atccaggcta ggggattgaa gaagcacttg aagaggctca   48360
atgcgcccaa gcattggatg ctcgacaagc ttggtggagc ttttgtaagt aaacatgtcg   48420
gggaccataa ttaggggtac ccccaagact cctaatctca gctggtaacc cccatcagca   48480
caaagctgca aaggcctgat gggcgcgatt caggtcaagg ctccgtccac tcaagggaca   48540
cgatcccgcc tcgcccgagc ccagcctcgg gcaaaggcag ccgacccagg aggattcacg   48600
tctcgcccga gggtccccctc aagcaacgga cgcaccttcg gctcgcccga ggcccaggct   48660
tcgcggagaa gcaaccttgg acagatcgcc acgccaacca accgtatcgc aggagcattt   48720
aatgcaagga tcgactgaca ccttatccta acgcgcgctc ctcagtcgat agggccgaag   48780
tgaccgcagt cacttcgccg ctccactgac cgacctgacg ggaaaatagc gccgcctgcc   48840
ctgctccgac tgctgtgcca ctcgacagag tgaggctgac agcagctaag tccagcctcg   48900
```

```
ggcgccatga gaagctccgc ctcgcccgac cccagagctc gggctcaacc tcgacgccgg   48960
acgacggact ccgcctcgcc cgaccccagg gctcggactc agcctcgacc tcggaagacg   49020
gactccgcct cgcccgatcc cagggctcgg gctcaacctc gacctcggag gagcctccgc   49080
ctcgcccgac ctcgggctcg gaccgaccac gtcgcagggg gagccatcat taccctaccc   49140
ctagctagct caggctacgg ggaacaagac cgacgtccca tctggctcgc cccggtaaac   49200
aagtaatgat ggcaccccat gtgctccgtg acgacggcgg ctctcagccc cttatggaag   49260
caaggagacg tcagcaagga tccgacagcc ccgacagctg tacttccaca gggctcaaac   49320
gctcctccga cggccacgac atcacatgaa cagggcgcca aaacctctcc gacagccacg   49380
acagcatgta cttagggctc tggctcctct ctgctagaca cgttagcaca ttgctacacc   49440
ccccattgta cacctgggcc ctctccttac gtctataaaa ggaaggtcta gggctctcgt   49500
acgagagggt tggccgcgcg ggagaacggg ctgacgcaca aggctctctc tctctctctc   49560
ccacacgaac gcttgtaacc ccctactgca agcgcatccg ccctgggcac aggacaacac   49620
gaaggccacg ggttccccctt tgctgttttc cccccctttgt gtttcgtctc gtgccgaccc   49680
atctggaatg ggacacgcag cgacagttta ctcgtcggtc cagggacccc ccggggtcga   49740
aacgctgaca gttggcacgc caggtagggg cctactgcat ggtgacgaac agcttcccgt   49800
caagttccag atgggtagtc tccagcaacc actccaaccc gggacggtgc tccatttcag   49860
gagtcttgag ttcatgtccc tcgacggcag ctacgacatg acactccttc ctccgccgcg   49920
cgacaacgac aatggcggcc gtcagcccgc ccgtcggcgg cggaatcgac gacgtcttcc   49980
ccacgtggcg gaagagcgat atccgggtct gtcccgtcac cttccccgct gacggaggag   50040
gaggcggggt aggcatggcc aatcaggagg cggcacctcg tcggctgtcg agcgagtcga   50100
cggcgccgac gccccaacgg gggacacgtc gggcgttgac ctcgcgtctg agacgaagac   50160
aagcgtcgtt tccccgcaac acgccaaccc caagcagacg gatgacgcca gcacgctcgc   50220
gaaggacttc ctgggcgtta acctcgtacc tgagacaacg gtgcagtccg tccctgacgc   50280
gacttcgtca ccacccgtcg atcaagaggt accgtccgtt tcccatccca tgcctttttag   50340 attcagttgt gacccaccaa gcgatcccgc ttcggtggac gctttcataa aggcatgtcc   50400
aaaccctccg gggtatcata tgcggtcaac ctgggaccga ctgacggccg tctcgaccta   50460
tgggcccccg ggttccgagg aagatgacga gcctgactct ggttgggatt tctccgggct   50520
cgataacccc agtgtcatgc gggacttcat gaccgcatgt gactactgcc tctccgattg   50580
ctccgatagc agccacagcc tcggcgacga ggactgtggc ccaaggtgcg aatgcttcca   50640
cgtcgatcta gggggtcttg acgaaggcaa ccatcttggt atgccggagg atggtgatcc   50700
ccctaggcct cgcgcctcgcg ttgacatcct tcggagctga gctgtggtcc cagtccctgc   50760 gggggggtcaa gacgcacggc ttgagcaaat ccgcgaggta caggccaggc tcgacgagga   50820
agcaggacaa cttgtgcagc ttcggcaaaa tatcggcag gagtgggcag gccgagcacc   50880
ggctggagaa gcgcgtcatc tggcccagga cgtccagcac cgcatcaccg acgatgccag   50940
ggcgaggctg cccccggctt ccagtggggt cggccagaac ctggctgcag cagcgatact   51000
actccgagcg atgccgaaac catccaccac cgaggggtgg cgtatccaag agagctcaa   51060 aaatctccta gaggatgtcg cggtccgacg ggccgagagc tctgcctccc gaaggcaggg   51120
gtaccccggg agcatcgcgc tgcgacttcc cgattcatgc gggaagcctc ggtccacacc   51180
gggcgcacgc gggacacagc gcctgcggcc ccaagacgcc tcggcaacga gcaccgccgc   51240
```

```
gaccgtcaag cccacctcga cgagaaggtg cgtcgaggct accaccccag gcgtggggga    51300
cgctacgaca gcgtggagga tcggagcccc tcgcccgaac cacccagtcc gcaagctttc    51360
agccgggcca tacaacgggc accgttccg acctggttct gaaccccgac taccatcacc    51420
aagtactcgg gggagtcgaa gccggaactg tggctcgcgg actaccggct ggcctgccag    51480
ctgagtggga cggacgatga caacctcatc atctgcatcc ttcccctgtt cctctccgac    51540
gccgcccgag cctggctgga gcatctatct cctgtgcaga tctccaactg ggacgacctg    51600
gtcaaagctt tcgtcggcaa cttccagggc acatacgtgc ccctgggaa ctcctgggat     51660 ctccgaaggt gccgcagca gccgagagaa tccctctggg actacatccg gcgattttcg    51720
aagcagggca ccgagctgcc caacatcacc aactcggatg tcatcggcgc gttcctcacc    51780
ggtaccactt gtcgcgacct ggtgagcaag ctgggtcgca agactcccac tagggcgagc    51840
gagctgatgg acatcgccac caagttcgcc tctggtcagg aggcggtcga ggccatcttc    51900
cggaaggaca gcagcctca ggggcgtcag ccggaagacg tccccaaggc gtccgctcag     51960
cgcggcgcga ggaagaaggg caagaagaag tcacaagcaa aacgcgacgt cgccgacaca    52020
gacattgtcg ccgccgccga gcacagaaac cctcggaagc ctcccggagg cgccaacctg    52080
ttcgatagga tggtcaagga gtcgtgcccc tatcatcagg gtcccatcaa gcacaccctt    52140
gaggaatgcg tcatgcttcg acgctacttc cacaaggccg ggccaccggc gaaaggtggc    52200
agagcccaca caacgacaa gaaggaggat cacaaggcag aggagttccc cgaggtccac     52260
gactgcttca tgatctatgg tgggcaagtg gcgaacgcct cgactcggca ccgcaagcaa    52320
gagcgtcggc aggtctgctc agtaaaggtg gcagcgccag tctacctaga ctggtccgac    52380
aagcccatca ccttcgacca gggcgaccac cccgaccgcg tgccgagcct aggaaagtac    52440
cctctcattg tcgaccccgt catcggcaac gtcaggctta ccaaggtcct catggacgga    52500
ggcagcagcc tcaacatcat ctacgccgcg accctcgggc tcctgcagat cgatctgtcc    52560
tcgatccggg ccgtgcgac gcctttcac gggatcatcc ccgggaaacg cgtccaaccc      52620
cttgggcaac tcaatctgtc agtctgcttc gggactccct ccaacttccg aaaggaaacc    52680
ctcacgttcg aggtggtcgg gttccgagga acctaccacg cagtgctggg gagaccatgc    52740
tacgccaagt tcatggccgt ccccaactac acctacctca gctcaagat gtcgggcccc     52800 aacgggtca tcaccatcgg ctccacgtac cgacacacgt acgaatgcga cgtggagtgc     52860
gtggagtacg ccgaggccct cgccgaatcc gaggccctca tcgccgacct ggggagcctc    52920
tccaaggagg cgccagatgc gaagcgccac gccggcaact tcgagccagc tgagacgatt    52980
aagtccgtcc ctctcggccc cagcaacgac gcctccaagc agatccggat cggctccgag    53040
ctcgacccca aataggaagc agtgctcgtc gactttctcc gcgcgaacgc cgaggttttt    53100
gcatggagtc cctcggacat gcctagcata ccgagggatg tcgccgagca ctcgctggat    53160
atccgagctg gagcccgacc cgtgaagcag cctctacatc gattcgacga agaaaagcgc    53220
agagccatag gcgaggagat ccacaagctg atggctgcag ggttcattaa agaggtattc    53280
catcccgaat ggcttgtcaa ccctgtgctt gtgagaaata aggagggaa atggcggatg     53340 tgtgtagact acactggtct aaacaaagca tgtccgaaag ttccctccct ctgcctcgca    53400
tcgatcaaat catggattcc actgctgggt gcgaaaccct gtctttcctc gatgcctact    53460
cagggtatca ccaaatcagg atgaaagagt ccgaccagct cgcgacttct ttcatcacac    53520
cctttggcat gtactgctac gttactatgc cattcggttt gaggaatgcg ggtgcgacat    53580
accaaagatg catgaaccac gtgttcggag agcacattgg tcgaacggtt gaggcttacg    53640
```

```
tcgatgacat catagtcaag acgaggaaag cctccgacct cctctccgac cttgaaacga   53700
cattcaagtg tctcaaggcg aaaggcgtaa aactcaatcc cgagaagtgt gtcttcggag   53760
tcccccgagg catgctcttg gggttcatcg tctccgagcg gggcatcgag gccaacccgg   53820
agaaaatcgc ggccatcacc aacatggggcc ccatcaagga cttgaaagga gtacagaggg   53880
tcatgggatg ccttgcggct ctgagccgtt tcatctcacg cctcggcgaa agaggcctac   53940
ctctgtaccg cctcttgagg aagaccgagc gcttcacttg gacccccgag gccgaggaag   54000
ccctcgggaa cctaaaggtg ctcctcacaa gcgcgcccat cttggtgccc cctgttgccg   54060
gagaagccct cttggtctac gtcgccgcta ccactcaggt ggtcagcgcc gcgatcatgg   54120
tcgagagacg agaagagggg cacgcattgc ccgtccagag gccggtctac ttcatcagtg   54180
aagtactgtc tgagaccaaa atccgctacc cgcaaattcc agaagctact ttacgcggta   54240
attctgacgc ggcgaaagtt gcgacactac ttcgagtctc atccggtgac tgtggtgtca   54300
tccttccccc tgggagagat catccagtgc cgagaggcct cgggtaggat tgcaaagtgg   54360
gcagtggaga ttatgggcga gacaatctca ttcgcccctc ggaaggccat caagtcccaa   54420
gtcttggcga actttgtggc tgaatgggtc gacacccagc ttccagcagc tccgatccaa   54480
ctggaactct ggaccatgtt tttcgacggg tcgttgatga aaacaggagc gggcgcgggc   54540
ctgctcttca tctcgcccct cgggaagcac ctccgctacg tgttgcacct ccatttcccg   54600
gcgtccaaca acgtggccga gtacgaggct cggttaacgg gttgcgaatt gccaccgagc   54660
taggggtccg acgcctcgac gctcgcggcg actcgcaact tgtcatcgac aagtcatgaa   54720
gaactcccac tgtcgcgacc cgaagatgga agcctactgc gatgaggttc ggcgcctgga   54780
ggacaagttc tatgggctcg agctcaacca catcgcccga cgatacaacg agactacgga   54840
tgagctggct aagatagcct cggcgcggac aacggttccc ccggacgtct ctcccgaga   54900
cctacatcaa ccctcagtca agaccagcga cacgcccgag cccgagaaag ccttggccct   54960
gcccgaggca ccctcggccc ccgagggtga ggcactgcgc gtcgaggaag agcggtatgg   55020
ggtcacgcct aatcgaaact ggcagaccct gtacctgcaa tatctccacc gaggagagct   55080
accctcgac agagccgaag ctcggcaact agcgtggggc gccaagtcgt tcgtcttgct   55140
gggtgacggg aaggagctct accaccgcag cccctcaggc gtcctacaac gttgcatatc   55200
catcgccgaa ggtcaggagt tattacaaga aatacactcg ggggcttgcg gtcaccacgc   55260
agcacctcga gccctcgttg gaaatgcctt ccgacagggt ttctactggc caaccgcggt   55320
ggccgacgcc actaggattg tacgcacctg ccaagggtgt caattctatg caaagcagac   55380
ccacctgccc gctcaggctc tgcaaacaat acccatcacc tggccgtttg ctgtgtgggg   55440
tctggaccctt gtcagcccct tgcagaaggc accgggggc tacacgcacc tgctggtcgc   55500
catcgacaaa ttctccaagt ggatcgaggt cagacccccta aacagcatca ggtccgaaca   55560
ggcggtggcc ttcttcacca acatcatcca tcgctttggg gtcccgaact ccatcatcac   55620
cgacaacggc acccagttca ccggtagaaa gttcctactg cgaggattac acatccggg   55680
tggactaggc cgccgtagct cacccccatga cgaatgggca gctagagcgt gccaacgaca   55740
tgattctaca aggactcaag ccacggatct acaacgacct caacaagttc agcaggcgat   55800
ggatgaagga actccccctcg gtggtctgga gtctgagaac gacaccaagc tgagccacgg   55860
gcttcacgcc gttttttcta gtctatgggg ccgaggccat cttgcccaca gactcactgg   55920
gccatcttca cgctgttttt tctagtctat ggggacgagg gcgtacgacg accgaagcaa   55980
```

```
tcgaaccaac cgagaagact cactggacca gctggaagag gctcgggaca tggccttact    56040
acactcggcg cggtatcagc agtccctgcg acgctaccac gcccaagggg ttcggtcccg    56100
agacctccag gtgggcgact tggtgcttcg gctacgtcaa gacgcccgag ggtgtcacaa    56160
gctcacgcct ccctaagaag cccggaacat acaagctggc caacagtcaa ggcgaggtct    56220
acatcaacgc ttggaacatc cgacagctac gtcgcttcta cccttaagat gttttcaagt    56280
cgttcataca cctcgtttac atacgccaac aaagtctaac catcaaggaa gggtcagcct    56340
tgcctcggca aagcccgacc ctccctcggg ggctagaagg ggggcacccc ctctacgtca    56400
aaatttcct cgaaaaaagt ctttctgcca gaacatcttt cgtgcttttc gactacttcg    56460
aaagtgggat cctgaaaacg acggagtaca cgtaagcagg caaggacgac cgagccgagg    56520
gactcctacg cctccgggat acggatacct cactcatcac cttctgcgat aagtaactca    56580
cgctcggata agcgatcccg ctggccgaac aagtcttaac gttcgaaagc ttttctgccg    56640
aaacgatttt ttgtgccttc tcgactatat cgataacaga atccaacgga cgagtaagag    56700
tacacgtaag cggcaaggcc gaccgagccg agggactcct acaccttcgg gatacggata    56760
cctcactcat caccttccgt gaaaagtaac tcttgctcgg ataagcaatt ctgttactga    56820
cgaacaagtc ccgatactcg aaacaagggg aaaagaaacg ccgctttaca acacgacgac    56880
ggtatgtttg ggcctcggcg gccgcaaaaa acatacgcac actacagata aattgttcct    56940
gcaggatcag acatcagtgg gggagcagca gcacccctcgg cgtcgactcc accttcggcg    57000
gagtccgacc cagcctcgga cggcgacacg gtcggaggat ctccatctcg aaggaacctg    57060
tcagcaccgc gcctgggcca tcgccgaggt gtcctccagg aacccggccc gagtagacga    57120
ctcgaccgac cgctctgtag cctcagccag ctgtcccccg aggacatcag cccggctcat    57180
ggcctcggca acccgactcc ggcgtcggtc ccaccagtgg acggcccgac caggctccgg    57240
ccgatgaagc ttcttttga gccaactccg cctctgtcca cgctgacacc gctgacaccg    57300
ctgcctctag ctccggctca tcgcagagcg gccgagggtt tctttaacta agcaagagaa    57360
gcctcgggcg gcaaggccga ccgatccgag ggactcctac gcctccggga tacggatacc    57420
tcactcgtca ccttccgcac gaggcaactc acacttggtt aagcggttca gctagccgac    57480
aggcgagtcc tagtgctcga aatgaggaaa aaatacggct ttagccaaaa tacacatctt    57540
caggccccga cagccgcaat gaacagacac cggcactcaa ggtgccatta caaacagaac    57600
tctggttccg cccccacagg tacgaacgac cccccacatt ggagggcctg cggggcaact    57660
gaaagctctc ttgtgagttt tggtgtttgg atgacaactc aattaaagga ctaacaagtg    57720
tactaagtgt tgaacaggtg cttaaggtaa agcctacagg gttcaacaca agtgaacaaa    57780
tgtgatggtc caagaactgg attatggata cataatggac atcacaagta agatggacat    57840
tgcacaaagt gagactcggg tgcgtagctc ggagacaact gatcaagcca aggacggagg    57900
caagaaaagc ttcgaggtac caaatgcacg ggagaaggtc aaggaggctg aggaacccaa    57960
agccaagggt gaagaagaag gcttgcaaag tcaagggtga tcgagttgag aacagctacg    58020
gcacatcaag gatcactaca taaggacgtg acttacagcc aatgaggtaa cagctatagt    58080
tatgtggtgt aagtcataag gctcaagatc aagctctaag gaggagatca aggtcactag    58140
aaggagaaca agtgtcgaaa ccagaactgg aagcagccca aaagagctaa gttcactttg    58200
atctttagtt tgggttgttc ctatgtttgg agatgttcta tgtgaccttt acaggatgtt    58260
ggagccaagc gatgtcaatc tagatcaagt caagctgact tgataattta tgagtccaac    58320
atcaaagctc aagcatgtga aatgctatag atgtaatgat taatagaagg tatgtttcta    58380
```

```
gacttagtac attggttttg gggactaata tacttgtcta agtgttagaa acagaaagaa    58440
gaagaaaagg gaagaggtgc gaaaggcttg gctgtgtaca gccaagactt agttcagtct    58500
ggcacaccgg actgtccggt ggtgcaccgg acagtgtccg gtgcgccagg ctgaactctg    58560
gcgaactggc cgctctcggg aattcaccgg cgatgtatgg ctataattca ccggactgtc    58620
cggtgtgcac cggactgtcc ggtgagccaa cggtcggccg ggccaacggt tggccgcgcg    58680
atctgcgcgg gacacgtggc cgagccaacg gctagatgga ggcaccggat tgtccggtgt    58740
gcaccggaca tgtccggtgc gccaacggct ccaagactgc caacggtcgg cttcgacgta    58800
gaaggaaaga atcgggcac cggacagtgt ccggtgtgca ccggacagtg tccggtgtgc    58860
accggactgt ccggtgcgcc acccgacaga aggcaagatt tgccttcctg gattgcttcc    58920
aacggcttct aggcccttg tgtctataaa agggacccct aggcgcctcc agcaaaatag    58980
aagtgcagcc aacaagtgta gactccactg gaatcaattc tcactctccc tcttgtgtgt    59040
aactctatag tttgtgtaga aggcacagct ataagcctta gagagaggag tagtgctgct    59100
aagagctaga gcaaggtctt gagcatatcg ttactctacc ggggtgctgc caagaagtct    59160
gtaagcagcc gcggttctgt tgtaaccca ctcaatagtg aaaggctcta tctgtcatac    59220
tgacagatct gagcaaacgg aggaaggagt tgaaatagac tccaagccca ggtgtggcta    59280
actccaacga ggactaggca agcatttcag gcttggccga acctcgggat aaatccttgc    59340
gtctgtgtgc tctgttctgt attgtatcct gactctcttt ctactcgcct ttatatctgc    59400
acttcaatac ttatctgtgg tataagcttt atttgaagtg caggacattt tgagacagga    59460
tcttctattc ggctgcaacc tacttgaaga gtcttctcac tccactgcat actaagtctt    59520
cgagtagagt aagaatttaa gttttaaagt gaaaagtttt attcgcctat tcaccccccc    59580
ccctctaggc gacatccaga tcctgttccc gggtcaaagg gaactttcaa ttggtatcag    59640
agctaggcct ctccagtgtg ggcttagccg tccggagatg acgatgtcgt cacaagaggt    59700
aactgtggaa cttcttttag acgatggctc taattacaag tcttggtctg tctctattta    59760
tagtgctttc atgagtgttg atcctgattt gagacaggtc tttagtagta gtattttccc    59820
ctccaatatt agtaaaaacc catccaatga agaactaaga tgtctaactc taaatcacca    59880
tgcttgcaac atcttagttg attctctatc tagaggtgcc tattttgcca tcatgagtag    59940
tgatagtgat ctatttgttg atgctcatga tttatggaat aggattaaag aaaaatattt    60000
tgtggcaaac tgtgatgctc ctactcccta tattacttgt gatactaacc attcaaaggg    60060
agaagaacaa gaacgatggc atccaaacga tgaatccacc tcgtcgacag gtttgttctc    60120
cactagtgat aaatgttta ttgctaacaa tgacggtgga gacgaaagcc atgataagga    60180
gaaatatgag gatgaatctt catcatcaca aggtacattt tcctatattg cttccactga    60240
cattaatgac agggaaaatg agaccgatga tgtggaggaa gaggagattc accgtttcta    60300
catccatctc aacaaagagg acaaggcact cttggttaag ctgttgagaa ggaacaagga    60360
acaaggcgag acgcttctca ggctagagga gtccctcatc aaaaccaaca acagcctgga    60420
gaagatgacc aaagaacatg agaagctaag gcgctctcat gatgatttgg tccaaaggta    60480
tgaatatgtt ttaattgagc aaagaaatag tcatgatgca ttatctaata ttgctcaact    60540
taaaacggaa aattctatgc ttaagagtca agtagaaaca atgaacttag aaaaacgtgc    60600
tctaggtaaa aagtatgata tgttgtcaaa ttctcataat aaattagttg atgaccatat    60660
catgcttaat gttgctcatg aggttataat tgcaaactta aattcatgtg aacctcattc    60720
```

```
tcgcacgtgt gcgcatttga agtgtatatc accatgtgct aacccctgtt gctcaaaaga   60780
aagccaatca ttgattgagc aacaagtttt agggtcacaa aagaaattct gtgggaacaa   60840
gaagcaaaga caactaagga gaagacacat tgctcaactc tctcaagata tccacgggcg   60900
cgtggtgaag aagcttgaga aaggaaaaac tgcagcaagt gttaagctca ataagaagaa   60960
tgttcccaaa gctataaatg aagaaatcaa catgaacaag gaaaaaggta aaaattcaat   61020
tagtcatgtt gtttgcactg atcatctctc catgtcattc aagcacaaaa agggaagagg   61080
aaaaaggagg tgcttcaaat gcaaggagac aggccacctc atcgcgtctt gtccgtacaa   61140
agacaaggat gaaagaacaa ggagttgttt tggatgcaac aataaggacc acatgatcac   61200
ttcatgtccg gtcatgaaga atcaaggata tgcatcctcc aaagtgaccc tcaccaagga   61260
aaatgacaca aaacaagcgt catgtcaagt tgagcgacgc ttctgctaca agtgtggtga   61320
gcaaggtcat ctatccaagg tatgttacaa aggtaagatt cctaaacaag tgaatttgtg   61380
tcaatcttat tcgcatagga gacccaaatc atacacttgt gctagatcta aacgagatc   61440 acctagaact agcacaaagg caatttgggt accaaaggca catttacatg atcattatgt   61500
acccatcccg agatggatac caaactgtgc caactagacc atgcaggtgc ctcgagatgg   61560
actggagacc atgggaaaga ttaagacggt tatctaaaac tctatgctta agctgttaat   61620
tgttttagtg tttattgacc caaggttgaa ttattgtgaa acactaatcc catgttcatc   61680
tcaagagaaa taaggtgtat aggtcctgaa tcattattgg tgaatcaagt aaaggatctt   61740
gatgagaatc tacaacctgc tctccaaagg acggtacccg tgtattttaa gtacataatt   61800
gcaatttagt attgctctta agttggcttg ttgtgctacc tgtccttaga gtagttatgc   61860
tttatgattg cctgtgttaa attgatcata atgatggttg cttaatcatg actggtgcta   61920
taaaggatat atcttttgaa tcattcatgg gtagctattt catttgttat atccacaacg   61980
ataactctct tgatgtatat ggataaacct gtaacttttg taagtcatgc tatgtgcaat   62040
tatgacattt tgtttagtcc atgttcacat gattacccta gtttggtact gtgtgaattt   62100
caaatccatg tcgtgcccct ttgagctatg aggtgcgtaa gcaaaggag ccctaaattg   62160 gcgataacaa gggctctcat aaaggcaaag gtatggaaaa tggagctatg caatttcatt   62220
aaatattctt gaaattccat tcattgtgat catagctatg ttcttgcctt tcaattggta   62280
atatcttggc ttaggtaatt tatgccttta aaatgttgtt tcttttgtgc acctaagaaa   62340
ccttcttaat tataacatgc ttagatattt cgattgtgtt tatctttaat tggtatatac   62400
aatgatagtt aaatatgaag catgtacaag ttgcgtaaat gttagacttc ctgtgagtat   62460
tcaattggct taggtgccac tgaggcgtgc attgttgtat ttagtcaacc tttcatttag   62520
ccttcaattg gtgttatgtg gcgtttcatt tgatattcaa attggcatct ttgggtgatg   62580
aaagtggtag agtatgcctt gaccaaggta tgttgtgatc ccctctaatt ctaaggaagc   62640
tagaatgtgc aaagtgcaag tcattcaaat acttgatgca caacttgagg gggagcacac   62700
ataacttgtg tcttttgaga ctaactgttt cttgagcaat cttgtatagt ctctaggtgg   62760
aaaagagaag ataagcaaga aatggagcaa tcaggacttg ggtacctctg taagtcaaga   62820
aaattggtat ctcaagttgt gagtaagtgc atatttttag attgctcatg ctctataata   62880
tctggtgata atagatgctt attcttaaat atcatggagc catgataata aatgaacttt   62940
gcaattggta tctttcaatt ggtagccgta atagttcgct tcaattgaca tcttttgata   63000
atcatgagaa tagaagtttc ttcttgtgcc caatactata acttgttcta agtttggtgt   63060
cttagcaaca agaaaaagtt aggagagaga atcaggcaca agtgtggaga agctctcgag   63120
```

```
agattaacta ctttcaagat gggaagtaca ctacatcatg gtaaaggtac aaaaggaagt    63180
attaatcttt ttgcatatat gtatcttacc taaatgttga taggacatat gttcaataaa    63240 taaggggag ttttgatagt cgttttccc cttaacaccc tgctgtccct tgacatcatc    63300
atatgttctt gcttgagtat ggttttggt gtttgatgtc aaaggggag aagttgtgca    63360 ttaaagctta tctcaacctg agaggaaagc ttatcctaat gggtgatgtg ttagtttgag    63420
ctttgccaag tgtgatattc atatgtttct tgcagtatta tacgtgttga tcatatggac    63480
tagactagtg ttttatattc atatgtttct tgcagtatta tacgtgttga tcatatggac    63540
tagaccagtg tttccgctgc gatgaattat ttggcttcta tagtgaaata gatagtcatg    63600
tggttaatgg tgctttaaga ttgctttaaa ttgatatctt agtttaagtt ggtatcttaa    63660
tggtgaatag tggtaggttg atattcctgt gatatatcca ctaatttgaa tggtgtttaa    63720
ctctgattat gtgcatttgt gtgttatagc atcatggttt gattcttgac ataatgcatc    63780
ctaaaaagtg ctaaggtgta gaaatgtttc aattttccta agtatgtgca aattgacgtt    63840
tgtggtcaaa attaggtttt tgaagtaagc acttatttag ggggagcatt ctataatctt    63900
agaattcaaa tttgtgcttc aaatcttatt cttatgtaag ctttaattgt gttgccacca    63960
atcaccaaaa aggggagat tgaaagctct cttgtgagtt ttggtgtttg gatgacaact    64020
caattaaagg actaacaagt atactaagtg ttgaacatgt gcttaaggta aagcctacag    64080
ggttcaacac aagtgaacaa atgtgatggt ccaagaactg gattatggat acataatgga    64140
catcacaagt aagatggaca ttgcacaaag tgagactcgg gtgcgtagct cgaagacaac    64200
tgatcaagcc aaggacggag gcaagaaaag cttcgaggta ccaaatgcat gggagaaggt    64260
caaggaggct gaggaaccca aagccaaggg tgaagaagaa ggcttgcaaa gtcaaggtg    64320 atcgagttga gaacagctac ggcacatcaa ggatcactac ataaggacgt gacttacagc    64380
caatgaggta acagctatag ttatgtggtg taagtcataa ggctcaagat caagctctaa    64440
ggaggagatc aaggtcacta gaaggagaac aagtgtcgaa accagaactg gaagcagccc    64500
aaaagagcta agttcacttt gatctttagt ttgggttgtt cctatgtttg gagatgttct    64560
atgtgacctt tacaggatgt tggagccaag cgatgtcaat ctagatcaag tcaagctgac    64620
ttgataattt atgagtccaa catcaaagct caagcttgtg aaatgctata gatgtaatga    64680
ttaatagaag gtatgtttct agacttagta cattggtttt ggggactaat atacttgtct    64740
aagtgttaga aacagaaaga agaagaaaag ggaagaggtg tgaaaggctt ggctgtgtac    64800
agccaagact tagttcagtc tggcacacca gactgtccgg tggtgcaccg gacagtgtcc    64860
ggtgcgccag gctgaactct ggcgaactgg ccactctcgg gaattcaccg gcgacgtacg    64920
gctataattc accggactgt ccggtgtgca ccggactatc cggtgagcca acggtcggcc    64980
gggccaacgg ttggccgcgc gatctgcgcg ggacacgtgg ccgagccaac ggctagatgg    65040
aggcaccgga ctgtccggtg tgcaccggac atgtccggtg cgcgaacggc tccaagactg    65100
ccaacggtcg gcttcgacgt agaaggaaag aaatcgggca ccggacagtg tccggtgtgc    65160
accggactgt ccggtgcgcc acccgacaga aggcaagatt tgccttcctg gattgcttcc    65220
aacggctcct aggccccttg tgtctataaa agggaccct aggtgcctcc agcaaaatag    65280
aagtgcagcc aacaagtgta gactccactg gaatcaattc tcactctccc tcttgtgtgt    65340
aactctatag tttgtgtaga aggcacaact ataagcctta gagagaggag tagtgctgct    65400
aagagctaga gcaaggtctt gagcatatcg ttactctacc ggggtgctgc caagaagtct    65460
```

```
gtaagcagcc gcggttctgt tgtaacccca ctcaatagtg aaaggctcta tctgtcatac    65520
tgacagatct gagcaaacgg aggaaggagt tgaaatagac tccaagccca ggtgtggcta    65580
actccaacga ggactaggca agcatttcag gcttggccga acctcaggat aaatccttgc    65640
gtctgtgtgc tctgttctgt attgtatcct gactctcttt ctactcgcct ttatatctgc    65700
acttcaatac ttatctgtgg tataagcttt atttgaagtg caggacattt tgagacagga    65760
tcttctattc cgctgcaacc tacttgaaga gtcttctcac tccactgcat actaagtctt    65820
cgagtagagt aagaatttaa gttttaaagt gaaaagtttt attcgcctat tcacccccc    65880 tctaggcgac atccagatcc tgttcccggg tcaaagggaa ctttcagcaa caaaaccccta    65940 gacagctcgc cgaggcccgc tctggcagca gcgacaacga cctccgctcc ggacagccaa    66000
acagcagcag cgatgacctc agtgcagacg ctgctgcgac aaggcccctcg cccacgtccc    66060 caccatcaaa ctggtggtca ccgtcttggg tgaccaccag cgaggggatg cagccgggcc    66120
gcctgatgaa aatccttgaa gccgagcgat ggctgaaagg taccaacttc cgcgaagttg    66180
cgttcctcca acgacgacaa gacgaaagca acgcgggcgc tccccatccg ggggctcgga    66240
agttggaagg gcgcgatgca tgaagggagt gtgaagacat ggttgccatc caaggggtc    66300 gccctccttt taaaggcgac tctccccact tgcgtcctca gccgtcgcgg actgagtctt    66360
caccaacacg ctccaaggtc ctcccctac gacatgggg ctgggtccca cgcgtcatgc    66420
aagctggccc agggcagaag aagccaaacc gtcgcgcgca gagtgcgtaa ctgcccagcg    66480
gttacaagca ctcctccact ttcgcccaga ccggcgggtg aaagggcgga ccgccatgca    66540
ggcggcatgc aaccgcacca agggggtgca cccttcgac tccgacgcgt ccagcacggg    66600
ggcccaggcc cacacgtcat gtaaccggcg cgccggttac tacgcgcgag aaactgcacc    66660
gccacttgtg ctagtaccgc gccttctcga ctgcggaacc ggtgccgcga ctcgaggcaa    66720
ccctgcgcat ggcccaacag tgccaaccga gcacatcgat cacgggtcag tcagccgcgg    66780
gagaaggcgc gatggttgat atggccaaaa gtgggccggc agtaatggcg gcggcaggcg    66840
ggcggaagca gcggtcaagt cgtctgtagg ctcacgtccc ctcctgggac agcgagagag    66900
ccccctccca cggcgtgaag acgacacgcc cgtgttccgt tcctcgaacg gctagcgcac    66960
gcacaacggc tgccccgcga accactcatc ccgtcgcatt aactctgcgg caggacaggc    67020
ggcacctttg gcaggcgaag caggtgacgc ttcacctccg ccttaatgac cgcgtcaaaa    67080
aaggtgcgcc acgtcgtttg atttcgtatc ctttttaccct tcctctttct ctctcttgct    67140
atagggaccg ggaaagagga tactccgaaa gggatccttc tccgcgaagg aagcgggccc    67200
cgagccctcc tactaatcag aggttcgaag gctggcccct cggaagggtt cgacagtcgc    67260
cttagagcac tcgggctccg cgccctccta ctgatcagag gttcgaaggc tggcccctcg    67320
gaagggttcg acagccgcct cagagcactc gggttccgtg cccactactg gtcagaggtt    67380
cgaaggctag cccctcggag gggttcgaca gccgcctcaa gccactcgag ctctgcgccc    67440
actactgatc aggggtttgt aggctggccc ccgaaggatt cgccagccgc ctcagagcac    67500
gcagagcgag ggatgactct gggtacgtcc gatacatggc cgaggctcgg gctacgctcc    67560
cgaggtaccc taggacattt ccgagaccaa caggagcgat tctgtaacgg aatcccatca    67620
gagggaggca tcgagccctc ggaccctatc aaacgggacc gggtccggca aatcacctgt    67680
aggtactttt ggagcgcgcc tctgggccac tagccgaccc ttatcgaacg gggcacgggc    67740
gtccactcga atcaaccgtt agcaactcac tggagacacc atgttcgacg ccctctgagg    67800
gcaacatggc gctttccccc ccctcctcct tgcggaaagg cgacgcaggg gcgtatgaaa    67860
```

```
aaagccgagt cagtccttgg ccgtcctctc gctctgtgcg gaggctcggg ggctgctctc   67920
gcatgaggga acaaccaaac cagcccgaga acttggaacc tgactatgca cccgggctac   67980
ggccagttcg catgagggaa caaccagacc ggccgaagca tcacgaaacg tgctaagacc   68040
tcgaaggagt caaaccactc ctccgaggcc tcagggcta cacccggcgg gtgcactcgc   68100
gcgcacccac cggaacgaaa cgcaaccgag aaaggccggt ccccttgcaa aaagtgcga   68160 caaaagcctc caagtgagta ccaacactcc cttcgaggct cggggctac tgtcggggac   68220 cataattagg ggtaccccca agactcctaa tctcagctgg taaccccat cagcacaaag   68280 ctgcaaaggc ctgatgggcg caattcaggt caaggctctg tccactcaag ggacacgatc   68340
ccgcctcgcc cgagcctagc ctcaggcaaa ggcagccgac ccaggaggat tcacgtcttg   68400
cccgagggtc ccctcaagca acggacgcac cttcggctcg cccgaggccc aagcttcgcg   68460
gagaaggaac cttggccaga tcgccacgcc aaccaaccgt atcgcaggag catttaatgc   68520
aaggatcgac tgacaccttc tcctgacgcg tgctcctcag tcgacagggc cgaagtgact   68580
gcagtcacat cgccgctcca ctgaccgacc tgacgggaaa atagcatcgc ctgccctgct   68640
ccgactgcta tgccactcga cagagtgagg ctgacagcag ctaagtccag cctcgggcgc   68700
catgggaagc tccgcctcgc ccgaccccag agctcgggct caacctggac gtcggacgac   68760
ggactccgcc tcgcccgacc ccagggctcg gactcaacct cgacctcgaa agacggactc   68820
cggctcgccc gaccccaggg ctcggactca gcctcgacct cggacgatgg actccgcctc   68880
gcccgacccc agggcttgga cttagcctcg acctcggaag acggactctg cctcgcccga   68940
tcctagggct cgggctcaac ctcgacctcg gaggagcctc cgcctcgccc gacctcaggc   69000
tcggaccgac acgtcgcagg gggagccatc attaccctac ccctagctag ctcaggctat   69060
ggggaacaag accggcgtcc catctggctc gccccggtaa acaagtaatg atggcaccccc   69120 gcgtgctccg tgacgacggc ggctctcagc cccttacgga agcaaggaga cgtcagcaag   69180
gatccgacag ccccgatagt tgtacttcca cagggctcaa acgctcctcc gacggccacg   69240
acatcacatg aacagggcgc caaaacctct ccgacagcca cgacggcatg tacttagggc   69300
tctgtctcct ctctgctaga catgttagca cattgctaca ccccccattg tacacctggg   69360
ccctctcctt acgtctataa aaggaaggtc cagggctctc gtacgagagg gttggccgcg   69420
cgggagaacg ggctgacgca caaggctctc tctctctccc acacgaacgc ttgtaacccc   69480
ctactgcaag cgcatccgcc ctgggcgcag gacaacacga aggccgcggg ttcccctttg   69540
ctgttttccc cccttttgtgt tctgtctcgc gtcgacccat ctgggctggg acacgcagcg   69600
acaatttact cgtcggtcca gggacccccc ggggtcgaaa cgccgacaaa acaatatttt   69660
ctagctttgg tacctacaat cttctgtact tccccatttg tctaatgctt caggttgttc   69720
ttttttttct gtagatctat gtaccttatc cttgctatac tgtccatata tgttgtgtgc   69780
atgaaagtct tgcattgaaa atgtcatgtg ctacaatcgt taggactatt aatagatgtt   69840
gctctgtcta tctatccatt tacatcgctg gaaattccca tgcccttttca tagtacgcct   69900 gtgaaattct cactgctttt ctattggttt gtgtgcagtt catgtctctgc aaggtaaggt   69960 ctgttcagtt tggccagaaa ggcatcccct gcctaaacac ctacgacgac cgcaccatcc   70020
gctaccccga cccgctcatc aaggccaacg acaccatcaa gatcgacgaa atcttctaga   70080
attgnnnnnn nnnnnnnnnn nnnnnnnnnn nnnnnnnnnn nnnnnnnnnn nnnnnnnnnn   70140
nnnnnnnnnn nnnnnnnnnn nnnnnnnnnn nnnnnnnnnn nnnntcttat gtatcagctt   70200
```

```
gattcgttgc acattgttga gatgggcctc tctttactcg ctaatggaca ataccgctca  70260
agttttggga ccaagcgttc ctcacctcaa cacatcttat caatagaact cctactaagc  70320
ttcttgatta tgacacatcg ctccaccgtc tcttaggtgc taccccagat tactctaatc  70380
tacgcgtctt tggctatgca tgttagccaa atttgcggcc atacaacacc cataaactct  70440
agtttcggtc catttggtgt gcttttctag tctatagcaa ccttcacaag ggttacaagt  70500
gtcttgacat ctcaacgggc cgtgtttata tttcacatga tgttgttttt gatgagacgc  70560
ttttcccttt gctgctctcc atcccacagt cggtgctcga tatacctctg acgtgcttct  70620
tctacccgat cctaataatt ctcgggccaa ctcagatgat cttgtgacta attctcctgc  70680
tgaatccagc atgcttgctc cgattttgtg gcctaaccag cttttgcagc caccaatgat  70740
ccctgctgca aattctgtcc cggctggtgg cctcaatccc ggtgctgatc tgttgctagg  70800
ctccacgcca cacccctccg acgcggctac aggtgcgccc agcaacgcgg tgcttcccac  70860
caccacggcc gcatcaatag cagcagccac ttcgggattg cctcgtgccg actctggcgc  70920
ggctggtccc tctctcactg acagccatct gccctcgcca tcagcctcgt gtcctattcc  70980
gcttcctgct aggcgcactc ggctacagag tggtattgtg aagcccagaa agtttacaga  71040
tggcacgatc aggtatggaa atttggcaat ttgtgaagaa ccctccagct tgtctgttgc  71100
attgtttgac ccaaactgga aaagctgcca tggacctaga attttctgcc cttatgcgga  71160
ataaaacatg gcacttggtt cctcccgcac ctgacagaaa tttgattgat tgcaagtggg  71220
tttataaact caagagaaaa gctgatgagt ctattgacca tcataaagct cgattggtgg  71280
ctaaaggttt taaacagcgc tacgacattg actatgatga cacttttagc ctagtagtta  71340
aatttgctac tgtccgcctt attttgtctc ttgctgtctc tcagggttgg agcctctgcc  71400
aactggatgt gcagaacgcg tttcttcatg gtgttctaga ggaagatgtg tgtcggcacc  71460
ctaaaactag ggtaccccct actactgtat aaagacgcag tacccacacg actatcttta  71520
gtcgcgtggt aaataagctg tatgtgggac cagaccatga ctcgccctag cctcgggcga  71580
ctactctggg ccagcaacag cacctgaccc caccacatgg gcgggttcgg ggccgccatg  71640
tgtccagaga aagtgatgta ctccaaggca tcaacagtga gtccggaccc catgggagag  71700
tgccggacca gtgccagacc cctgtatata cggtccaggc ctccaagttt ggtccaggac  71760
ctccacgtgt acaaaccgga cccctaggat gggatccgaa ccccccgtat gggtctgggc  71820
cacccatagt ggggtcccag ggttctagga cagaacatac ccgggccttg attaggaccc  71880
aggtgggggt ccgagccga cacgtgtcta gacctggtct ggtgggatcc ggacctatcc  71940
gcatacactc cttctccctg ctcaggcgga gacccgatgc tgccacgtgg catactgcgc  72000
gcggcataaa ccaacgggtg gaacctggca tgatgcctct gggctacgcg tgccttcgca  72060
ttcattacgg agaagatgtg cgcctgtcca ttccactgac aggcggcatg ctcagtccac  72120
gatacgtggg ccatgcagtt actcacacgt taccatatcg agggcaatga ctcaccatta  72180
ctcgtatgtt tccaagaaaa gggttactgt ctatcaatgc tgcatggact gcagccatca  72240
tgactcccgc tgattactca tgtgttactc tgtcagcatt agttattcac ataatgtatt  72300
tcttccatta tgctcctggg cccacatgtc ggggctcagc atccttgtat gtgcctccct  72360
taaactataa aagggaaggc acacaacgtt acaagggaca cgctgtacac actcaataca  72420
acatacacac agtggaggta gtgtattacg ctccggcggc ctgaaccact ataatccctc  72480
gtgtcctctt gtgttcatcc cgaattcacc aaacaggcaa ccgcttaggc cccctcctca  72540
tcttaggatt agggcgggtg cattccgcca cccggccgga ggattttccc ttcgacattt  72600
```

```
ggtgctccag gtaggggct ttggctttag gttttgcct gttttcttgc tcgacacgat   72660
ggttcagatc gtcgagcacc gtggcttgtc tcccgaggac ttcttgatgg aggaaggggc   72720
attatcttcc atgccacgag gctccaaccg cgctgtgcct ggtgctgctg ctatgcacgc   72780
tgcgcagcaa cacacgcccg cacagacctc taggactccg tcgagggcta cctatggtgg   72840
gccattgtct gcagccaggg agttgctgcg taacccacca agttccacgg cctccccggg   72900
ggccatgagg cagtggcgtg aagatgtcga ccgtctcctc ggcatggccc atcctagctc   72960
ggccaggtcc aggcctcgat cattccggca tcagcgcgag gcgtcaacgt ctgtgcattc   73020
accctcagtg aggggcaca gactaacgac ctgcgagcag aactcaacca caggcgtgca   73080
ggcgaggatg ctcgaatctc tctggagagg gcgcgtgagc gccggcaaaa cttcgagggt   73140
cgcaacctcg accaagactt cactgcaagg gacgcccgaa tccagatggg tgtcccattg   73200
gtcggcgtgg gctgcgccgc actagcagat catctccgcg cggcgacttg gccacccatg   73260
ttccggccac acctgccgga gaagtacgat gggacatcga acctgtcgaa attcctgtag   73320
gtctatgtca ccgccattac ggcagctggt gggaacactg ctgtaatggt aagctatttc   73380
catgtagcct tgaatgtgcc ggcacagacc tggctcatga acctcacccc ggggtcgatc   73440
tactcctggg aagagctctg tgcacggttc acaatgaact tcgccagtgc ttatcagtag   73500
catggcgtgg aggctcatct ccatgcagtg aggcaggaac ccgaggagac tctccgggct   73560
ttcatctccc gcttcaccaa ggtacagggg actatacctc gcatctccga tgcctccatt   73620
atcactgctt tccaacaggg gggtgcgtga taagaagatg ttggagaaat tggcgacgca   73680
tgacgtggaa accgtcacta cgctcttcac tctggccgac aaatgtgcca gagctactga   73740
gggccgtgca tggcactcga cgctgcaaac cagagtcacc caaatgggtg gctcaggtgc   73800
tgccacccag ggtggtggca agaaaaagaa gaagcaccgt gtcacgatag gccgtagtct   73860
ggtgctccag ttgctgtagc tacggctggg gaccgggacg agcgcggcaa gcatccacgg   73920
caacagggaa gtgacattgg gtcatgccct gtccaccca acagtcgcca cagtgcctca   73980
gaatgacgag agatcctgaa gctcgtgaag cgcatcagtg agcggcgcga gcatgcctcc   74040
agggatggct cgccgcctcg gcgccggcct ggcaaggaga aggtcgacga aggtgacctg   74100
gccacgggag aatgggacct cgagaattag gcccccgagc aagtcctcaa ggatatcctc   74160 actgagagact ccgactccgg tgatgacaac gaccgccgca agaagctgta cgtaatgtat   74220
ggtggaagct gggagctcac ctcccgtagg aacgtgaagt ccctgcgccg cgaggtcctt   74280
ttggcgaccc caggggtccc gaaggcagcc ccacatcagc ggtggcggag caccactatc   74340
tccttcgggg cacccgactg ccccgaaaac atggcagggg ctggtatact accactcatc   74400
actgcccctg tcatcgccaa catgaagttg catcatgtgc tgattgatgg tggggttggg   74460
ctcaacgtca tcagccacgc tgcgttcaag cagctgcaga tcccaggatc ccgactagga   74520
ccctctcgca cgttctctgg agtgggccct aaaccggtgt atcccccttgg gagcatcaca   74580 ctcctggtta cattcgggac tgaggataac ttccacacta agaatgtcta gttcgatgtt   74640
gcggaggtta acctcccttt caatgccatc attggcaggc cggccctgta ccggttcatg   74700
tccattgccc attacaggta cttggtcctc aagatgccat ccctgctgg gtcctcacc   74760 atgcggggcg accgtcccgc tgcgcttgca gctatcgaga agttgcatgc cctagcggca   74820
gaagctgctc gcccggatga cgaggggagg gaccccctcga cttcctgtac caagatgcct   74880
gctaaggtgc ctaaggtgca accatctggg gcagacggcg tccctgtcaa gaccatccgg   74940
```

```
ctcaacgggg attcctccca gaccactcgc atcacgggcg atctggagga gaaataggaa    75000
atcgcgctca tcgccttcct ccaggcaaat gccaatgtat tcgcatggga actatcgcag    75060
atgcctggga tccctaggga ggtgatcgag caacatctga agatccaccc tgacgccaaa    75120
ccggtgagtc agaagcctca aagacagtcc atcgagcggc aggatttcat ccgtaaggag    75180
gtccggaagc tgctggacgc tggtttcatc gaagaggtcc atcacccagt atggctggcc    75240
aatctagtca tcgtcccaa ggctaacggg aagctttgga tgtgcatcga ctacaccagc    75300
ctcaataagg cctgtcccaa ggacccatat ccacttccac gaatagatca aatcgtggat    75360
tctacctctg ggtgcaacct cctatccttc ctggatgctt actctagttt ccatcagatc    75420
gagatgtcta ggcaagatag gaagcatacc gcttttgtaa ctgtggatgg actttactgt    75480
tatgttgtaa tgccttacag tctgaaaaac gccttgccaa catttgtacg ggcgatgagt    75540
aatacttttg gtgacttgat tagggacagg gtagaggtat acgtcgatga catcgtagtc    75600
aagactaagg gagggtcgac cctagtggaa gacttaaccc tagtctttga caagctgcag    75660
gcaacacgca tgaagctgaa cccggacaag tgcgtctttg gtgtctctgc agggaagttg    75720
ctaggattcc tggtttcaca ccggggcatt gaagcaaacc cagagaagat caaagcaata    75780
gagacaatga ggcctccggc ctgaatcaaa gacgtccaga agcttacggg gtcactggcc    75840
gcccttagtc gcttcatctc aagactggtt gagagggcac tacccttctt caagctattg    75900
cggaagtccg acccattctc ttggaccaaa gagacagaac aagcctttca agagttgaag    75960
cagcaccatg tgtccctatc aatactggta gctccagagc caggagagcc attatactag    76020
tacattgcag cggctacaga ggcggtgagc atggtgctgg tcgtcgaaag tacgacacaa    76080
catccctagg ggagtcataa agttcccta ggagaaggtg gtggtctgac caccacgatg    76140
ttgacagaag gccaggagtt tgaggactcg ggactgaatg caggggtccg aaccatccag    76200
aagccggtct actacgtcag cgaggtcctc catgaggcaa aagccaggta ccttgagacg    76260
cacaagctta tctatgctat acttgttgtg tccaggaaat tgcgccacta tttttaggca    76320
cacagagttg tggtggtgac ctccttcccg ttaagggcca ttctccacaa ctcaaacgcc    76380
acaggcaaca tcgccaagtg ggccacggag cttgctgagt tccaactgga gttccagccc    76440
cgccacgctg tcaagagcca ggtcctggct gacttcatcg tggagtggac cccttccccg    76500
agcgctcctg ggggtccaga tcccgattcg gacaccacac ctgcggagcc aagggcttcg    76560
gtcttcactg agccccactg gatgcttttc ttcgacggat ccgcctgcca gcagggtggc    76620
agtgctggag ttgtgacacc ccaggtgtca gtttcgtgtt acgtcgcgag atttatccta    76680
atctcggatg ctcagtaaaa atttctattt ctcgctcgcg tatgtccctg attatccaga    76740
ttattcattc atgtttcacc gaattcggag ttactcagtc tcatagaagg ccaattttgg    76800
agcctgttaa aactttatc cttggcacaa atgcgaactc aaaaatcatt ctcgaattat    76860
aaacctcatc tgaagctcaa taaatcaaac tctcgacggc tgttatttga tctgtgtccg    76920
aatccaattt ctcgatgttc gatcgatgtc caactatttt aatccgagtc catactcaca    76980
aacgaaataa tcaatatgtc gtcctctgat caaatcttac tcgactcagc ttagcatctc    77040
tgtatccaat ccgatttcaa aatcaacatc ggcaacgatt tttatatatc acgattcgct    77100
ttctccgact aaaaatccaa aaccgatcaa atctcaggac ggtttatttt cgatttacgc    77160
gtagggaatt attttcaagc aaaatctaaa cagactctcg gctgagttaa tcgcgcaacc    77220
ttccgttcgt ccgaactctt ttcgctctgt ttctcagtag cgacgaattc cgcaggaaca    77280
tttttagtcc ggaaattatt tagcgcgacc caatttagtg tttttgggcca aatccagtcc    77340
```

```
agcccgtttg gcccataaga aaccctaccc taatttctcc tctataaata tgggcttccc   77400
taccttgcat tctgaaaatt ttccatttcc accccagccg ccaacaccct tctcttcctc   77460
ctctaccatt ttccagccat gggctccttc aagcacgtag agctggagct ccttccccag   77520
cgcgcagggg cttccatggc cgggcgttcc ttccctccag cgcgtcgaag ctcttctcgt   77580
agcgtcctct gcctttcttc ttccccgctt cacggcagca aggccaccag caggctccct   77640
gctcccgcg cccccagcca tggcatcctt cactcccta ctgttttct cccagggcgc     77700
agcagcaaat ccatgcagcg gctccatggc cgagcaccct gcccggtgct ccagccggcc   77760
tcctctgccc ctgccatttt cataggagt cgagctccta cctgcagcag gcgcccctg    77820
ctctttcctg tccgcgacca gggagcttca gctggcgtga aacttcactt gcgcacggcg   77880
gccagcaccc tctccttggg ctccaacagc ttggatgccg aacccctttc ttccttccc    77940
tggccgagct cgagcttccc atggagccat tcctccctct ctctgttgta catagtgcca   78000
agcagcaact ccatttttccc tggccgcgcc caaggtcggt gaccagcctc cccttccctg   78060
ttcttgccgt ggccgagcca ccacttcccc agccgtagcc ctctccccct ccattgtttc   78120
agcgcctgaa acaaacacct ggccgccatc cacacttgtg ctcgatgaaa tgtgcagcag   78180
ccccgacggc tccgcgtgct gccggcttgc tgttttgttg cgtagtgagc agcacgccgt   78240
gatgccgccg tgtgttcgct gtttttgcgc agccccaaac gtcgtcgtcg ttcaccccgg   78300
tgagaccgcg acgctccttg tttgattccg catcgatgtt attttcctat gattaattat   78360
gtatgtgtgt tgctttgttt tattttttgtg gaggagagaa ccccgtgttt tgcgaggaga   78420
aagcaagtcg cttaacgctc gttggatgtt tggagcgatg cacgaatcgg aatcaccgtc   78480
attcttgcaa acatcatttg ggtttgttta tggtgagccg atgcatgtcg ctctcgatcg   78540
actcgattaa tcattttgta tggatgtgtg taaaatgttc gattatgcgc attggtagga   78600
tcacgtttgc gattggagaa caagaggtta attgatgtgc acgatttgta gttgtctaat   78660
tatgttttgg tcgatgatgt gcatgtggtt atatgtgtgt aactgtataa ttttataaat   78720
ggacgcgtgt agggaagaaa ttgaaataga aagaactcg agtattttta ttttgatagg   78780
aaaatatgcg atgcgttgtt tgatgcgaaa actaagttac aaaatgtgga ttttgttttg   78840
ggaaatgcat cgatgtgttt atgtgaaaag tgtatttgtt ttaagcaatg tgatgggatt   78900
cataatttta gaggggatat atttattgat gtgacgagta gtttagagaa tgctagtttg   78960
cgtagaggat gtatcgttaa gacatgagtg tcagagtcca tttatactag tggtcgcgcc   79020
acatggattg aagtgtctcg agtgcacgcc ataatatggt tgtatgcgag acagggttat   79080
gcgtacgatg agtttagtaa aaattccatc ggtgtcagtt gtgttaagtt gaagtttatt   79140
tgtgcgtata aagtagtaag gtatttaatg cttacgactc ttaatcgatg gtagaaattg   79200
tcttgactta aatagagagg tggtgacatg ccagagtagt catcgctttc tctatattta   79260
taggtcaagt catgacgatg cgtattatgc gttcgttaaa attatgtttc gtatatagtg   79320
tatgattgtg ctcacgattt cgagtagaca cttcaaataa gtcaagtagc tttgtaatgc   79380
aagatgtgtg atgaagttag tttgttttag gatatgtgtt gaaatgctcc attcctgtga   79440
tagacatgta gggttatttc aaaacgggtc gatgtgtgtg atgatgatat tcatgattta   79500
agtagatgtc ctgaaattat gtggcgaagc ttaggttaag ttgcaagcga tgtggaaatg   79560
ttttcgtaaa gatatatgtg gaatgtgaac gagtcattca atgtattcgg tatgtcatgt   79620
agtggtggta tgaaaaatgg gttaggaatc gatcggctaa atgccaagtt cggttagagt   79680
```

```
tattgtcggc gtttcgagac cgggggggtcc ctcaggtcga cgagtgagtg ccgcgtgcgc   79740
cagcccagat gggtcgagcg cgtgggcgag cgcgaagggg ggaaaggagc gaggcggccg   79800
gagaccggcg tgagagaggt gggaatcccg cggccttcgt gttcgtcccg cgcccaggtc   79860
gggtgcgctt gcagtagggg gttacaagcg tccacacggg tgagggaagc gagcggcccc   79920
aagagagcgc ctgtcccgtc ctcgtcccgc gcggccaacc ctctctaaga ggaccctggt   79980
ccttcctttt atagacgcaa ggagaggatc caggtgtaca atgggggtgt agcagagtgc   80040
tacgtgtcta gcgagggaga gctagtgccc tgagtacatg ccaatgtggc agccgaagag   80100
atcttggaac ccagctagtg tgatgtcgtg gccgtcggag gagcggcgga gcctggcgga   80160
gggacagctg tcggagcggt tgtgtccttg ctgacgtcct cctgcttccg taagagagct   80220
gagagctgcc gtcgtcacag gcatgcgggg gcgccatcat tgcctatctg gtggagacag   80280
ccagatggga caccggtctt gttctctacg gcccgagtca gctcggggta gggtgatgat   80340
ggcgcttcct gttgacgtgg ctggcctgcg ccctaggttg ggcgacgtgg aggctcctcc   80400
gaagccgagg tcgagtctgt cttccatggc cgaggacgag tccgagcccc tgggtcggcc   80460
gaggcggagg tcgtcggcag aggccagggc ggtgtccgag ccctggggtc gggcgaagcg   80520
gagttcgtcg tcttctgggg ctgagcccga gcccgagccc tggggtcggg cgaagcggag   80580
ttcgtcgtct tccgggtctt agcccgagtc cgagccctgg gtcggttgga gcggagttcg   80640
ccgtcttccg ggtcttagcc cgagtccgag ccctgggtcg gacggagcgg agttcgccgt   80700
cttccgggtc ttagcccgag tccgagccct gggtcgggcg gagcggagtt cgccgtcttc   80760
cggggctgag cccgagtccg agccctgggt cgggcggagc ggagttcgcc gtcttccggg   80820
gctgagcccg agtccgagcc ctgggtcggg cggagcttcc tatggcgcct ttggcagggc   80880
ctggcttcct gtcagtatct ctctgtcaag tggcactgca gtcgaagtgg cgcaggcggc   80940
gctgtccttc tgtcagaccg gtcagtggag cggcgaagtg acggcggtca cttcggctct   81000
gccggagggc gcgcgtcagg ataaaggtgt caggtcacgt ttgcgttaaa tgctcctgcg   81060
acttggtcgg tcggtgcggc gatttagtca gggttgcttc ttagcgaagg cagggcctcg   81120
ggcgagccga agatgtgtcc gccgttagag gggggcctca ggcgagacgg aaatcctccg   81180
gggtcggctg cccttgtccg aggctaggct cgggcgaggc gtgatcgagt cgctcgaatg   81240
gactgatccc tgacttaatc gcacccatca ggcctttgca gctttatgct gatgggggtt   81300
accagctgag aattaggagt cttgagggta cccctaatta tggtccccga cagtagcccc   81360
cgagcctcga aaggagtgtt agcactcgct tggaggcttt cgtcgcactt ttttgcaagg   81420
gaccagcctt tctcggttgc attttgttcc ggtgggtgcg cgcgagcgca cccgccgggt   81480
gtagcccccg aggcctcgga ggagtggttt cactccttcg aggtcttaat gccttgcgta   81540
atgcttcggc tggtctggtt gttccctcat gcgagctggc cgtagcccgg gtgtacggtc   81600
ggggcccaag ttctcgggct ggtatgttga cgctgtcaac ggtttggccg gagccggtt   81660 tgcgagagca gccccctgagc ctctgcacag ggcaagaggg cgatcaggga cagactcggc   81720
ttttttacat atgcccctgc gtcgcctttc cgcaaggagg actaggggga gggcgccatg   81780
ttaccctcga tgggcgccga acatggtgtc tccggtgagc tgcaagcagg taatccgagt   81840
ggacgtccgt gccccgttcg ttaggggtcg gctaggggcc cagaggcacg cccaaaagta   81900 ctgcgggtg atctgccgga cccggtcccc tggcgacggg gtccgagggc tcgatgcctc   81960
cctccgatgg gattccatta caagatcgct cccgctggtc tcgaaatgt cctagggtac   82020 ctcaggagcg cagcccgagc cttggttatg tatcgaacgt accccctggtc atccctcgct   82080
```

```
cggcgtctga ggcggctgtg aacccttcgg gggccagcct tcgaacccct gatcagtaat    82140
gggcacggag cccgagtagc ctgaggcgac cgtggaaccc ttcgggggc cggccttcga    82200 acctctgacc agtagtgggt gtagggccca cgcgatctga ggcggctgtt gaacccttcg    82260
gggggccagc cttcgaacct ctgatcagta aggaggctcg gagcctggtt ccttcacggg    82320
gaaggatccc tttcggggta tccccctttc ccggtccctg tcgcaagaga tagagaaaga    82380
ggaaaagggg aaaaggatac gaaaccgaac gacgcggcgt accttttttg gcgcggttat    82440
ttcggcgaag gcgaagtgtc gcccgctgct cctgccagaa gcgccgcctg tccagccgcg    82500
gagttaatgc gacgaggcga gtagttggcg gggcagccgt tgcgcgtgcg cgagccgttc    82560
gaggaacgga tcacgggcgc gttgtcttca cgccgtgaga gggggttctc ttgctgcccc    82620
cggatgggac gtgagcttgg ctgacgacgt gaccgctgct cccacgcgcc tgccaccgtc    82680
attactgccg gcccactttt ggccgtgttg accgccgcgt caggctggcg ctgctgggtc    82740
gcacgctggg tcgcctcgag tcgcggtatt ggttccgcaa tcgaggaggc gcggtggtgg    82800
cgcaagtggc ggtgcagttg cttgcatgtc gtcgtagtca gagcgggcgg cggcgagccg    82860
ctcgtcagtc ttctgttgct ccgtaggccc acccctatcg agtggggctg ttcgtacctg    82920
cggagggggg aaccggagtt ccgtttgtaa tggcacttcg aatgccggtg ttttttgttca    82980 ttgcggcttt cggggcctga acatgtatgt aattccggca cggagccgtg ttttttcctca    83040 ttttttgagcg ctaagactcg tctgttgatt atctgaaccg cttcaccaag catgagtcgc    83100
cccgtgtcaa ggtgacgagt gaggtatccg tatcccggag gcgtaggagt ccctcggctc    83160
ggtcggcctt gctgtccgag gctcctctag cttagttaaa gggacccctc ggccgctctt    83220
cgacgagccg aggccagggg tagcgatatc agtgtgaaca gaggcggagt tggctcgaaa    83280
atgaaacctg gttggtcgga gcctagccgg gttgtccgtt ggcgggaccg acgtcggggc    83340
tgatcagccg aggcctcagg tcgggctggc gcccttggga gatggtcggc cgaggccca    83400 ggggtaaccg gccgagccgc ctgctcgggc cggattcccg gagaagtccc tggcagcgat    83460
tgcccgggcg tggtgatgac atcgtccttc ggagcggaga tcctcggacc gcgtcgccgt    83520
ccgaggctag gtcgggcctc gctgaaggtg tcatcgatgc cgagggtgtt gctgcccct    83580 tccagcgtca agacccgagc ctgtagggtc agattgtctt gtagcgtgtg ccttctgcag    83640
ccgccgaggc cagaatacac gccctcgctg tgttgtaaag ctgcgtctcc tttcctcttg    83700
tttcgagtat cttgactttt ttgtcggtaa cagggatgtt tgtgtgagtg ggagttgctt    83760
ctcgcggaag gtgatgagtg aggtatccgt atcccgagg cgtggaagtc cctcggctcg    83820
gtcggccttg ccgcttacac gtactttcac tcgtccatga ggccctgcca ccgactcagt    83880
cgagaaggct cgaaggattg cttcggcaga agaacttccg aacatgaaga cttgttcggt    83940
ccgcggaatc actttatccg aacgcgagtt acttatcgca gaaggtgatg agtgaggtat    84000
ccgtatcccg gaggcgtagg agtccctcgg ctcggtccgc cttgactgct tacgtgtact    84060
ccgtcgtttt caggatccac tttttcgaagt agtcaaaaag cacgaaagat attctggcag    84120
aagagacctt ttttcgagga aaatttcgac gcagagggg ttccccccct tttagccccc    84180
gagggagggt cgggctttgc cgaggcgagg ccgacccttc cttgatgact aaactttgcg    84240
tgggtgcgag gtatatgaac gacctgaaaa catcttaagg gtagaagcga cgtagctgtt    84300
ggatgttcca agcgttgccg tagacctcgc cttgactgtt ggccagcttg tacgttccgg    84360
gcttcagaac tttggcgatg acgaatggcc cctcccaggg gggcgtgagc ttgtgcctcc    84420
```

```
ctcgggcgtc ttgccgcagc cgaagcacca ggtcgcccac ctggaggtct cggggtcgga   84480
cccctcgggc gtggtagcgc cgcagggact gctgataccg cgccgagtgt agtaaggcct   84540
tgtcccgagc ctcttccagc tggtccagcg agtcttctcg gctagcttgg ttgctttgat   84600
cgtcgtaggc cctcgtcctc ggggagccgt attctaggtc agtgggcaag acggcctcag   84660
ccccgtagac caggaagaac ggcgtgaaaa cccgtggccc ggctcggcgt cgtcctcagg   84720
ctccagacca ccgaggggag ttccttcatc catcgcttgc cgaacttgtt gaggtcgttg   84780
taaatccgag gcttgagccc ttgtagaatc atgccgctgg cacactctac ttgcccattc   84840
gacatgggat gagctacggc ggcccagtcc acccggatgt ggtgatcctc gcagaagtcc   84900
aagaattttc tgccggtgaa ctgggtgccg ttgtcggtga tgatggagtt caggaccccg   84960
aagcgatgga tgatgttggt gaagaacgtc accgcctgct cggacctgat gctgttcaga   85020
ggtcggacct cgacccactt ggagaatttg tcgatggcga ccagcaggtg cgtgtagccc   85080
ccgggcgcct tctgcaaagg gccgacgagg tccagacccc acacagcgaa gggccaggtg   85140
atgggtattg tctgcagagc ctgagcgggc aggtgggtct actttgcata gaattgacac   85200
ccttcgcagg tgcggacaat tctagtggcg tcagccaccg ccgttggcca gtagaagcct   85260
tgccggaaag cattcccaac gagggctcga ggcgctgcgt gatggccgca agcccccgag   85320
tgtatctctt gcaggagttc ctgaccttcg gcgatggaga tgcatcgctg gaggatgccc   85380
gagggattgc ggtggtagag ctcctgctca tcgcccagca agacgaacga cttggcgcgt   85440
cgcgctatcc gtcgagcctc ggctcggtcg aggggtagct ctccttggcg gagatattgc   85500
aggtacgggg tctgccaatt tcgatcaggc atggccccac ttcgctcctc ctcgatcgcg   85560
gatgcctcgc cctcggagac cgagggtacc tcggttgag ctgagggtgc ctcgggccgt   85620
gccgagcgta cctcgggctg gtccgaggc gcctcgggct cggagggtc atcgatcttg   85680
acggagggct aatgcagatc ccgggagaag acgtccgggg aaccgttgtt cgccccgagg   85740
ctattttgc cagctcgtct gcagtctcgt tgtagcgccg agcgatgtga ttaagctcga   85800
gcccgtagaa cttgtcttcc aggcgccgaa cctcatcgca ataggcctcc atcttcgagt   85860
cgcgatagtg ggagttcttc atgacttggt cgatgacgag ctgcgagtcg ccgcgagcgt   85920
cgaggcgtcg gaccctagc tcgatggcga ttcgcaatcc gttggtcaga gcttcgtact   85980
cagccacatt gttcgacgcc gggaaatgga ggcgtagcac atagcgtagg tgtttcccga   86040
ggggtgagac gaagagtagg cccgcgccgg ctcctgtctt catcaatgac ccgtcgaaaa   86100
acatggtcca gagctccggt tggatcggag ccgtcggtag ctgggtgtcg acccattcgg   86160
ctacgaagtc cgccaagacc tgggacttga tggccttccg aggcgcgaac gagatggtct   86220
cgcccatgat ttccaccgcc cacttcgcaa tcctgcccga ggcctctcgg cactggatga   86280
tctcccccag ggggaaggat gacaccacag ttaccgggtg agactcaaag tagtgtcgca   86340
acttccgcct cgtcaggatc actgcataca gcagcttctg aacttgtggg tagcggatct   86400
tggtttcgga cagtacctca ctgacgaagt aaactagcct ctgaatgggc aatgcatgcc   86460
cctcttcttg cctctcgacc acaatcgcgg cgctaaccac ctgagtggtc gcggcgacgt   86520
agaccaagag ggcttttct ccatcagctg ggggcaccaa gataggcacc ttggtgagga   86580
gcgccttcag gtctacgaga gcttcctcgg cctcaggggt ccaagtgaag cactcggcct   86640
tccttaagag gcggtacaga ggcaggcctc tttcgccgag gcgtgagatg aagcggctca   86700
gggccgcgag acatcccatg accctctgta cacctttaa gtccttgatg ggccccatgc   86760
tggtgatggc tgcgatcttc tccaggttgg cttcgatgcc ccgctcggag acgatgaacc   86820
```

```
ccaagagcat gccccggggc accccgaaga cacacttctc gggattgagc ttgacgcctt    86880
ttgccttgag acaccggaat gtcacttcaa ggtcggagag gaggtcggaa gctttccttg    86940
tcttgactat gatgtcatcg acgtaggcct cgaccgtgcg accgatgtgt tcgccgaaca    87000
catggttcat gcaccgctgg tacgtcgcac ccgcattcct caaaccgaac ggcatggtga    87060
catagcagta catgccgaag ggcgtgatga agaagtcgc gagctggtcg gactctttca    87120
tcctgatttg atgataccct gagtaggcat cgaggaaaga cagggtttcg cacccagcag    87180
tggaatccac gatttgatcg atgcgaggca gagggtaagg aaccttcgga catgctttgt    87240
tgagaccagt gtagtctaca cacatccgcc atttcccccc tttctttctc acaagcacag    87300
ggttggcgag ccattcggga tggaatacct ctttgatgaa cccggctgcc attagcttgt    87360
ggatctcctc gcctatcgct ctgcgcttct cctcgtcgaa tcggcgcaga ggctgcttga    87420
ccggtcgggc tccggcccga atatccagcg agtgctcggc gacatccctc ggtatgctag    87480
gcatgtctga gggactccac gcgaagacgt cggcgttcgc gcggagaaag tcgacgagca    87540
ctgcttccta tttgggctcg agcccggaac cgatccggat ctgcttggag gcgtcgccac    87600
tggggtcgag ggggacggcc ttagccgtct ccactggctc gaagttgccg gcatgacgct    87660
tcacgtctgg cacctctttg gagaggctct ccaggtcggc gatgagggcc tcggactcgg    87720
cgagggcctc ggcgtactcc acgcactcca cgtcgcattc gaacgcgtgt ttgtacgtgg    87780
ggccgacggt gatgaccccg ttggggcccg gcatcttgag cttcaggtag gtgtagttgg    87840
ggacggccat gaacttcgcg tagcatggcc tccccagcac cgcgtggtag gttcctcgga    87900
acccgaccac ctcgaacgtc agagtctccc ttccgaagtt ggagggtgtt ccgaaacaga    87960
cagggaggtc gagtcgtccg aggggctgga cgcgcttccc gggaatgatc ccgtggaagg    88020
gcgcagcgcc tgctcggacg gaggacagat cgacgcgcag gagcccgagg gtctcggcgt    88080
tgatgatgtt gaggctgctg cccccgtcca taaggacctt ggtgagcctg acgtcaccga    88140
tgacagggtc gacgacgagt gggtatttcc ccgggctcgg cacgtggtcg gggtgatcag    88200
cttggtcgaa ggtgatgggc ttgtcggacc agtctaggta ggctggcgcc gccaccttca    88260
ccgagcagac ctcccggcgc tcttgcttgc gatgctgagc cgaggcattc gccacatgcc    88320
cgccgtagat catgaagcag tcgcggacct cgtggaactc tcctacttgg tgatcttcct    88380
tcttgtcgtc gtcgcgggcc ctgccaccct ccgcgggtgg cccggccctg tggaagtggc    88440
gccgaagcat gacgcactcc tcaagggtgt gcttgacggg ccctgatga taggggcacg    88500 gctccttgag catcttgtca aagaggttgg cacctccggg gggctttcga gggttcttgt    88560
actcggcggc ggcgacaagg tccgcgtcgg cggcgtcgcg tttcgcttac gacttcttct    88620
tgcctttctt cttggcgccg cacggagtag acgcctcggg agcatcttcc gacgggcggc    88680
cctggggctg cttgtccttt cggaagatag cctcgaccgc ctcctggcca gaggcgaact    88740
tggtggcgat gtccatcagc tcgctcgccc tggtgggggt cttgcgaccc aacttgctca    88800
ccaggtcgcg gcaggtggtg ccggcaagga acgcgccgat gacatctgag tcggtgatgt    88860
tgggcagctc ggtgcgctgc ttcgagaatc gccggatgta gtcccgaaga gactctcccg    88920
gctgctgtca gcagcttcgg aggtcccagg aattcccagg gcgcacatac gtgccctgga    88980
aatttccggc gaaggcttgg accaggtcat cccagttgga gatctgcccc ggaggcaggt    89040
gctccaacca ggcgcgagcg gtgtcggaga ggaacagggg gaggttgcgg atgatgaggt    89100
tgtcgtcgtc tgttccaccc agttggcagg ccaggcggta gtccgcgagc cacaaatccg    89160
```

```
gcctcgtttc ccccgagtac tttgtgatag tagtcggggg tcggaaccgg gtcgggaacg   89220
gtgcccgccg gatggcccgg ctgaaggcct gcggaccggg tggttcgggc gagggactcc   89280
gatcctcccc gctgtcgtag cgtcccccac gcctggggtg atagcctcag cgcaccctct   89340
cgtcgaggtg ggctcgacgg tcgcagtgat ggcgctcgtt gccgaggtgg cccggggccg   89400
caggcgcggt gttgcgcgtg cgcccggtgt agaccgaggc ttcccgcatg aatcgggaag   89460
tcgcggcatg aggttccgag gggtatcctt gccttcggga ggcagtgctc tcggcccgtc   89520
ggaccgtggc gccttccagg agattttga gctctcccta gattcgccga ccctcggtgg   89580
tggatggctc cggcatcgcg cggaggagca tcgctgctgc gaccaggttc tgaccgaccc   89640
cactggatgc aggtggtggc ctgaccctga cgacatcggc gacgcggtgc tggagaccct   89700
ggggcaggtg acgtatttct ccggccgggg gttggcccgc ccatgcctgc ccgacgtccc   89760
ggcggatcgg ctcaagcgct cctgctccct cgtcgatcct ggcctgcgcc ccgcggactt   89820
gctcgagctg tgggtcgtaa ccccccgccg gaacagggac cacaactagc tcccgcggga   89880
tgtcagcgcg aggcaccggc ccaggggag caccgtcctc cggcatgccg agatgattgc   89940
cttcggaggg acccctaga tcgacgtgga aacattcgcg gcttgggccg cagtcctcgt   90000
cgtcgaggct gcggctaccg tcggaacagt cggagaggca gtagtcacat gcggtcatga   90060
agttccgctg gcactagggt tgccaaatcc agagaaatcc caacagatgt tggggtcgtc   90120
atcttcctcg gacccagagg gccgtaggt cgagacgtcc gtcagccggt cccaaggcga   90180
ccgcaagcga aaccccagag ggtttgtact cgcctctaca agggcgcccg ccaaagcaag   90240
attgctagac gggttgaggc tgagtacaaa tgacgtagga tgggaatcgg ttggtaccttt   90300 ttggtcgtcg agcggcgatg aagtcacgtc gaggactgac cgcatcgtcg cctcaggtac   90360
gagggcgatg tcctgcaagc ttttcgcaag cgcgctggcg tcgtccactt gctcgggatt   90420
ggcgtgtcgc ggggagacgg cgctcgcctt tgtctcaaac gcgaggtcga cgcccaacgc   90480
gccccccgtt ggggtgctag ggacgtcgac tcgctcgaca ccgacgagg cgcggcctcc   90540 tgcttggcct ttgttgcccc gcctcctcct ccgttggcgg gggagaggac ggggcgagct   90600
cgaatgttgt tcttccgcca cgcggggaag acgtcgtcga ttccgccgcc ggcgggcggg   90660
ctgtcggccg ccatcgtcgt tgtcgcgcgg cggtggaagg agtatcatgt cgtagctgcc   90720
gtcgagggac atgaactcaa gactcccgaa acgagcacc gtcccgggtt ggagaggttg   90780
ttggagactg cccatctgga gctcgacggg aagctgttcg tcaacacgca gcaggcccct   90840
acctggcgcg ccaactgtag gcgtttcgag accgggggt ccctcaggcc gacgagtgag   90900
tgccgcgtgc cccagcccag atgggtcgag cgcgtgggca agcgtgaagg ggggaaagga   90960
gcgaggcggc cggagaccgg cgtgagagag gtgggaatca cgcggccttc gtgttcgtcc   91020
cgcgcccagg tcgggtgcgc ttgcagtagg gggttacaag tgtccacgcg ggtgagggaa   91080
gcgagcggcc ccaagagagc gcctgtcccg tcctcgtccc gcgcggccaa ccctctctaa   91140
gagggccctg gtccttcctt ttatagacgc aaggagagga tccatgtgta caatgggggt   91200
gtagcagagt gctacgtgtc tagcgaggga gagctagtgc cctgagtaca tgccaatgtg   91260
gcagccggag agatcttgga acccagctag tgtgatgtcg tggccgtcgg aggagcggcg   91320
gagcctggcg gagggacagc tgtcggagcg gttgtgtcct tgccgacgtc ctcctgcttc   91380
cgtaagagag ctgagagctg ccgtcgtcac agggcatgcg gggcgccatc attgcctatc   91440
tggtggagac agccagatgg gacaccggtc ttgttctcta cggtccgagt cagctcgggg   91500
tagggtaatg atggcgcttc ctgttgacgt ggctggcctg cgccctagtc tgggggtacg   91560
```

```
tggaggctcc tccgaagccg aggtggagtg gatcttccat ggccgagggt cgagtccgaa    91620
gcccactggg tcgggccaag gcggaaggtc gtcggcaaaa gtccagggcg gtgtccgagc    91680
cctgggctcg ggtgaagcgg aattcgtcgt cttctgggc tgagctcgag cccgagccct     91740
ggggtcgggc gaagcggagt tcgtcgtctt ccgggtctta gcccgagtcc gagccctggg    91800
tcgggcggag cggagttcgc cgtcttccgg gtcttagccc gagtccgagc cctgggtcgg    91860
gcagagcgga gttcgccgtc ttccgggtct tagcccgagt ccgagccctg gtcgggcgg    91920 agcggagttc gccgtcttcc ggggctgagc ccgagtccga gccctgggtc gggcggagcg    91980
gagttcgccg tcttccgggg ctgagcccga gtccgagccc tgggtcgggc ggagcttcct    92040
atggcgcctt tggcagggcc tggcttcctg tcaatatcac tctgtcaagt ggcactgcag    92100
tcgaagtggc gcaggcggcg ctgtccttct gtcagaccgg tcagtggagc ggcgaagtga    92160
cggcggtcac ttcggctctg ccggagggcg cgcgtcagga taaaggtgtc aggccacctt    92220
tgcgttaaat gctcctgcga cttggtcggt cggtgcggcg atttagtcag ggttgcttct    92280
tagcgaaggc agggcctcgg gcgagccgaa gatgtgtccg ccgttagagg ggggcctcgg    92340
gcgagacgga aatcctctgg ggtcggctgc ccttgtccga ggctaggctc gggcgaggcg    92400
tgatcgagtc gctcgaatgg actgatccct gacttaatcg cacctatcag gcctttgcag    92460
ctttatgctg gtgggggtta ccagctgaga attaggagtc ttgagggtac ccctaattat    92520
ggtctccgac agttattttg atagttggga ttgtggggtg aagtgatggc atgactacgt    92580
agccgtcacg tcatctattg cgtggctatg cttaagcgtg ccttgatata atttagaata    92640
agtcgagtct ctagaacgcg gcaatttta aaagtaaata gaagctgaat ttattgattg    92700 ctgtttggg ctgcacgcac tgttttagtt gtgctgtttg tttgataaac caaatcatgt     92760
tttctataga aaagtcatat agaagagttg tagatgacat gattatcttg cttgtactaa    92820
aatttgacag ccataaacct gattgtttag gagttgtgct tttcacaagc ccagcacctg    92880
aatctgtcaa atttctgaac atatttcaga aattgcaatg attgcttaag ttaatgttga    92940
aattagttat tggtggtcac aaaaaagttg tagataactt tattatcgta cttgtgttaa    93000
aatttgacag gcataagtct gattgtttag gagttatgtt ttttacaaat tcagtaactg    93060
aatctgtcca ctttctgtac agatttcaaa agctgcattg tttgcttaag ttaatgttag    93120
aatcagccct tgtcaattat aagaaagttg tagaggcttt tcttgtcttg cttgtgttaa    93180
aatttcataa ctataggcct gacggtttaa gagttatgaa ttttacaaac tggttgctgt    93240
gttctgtcca ccgtcagaac agatttcgaa aactgtaata tttgatttag ttaaacctgg    93300
aatcacttct tggtgattat aaaagttgtg tagtactttt gctaagcttt tcaaaaagtc    93360
ttagatcact ctttttggtg gtctgaagat taagttacat gtgtttgaag tgtgaagact    93420
gaatctgtcc agttttggac agcacagcct tcatagtata ttttaacctt gatacatgct    93480
aaaccagcct gggatgttta taaataattt gtagaacatt taattagctt tccagaaagt    93540
ctaggatcaa tttgtttgga tgtctgaatc ttcagttatg aattttaaa atcacaagtc     93600 tgaatctgtc caaatctgga cagagctgct gtgattgcac ttttgacct tgctaagtgt     93660 ttaatcatgc tgtgatgaaa ataccaaaat tgtagagcac tttctaaact ttccagaaag    93720
ttttagtttg ctattttgg attaatattt taaagttat gattaaaaca agtagctgct      93780
gtgctgctgt cctaaaaatc tgcacgtgct caaatgaata tttagttcac cattttggct    93840
aaaaacgctt tagtaagcac ttaacggaca tagacttgtg atggctaaac ttaggttaac    93900
```

```
atgtgttcca taattaatgt gtttgcttgc tgtagttgat tgtgatagag gagtccatcg  93960
acattgatgc atcggtcctt ttattaaact tgtgtttgtg atgtttttgt gtgatcaata  94020
taagaattaa tgaaaagccg tagcaactaa ataaatgctt gtacatatga tatcgtgttg  94080
cgttggttaa ttgtaggtag tgatcattgt ctttccagtg gtagtgttta cgtgtgccca  94140
atgacacata ataactagt gtttgcgtat agttgttgca gtgtcttact aattaatgtt  94200
tagttcgcca ctgtgtcttg gtatatctta tgttactttt attatattca tacatatgca  94260
tcttgcacct catataggac cgagagatga tgatcgagcc agtgatgtgg tgccaaccac  94320
aagatgccgt tgatggacga cctgaagaat ggacttaacc agtggatgct caccaagcga  94380
gtacctcccc cagcaaacac tacctaagtg ttaaattaaa ggcaagcccc ggttttatgc  94440
ataaccatta tatatatgct attttactgc acttaatgtt tgtaggcttg taccgtgcac  94500
ttaagtgtag gagttgaatg aaaccctagt tgcatgaact caggattccc tttgagatgg  94560
atactagtat gctaggtcga gtagctnnnn nnnnnnnnnn nnnnnnnnnn nnnnnnnnnn  94620
nnnnnnnnnn nnnnnnnnnn nnnnnnnnnn nnnnnnnnnn nnnnnnnnnn nnnnnnnnnn  94680
nnnnnnacag tgcacagtgc accggacttt ccggtgagcc taggcagagg tgattttgaa  94740
aattttcaaa ttttcgatc taaattttaa ccaaaccaaa tcccaactta taatcataca  94800
aaagaacacc tattgggata ggtattggcc ccctcatata ttttcccata attttcaaaa  94860
atattttgcc ataggctagt caattttag agaaaatagt caaatggtga gattggcatt  94920
ttagctttga actaggggtt ttcatgaata atttgagttt tgaatactcc cccctaagt   94980 gtagtactac atgcatatct caagaaccaa caatggcata gtaaataaga atttaagtac  95040
taaaagctta aagctaagac ttgtcaagtt tgagcccgag ttaagctttt ttcactcgct  95100
ttgttggcgg ttatcttaac taggttagac aagccctaga tgcaatacaa gaaatttaaa  95160
tatgcaatgc aggcttgaca acactatttt gagatcttta aataaaattt ctgagatcaa  95220
gtatgtttaa ttcatttctc aacatgcaaa agcgggtttt atcaagaggc ttagtgaaaa  95280
tatcctctaa ttgatcttcc gacctcactt cttctaaaat aatgtctcct ttagcaatat  95340
gatctctaag gaagtgatga cgaatatcaa tgtgcttggt gcgagagtgt tgtacaagat  95400
tattagcaat tttaacagca ctctcattgt cacacaacaa aggtacctt tctagaacta   95460 caccatagtc tagaagagtt tgtttcatat ataaaatctg tgtgcaacaa gcaccagcgg  95520
caatgtattc cgcttcggcg gttgacaagg caacactatt tttctttttg gatgtccata  95580
atagtagtga tctcccaagc aaattacacc cctagaagta cttttttctat caattttgca  95640 accggcataa tccgaatcgg aatagccaat taaatcaaaa gtagctcctt tgggatacca  95700
aaggccaaca cttggggtgt gcttgagata cctaagaatt cttttaagag cgcaaatatg  95760
agctttctta ggatttgatt gaaatctagc acacatgcat acactaaaca tgatatcggg  95820
cctagatgca ataagataca ataaaactacc aatcatagaa cggtagagag ttaccatctt  95880
ttcaacaagt gatctccatg ttgaaccttt tcaacaagtc tttggtatac ttctcttgtg  95940
agaggaagtt accatctttc atttgcttca cttgaaagcc gaggaaatac atcagctcac  96000
caatcattga catctcgaac tccttcgaca tcaactcacc aaattccttg caatgatagc  96060
gatttatcga gccaaagatt atgtcatcaa catatacttg acaaatgaaa atatcaccgt  96120
tatgtttctt tgtgaataga gttgtgtcga cggtcttgat cttgaagccc ttttgatga   96180 ggaagtcgcg aagacgctca taccaagccc ttggagcttg cttttaaccca tatagcgcct  96240 tggacaacct ataagcatgg ttaggatatc tagggtcttc aaacccgggt ggttgctcaa  96300
```

```
catatacaag ttcatttatg aagccattta aaaatgcact ttttacatcc atttgataaa    96360 gcttttatc atagcatgat gcatatgcga gtaggataca gatggcttca agtcgagcaa    96420
ccggtgcaaa ggtctctcca aaatctaaac cttcaacttg agagaagccc tttgcaacaa    96480
gtcttgcctt gttcctcaca atcacgcctt gatcatcttg tttgtttctg aataaccact    96540
ttgttccaat gatccttgca tcttgtggag gcttctccag ggtccaaact tggttacggg    96600
tgaagttgtt tagttgttca tgcatggcat tcacccagtc cggatcctgt agcgcctcat    96660
ctatacagta ggctcaacac aagaaacaaa ggagtgatgt tcaataaaag aagcatgttt    96720
atgtgatcga gtaataaccc cttgtgaagg acttccaatg atttgatctt gtgggtgtgc    96780
ttgaagcagt gatgagtttc tcctatcaac cacttaggaa gaagatcctg gagcatcaac    96840
atcttcggct tgtatccttg cttgttcatg agagacaaat gtatcttcat ttgcatgcct    96900
ctcatctttt tcatcatctt gtggtacact tgatgaagaa ggcctattaa tgttttgcac    96960
ctcttcttca tcttcttttg gtttgatagc tccaattggc atgttcttca tggcttcctt    97020
aagtggctca tcacctacat catcaagatt ttcaagtgct ccttgggagc cattagtctc    97080
atcaaactcc acatcatatg tttattctac cacgccagtg gcatgattga atactcgata    97140
tgctttggac tttaatgaat aacccagaag aaaaccaata tcacaacgtc tttgaaactt    97200
ccctaggtga tggcgtttct tgtaaatgta gcatttgcat ccaaacaccc aaaagaatga    97260
gacgtctggc tttttcccat ttagcagttc atagagagtc ttcgcaagta gccagtgagg    97320
aaatagcctg tttgatgcat aacatgcagt gttgatagct tcggcccaaa acctctccgg    97380
tgtgttatac tcatcaatca ttgtccttgc aagtgtgatc aaggtcctat tttccttttc    97440
aacaactcca ttttgttgag gtgtatatgt tgctgatact tcatgcttga tcccaatctc    97500
atcacagtat tcatgaatgt tggtgttgtc aaattctttt ccattatcac ttctaatctt    97560
cttgatcttg taatcaaatt cattttgagc tttcttggca aacttcttga atatagatgc    97620
aacttcagat ttatcatgga gaaaaacacc caagtgtatc ttgagaaatc atcaactatc    97680
accagacagt agaggttgcc accagcactt gcataagttg ttggtccaaa tagatccatg    97740
tgaagtagtt ccagtggcct tgatgttgac atgaaagctt ttgtaggatg tgtgttagca    97800
acttgctttc cagcttgata agcactacaa ggcttgtcct tttcaaatat aacatccttt    97860
agtcctctaa ccatgtcctt ctttaatact ttcttcagtg tgctcattcc aacatgtgca    97920
agccttctat gccatagtca tccaagagat gctttggtaa agaggcaagt tcttaagtct    97980
gcatcttcag aggtgaaatc cactaagtag agattgttgt atctaaatcc tttgagcacc    98040
atttattcat catccatttt tgatacaata acctctgttg gagtgaataa gcattgaagt    98100
ccaagaacac agagttgacc cactgataat aagttgaatc ttaaaggtgc aaccaagaga    98160
acatttgaaa ttgatagatc atttgaaatt gccaccttgc caagtccttg aacttttccc    98220
tttgaattgt ccccaaatgt gattttgtct tgtccatcaa cattatcatc aagtgaggtg    98280
aacatccgtg ggttgcctat catatgttat gtgcatccac tatcaataac ccaatggctc    98340
ccaccggtct tgtagttcac ctacatccac agacaaatca agcctaagtt tgagggccc    98400 tatattgcat aggaccagtg actttctcaa tcaaggactt gcaacccaa atttgtctag    98460 gtctactctt gcttggtgga cctaggaatg taacttcgac ttttccattt gctacttctt    98520
aaaacataat gagcattgaa ggcaaatggt cttgagtgct ttggcagggg agttggtggt    98580
ttggctttgc agttgtggga aaaatgacct tcttttccac actcaaagca tttgatatgc    98640
```

```
ttatgagtct gatttggctt gtattgagtt gtagctttct tttgcacaaa ggagttatat    98700
ccaataccac tcttgttgtt tttcatgaca gtgttcatga gcaattcatt ttagaggtat    98760
tggcccttgt tgaacttttg cacacttgtt gcaagatgtt cattttcacg cttaagtttc    98820
ttgacctcat tttaagcctt tctttatcca ctgccaactc attgttgaag tcattgttct    98880
caatggcaac ctttcctcta gtagttgcat cagtcaagta tctcttcaat ttttggttgt    98940
ctaatgtcaa gacttcaact ttttcagtca attcatcatg tagactagtt tgatcacctt    99000
gactcaaatc atcacatgag gttgctacat caatattaac aacagggtta atagcctcat    99060
gtgtattgca agataaaagt tcattttcaa caagaagatt atcatgatca aatttaatct    99120
tagtatagtc ttccttattt tttactagtc tatctttcaa ctccctatta gcttcattta    99180
acttgtcaca tttatcctta gcatctttta gggaggatgt aagctcattt acagtggatg    99240
acatagtttt gttttcttct ttcatttcat tactagcttt cataactatg tcatatttag    99300
catttaaaaa ttcattttca tctttcaact tatcacattt agcttttgac ttcctaatga    99360
gttgagtgta ttcattaagc aagtcaacta gttcatcata ggaaggtgaa gcaaattctt    99420
catcactatc actatcacta tcatcaataa tatcattatc attttgtact tttcgttcac    99480
ctctagccat gaggcatagg tgagaagtcg atgatggaga tggtggtggt gaagagaagt    99540
ccccagcgat ggcggtaact ttttcatcat tttcttcttc acttgaagaa gatccacttg    99600
acgactcaat gtcagtgagc caatcaccaa caatgtatgc ctttacattt ttcttttgt    99660 ggaacctctt atgctttcca tccttcctct tgaagaatct cttttcattt ttctcatcat    99720
cactgtcatc ttctttcttg cccttgaact tgttcttctt ggacttgtta cattgatgag    99780
caagatgacc aagctctcca cagttgtagc aatccattta agaaatgggc tttcttttgc    99840
tggaaaagaa tttcttcttt cttgagtcaa atttgatgcc ttctctgttg agcttcttta    99900
atatcttggt ggtcttcctc accatcaagg caatgttagc attaagatca tcgtcacttg    99960
aggattcctc ctcaacttgt actttagctt ttccttctct ttcttgattt tctttggagag   100020 ccaaatcctt tctcttgtaa gatgactcat ccttgtcatt gatgtgcatg tacatctcat   100080
gtgcattgat ctttcccaaa atttgtgtag gagtgacaac tgaaagatcc atctgatgca   100140
gcacagtgac aatgtgtcca tatttatcaa ttgggaggac actgagaatc ttcctcacaa   100200
catccggttg tgaaatttgt gtaagcccca agccatttac ttcctctaca agaatattga   100260
gacgtgagta catagcattg gcattttcat tagcaagcat ttcaaaagaa tttaattttc   100320
tcatagcaat gtgatatctc tcctcacgct caattctagt tccttcatgt agagcacata   100380
tgtccatcca caaatcatga caattttat ggtttctaac tctattaaac acatctttgc   100440
aaaggcctct aaaagggtg ttttggcct tagcattcca tttctcatag ttcaactctt   100500
cacctacaag atttgtggga tctctaggtt cggggaatct ttgtgtggcg ctttgtaga   100560 caccaatgtc tatagcctct aaatatgctt ccatacgaat tttccaatat ggaaaatcgt   100620
caccataaaa aacgggagaa ggtccatccc caccggacat cgttactcta gcggttaagc   100680
taatctaaga gcaacaaggc tcttatacca attgaaagga tcacgatgcc caagaggggg   100740
ggttgaattg gcttttcta aaaatcaaca ctaactaaaa tctaagcaag agcccaactt   100800
caccccgaca actagcacta agagaataat actagaaata caacaatgct aagataatac   100860
ttcaaatact tgctaaacaa atacacaatg taaaatactt gaattaagtg cggaatgtaa   100920
agcaaggttt agaagactcc tccaattttt ctagaggtat caaagagtcg gcactctccc   100980
ctagtcctcg ttggagcacc tgcgtaaggg tatcgctctc ccttggtcat cgcaagaacc   101040
```

```
aagtgctcac aacgagatga tcctttgcca ctccggcgcg gtggatccct cacgaccgct    101100
tacaaacttg agtcgggtca ccaacaagat ctccacggtg atcaccgagc tcccaacgcc    101160
accaagccgt ctaggtgatg ccgatcacca agagtaataa gccatagact ttcacttgac    101220
caagagaagc ctaatgcatg cggtgtgtgc tctaggtggc tctcgctagc gttaatgagg    101280
tccaaatgcg ggattaagat tctcaagtca cctcactagg ctttgtggtg cttgcaatgc    101340
tctaccaatg tgtaggagta aatgtgggca gcaagaccat caatatggta ggtggatggg    101400
gtataaatag ccctcaccca ccaactagcc attaccagga atctgctgcg catgggcgca    101460
ccggacagtc cggtgtgcca ccggtgcgcc aacggtcgac tcaaacggct agttctgaca    101520
gctagccgtt ggacagatgg cataccggac agtccgatac gctgtccggt gtgcctctaa    101580
aattcaactc acgaacagcg cgctctcggg tttctgcgcg cagggaaccc tcttccctgg    101640
gccaggctgg gcccactggc aaagggtgca ccggacagtc cggtgcccca agccagaaa    101700 ccctagcttc tgttttgtgc tgttttttca atttggtttt tgttctaact tgtgagtatg    101760
ttctagagtt acacctagca ctatatgtga gtgtgaatat gcaccaacac tacactagaa    101820
ctcttttggt caaactactt atcgacaacc cctctttata gtacggctaa acaaaataa    101880 aagacctaac tatatcacga gtgtccgcaa ctccttgaca ctcggaatac gaagaccttc    101940 acttttttgtt tcgtcgcttt agccgttgct tcaagttttt atctccggga ttgttttcac    102000
cattgtagta catctacctg taatgcgacc taacttacca tttgcctctg caaaacacat    102060
gttagtcaca tataaaatta cgttgtcatt aatcactaaa accaaccagg ggcctagatg    102120
ctttctagtt taaatcccca acaagtcaaa attctttcta ttttttttttg caagttccaa    102180 ttgacatctg aaaggttgta aggtacacgt ttggctctca ttgataacgg gggaaagata    102240
cagtgcaaac caccatataa tgacccactt ctaatcgaat ggacctgtaa cgacgaaata    102300
ccctgtgaga actatggttc actcatgtta attcattgaa attgttgtag tgaattgaca    102360
tggttgggag cctgcttaga gagtatagat tgtcactttt ttttggaccg caacttattt    102420
ttaaaagata ttgcgatcgc ttgtttagta gctgtttcag gccccaatgc agtttctatc    102480
gtgatccatt taagtcactc aacattctca tacttctcat tttgcattaa ttcattccaa    102540
tctccactac tataaaatac tagcttcgat ggtcgtcata cgccatgcac gaagcatgta    102600
gatcaatccg cataccagtg ggcatctata gataggctgt gaaaaccacc caaatcccta    102660
ctagtggaca tttttatctat agatggaccg tgagaaacca cacaagtcta acacgacagg    102720
gaagccaaac gcagcgcagc gctcccacat agaaccacct cactacctaa aggaggacaa    102780
gccatcgagc aagctttaaa aaagtagtca ggcttctttc aactcatacc tttcctgata    102840
ttttagctaa gataaaagcg taatatttgt ttttatcagt ttagtatctg atatatggac    102900
catatgttca ctttgatatt tgatattatt tttttattgg tatcaaatat gattgtatgt    102960
cgtcgcagcg cacatgtgtt gtactagtta ttttataaga taatcaagta tttcttaatc    103020
atttaagaca ttttgatgat tatttaaaac attctatttt tttctcagtc attcactcgt    103080
taggtcattc agtacatatt atgttaaatt aagtcattct gttacaattc tagtcatcac    103140
atgtcattta gtcattttat gacttattta aaatatttca tattgtcaac agttgttaca    103200
agactttctt acaaatattt taagtcatcc aatagtttat tcatccagag actcataata    103260 tgttttttaag tcattccttt ctattaaatt gatgtaatta ttttttatcac gattggactt    103320 cttttctttta tcacttagaa gccgtgcgag atgaaagtct catgcacggt tttgcatgag    103380
```

```
agaaagaagc gaggaattct cttttttgact ctgactcccc cactccaatc gttgcttttc   103440
tttctgttac ttcgaaagta gttgcttcag ctttagccac gcgaattctc gatattcctt   103500
tttatttctc atcaaacgaa tgacatcttc ttctggaaat cctagctatt cttagcatga   103560
tattggagaa tctccttgct attagtcaaa caagcatctg attggagcac aggcgtgtgg   103620
ggggagggat gctcaatggg ttattgaggt gtgatggata gagcatccgg ttagagcgca   103680
gggcacgcag tggatactat ttggcaccac gctcagcgag tatgcgtgta tgcagtcatg   103740
caacccgcat atataggcat aaaaaaccaa aatcccttt tttgttatat tcgtgtttat     103800
gagattttcg aacaaaacta gacactcatg ctatatcttt ttcaattttt tatttaatcg   103860
caatgtccga ccctaataaa tacaatgatt ggtcctaata aatacgatga ctggctctaa   103920
taaaaaatac aatgacttat cttgatagct ataatgagtg accctgataa aatcaaatga   103980
ttgaacctaa taatacaata actaaccctg ataaaaatat cctgctaaat acaatgactg   104040
accctaataa aaaatacaa tgaccgacct tgataactat aatgagtgac tctgatataa    104100
atacaatgac tgatcctaat aatacaatga ttgaccttaa taaatacatt gactgacact   104160
gattaaaata taatgattga tcctgataac tacaataact gaccttgata aaatgtagac   104220
cctaatagaa gaagtacaat gactgatcct gataaaatac aatgactggc cctggtaaaa   104280
aataaaatga ccctaataat tacaatgaat gaccctgata aatacacgac tgatcctagt   104340
aactataatg attgaccttg ataaaagtac aagtgattca ccttgataac tacaaatgat   104400
tgatcctaat aacataaaga taaggagaa caaatgagag gttggttatg aaataattgg    104460
ggaaatttgg gctagccagt tgcatgggtc cgacctagtc acgaaccagc cagccaggcg   104520
cgtggaataa ccacacaaaa aataggacgt ggggattcaa accatgctct ttcgatacaa   104580
gcgagcgtct tctaccacta taacttatgt ctgtttatgt tatataaagg agagatattg   104640
tatgtgtgca cacatatata cacacataca ctataaaact gatgtcagcc attcacattt   104700
tgttcaacca tccattatct tttgttgagc catttctaat caataccact tgtcgggtat   104760
cataattagg ggtacccaga ttatgcccct aaaacacact taaccccttag accaccttca   104820
agacacattc cccgagatca aaggatcata aaccgcgctt cgcccgaggc cccgctcagg   104880
ggtcaccata ggtccgcttc gctcaagcct gccctcggac atggtgtgct ctaggagaa    104940
ttctcgtccc ggccgaggct ccatctccca gaacaaaagt cttgcctcg cccgagcaca    105000
tctcgggtaa ggaagacaac cccaatgcaa gactcaacca aagtctgcag ggggcaggag   105060
cattcaatat gcatacctac cccacgtaga gttgcaggtg aacaggagca acaagaccgc   105120
ggtcctgtca agcttcacca actacgatga cgcatgcgac cactattccc acatgccatc   105180
tgtcaacccc tgatgggacg tacaatacga caagagtgca ggatggctct cggacgtgaa   105240
ctctgcctcg ctgaaggcga cctcggcctc gggacaaact tcgcctcgcc tgagcccggc   105300
ctcgtttacc tgctcccgc gaatactgga gcgggctcgg tcgtgacctc gggcggactt    105360
ctgcctcgcc cgagcccgac tctagcctca atatccacaa cggaaaggcg cccaacgtca   105420
ccatatactg cagagctgac atattactta gggactttt gccatactca gtactgtgtc    105480
aaccactacg gcatgggcaa ccccccttgtc aggggggctc gggtacgtga ccaagcgctc   105540
agcccttgcc tcggctctca gcagaaatca gcgggcaca agtcaccaaa caagtacaag    105600
accatgcttc ttgaagatct ttgagtgatt tctgcagatt tgaacttttt tcaacttcag   105660
cttcgagttt tgtttcgaaa tctttcttct cttgctcaat gcttttgac ttcatggaaa    105720
gttcactatt cagtctggcg atctcggctt gagcttctgc cagtgaacct tccattgttt   105780
```

```
gaattatgaa gtctttcttt tctagggcag cttcatgatc tttaatcttg ttctctaagc 105840
cctcaattat aacttcgttt ttcttgtcct cgaggtcttg ttgcatcctc aaggttttgc 105900
ttagtagtag gctctgacaa aataaccttc atcagaaaac atcttcatat caaaacaata 105960
aaaagttaag ggaagaattt taccttaaag ttagaataaa ataggctacc gacgatatgc 106020
tgtcgtcggt atctgctgag atcggcttcg agtttcggaa aaccaacact tttcgataaa 106080
gtcctgacaa ctttctcccc agtccggtct caaaggcaac ctaagctctc ttcgtctata 106140
ccaccgaaga gcagtgcccc tggctggtac ccgcaagata tagcaaagtc cctcagctct 106200
tcttttttag ccttagacaa ctcttgtcca attatgtttt gaaagttgat atttcttcct 106260
tccgaagcat cttcggcaag ctccttctcc ttttcaggca ctgtagccgg ggtttcctca 106320
gcagctgcag cagtttcttc ctcagccata ttcaaaatta tttcatcaat gtcagtaagc 106380
gtgttttcca aatttgtggc ttcggctgct gcaacttcgg aagtagaagc ttcggctgga 106440
gcagctttgg ctgctgctgt ttttagcact gaggccgacg atggtgtttc ttcaatagcc 106500
tcaatgatag taataatcct tcgctttttt ggttcagcgg gcttctcggc aaccgaaggt 106560
tccttcttct tcttctgtaa aagcttcatc agttccggtc ccagcgggct tagcttatta 106620
ggtagagatt cggtcattac cttttaaaatt tcttctgcgt cagtggcaga aggtgttgag 106680
ggaacttctt ctaaatcagc ttttggcttc ggagctgtag cttttctttt cttgaaacg 106740 gccaccttcg gctcagggct ggattttttt tcttttttgc taaattttca tcttctttta 106800
tcattctggc agcttgtctt tgcataacac tgacagctct tttttgtttt ggcccttcgg 106860
cacctttact taaccgttca tagtctgggt attcaaattt cagagtgttc attactcggt 106920
ttagccttcg tttcggtcgg gtgccgaagg ctgccgtcat caattgatct tctttcttcg 106980
tataattgcc caatatttca ttgcacataa cttcgatcgt atccaaccat tcttggcagg 107040 gttcttgaa gtgtttcttg aacttaaaat gataggcag tcgaacaagt tcattctttt 107100
tcttctctcc tttaagcttc ggcatactcc attcctttaa cgttgggaat actctattgg 107160
ctaagtattc ctgaaccaaa tccctagttc cgatatgctc ggacacaact ctaaattcac 107220
ccacaacatc tgggcatgat gatcccagcg tcatgcgaca ctggggccta gttaacccga 107280
aggttaggcc cagtgggctc taaactagct tctccttctt ctcatcaacc ttaacataaa 107340
accattcagt tttccaaccg gttgtccatt tggtgcggta gctaaccaac ggtgtcttca 107400
tgtctttgcg gtaggcaaaa ttatagcagc cgaagttctc gtgcagtcca tcttctctag 107460
ccttcgtctg atagtgaagt tcgtgcaccc ggtagaaggc ttcggcaagc ggctccactc 107520
cttggcttcg aagagcccag ataaagacgc taagcctaac gatagcgtta ggagtcagct 107580
gatgaaaata aatttcgaaa ttttccaaaa catccacaat catcccatgc agaggaaacc 107640
tcagtcctgc tttaaagaaa cttctgaaaa ctaccacctc atcattttct agcttcggag 107700
tgatttattc tccgccaaaa cgaattagct tcttctcggc ttccccgaag tagcctagct 107760
tcgtcatcat gggcatatcg gcctcagaga cggtagactt tccaaattcc aagtggctgg 107820
gtttagatgg catgacgaaa taatctatct cctcttcatc agcctcacct tcttcaatgt 107880
cagcctgctc ggtttcggca gcacgtgcac cttcgtcaga aacaccctct agcacaacca 107940
agcctgattg tctcattact tcggagattg gggcggtctc ggcagcttcg gcctcctccc 108000
cgtcgcgtgt gactctagca gttgaacgca ccctggccat ttgatgctga atttctcgcg 108060
gttttgacaa agttgattac ttttttgattt tgccgaagct ccctcttttg acgaagctaa 108120
```

```
agaacaagac gatgctctaa ttgagaatac gaagaataag cttcggctat ggtcaaattt   108180
ttcagcagca caacaatacg atagtaatga atgctgtggt aacttcacac ctacccgtct   108240
gtttatatag tgctacaggt gggaaggtga atcatcaagc cacctgcacc cgccgaacag   108300
tcgctcgcat tcactgaacg gtggaccgca tggcgcgaga aggagaatca ccagatcgtg   108360
cgtacccgtc ctatggtggg accacctcgc actaggaata cttaaatcgt ttctcgacaa   108420
cgagctcagg gaaggtgttt ttcggacctt cggcattccg aagcctaaaa gaatttttca   108480
cgggtcgagc tcgttacaaa aaatgatctg gcaccgtgaa ggggctactg ttgggggtct   108540
gtttcgtcgc cgaaggtcct gtgagaaaaa acaccttcgg aaggccagaa caggaatgat   108600
gccgaagcta ccaatcagag agcttcgtag cgtatttcca gatgcaccga cttaaagatg   108660
aaatgacgaa ttgggcccat gataatctat gttatgattg taatcatttg tagaggacat   108720
gaatgtaaat ttacacaggc tgcgccctgt gcctataaat aggtgaacag taccctcgta   108780
ctgttcacgc tttcgcatct tacttttatc tttgccttct atcaagctca aggtatataat  108840 gtaatttgat attattctta tgttcttatg attatttaat aataaatatt tatgttaaga   108900
tgttatataa ttgtttatgt tgtcttccta tgtttcataa gcttcatcct ttgtttatac   108960
atgtcatact tatgaaggta tgtccttcat aaccttcgtc cgaagatcgt tatctcctaa   109020
gggaaataat gcttcgaagg acgaaggaca ttaacattta acattttgtg ttgccttgtt   109080
cttaactcat agcatttgag aacaagtccc caacaattat tatgatatcc tcgccactaa   109140
caagtgaatt tttgggagaa ggactaaaat gcagtcaacg ataatgtata agactttgga   109200
gcaaaaacaa agacaagaga cataaatatc caatacaaaa ggaaaccaga gaggtagtgg   109260
tatttttttc tttcttggtg gctaagcatc gctcaccctg tgatgcaaaa atctaccaga   109320
gacaagtata gccaagacca tcaaataaag agacaattta gcaaacaatc caaatcaaga   109380
tcagtgtttt tatgtaaaat agagcatttt tatcatctcc aattgcattg acaattataa   109440
atatgatgaa attgagaaat agataggctg agtaccctag ctcagcctca tctttggcag   109500
aggcatcacc atcaacatct tcaaagtcac aatcttggaa gagtttcttt gcccttttttt  109560 ggcaggggaa gggtgggtaa gtcctatcag tagattgcaa tcaacaatag gataagatct   109620
catatgtatt atggaaacaa ataagtagat ttttgcgtta caaaggttac cttttttata   109680
ccactcttct gtgtcccggt tatagaacca ccccaggttc acactagcat caaagatctg   109740
tagcaacccg cgatcaagca catagattac cattatattt tagacatggt gtctcatgtt   109800 atttttatttt caagtactat gtaaattcaa tgaaatgcta agattaatat ggcaagaaca   109860
tttgacagaa attagcatca tactgctggt gacattggaa tgagagaatt ccatcatct    109920 cttagtatta gctaaaggaa tgagttccaa ggcgaaaaga ggcttcagtt agaagaaaaa   109980
tttaccttag gtataagggc atcaccatca gtttttctgtg tttctgttga cctcgcaaag   110040
caacttgcag aaactgcact catgatgtgc agattcatat catcttccac agatttaaga   110100
ataaaatatg agtgtacaaa aaatcaaatt ggtagtcaaa catgcgaact gtattctgtt   110160
gtttgagtga tttcacaaat tactgtcaaa tgtgagttag aatataccttt agaagtggtc   110220 ctggcattcc tgctttgtgg tgtcactgtt ggttcagtga ttttcatcaa cattttgttg   110280
ttggtattct cgaagcatgg ctagcctctg aagctggtag ttaaggcatc actttttga    110340 agagtccctt gcatattgct tgttgtaact tgagagacca tgatcagtgt tgattgtgat   110400
cctgctggtg acatttccat aatctagctc aacccctag ctgatataaa acagatcaac    110460
cataaatcaa atataacata ttgcaacaaa caattacaca atcatgattt ctatagcaga   110520
```

```
atattatatt gtgttcatga gttgtaactg ttagatgaag ttacgatatt ctagaagttt   110580
cttgtgcatg taatctttag ccaaccgaat caatctccta tagatagaaa ggatatattc   110640
taggctgtgc atagatagaa actccaacaa tagattgatt cggttacctt attgtataag   110700
ttgttgcacc cagccttgtg cctatataaa catgcaatcc ttggccacct agtgtggtag   110760
aacgcttcaa ctgtgacacc ccagtgtcac gtagggtttt tcctagagtt gactccaacc   110820
attatcacat gtgaaccaaa aagaggaatg aacataaaaa aattaagaac aaggtttaag   110880
tgagtctttt tcatcttaag aaattctcct taatcatgcc atgcacctca aggtaagaag   110940
aactctcaaa ccctaattaa tcctaagtgg accatttaag cacataaagg gaatttggga   111000
aaagacttgg gaaaatacaa aattttggta agaaccaaat aacaaagttt tagtgcacta   111060
aataaccaac aaaatatagt aagaaagttt tgccatttga attttccaaa atcccaaatc   111120
agcccatgaa ccaatgccct atggggaaat tcagaaattc agaaaactga atttcaaacc   111180
ctttcccaaa gttcagatgt gttccctgtt ttccaaaact cgaatccaca aagtccaaat   111240
atcaaagtgg cgccaaaata ccctaggaac actttggaga agtttgagat caaacccgaa   111300
tcgtttgaca cgacttgaca taagttttgt ctcggtttgg acagtgctaa cagagctatc   111360
ttcaggccat catatcttct cacctaggcc atatcttcac tcgggactca cacgacag    111420 gaagaccttg gcacggtgaa gagacgctac acaggatcct tggcaagata tgcacgtttt   111480
ggtcggccaa caggcgtttg aactcgggca gaatcacact tccacgtgtt cgatcgcgtg   111540
ctcaagcgct tggccgcgca ctggctgccc tctgatcgcg cgccatgcac ggtcggcttc   111600 tgtccccgc gcctgcactc agccatgcct gagggcgcct ataagtaccc tggatgcaca   111660
atggtctgcc cttcactccg cctcacgcct cgagcaagaa ctccaactcc gcgagctctc   111720
ccccgcccgc catcaccgcc cgagcctcgg ccaccgcggc cagctccctc cagccacttc   111780
caagctgcac cagtcactcg gttagcttcg ccagtggccc gtgaagcttt ccaagtcctc   111840
ggacccaaca gagtttcacc agagacccag gatcgacctc gctggacttc ggtcacccgc   111900
agccgcgcgt agaccgagca atccggtgat tcattctcaa attcctcgcg cgcatgtctt   111960
ccttgacctc tggtgaagct ccctaacctg ttcaattgga ctatcgcgcc gtgagcaggc   112020
cggatccctc gccgccgacg agctccccgc ctgtgcacgt ggaccaacct actccgacca   112080
ccaccgccga cgatccgcac ctcgacgtga tcgccagaga ccccgaccct cacccgaccc   112140
ctcaccggag caacctcgcc gccggtaagc ccctccgccc ttttcttcca ctgcggtcac   112200
tattccatta ggggaaggat cgcgggttcg atttcgcaaa accctagggg ttttctgcag   112260
agtcatagac tcagataaat agtgaaccaa ggacctgtct gtaatacact taaaaccttt   112320
cgccagggac cccagtgcaa aaccctttt cctttatcca tttctgttta ttcttttta    112380 attcagtaaa ggacttagga aatttgtatc ttgagaaata ttcaaccaaa tttagtcaaa   112440 ccaatttac tagattcaaa atattatgaa ctatcacata aaaatattga accctgtgct    112500
ttctgtttta aattttggag tttagaatta attaaagaaa ctgaccaaac cttattaaaa   112560
tgaagaaaat tagttatgct tctgtgctga acttaagaaa atttgtagaa gttcaaaccc   112620
cacttagaca ctgtttaaaa atattgagca ccctagtatt gaagatttaa acagggttat   112680
ctattaaaag ccataattgt ccaaaactta ggaaaataag aaaggtacta gaaaataatg   112740
aacagtggat gcaaatattt ttcctagccc acttaagtaa tgaagaacct agaaaaaata   112800
aaaggaacac tagtccagag caaattcaag gtgaaatgtt ttattaggca ctaataaagc   112860
```

```
tagaagggca attattagaa atatgagaac aatttcaaaa ttggtaagaa aaattcagta    112920
gacttgtaac cactaggaca ccactacaaa aatgataaat acctagccca tcattttaag    112980
tgggttgaac aaataaaact tgatattgag ccatattcca attaaatcat aagcaagcca    113040
aaaagtgtgc aacaatgggc gaataaattt ttactagatt attaatggaa tagatcacca    113100
gagcaaaatg caaaacctat tcaaactaca aagtaatacc cattgcccct acttcatgaa    113160
aaaggccatt taattcaaga aattcctacc acccttccct taagaaaaag gttaccaaat    113220
tttagaatga ttgctcttgc gcaaagaaga agataggaaa aattggaaat ctgttgtttg    113280
atatttttca gtatagtgg tagtagaaag cacccctttg gctagaaact ttagaaaatc    113340
ataataaaat aactaataaa tattagtggc tgaaaatttg tacaaaatca tgttataaca    113400
tctaaatgcc agcaaaaata agtcttaaag aataacccac tgttaaaaga gagttgtagt    113460
tcaaaacatc cccttttgccc taacacttgc taattttgta cagagagaac ccctcacttt    113520
ttaagcccca aattttgaga cagaaaatta tacaccagta agaagctact gtaatgtttg    113580
cagaatttct ggaaatttat taagctatct tgtagttcaa acccaccta aaagcataaa    113640 aggaataaag aagggaggaa ttagaaagat taataagtat taccccaaca tggcagctaa    113700
gaatcttgtt aaaatatcca taagatataa agaagaaaat cagtagaaca ctaaaaatgg    113760
gttaaccatt cagtaatcaa cttgacccta agttggtgag tgtaccacca aaaatctcca    113820
gtagtgagaa tgaggtctac cctattaaat tgatcatcct ccatcaaatt ttaattgcta    113880
aattaaatat catgccatgc atatatctta ctcattgcat tcattagatt gcaacctcgc    113940
tgatggagag tacgtgctca tccctgagca aggagctgtc cacgaggaag accaggagca    114000
agctcccgag actgccatcg aggatctccc cgcagcccca tcatttggag gcaagccccg    114060
gttttatgca taaccaattt atatatgcta ctttactaca cttagtgttt gtaggcttgt    114120
aatgtgcact taagtgtagg agttgcttga aaccctagt tgcatgaact caggattcct    114180
ttttgagatg gatactagta tgctaggtcg agtagctgct ttactaatta ggatctcggt    114240
agaagtcgag tgattttttct agcaatcgcg cgaggtcagg aattgattgt attcatcttg    114300
ataatgggat ctatgatggt ctatggtctt ggatccaggg tggatgcctt gtccatgaga    114360
caggaaaatg aattaaggat taatgtgtgg atacctgagt caagcgtttg aacgtactaa    114420
acacatgtcg ggaaatatgg taaccggtaa acctagtacc tgattgaagc tgggcgcgga    114480
cttttctcct cactcgtcct gagactgggt ctcctatgct agctttggtg ggtacaagtg    114540
cggtcactgc acggcggcag cccgggtcag tggagcattg tatgccaagg cggtgagccc    114600
tggccgcgaa aggggaatcg atggggacgg agtgccctga catgtcgtgt gtttaggttt    114660
accttgcaag gttaatactc gatttgaatc gtctgcttct cgcagctaat gagactgctt    114720
gaccccttgt actacattga gtaagaagtg aaatgaggat tacatgagat aacttgttga    114780
ttgtattaaa tgattgttac catgtatgct tagaaagagc aaacttagct acaataatga    114840
tactagaaat ggaaaagata aagttgacct tagatacaac tagtgctttt ggcaaaccaa    114900 accccctcaac caaacagcta catggtctag aggtagaaga gtagattcct cacaccgggt    114960
aagtctagct gagtattagt atacttagcc ttgcttgtgg cataattttt gcaggtacgc    115020
tctaggatat ggttgacggt gtaacttggc ctacaaccct gtcaccgggt tggacggtcg    115080
agtgggatgc tgctccggca ggagaggagc aggagaagta gtgggccagg ccttgcccta    115140
ttcctcgctt ttgacgacat cgattatccg ctgcagttta ttttgtgaac ttttctcagc    115200
tacttgaaaa actctgattt atgtaataac tccagtactt taatttgagg ttttcctgtt    115260
```

```
ttattgtatt tcttctgtga ctcaccttcg agtgagcttg tggtatttga tcctggataa   115320
gtggctttat tagactagat ctgagggact gatggcttat tccgatttaa gtgcattgcg   115380
gcctttaagg cgtgacttgg gcacttaaac tggaataatc cggcggttc tgccacatca    115440
accattccaa tctacatggt accatagcca ggtcctctac aacacatcca tcatggcgag   115500
tagattctca aattccacca ccatcccctc ctccttctcg atcccggtca ccgaaaaact   115560
caccaaaacc aactaccgcc tatggagtgc ccaaatccta ccgcccatcc aatctgcaca   115620
gctctacggt ctgctcatcg gcaaagaaaa gatgctggtt aagactgtct ctgtgatgac   115680
taacgacgcc tatatggaga cgcccaatcc cgagtacatc aactgggtga ctcacgatca   115740
agcgctgctg ggatatatcc tctcctctct gatgcgtgag gtcttgatgg gtgtcacgac   115800
agccacgacc tcggccgacg tctggagctc cctcgcggct atgtacggat cttgcacacg   115860
tgcgcgttct gtcaacacgc gcattgcgct cgccaccacg aagaaaggca cgaccacaat   115920
ggccggattc taatccaaga tgaagagtta tgccgatgag atgtcggcgt ccggccaacc   115980
tctgggcgat gaggagttcg tcgcctatgt cctcaccgac cttgatgaag aaatctacaa   116040
cccgcttgtg tcgtccatcg tcacttgcgt cgagccaatc tcctctgcca agttatactc   116100
gcagatgctc agctatgagc ttcggcttgc gaagcagtcc ggcggcaggt acgctgctca   116160
tggatcagcc aatacggcta ctcgtggccg tggtggctcc tggcatgatg gttctccaaa   116220
atcacggtcg cggacgctcg cgcggaaatg gccatggcta tccttcgtcg tcttcgcgcg   116280
gcaactacag caacaacaac tacttcaggc gcagttccgg tccaccgaca gatcaatccg   116340
gtggccagtc ttgtccacgc tgctaggtct accttaaagt cggtcacaga gctaatatct   116400
gttggtaccg cttttatgaa gaattcactc ctgatgatcg ggttgcggcc atggcatcat   116460
cctccactgc tgctgatcca aactggtacc ttgacttcgg tgtgactgat cacatcaccg   116520
acgagctgga aaagctaaca gcatgatcgt tacaatggca atgatcagat tcgggcggct   116580
aatggtgcag gtatggagat tactcacatt ggttattctg ttttgcccac ttccttccgc   116640
cctctgcacc taaatcatgt ccttcgtgtc cctcataccc ataaaaatct tgtttccatt   116700
catcgtttca atcttgataa taacaccttt attgagttcc atccgttctt tttcttgatt   116760
aaggatcagg ccacgaggca agtgctggtg cgcggaccat gtaggggtgg cctctaccca   116820
ttgacatctc ttgcacacct acccagaagc acgaccttgc cgcaataaag ccatcctatg   116880
agcgttggca ttgcagatta ggtcatccat cgcgtgatat tgtcgctcgt gtcattagaa   116940
ataataattt agtgtgttca ggcttagatt cctcggagta tgtttgtgat gcctgccttc   117000
gtgctaaggc ccatcagttg ccttatccta agtcgaccag tcagtctgct gctccttag   117060
atctggtgtt tttcgatgtc tggggacccg ccattgattc tttttgtaat aaaaggtatt   117120
atgtcagctt cattgatgat tatagtaaat ttacttggat ctatcttctt cgccataagt   117180
ctgaggtgtt tcagttcttc aaagaatttc aaagccttgt tgagcgcttg ctcaataaa   117240
aaatcattgc tatgcaaacc gattggggtg gcgaatttga gcggcttatc tccttttttc   117300
ttatcactcg gcgtccctca tcgtgtctac tgcccccatg ctctgcaaca aatgaggact   117360
cctatcgtga attaatcgcg cttgtttata tgatcctttc tttatttctg aacatagtca   117420
taaactttat tctctttgga cgaccggtcc taccgctctt ggcaatattg ctcagcnnnn   117480
nnnnnnnnnn nnnnnnnnnn nnnnnnnnnn nnnnnnnnnn nnnnnnnnnn nnnnnnnnnn   117540
nnnnnnnnnn nnnnnnnnnn nnnnnnnnnn nnnnnngaaa tctagagtaa tcgttctcat   117600
```

```
cgcctaattt atgttttaaa aaattaggca tgtgagtttt aacaaatgca tgtgtcatcc   117660
tctctatatc ctccgtgata cttttaatcc gattatcaaa agaaatttta atagatggaa   117720
tatcatcggc tgacctggca tcacctattg tggggagctg ttgcagcacg gctaacatat   117780
actcggcgtt tatctccctc tcttggacgg tcttctggtg gcagtctacc ttgaagtgcg   117840
agaggtacca cttgtccgcc accttgagca cctgatcctt ttgtcggtgg gcctcctcgt   117900
ctattttctt catgtcatct tctaattttt tatgctcagc ggccgataaa ttagtcagcc   117960
ttgtgttgct gtttggagaa gcactgttga gatctttaga atcggccatg taagcctgat   118020
tttgtagatc tgcaacttct tccccagcgg agtcgccaaa aagtatgttg acgccttttt   118080
ggagcgccaa acactcaaca agaaccgtgg cggtgccctc tggtcaggcg cggacggtct   118140
gcagccttgg gccggacgat ccgcagcctt gggccggacg gtccgcgacc tgggcgcagg   118200
agtggtgtct tccctgcgtc acaccggacg gtccgcagct ctgggccgga cggtccgcga   118260
cctggcgaca gggtcgtctt cctactcctt gctggaatct agatctcgtc cctgggggg    118320 aaagatctta aggtgctccg ggtcgacagg tcacccgggg cgtccccaga cgacgtggag   118380
tcgcctagga attaagagat caaatcgagg aagaagtctt ggatggacaa ctagatcttg   118440
ccccccggga ggggtgagat cctagggtcg tcttgggatc ggcaggccac ccaagacgga   118500
tctagacgac gtagagtcga ataggggtgg aggtggatat gtggaagact acaactagaa   118560
ctatgctaca tctactccta gggcaggaaa agtaaataag gtaattggtt cgattggaat   118620
gtgttcgggg gttctcaatc ggccgtaccc ctttatattt atagggagg aggtctggac    118680 cttttcctaa gagatagcca acaaactccc acgtgattag atggataacc acgcacgaga   118740
taaggataaa catccgagtt aatctaatct cgggacacgc ggaccgtccg ggcccatggg   118800
ccggaccgtc cgctcatttt ggtgtccaac agctacgtag tcatgccatc acttcacccc   118860
acaatcccaa ctatcaaaat aactctaacc gaacttggca tttagccgat cgattcctaa   118920
ctcatttttc ataccaccac tacacgacat accgaataca ttgaatgact cgttcacatt   118980
ccacatatat cttacgaaa acatttccac atcgcttgca acttaaccta agcttcgcca    119040
cataatttca ggacatctac ttaaatcatg aatatcatca tcacacacat cgacccgttt   119100
tgaaataacc ctacatgtct atcacaggaa tggagcattt caacacatat cctaaaacaa   119160
actaacttca tcacacatct tgcattacaa agctacttga cttatttgaa gtgtctactc   119220
gaaatcgtga gcacaatcat acactatata cgaaacataa ttttaacgaa cgcataatac   119280
gcatcgtcat gacttgacct ataaatatag agaaagcgat gactactctg gcatgtcacc   119340
acctctctat ttaagtcaag acaatttcta ccatcgatta agagtcgtaa gcattaaata   119400
ccttactact ttatacgcac aaataaactt caacttaaca caactgacac cgatggaatt   119460
tttactaaac tcatcgtacg cataaccctg tctcgcatac aaccatatta tggcgtgcac   119520
tcgagacact tcaatccatg tggcgcgacc actagtataa atggactccg acactcatgt   119580
cttaacgata catcctctac gcaaactagc attctctaaa ctactcgtca catcaataaa   119640
tatatcccct ctaaaattac gaatcccatc acattgctta aaacaaatac acttttcaca   119700
taaacacatc gatgcatttt ccaaaacaaa atccacattt tgtaacttag ttttcgcatc   119760
aaacaacgca tcgcatattt tcctatcaaa ataaaaatac tcgagttctt ttgtatttca   119820
ttttcttccc tacacgcgtc catttataaa attatacttt tacacacata taaccacatg   119880
cacatcatcg accaaaacat aattagacaa ctacaaatcg cgcacatcaa ttaacctctt   119940
gttctccaat cgcaaacatg atcctaccaa tgcgcataat cgaacatttt acacacatcc   120000
```

```
atacaaaatg attaatcgag tcgatcgaga gcgacatgca tcggctcacc ataaacaaac  120060
ccaaacgatg tttgcaagaa tgacggtgat tccgattcgt gcatcgctcc aaacatccga  120120
cgagcgttaa gcgacttgct ttctcctcgc aaaacacggg gttctctcct ccacaaaaat  120180
aaaacaaagc aacacacata cataattaat cataggaaaa taacatcgat gcggaatcga  120240
acaaggagcg tcgcggtctc accggggtga acgacgacga cgtttggggc tgcgcaaaaa  120300
cagcgaacac acggcggcat cacggcgtgc tgctcactgc gcaacaaaac agcaagccgt  120360
cagcgcgcgg agccgtcggg gctgctgcac atttcatcga gcacaagtgt ggatggcggc  120420
caggtgtttg tttcaggcgc tgaaacaatg gaggggaga gggctacggc tggggaagtg  120480
gtggctcggc cacagcaaga acagggaagg ggaggctggt cgccgacctt gggcgcgggc  120540
agggaaaatg gagttgctgc ttggcgctat gtacaacaga gagagggagg aatggcgcca  120600
tgggaagctc gagctcggcc aggggaagga agaaaggggt tcggcatcca agctgttgga  120660
gcccaaggag agggtgctgg ccgccgtgcg caagtgaagt ttcacgccag ctgaagctcc  120720
ctggtcgcgg ataggaaaga gcaggggcg cctgctgcag gtaggagctc ggctcctgtg  120780
gaaaatggca ggggcagagg aggccggctg gagcaccggg cagggcgctc ggccatggag  120840
ccgctgcatg ggatttgctg ctgcgccctg ggagaaaaac agtaggggag tgaaggatgc  120900
catggctggg ggcgcgggga gcaggagcc tgctggtggc cttgctgctg tgaagcaggg  120960
aagaagaaag gcagaggacg ccacgggaag agcttcggcg cgctggaggg aaggaacgcc  121020
cggccatgga agcccctgcg cgctggggaa ggagctccag ctctacgtgc ttgaaggagc  121080
ccacggctgg aaaatggtag aggaggaaga gaagggtgtt ggcggctggg gtggaaatgg  121140
aaaattttca gaatgcaagg gagggaagcc catatttata gaggagaaat tagggtaggg  121200
tttcttatgg gccgaatggg ctggactgga tttggcccaa acactaaat tgggtcgcgc  121260 taaatatttt ccggactaaa aatgttcctg cggaattcgt cgctactgag aaacagagcg  121320
aaaagagttc ggacgaacgg aaggttgcgc gattaactcg gccgagagtc tgtttagatt  121380
tcgcttgaaa ataattccct acgcgtaaat cgaaaataaa tcgtcctgag atttgatcgg  121440
ttttggattt ttagtcggag aaagcgaatc gtgatatata aaaatcgttg ccgatgttga  121500
ttttgaaatc ggattggata cagagatgct aagctgagtc gagtaagatt tgattagagg  121560
acgacatatt gattatttcg tttgtgagta tggactcgga ttaaaatagt tggacatcga  121620
tcgaacatcg agaaattgga ttcggacaca gatcaaataa cagtcgtcga gagtttgatt  121680
taatgagctt cagatgaggt ttataattcg agaatgattt ttgagttcgc atttgtgccg  121740
acgataaaag tttttaacagg ctccaaaatt ggccttctgt gagactgagt aactccgaat  121800
tcggtgaaac gtgaatgaat aatctggata atcaggaca tacgcgagcg agaaataaa  121860 attttttactg agcatccgag attaggataa atctcgcgac gtaacacgaa actgacacct  121920
ggggtgtcac agccttcccc ccttaaaaag aatctcgtcc cgagattcga atgaggatat  121980
ttatgggtgg agaagcatgt aactcccaga ctgaagatag atgcaaattc atgagagggt  122040
atctgacaag atactggaga cagatttggt tagaatatcg cgacatatcg agacaaaatg  122100
cagcgatcat tctgagagtg tccacaaaaa aatagcacat cagtatagtc tcgtaatgga  122160
tcacgactat taaccgcgat actagcgcgt gccgagcagc tcaaccatgt gtgcaccata  122220
gtaggctctc ggtttcgtcg cggcaccatc agtcgttagt catgacatca ttaccaaacg  122280
caaccaataa gaaattcaca tagcactgat agttggagcc catgagagta tggctcagaa  122340
```

```
aataagaatg tgatcagagt tgaagcagag attattggca aaagatcatc acatgagaat  122400
tttcttcaac tcatagagtt attttatgat catcacgggg attagcaggc cagcgattag  122460
tacgagattt gatatgagaa ggaagcactc cagagatcat gttgatgaac ttgtagagac  122520
atgagagaac cacaagatga caacaacatc ccttgaacca aatggataca ctgtttagag  122580
ataaagttga taaacatcgt catgatcctc agagaacgag tatgagaatg accagaattg  122640
agagacttag gtagatcaac attcgatact tgagaacggg ttatagtaga taacaagata  122700 ataggggcaga atcatgaaag atcagagatt cggatgataa ggtcacaaca tgattcacaa  122760
ggaaaaagat cactagatcc atgcgaaagg agaggtaggc aacaagatca gctggatgat  122820
caacaggaat gctatgaagt tttaggggca aggaatttat ggaaagaaac atggccttga  122880
tagggtttgc gcaactagac accaaacaac aaattttttt tgacgtaacc agtgcacaag  122940
gaagctttgg tcgatctagg agtcaagcta tgggaatcta caagctgtgc aggtgtaact  123000
tcaagggtaa aacccacaag ggctagaaaa cgccaacaca agcattttt taaaagcggg  123060 ttcacttgct aaactcaagg ttgtttggag gagtctttt atgaacagaa caagcaacaa  123120
aatgttttgc aaaagggtt gaacaattac aatactacct agatagcaag acaagagaag  123180
cacataacat aacctagtaa agactatcat gacacacaag ataagacatt tttttttgcag  123240 ttcctagcaa tacagcacat tattcacaat tttttttatt atttgaataa aggtgagaga  123300
agcatgttgg tgcacaaaag acaattataa tgcgacaatc atgatgcatg ctcattctag  123360
tcgtcttctc agacctaact acttttttcgg ttgcttctac agcatcctta ttaatagtag  123420
tagtagcctt tatggcctat ataaatagcc acctagctac ccatctattt cctaaggctt  123480
cacgtcctaa gtctatcctt atcgtcctga catctatcca acattggttt ctagcaagtt  123540
ttacttttag aaaaggttgg taatcatgac ttattgactt ctctgtgatg gtattcgctc  123600
cgataccagc tgtggcggaa ccgcccgaat tattcaaact taagtgccca agtcccgcct  123660
tagaggctag accacactta aataggaata aaccgtcagt ccctcggatc tagtccgata  123720
aagccactta tccaggatcg aataccacta gctcactcga aggtgagaca cagagaaata  123780
caataaaaca taataccaca aatttaataa gtatcattag tgattacatt atcggagttt  123840
cagaaataat aaccataaat tttaatgcag cagaaataac taacggagaa gaaccgagta  123900
acatggcgaa gcctggccac tctactcctc ctggtcctct cttgcggaag cagtaaccca  123960
ctcgaccatc tatcccggtg gtagggatgg aggccaagtc acaccatcaa ccaatcatcc  124020
taatgaatat ctgcaaaaat tatgccacaa gcaaggctga gtatacatta ctcaactaga  124080
cttacccggt gtgaggagtc tacttctcta cctctagaca tgcagctgtt tggctgaggg  124140
gtttggtttg ccaaaagcac tagctgagtc taaaatcaag ttttagcttt tcaagtttta  124200
gtatgatcct ttttgactag atgtgtacct agctaatcat acatgatatc aagaattttt  124260
atcaaacaac atcttttgcc aatcacctca tttccactta ttactcaatg cagtacaatg  124320
gatcaagaag tctcattagc tgcgagaagc agacgattcg aatcaagttt ttaaaccttg  124380
caaggtaaac ctaaacacac gacatgtagg ggcactccgt ccccacacac atcaaccgtc  124440
cccatcgatt ccctggcaac agaaagggggc tcaccgcctt ggcgtacaat gcctcactga  124500
ccccgactgc cgtcgtgcag tgaccgcact tgtacccacc ataaccggaa tgggagacca  124560
cgtctcaggt cgcctgagga gggcaatctg cgggcaggtt cactcaggta ctaggcttac  124620
cgatttacca tatttctcgg catgtgttta gtacgttcaa acgcttgaca caggtatccg  124680
cacgttaatc cttattccaa tttcatctcg tagaccacgc gtccccatgg acccgtgtcc  124740
```

```
acagaccatc accattatgt tatcaaagtg gatacaacca attcctgacc tcgcgcgagt   124800
gctagaaaaa tcactcgact tctaccgaga tccctaatta gcaaagcagc tactcaacct   124860
agcatactag tatccatctc aaagggaatc ctgagttcat gcaactaggg tttcattcaa   124920
ctcctacact taagtgcatg gtacaagcct acaaacatta agtgcagtaa aatagcatat   124980
atataacagt tatgcataaa accggggctt gcctttaatt taacacttag gtagtgtttg   125040
ctgggggagg tactcgcttg gcgagcatcc actggttaag tccattcttt aggtcgtcca   125100
tcaacggcat cttgtggttg gcaccacatc actggctcga tcatcatctc tcggtcctat   125160
atgaggtgca agatgcatat gtatgaatat aataaaagta acataagata taccaagaca   125220
cagtggcgaa ctaaacatta attagtaaga cactgcaaca actatacgca aacactagtt   125280
atttatgtgt cattgggcac acgtaaacac taccactgga aagacaatga tcactaccta   125340
caattaacca acgcaacacg atatcatatg tacaagcatt tatttagttg ctacggcttt   125400
tcattagttc ttctattgat cacacaaaag catcacaaac acaagtttaa taaggaccg    125460
atgcatcaat gtcgatggac tcctctatca caatcaacta tagcaagcaa gcacattaat   125520
catggaacac atgttaacct aagtttagcc atcacaagtc tatgtccgtt aagtgctaac   125580
taagcgtttt tagccaaaat ggtgaactaa atattcattt gagcacgtgc agatttttg    125640
gacagcagca cagcagttac ttgttttaat aataacttt caaatattaa tccaaaaata    125700
gcaaactaaa actttctgga aagtttagaa agtgctctac aattttggta ttttcatcac   125760
agcatgatta aacacttagc aaggtcaaaa agtgcaatca caacagctct gtccagattt   125820
ggacagattc agacttgtga ttttaaaaat tcataactga agattcagac atccaaacaa   125880
attgatccta gactttctgg aaagctaatt aaatgttcta caaattattt ataaacatcc   125940
caggctggtt tagcatgtat caaggttaaa atatactatg aaggctgtgc tgtccaaaac   126000
tggacagatt cagtcttcac acttcaaaca catgtaactt aatcttcaga ccaccaaaaa   126060
gagtgatcta agactttttg aaaatcttag caaaagtact acacaacttt cataatcacc   126120
aagaagtgat tccaggttta actaaatcaa atattacagt tttcgaaatc tgttctgacg   126180
gtggacagaa cacagcaacc agtttgtaaa attcataact cttaaaccgt caggcctata   126240
gttatgaaat tttaacacaa gcaagataag aaaagcctct acaactttc ttataatcta    126300
caagggctga ttctaacatt aacttaagca aacaatgcag cttctgaaat ctgtacagaa   126360
agtggacaga ttcagttact gaatttgtaa aaaacataac tcctaaacaa ttagacttat   126420
gcctgtcaaa ttttaacaca agtacgataa taaagttatc tacaactttc ttgtgaccac   126480
caataactaa tttcaacatt aacttaagca accattgcaa tttctgaaat atgttcagaa   126540
atttgacaga ttcaggtgct gggcttgtga aaagcacaac tcctaaacaa tcaggtttat   126600
ggctgtcaaa ttttagtaca agcaagataa tcatgtcatc tacaactctt ctatatgact   126660
tttctacaga aaacatgatt tggtttatca aacaaacagc acaactaaaa cagtgcgtgc   126720
agcccaaaac agcaatcaat aaattcagct tctgtttact tttaaaaatt gccgcgttct   126780
agagactcga cttattctaa attatatcaa ggcacactta agcatagcca cacaatagat   126840
gatgtgacgg ctactgttga cgccttttg gagcgccaaa cactcaacaa gaaccgtggc    126900
ggtgccctct ggtcaggcgc ggacggtccg cagccttggg ccggacggtc cgcagccttg   126960
ggtcggacgg tccgcgacct gggcgcagga gcggtgtctt ccctgcgtca caccggacgg   127020
tccgcagctc tgggccggac ggtccgcgac ctggcgacag ggtcgtcttc ctactccttg   127080
```

```
ctggaatcta gatctcgtcc cctgggggga aagatcttaa ggtgctccgg gtcgacaggt   127140 cacccgggc gtccccagac gacgtggagt cgcctaggaa ttaagagatc aaatcgagga    127200
agaagtcttg gatggacaac tagatcttgc ccccgggag gggtgagatc ctagggtcgt   127260
cttgggatcg gcaggccacc caagacggat ctagacgacg tagagtcgaa taggggtgga   127320
ggtggatatg tggaagacta caactagaac tatgctacat ctactcctag gcaggaaaa    127380 gtaaataagg taattggttc gattgacaag ttttcggggt ttctctcact gccgaccctt   127440
tttatcataa ctgagcacca ggtctgaaac tcaaacctct ccgaaaggga agcgtatcac   127500
ctgatccgag ctggataagc tccgactatc gacggatgac atagcatcac aactgatctc   127560
gggacagcag gtgctgccgg ttccctggac caagcaagcc catatcattt gatgtccacc   127620
agatgccccc tgccgcaagc gcgcaaaaag ctgcacccgg gagcctgaat tacactccga   127680
aaagcgtgag cccgtgattg cctttcatg tcaaggatc gatacggatc gatgggagat    127740
cacgcccgat gggcctggat tgcttctgtt accttggcga gcgtttggtg cagaggccat   127800
cctctggaac ggattccact gcaccatggc tgatggaata tcctgcgtca tgcagaccat   127860
tgatggaggt gggtccccag cccagatagt gaagcgcgaa ctcgcatggt gtccacatgg   127920
attgaccgca ccgtcccgca gcttgaaata gaagcccggt cccgaaggag acatgtcggg   127980
gagctcggcg gctgtcccta ctggacggct gctagctgca aaatgggggg ttggccgctc   128040
ctacgggacg ttccgcacgc gtctctcgtg cgaccggacg caatggccat cggatagtgt   128100
tgctctggac tggttcatga ttagcacccn nnnnnnnnn nnnnnnnnnn nnnnnnnnnn   128160
nnnnnnnnnn nnnnnnnnnn nnnnnnnnnn nnnnnnnnnn nnnnnnnnnn nnnnnnnnnn   128220
nnnnnnnnng aattctttat tcctaagtta atttgatcct catgcttact ttggttcaca   128280
taaaataatg gttcttggtt tggcattttt aagagaaacc gtaggtgaca ctagggtgtc   128340
acagccttcc cccettaaag gaatctcgtc ccgagattcg ggccagagtc ctcccagggt   128400
gaagcgaagg gtgagactta taggaaaagg gtggggattg ttatgcttca aatcatggta   128460
catcttggtg cttcccggat gcatagagaa tttggagaga tgagcctcat ccaaaatttt   128520
cttcttgaga tcctggtcct taggaattac caatctgctt ttgaaccata acacaccctt   128580
ctcatcctgg cggaaacaat tatacttctc aaccttctga tggagattct tcttgataat   128640
ttgcactccc ttgtcactga gctgggccat gataatctgg tcttgcaagg ctggctcaac   128700
agcaatgtga gacaaagaac cagaaggaat cacttcaatt tgcatcttgc tcaactcatc   128760
acacaaggtg ttaacacgag aatccatcag aatacagttg cactgcaact tccgactcaa   128820
ggcatctgct accacattag ctttccctgg gtgataatgt acctccaggt cataatcctt   128880
gatcagctct agccatcttc tctgcctcat gttgagatca gcctgagtaa aaatgtactt   128940
aaggctctta tgatcagtga agatgttgca gtgggttccc attagatagt gcctccacat   129000
cttcaatgca tgaaccactg ctgctaactc aaggtcatga gtaggataat tttgctcatg   129060
aggcctgagt gctcttgagg cataagcaat gactcggttg tcttgcatca agacacaacc   129120
tagcccggtg ccagaggcat cacaatatac atcaaaaggc ttgctgctgt cgggttgcgc   129180
caatactggt gctgtggtca gatgctgcct taatgcatgg aaggcatctt cgcacttctg   129240
actccacaca aatttgactt ctttcttcag caactcagta ataggcttcg caattcgaga   129300
gaagtccgga ataaatcttc ggtaataacc agccaatccc agaaaactcc gaatctggcg   129360
aacagtcgtt ggtggcctcc agttcatcac ctcttgcact ttatcaggat caacagctat   129420
tccagcctga gagatagtgt gacccaagaa tttgatttcc tttagccaaa aatcacattt   129480
```

```
ggataacttg gcataaaggt ggtgatctcg cagacgttga agtactacat gcaaatgccc    129540
ggcatgttct tcttcgttcc ttgagtacac cagaatatca tcgatgaaaa ccaccacgaa    129600
cttgtccaat tctggcatga aaacagaatt catcagatac atgaaatatg ctggtgcatt    129660
cgtcagcccg aatgacatca ccaagaattc atatagccca tatctggttg agaatgccgt    129720
cttcggaata tcacttgctc gtattttgat ctgatggtag ccagagcgaa ggtctatctt    129780
ggaaaacacc ttggccccga ccaactggtc aaagagaaca tcaatacgag gcaaaggata    129840
cttgttcttg atagttaccg cattaagagg gcggtaatct atacacaacc tcaagctttc    129900
atccttcttc ttcacaaaca gtgctggaca gccccaaggc gaagtgcttg ggcgaataaa    129960
tcccttatcc agcaactctt gcaactgctt cttcaactct gccaactcag cgggtggcat    130020
tcggtagggc ctcttggaaa ttggggccgt tcccggttgc aactcgatgg cgaactcaat    130080
atcccggtcc agtggcattc ttggcaattc atcaggaaag acatctgcat actcacagac    130140
cactgggatc ttcttcaggg gtaattccgt catagagaaa gcacatgact gagaagaacc    130200
ctgactaggc agaatcaaag tgaaattccc gcagaaggga gaattaactt ccacggtacg    130260
actggctacg tcgagcacaa cttggtgcaa ggtcatccaa tttgctccta gaataatgtc    130320
cacattttcc aatcccaaca caagaagagt ggttttgata atgtggcttc ccagttgaat    130380
aggcacactt tggtttaatt gattagttgc aattttaccc ccaggtgtga ctatcatgaa    130440
tgaccctttt gagtgagaga atggaagttt gcaattagca ctgaactttt ggctaatgaa    130500
actatgagat gcaccagaat caaacagaat taaagcaggt tgattataaa ctgaaaaggt    130560
accggtcatg atgggagctc cttctggcac ttcctctaga gcagtgaagt tgagcttccc    130620
ttgcctgact tgtaccttct gctttcttcc cttgtcttga tttggtgctg catctgcct    130680 ctgctggttc ctgggacaat tcttggcata gtggcccaca ttgccacaag tgaaacactt    130740
gttcccattg ccctggcgga actgctgctg ctgcggaggc tgattgtttc ttggggcggg    130800
agctggatag cggttgggtg ccggctgctg ctgctgctga ggtggcctga tcacccatct    130860
gcctgcctgc tgctgaaaac ccctgctctg attgtgagaa acaatccgga acctctgagc    130920
ctgagcggat ggtgctgcca ttggtgcctt tctcttcttc tctgcccggt gagcaacaat    130980
gcaatcctcc tgagagatgg ccatgttgac caactcattg aagctatcgg cccggacagt    131040
gttgagtcgt tcccgcagct tggtattgag accctgcgg aagcgatccc tcttcttttc    131100
atcagaatca gcatgatacc ctgcatactg gcataagtcg ttgaaggctt gcgcatactg    131160
cagtaccgtg cgggttcctt gattgagggc caggaattcg ttcaacttcc gatcaagaat    131220
gccagctgga atgtggtgcc ctctgaaggc agtcttgaat tcctcccaag atacttcacg    131280
atcaccgggg agcatagcac ggaagtgatc ccaccaagtc cgagcagggc cgcgaagctg    131340
ctgtgcggcg aagcgagcct tggcctcatc agggcagtct cctgtgagga ggggaaactt    131400
ggactcgacg acgcgaagcc acacgtcggc gtccaatgga tcctctgcct tggtgaacaa    131460
gggcggctgc gtgctcagaa actcctggta tgttgccata gccggaggtc gctgatgctg    131520
gcctccacca ggatgctgag ggtggggctg gcgctgcaag agctgtcgca gaatctcatt    131580
ctgctgggcc atcagctcct gcactgtggg agctggagga ggtggcgggg gagcttgctc    131640
attttgcccg cgacgctgcc tcgctgccat ctgaaaacag agattgtcgc cattgttatc    131700
ccaattcaca tttccgaacg acaagatatc atctcatatg gaaggaaaat gccataatca    131760
taatattagg ttcgaatgaa gataacatgg tgacaaggat cccacagata tcaaaagttt    131820
```

```
acagggttac attaatcagg ggaaggtacc cacaagccta gtccaaaatg tgataccact    131880
aagctcgcat aggtttctat ccgcctaaaa atgtcaaagc gactgcttaa ccctgagcgg    131940
tggaagcgac actggatacg ggtgaaggag gtatcgcgga ggtagtccca ttggcaccag    132000
gggctggtcc tagctcctcg ggagcctctt ctccctcgct tcctgcttca ttggcctcca    132060
tctccaggtg gtgcatgtcc aagtggtcat ttgcttcctc gagttccctc tgcacgtcgt    132120
gaagctggtt ctccaagaca tcaatagtgt tatctcggat ctccacttgc tgctccaggg    132180
tggtaatacg ctggttcagc ctctccacct gcagatcctt ttccaccaac tctgtggata    132240
ggtcgaccac aaaatcttcc cgactgtcga gggtgagctt ggctgcctga gcggtattgg    132300
caagaagtgt catagcatcg ctctgaaggg cctgaaggcg gtacagcgca ctcatgcact    132360
gaacagtgac cctcccaacc aagtcaggat acattgccca cacatccttc acatggctca    132420
cgcggttaca ccacatggga tcatccttct tctcagcggg gaagagtccc aagggggtgca   132480
tcaccatctc caggggatgg tagccacaaa aagtcgtcag agtcttcatg gctgctgcct    132540
caacggtgtc gtccgtcctg agtccaatcg tctcagagtc aagagaacgc caacccggct    132600
gaaggggatg agcctccaaa gttagccaga cccgacaacg aggtacccga tgctcctcat    132660
acaactgcac cgtgtacaaa gggggcgtag ggtaaccggc ggaattaagc acttcccaca    132720
aaatggaagg gaagccatcg cgagaaagga agtcagaact gaaacgagag tctcctccac    132780
tggcgggggt gggtgaattc atctgcggaa gggaatcaaa gataaagatt atggtggaag    132840
gaaaaagaaa aagagagccc ggatgatttc gaagaaaagg gggttagctc aattttaatt    132900
cctctttatg ttttataatg catgcatgcg gaaagaaacg ttgcctctca aaaggaaaat    132960
agggtgcctt tttagggcat cctaaaatat aagtattggc ccacagggcc taattagtta    133020
gccacctatt tctccctcta tgcctaaggc ctttcgtcct aggtctagcg gtctagtcct    133080
gacgatccgt agtagcttct aggcaggttt tagattttga aaattggtat tcatggttta    133140
ttgcccttct ctgtggtgga atttgctctg ataccagctg tggcagaacc gcccgaatta    133200
ttccagctta agtgcctaag tcacgcctca ggggccgtaa cacacttaaa tcggaataac    133260
ccgtcagtcc ctcagatcta gtctgatgaa gccacttaac caggatcaaa tcccacaatc    133320
tcactcgaag gtgagtcaca gaagaaatac aataaaacag gaaacctcaa attaagtact    133380
gagttattac ataaatcgga gtttttgagt agcgaataaa gttcataaat taaagtgcag    133440
cggataatcg atgtcgtcgg taatgaggaa atgggcaagg cctagcccac tactcctcat    133500
gctcctctcc tgccggagca acatcccact cgaccgtcca acccggtggc agggtggtag    133560
gccaagtcac accatcaact acatcctgca tggtacctgc aaaaatggtg ccacaagcaa    133620
ggctgagtat actaatactc agctagactt aaccggtgtg aggagtctac tcctctacct    133680
ctagactatg cagctgtttg gctgaggggt ttggtttgcc aaaagcacta gctgtttcta    133740
aaatcaactt ttagctttc aaattctacc atcattaact tagctagatt tgctccttct    133800
aagcatacat ggtaacaatc aattagttca gtcaacaagt tatctcatat aatccacatt    133860
tcacttctta ctcgatgcag tacaaggaat caagcagtct cattagctgc gagaagcaga    133920
cgattcgaat cgagttttta aaccttgcaa ggtaaaccta aacacacggc atgtcagggt    133980
actccgaccc cacacatgac aaccgtcccc atcgattccc cgttcgcgtc caggcctcac    134040
cgccttggca tacaatgctc cactgacccc gactgccgtc atgcagtggc cgcacttgta    134100
cccaccatag ctagcatggg agaccctgtc tcaggtcgca tgagggataa agtccgcgcc    134160
cggcttcact caggtactag gtttaccggt taccattttt cccggcatgt gcttagtacg    134220
```

```
ttcaaaagct tgactcaggt atccacacat taatccttaa ttcattttc ccgtctcatg   134280 gacatggcat cctccctgga cccaagtcca cggactaaca tataccccat tatcaagatg   134340
aatacaatca attcctgacc tcgcgcgagt gctagaaaaa tcactcgact tctaccgaga   134400
tcctgattag caagcagcta ctcgacctag catactagta ttcatctcaa aaaggaatcc   134460
taagttcatg caactagagg tttcaagcaa ctcctacact taagtgcaca ttgcaatcct   134520
acaagcatta agtgtagtaa agtagcatat aataacatgg ttatgcataa aaccggggct   134580
tgccttcaat tgctggggct gcggggagat cctcaatagc agcctctgaa gcctgctcct   134640
ggtcctcctc ttggataggt ccttgctcag ggatgagcac gtactctccg tcggcaagat   134700
tacaatctaa tgaatgcaat gcgtaagata tatgcatgat atgatatgtg ctttagaatt   134760
tataacttta aagatgtatg atcttttgat ttaaaaccag ttaactttac ttatgtaaaa   134820 cccctttagtg gtatacttgg taaattgggt tagtcttatt gggatgaggt ttatttcttc   134880
ttctcttttc ttttattctc tttaatgttt tggagtaggt ttgaactaca agttgctttt   134940
ataaaattcc aaaaattctg caaaaattac agtggcttgt tactggtgta tggttctctg   135000
tctcaaaatt tggggttcag aaagtgaatg gttttctctg gacaaaatta ccaaattta   135060 gggcagaagg ggtactttga actacaacta ttatttaata gtgggtaatt ctcaaaaact   135120 tattttgct ggcttttagg tgttataaca tgacttgata caaatttcta gtcattaata   135180 cccctttaatt ctttccctaa gattttctta aggtttctag ccaaggggt gctttctact   135240 accactatac ttgaaaaaca tcaaacaaca gagttcttat ttttcttagc tagtattttg   135300
tgcaagagca atcattctgg agtttggctt ccttttgcct aagggaaggg gtggtttgca   135360
ttatttgagc taaatggcct tcctcacaaa ttactagcaa aaggcatggg ttcacttctt   135420
tttcatgggt ttgtattttt ctctggtggt ttatctcatc atggacttag caaaattttg   135480
gttgcccatt atcacattat ttggggttgc tcatgattta gtgggaaaat gccttattat   135540
cattctgtat ttattttccc tacttaaaaa gttaggctgg ggtgctctgt attttgtag   135600 tggggctctg gtggttataa gttcactgga tttttgttaa ccactttggt tatagttttg   135660
caattctaat aattgatttt cagtctacat aatgctaatt aaagcatctt aattagaaac   135720
tggtccaaat taatggtctc tgcatttttc ctaggttctc tgctgcataa gtaatctagg   135780
aaaaatatta ctaatcactg ttcattaatc tctaaggcct ttctgatttt ctctaagttt   135840
tggacaaaat ggctttaaat gaataactac atcataatct ctaatgctag ggctcctact   135900 attttttaaac agtgtctaat taaggtataa gcatctacaa attttcttaa gctcagcaca   135960
aaagaaaaac taattttcct taattaaaca aggtttaggg ggtttctgtt tttaatttta   136020
aactctaaaa tttagaacag aaagcatatg gttcactatt tttaaatgat aggtcataaa   136080
attccagagc tagcaaaatt ggtttgacag cttttcatta agatttcatc aagttatgga   136140
ttttctaagt tctctggtca tttaaaaag aaataacaaa attgattaaa tgaaatcca    136200 ctttgcactg gggtccctgg cggttttcta agttttcctc gcaattcagt ccttaggtta   136260
ctattctcat gagtcgctga cattacgaaa acccctcgg gttctacaga acctaacccg   136320
aggtccttct tctaccttaa acagtagccg cggcgaagaa aagggcggag gggcttaccg   136380
gcggcgagac tgttccggtg aagtggccga gggtgaaggg gaggtcgcgg ggatcacaac   136440
ggtgtgcgga acaccgtcgg agatggccga agtcggtcgg tccacgcgcg caggcgggga   136500
tgctcgtcgg cggcgaggag accggcctgg tcgcggcgag atagttcaat caaataggtc   136560
```

-continued

```
atggaggtcc acgggatgcc agagaagaca tgagcgaaag gaatcgggcg ggagactcac   136620
tggatagctt ggtccacgcg cggcggcgga agaccgaagt ccggtgaggt tgattcttcg   136680
ggcctcccgg tgaagttccg gtcgggtccg agggcttggc aagcttcacg ggctactggc   136740
ggagctagcc gagcactggt tgggctggag ggtggctgga gtgggctggc cacgcggccgc  136800
gtagttctgg cggcaatggc gggcggaaat gagctcgccg gagctaagga acagtggctg   136860
gccggtgagg gtgagtgcgg ggcgaagaga ggtgcgcccg gggaggcttt ataggcgcgg   136920
gcgggcacgg ccgagggcgt gggcgcgcgg cggacttgac cggacgccgg ggcgagcgcg   136980
cgcgcgggtt gggcgagctc tggcgtgccg accagggtcg aacacgtgtg cccgtgcgtt   137040
ctgcccaagc tctggcgcgt gtggtcgctc atccgagcct gctctcgcct tggtcagtgc   137100
acaaaacctc ttctcctccc tacaagctac cattcttgtg tggaggtcat aggattttgc   137160
ctactggttg cagagatatg gagccaggaa atctggtctg tctccctgcc caaacccgag   137220
gcaaatccca agttttgtcg tgtctagggc tcgcgtccca atgccatctt ctggcacaag   137280
acagaggggt tagttagaca caattttgtc aatgggccca ttaggattcg agttaggat    137340
caaggtgaac atccctgatc tttggctcaa ggtctgaatt tcagaattct gaaattcaga   137400
attcccaatg agtcccaaca aaagaagctt gatttggggg ttttcttgaa ttattttggc   137460
taagctttct caatctatct tgttgcttat caaatatact ttaacttata taattggctc   137520
aactcaaaat tttaaacttt tcattccctt ttgcttattt tcttgaattt tgttcatggg   137580
gttcacttag ggttcttaat tagggttgca cattcttatc ctttaagaga ctcaattgtc   137640
ttgatcatga cactttttaag catatacttg gtgaattctt tcttacttaa gttatttga    137700
tgctcatgct tactttggtt cacataaaat aatggtcctt ggtttggctt tttaagagaa   137760
accctaggtg acactgggt gtcacaggag gcacatacaa ggatgctgag cctcgacatg     137820
cgggcctagg agcataatgg aagaaataga ttatgtaaat aactaatgct gacagagtaa   137880
cgcatgacca aacttggagg cctggaccgt atatacaggg gtctggcatg ggttcggcac   137940
tctcctatgg gggtccggac tcactattga tgccttggag tacatcactt tctctggaca   138000
catggcggcc ccggacccgc ccatgtggtg gggtcaggtg ctgttgctgg cctagagtag   138060
tcgcccgagg ctagggcgag tcatggtttg gtcccacata cagctctttt accacgcgac   138120
taaagatagt cgcgtgggta ctgcgtattt atacagtagt aagggtaccc cttgtttcag   138180
ggtgccgaaa gtggcccccg gacccacctt aggggaggat gcgagcctgc atgtggggcc   138240
aaagcttgta ctttgcttca acgtgacctg atcggtgatt ggcatgccgt tttagcgcgt   138300
ctgcagacac gcccgctgtc aatccgcctt cagtcacgtc aactgccata tctgtctctg   138360
cagctgactg acccatggcc ccatgcctgg tggtttcgtc gggccacgcg tgggacgcct   138420
cgttgccgct gcataacctt ttgtcttctg cagcggcccc gaggaggtgc gctatcgtgc   138480
gcggcagttc gcatggcgat tcgctctttc cgcactcgaa atccagcaca caatctgtat   138540
gacttgtgga cccgggccac cgtgtcatag agtgggctgc ctgggtccta tgtgcgcatc   138600
gggcgagatt tcctgtggca attcaagggc gcacggaagg gtttccctga caaggactc    138660
aggtttcctt gaaaaaggat tcaccccgcg tgcagcagtt accttttcgc attctctccc   138720
aatcgcctgc acccctttgc cttcgtgctc ctctgttcca cgctcgcgcc gccgcacacg   138780
ccatggcctc gcttggtcat cctgactgct ttcagtctaa ggaggcgctc aacctggtgc   138840
gcggcctgct tggatggagc gcgccagggc tcgccggaag ttccgcgccg gcgccgtccc   138900
tcatggcgat ctcaccgccg gggagttcgt gctgttcacc tcctacatct tctacgggtt   138960
```

```
ggcgttgccg attctcgccc ttcttcttgc tgctgctgga ggagtttggg cttcagcttc 139020
aacacctcac accccactcc gtcctccagg cagccatctt cgtccacctc tgtgagatgt 139080
tcgtaggtgt ggcccctgt acttccctct tccgctgctt cttcgtgctg gtcaagttcg 139140
ggaagactag ggaccacatc ggtgcctact acttccagac gaggccagat ccagccgtcg 139200
tatacatccc cacctttggc ggtgcgaggt gggaaaactg gcgcaacgat tgggtgattg 139260
ccagcgccga ggccaacgac cgcctcgtcc tgccgagcga tgggccagcg ctcgaccgca 139320
agcagtggag gactaagccg tccctcttgc tagagttcct gcctgtattg gacagaatca 139380
agggcttggc tacgggcggc ctgccatcaa tgcacgtggt cggcgatctc ctgaagcacc 139440
ggatcgcgcc gctgcagagg agaccgcgta tgtgctgttg gttcaccggc ccaaacgaca 139500
tcgataggat ccaacgcagg ccgggcaccg ttctgtcctg ggacgagcta gcagtcctga 139560
tgggagggat tattggggaa acttttgtcc ctgagtccct gatactcccc cagaacatcc 139620
ctgcgctctg cgacgatcca ggcctgagga tggtgatctt ggccacgttg ccgaccctcg 139680
acgagagcgg catggcggtt cgctagaccg gtggccggga ccccctccgt gggatccaga 139740
tttctaatgc accgattgga ggttcccagc ccactggtgc ggctcccagc accaaccccg 139800
ccgtggcccc tagccccttg gacaaaggca aggggctgc gagcagtgcc tccgcccag 139860 gtagctccga gggggtcgga ggaggagagg caacgcaggc catgtcgcgc tgatgggtcg 139920
ctcatttcgg agccccccc agaagcgtca gagggctgca ggtggggccg aggaagctag 139980
ctcccaggcc cacggcgcgc agaggcgcgt cagtcctcac ccccaggggc accagcagca 140040
gcaacagcaa cagcaacagc gatagcaaca gcaggagcgg tgatcgcccc gcttccaggg 140100
tcactagaaa gtctagggcc ccaagtaagc gtagccccctt ttccatgagt ctaatcatca 140160
tgccgaccag ttttaaccca tcatctgttc gctagggctt cttccttcgc cgctcccaag 140220
gtcatgcctc ctccaccaga taccaggccc accgacgggt ctggctctca acagcaggaa 140280
cctgctgaga gtggtgccgg cggcccaccc ccagctgctg ccaagacagc accagcggct 140340
tctcatgccc cagccggggg tccggtggca gcgtcaggcg gcgtcgcagt ggcgaaggag 140400
gtcccagctg ggggatccgc gcccgctctc gacactgggg gtgacgcagt aggcatgtcc 140460
agctccaacc ccccgcctgc tccggaggag atggaggtgg tgtttgggcg gcgactccgg 140520
tcgggtgcca gcaagaagc ggcgccagtc cccctccctc gcataatgtc tcgtgcccac 140580
taggtcctta gtgacactgg ggcagcaatc ttgcgggagt gggaggcgct tgaggctgag 140640
caccagcgcc taagtgactg gcgcacccaa ctggaggagc gcaccagaac ggcgtcccaa 140700
caattcatct ccgagcggtc ccaactcgag caggaccata aggagtacaa gagggacctc 140760
cagagggtgt gcgccaggga gctggaggcg tcccggaggg agaagaaggt gaccaggaag 140820
gaggaggtcg tgacccagcg ggagaccctc acaacagagt accaggccaa gctgagtgcc 140880
ctggaccaga ctctggaagc ccagcgggcc cagcaggtca gggtcgtgga gaggctgcaa 140940
aagtggtagc aggagctcga gggcaaggct agcaatgcca ccctcgccga ggaaaatctt 141000
aaggcgaagg agcagtcctt ggaccggtgg gagacggacc tcgccaggca agagacggat 141060
ctcagcttca gggaagaaat gctcaccccgg cgaggcgagt tgctggccaa gcacaagctc 141120
gaggcagagg agaaagagag gaagctggag gagcagatcc gctagttcaa tgcagcgcag 141180
gcggcaccgg gtcccaagc gatggaggcc accaggaagg cccttgaaga tctccaagcg 141240
gagcaccgcg tcgaggtcca gtgtattgtc gcgtgggccg gcgaggcaag cacggcacta 141300
```

```
gtgccactag ggatgagccc catcccaatg tcggagctac cagcgtcgat ctctgatgcg   141360
ctcccggtgc tggactctac cgccgatcgc ctccgtcgcc tggatcagat cctcggggcc   141420
cgcctagagg cagagggcag caagctctgt cgggcagtgg ttgaataagt cctaacatgc   141480
ttccggagtc acgaccccac catatccttg gcgctagtga tcgctggtcc ggtagccgcc   141540
atagaagacg ccgcctggga gagtgtacaa gacgccgtgg agctggtggc cgagcgcttc   141600
cagcacgatc ctgctgacga cctatagaga caaagcaagg gttccactgg gaagcggttg   141660
taataacttt tgattttgta agatattata agaaccgcta atgaggtagc attggaactt   141720
aaacttattt gtatgttatt tgtccttgtt atgtgtagtg tcatcaactt ccccttggta   141780
cttggccccc tgggaggtag gctcgacgtg tcgaggctgg ataccagtat accaaagata   141840
aaattggtgg tccggcccct aggaggtagt ctctacagtt tgagactacc tactactgga   141900
ctgggacctg gacttgtaca cagcttcggc tttaaagtgt taggagcaca ccataggatc   141960
catcgtctgg tatctgccat cctttgattt atgcaacagg acctgcagga tttagcctgg   142020
gaagccaagc cgtatgcctg gacccatagg atcacagttc caaatactag ggcacccgtt   142080
atagagtggt ggagcatgca ggcttagggt acggaaccat gctaagcggc tacacaactc   142140
cggacccctc caggaggcta gcgcccattc tctagaactg gtccgcagtt tgccggaccc   142200
cctgtagcag taaaggggtc ttgaactgca agcctgtcta ctcaattcgg atgtcatcat   142260
accaacaagg gtgggaaact atatgggtgg gttagataaa aataatgca tgtaaaccga   142320 agtagaataa aaccatcaca aaatcacatc taggggtaa atcctttcct tataactcga   142380
tatacatggg tgtagaccaa cagatgggct tacgagggcg ggcctcaccg aattgacata   142440
cacatatgcg taacctagtt acaaaggaag aaaactcaac ccccagtttt gctattatg   142500 gatagaactt acagagatgc tctatattcc agggattggg aagaggcact ccttctgttg   142560
tggcaaggcg gacacaccat ggtcggcata tttctgtcac cttgaagggt ccttcccaac   142620
tgggggagag tttgtggagc ccttctcggt tcagtactcg ccttaggact aggtcccga   142680 ccctgagctc cctactatgc acaaaccgtt ggtggtagcg cctgagcgct tggttgtacc   142740
gtgcatttcg gatcaccgct tgccatctgc gttcgtcgat gaagtccatg tcctcacgtc   142800
gtagctattc ctgcatagac tcatcgaaag actggactca tggggagccc ataatgattt   142860 ccggagaag gcaggcttcg gccccgtaga ccaagaagaa cggggtctcc ccggtagctc   142920
ggctgggtgt ggtccggttc ccccatagta cggacggaag ctcattggcc caattggcac   142980
catgcttttt taagcagtcg taggtgtgtg ccttgagtcc cctaaggatt tctgtgttg    143040 ccctctcagc ctggtcgttg ctcctgggat gagacacaga tgtaaagcag agctgggtgc   143100
caatgccctc gcaatactct tggaagagtc gacttttgaa ctgggtccca ttgtccgtaa   143160
tgatatggct tgggaccca aatctgcata caatcgaatt gaggaaggca acagcagcac   143220
cttgggtgat actgaccata ggggtggcct ccgaccactt tatgaatttg tagatggcga   143280
caaagagaaa acggtacccg ccgacagccc taggaaatgg tcccaggata tccaccccc    143340 atacggcgaa tggccaagag ggtggaatca tttgcagagc ctgagctggt gtgtgtgt    143400 gtctgctttg catgaaactg acatgcttcg caggacttca ccaactcggc tccctcctag   143460
agagcagttg gccagtagaa gccatgccag aagaacgaat caagctgatt ctcagagttg   143520
aaaannnnnn nnnnnnnnnn nnnnnnnnnn nnnnnnnnnn nnnnnnnnnn nnnnnnnnnn   143580
nnnnnnnnnn nnnnnnnnnn nnnnnnnnnn nnnnnnnnnn nnnnaattct tagaaaattc   143640
gtcctcaaac ccaagagaca ttaaagggat tcttgagacg ggctcaaaat gagttcggct   143700
```

```
taagggtcaa gaaaataaga agcgacaacg gaacggagtt caagaactct caaattgaaa   143760
gctttcttga ggaagaggga atcaagcatg agttctcttc tccctacacc cctcaacaaa   143820
atggtgtagt ggagaggaag aatcgaactc tattggacat ggcaaggacc atgctcgatg   143880
agtacaaaac ttcggatcgg ttttgggccg aggcggtcaa caccgcctgc tacgccatca   143940
accgattgta tctacaccga atcctcaaga agacatcata tgaactccta accggtaaaa   144000
agcccaacat ttcatacttt agagtttttg gtagcaaatg ctttattctt gttaaaagag   144060
gtagaaaatc taaatttgct cctaaaactg tagaaggttt tttacttggt tatgactcaa   144120
acacaagggc atatagggtc tttaacaagt ccactggact agttgaagtc tcatgtgacg   144180
ttgtgtttga tgaaactaac ggctctcaag tagagcaagt tgatcttgat gagataggtg   144240
atgaagaggc tccatgcatc gcattaagga acatgtccat tggggatgtg tgtcctaagg   144300
aatccgaaga gcctccaaat gcacaagatc aaccatcctc ctccatgcaa gcatctccac   144360
caactcaaga tgaggaagaa gctcaagtcg atgaagaaga agatcaatca aatgagccac   144420
ctcaagatga tggcaatgat caaggggag atgcaaataa tcaagaaaag gaggatgagc   144480
aagaaccaag ggcgccacac ccaagagtcc accaagcaat acaacgagat caccccgtcg   144540
acaccatcct cggcgacatt cataaggggg taacaactag atctcgtatt gcacattttt   144600
gtgaacatta ctcgtttgtt tcctctattg agccacacag ggtagaggaa gcactacaag   144660
attcggattg ggtggtggca atgcaagagg agctcaacaa cttcacaagg aatgaggtat   144720
ggcatttggt tccacgtcct aaccaaaatg ttgtaggaac caaatgggtc ttccgcaaca   144780
agcaagatga gcatggtgtg gtgacaagga acaaagctcg acttgtggcc aagggatact   144840
cccaagtcga aggtttggat ttcggtgaaa cctatgcacc cgtagctagg cttgagtcaa   144900
ttcgcatttt attggcatat gctacttacc atggctttaa gctttatcaa atggacgtga   144960
aaagtgcctt cctcaatgga ccaatcaagg aagaggtcta tgttgagcaa cctcccggct   145020 tgaagacag tgagtaccct aaccatgtct ataggctctc taaggcgctt tatgggctca   145080
agcaagcccc aagagcatgg tatgaatgcc taagagattt cctttattct aatagcttca   145140
aagtcggcaa ggccgatcct acactcttta ctaaaactct tgaaaatgac ttgtttgtat   145200
gccaaattta tgttgatgat attatatttg ggtctactaa cgagtctaca tgtgaagagt   145260
ttagtaggat tatgacacag aaattcgaga tgtctatgat gggggagttg aagtatttct   145320
taagatttca agtaaagcaa ctccaagagg gcactttcat tagccaaaca aagtacactc   145380
aagacatcct aagcaagttt ggaatgaagg atgccaagcc catcaaaaca cccatgggaa   145440
ccaatgggca tctcgacctc gacacgggag gtaagtccgt ggatcaaaag gtataccggt   145500
cgatgattgg ttcattgctt tatttatgtg catctcgacc ggacattatg ctctccgttt   145560
gcatgtgtgc aagattccaa tccgacccta aggaatccca ccttacggcc gtaaaacgaa   145620
tcttgagata tttttggctt at acacctaagt ttgggctttg gtaccctcgg ggatccacgt   145680
ttgatttgat tggttattcg gatgccgatt gggcggggtg caaaattaat aggaagagca   145740
catcggggac ttgccagttc ttgggaagat ccttggtgtc ttgggcttca aagaagcaaa   145800
actcggtcgc tctttccacc gccgaagccg agtacattgc cgcaggacat tgttgcgcgc   145860
aattgctctg gatgaggcaa accctgcggg actatggtta caaattaacc aaagtcccctt   145920 tgctatgtga taatgagagt gcaatcaaaa tggccgacaa tcccgtcgag catagccgca   145980
ctaagcacat agccattcgg tatcattttc ttagggatca ccaacaaaag ggggatatcg   146040
```

```
agatttctta cattaatact aaagatcaat tagccgatat ctttaccaag ccacttgatg   146100
aacaatcttt taccagactt aggcatgagc tcaatattct tgattctaga aatttctttt   146160
gctagcttgc acacatagct catttgaata cccttgatca tatctctttt atatgctatg   146220
actaatgtgt tttcaagtct atttcaaacc aagtcatagg tatattggaa gggaattgga   146280
gtcttcggcg aagacaaagg cttccactcc gtaactcatc cttcgccatc actccaacca   146340
tctctctatt ctttggggga gaaatgagca tcaaagaaaa ggacttcgtc tttggtataa   146400
tcttaactca tttacttatg accaaaggag aagaaattac ttcgagggct ctaatgattc   146460 cgttttggc gattcatgcc aaaaggggg agaaaggagc ccaaagcaaa aggaccgcac   146520
caccaccaat ttcaaaaact tagtgttttc caagaaatat ttatcaattg gcatcctatc   146580
gtgttcaaaa gggggagaaa gtagtatttc aaaaatgata tatcaaaacc ctcttgaaca   146640
ctaagaggag gatttaattt agggggagtt ttgtttagtc aaaggaaaag catttgaaac   146700 aggggagaa aacttcaaaa tcttgaaaat gctttgcaaa atcttattc attcaccttt   146760 gactatttgc aaaagatctt tgaaatggac ttacaaaaga atttgcaaaa acaaaacatg   146820
tggtgcaaac gtggtccaaa atgctaaata aagaaagaaa cattccatgc atatcttgta   146880
agtagttata ttggctcaat tccaagcaac ctttacactt acattatgca aactagttca   146940
attatgcact tctatatttg ctttggtttg tgttggcatc aatcaccaaa aaggggggaga   147000 ttgaaaggga attaggctta cacctagttc ctaaataatt ttggtggttg aattgcccaa   147060
cacaaatctt ttggactaac ttgtttgccc aagtgtatag tgtatacagg agtaaaaggt   147120
tcacactcag ccaataaaaa gaccaagttt tggattcaac aaaagagcaa aggggcaacc   147180
gaaggcaccc ctggtctggc gcaccggact gtccggtgtg ccaccggaca gtgaacagta   147240
cctgtccggt gcaccagggg actcagactc aaactcgcca ccttcgggaa tttctaaggc   147300
gactcggcta taattcaccg gactgtccgg tgtacaccgg acagtgtccg gtgcgccaag   147360
ggaggtcggc ctcaggaact cgctagcctc gggttcgcgc ggcagccgct ccgctaaaat   147420
tcaccggact gtccggtgtg caccggactg tccggtgtgc cagcggagca acggctccct   147480
gcggcgccaa cggctccctg cggtgcattt aatgcgcgcg cagcgcgcgc agacgccagg   147540
cacgcccata ccggtgcacc ggacatcaaa cagtacatgt ccggtgtgca ccggacaccc   147600
aggcgggccc acaagtcgga agcttcaacg gctagaatcc aacggcagtg atgacgtggc   147660
aggggcaccg gactgtccgg tgtgcaccgg actgtccggt gcgccatcga gcagacgcct   147720
ccagccaacg gtcaagtttg gtggttgggg ctataaatac cccaaccacc ccaccattca   147780
tagcatccaa gttttccact tcccaactac tacaagagct aggcattcaa ttctagacac   147840
atacaaagag atcaaatcct ctccaattca tcacaaagcc ctagtgacta gtgagagtga   147900
tttgtcgtgt tcatttgagc tcttgcgctt ggattgcttc ttttctttct cacttgttct   147960
tgagatcaaa actccattgt aatcaaggca agaggcacca attgtgtggt ggcccttgcg   148020
gggaagtttt gttcccggct tgatttgag aagagaagct cactcgatcc gtggatcgtt   148080
tgagagaggg aagggttgaa agagacccgg cctttgtggc ctcctcaacg gggagtaggt   148140
ttgcaagaac cgaacctcgg taaacaaat ctccgtgtct cacttgctca ttcgcttggg   148200 atttgtttttg cgccctctct tgcggactca ttccttatta ctaacgctaa ccccggcttg   148260
tagttgtgtt tatatttgca aatttcagtt tcgccctatt caccccccctc taggcgacta   148320 tcaattggta tcggagcccg gtgcttcatt agagcctaac cgctcgaagt gatgtcggga   148380
gatcacgcca agaaggagat ggagaccggc gaaaggccca ctacaagcca cgggagcact   148440
```

```
tcatcggaag agtctcgcac caaaaggagg gagaagaaga agagctcctc caacaaaggg   148500
aaggagaaga aatcttcttc tcaccacaaa gagaagaagg aaaaatcttc ttcccacaag   148560
ccgcatcgga aaggcgacaa gcacaaaagg atgaggaagg tggtctacta cgagaccgac   148620
acttcatcaa catcgacctc cgactccgat gcgccctccg tcacttctaa gcgccaagag   148680
cgcaagaagt atagtaagat ccccctacgc taccctcgca tttccaaaca tacacccttta  148740 cttccgtcc cattaggcaa accaccaact tttgatggtg aagattacgc taggtggagc   148800
gatttaatgc gatttcatct aacctcgctc cacaaaagca tatgggatgt tgttgagttt   148860
ggcgcgcagg taccatccgt aggggatgag gactatgatg aggatgaggt ggcccaaatc   148920
gagcacttca actctcaagc aacaacaata ctcctcgcct ctctaagtag agaggagtat   148980
aacaaagtac aagggttgaa gagcgccaag gagatttggg atgtactcaa aaccgcgcac   149040
gagggagacg agctcaccaa gatcaccaag cgggaaacga tcgaggggga gctcggtcgg   149100
ttccggcttc acaaaggaga ggagccacaa cacatgtaca accggctcaa gactttggtg   149160
aaccaagtgc gcaacctcgg gagcaagaag tgggacgatc acgaagtggt aaatgttatt   149220
ttaagatctc tcatttttct taatcccact caagttcaat tgattcgtgg taatcctaga   149280
tatactaaaa tgaccccgga ggaagttatc gggcattttg taagttttga gtgcatgata   149340
gaaggctcga ggaaaatcaa cgagcttggc gactcatccg aagcccaacc cgttgcattc   149400
aaggcaacgg aggagaagaa ggaggagtct acaccaagtc gacaaccaat agacgcctcc   149460
aagcttgaca atgaggagat ggcgctcgtc attaagagct tccgccaaat cctcaaacaa   149520
aggaggggga aagactacaa gtcccgctcc aagaaggttt gctacaaatg tggtaagccc   149580
ggtcatttta ttgctaaatg tccaatatct agtgacagtg accgaggcga cgacaagaag   149640
gggagaagaa aggagaagaa gaggtattac aagaagaagg gcggcgatgc ccatgtttgt   149700
cgcaaatggg actccgacga gagctcaagc gactcctccg acgacgagga tgccgccaac   149760
atcgccgtca ccaagggact tctcttcccc aacgtcggcc acaagtgcct catggcaaag   149820
gacggcaaaa agaagaaggt taaatccaac tcctccacta aatatgaatc gtctagtgat   149880
gataatgcta gtgatgagga ggaaaatttg cgtatcctct ttgccaacct taacatagct   149940
caaaaggaaa aattaaatga attagtcagt gctattcatg aaaaggatga ccttttggat   150000
tcccaagagg attgtctaat taagaaaac aagaaacatg ttaaggttag aaaggcttat   150060
gctctagaag ttgagaaatg tgaaaaattg tctagtgagc taagcacttg ccgtgagatg   150120
attgacaacc ttagaaatga aaatgctagt ttaaatgcta aggttgattc tcatatttgt   150180
aatgtttcaa ttcccaatcc tagagataat aatgatgagt tgcttgctag gattgaagaa   150240
ttaaacattt ctcttgctag ccttagatta gagaatgaaa atttgattgc taaggctaaa   150300
gattttgatg tttgcaaagt tacaatttcc gatcttagag ataagaatga tattcttcat   150360
gctaagattt ttgaacttaa ttcttgcaaa ccctctacat ctattgatga gcatgtatct   150420
atttgtacta gatgtagaga tgttgatgtt aatgctattc ttgatcatat ggctttaatt   150480
aaacaacaaa atgatcatat agcaaaatta gatgctaaaa ttgccgagca caacctagag   150540
aatgagaaat ttaaatttgc tcgtagcatg ctttataatg ggagacgccc tgacattaag   150600
gatggcattg gcttccaaag gggagacaat gtcaaactta atgcccctct taaaaacttg   150660
tctaactttg ttaagggcaa ggctcccatg cctcaggata acgagggtta cattttgtac   150720
cctgccggtt atcccgagag caaaattagg aaaattcatt ctaggaagtc tcactctggc   150780
```

```
cctaatcatg cttttatgta taagggtgag acatctagct ctaggcaacc aacccgtgcc 150840
aagttgccta gaaagaaaac tcctattgca tcaaatgatc atgctatttc atttaaaact 150900
tttgatgctt cttatgtgct tacaaacaaa tccggcaaag tagttgccaa atatgttggg 150960
ggcaagcaca aggggtcaaa gacttgtgtt tgggtaccca aagttattgt gtctaatgcc 151020
aaaggaccca aaccatttg ggtacctaaa gtcaagaact aaatttgttt ttgtaggttt 151080
atgcatccgg gggctcaagt tggatactcg acagcgggtg cacaaaccca catgaccggg 151140
gagaaaagga tgttctcctc atatgagaaa aaccaagatc cccaacgagc tatcacattc 151200
ggggatggaa atcgaggttt ggtcaaagga ttgggtaaaa ttgctatatc acctgaccat 151260
actatttcca atgttttct tgttgattca ttagattaca acttgctttc tgtttcccaa 151320
ttgtgtcaaa tgggctacaa ctgtcttttt actgatgtag gtgtcactgt ctttagaaga 151380
agtgacgatt caatagcatt taagggtgtg ttagagggtc agctatactt agtagatttt 151440
gatagagctg aactcgacac atgcttaatt gccaagacta acatgggttg gctctggcac 151500
cgccgactag cccatgttgg gatgaagaat cttcataagc ttctaagggg agaacacatt 151560
ttaggattaa caaatgttca ttttgagaaa gacaggattt gtagcgcatg ccaagccggg 151620
aagcaagttg gcactcatca tccacacaag aacataatga caagtgacag gccactggag 151680
ctcctccaca tggatttatt cggcccgatc gcttacataa gtatcggcgg gagtaagtac 151740
tgtctagtta ttgtggatga ttattctcgc ttcacttggg tattcttttt acaggaaaaa 151800
tctctaaccc aagagacatt aaagggattc ttgagacggg ctcaaaatga gacgaatctc 151860
agatcgtctg tatagattan nnnnnnnnnn nnnnnnnnnn nnnnnnnnnn nnnnnnnnnn 151920
nnnnnnnnnn nnnnnnnnnn nnnnnnnnnn nnnnnnnnnn nnnnnnnnnn nnnnnnnng 151980 catcttgcaa cctcacagac cgtggcgtgc tctggtcagg cgcggacggt cccagccttg 152040
ggcggacgtc cgagccttgg gtcggacggt ccgcgacctg ggcgaggagc ggtgtcttcc 152100
ctgcgtcaca ccgacgtcc gcagctctgg gccggacgtc cgcgacctgg cgacagggtc 152160
gtcttcctac tccttgctgg aatctagatc tcgtcccctg ggggaaagat cttaaggtgc 152220
tccgggtcga caggtcaccc ggggcgtccc cagacgacgt ggagtcgcct aggaattaag 152280
agatcaaatc gaggaagaag tcttggatgg acaactagat cttgccccc ggagggtga 152340 gatcctaggg tcgtcttggg atcggcaggc cacccaagac ggatctagac gacgtagagt 152400
tgaatagggg tggaggtgga tatgtggaag actacaacta gaactatgct acatctactc 152460
ctagggcagg aaaagtaaat aaggtaattg gttcgattgg aatgtgttcg ggggttctca 152520
atcggccgta ccccttttata tttataggg aggaggtctg gaccttttcc taagagatag 152580
ccaacaaact cccacgtgat tagatggata accacgcacg agataaggat aaacatccga 152640
gttaatctaa tctcgggaca cgcggaccgt ccgggcccat gggccggacc gtccgctcat 152700
tttggtgtcc aacatatgcc cccctgcctt ttggtggagc atggcgaacc aaaagcatta 152760
gcgaaaactt cggaaacaat tgacctcatg aggttttttt ttccgaagta aggactcagc 152820
tcgatgcaag tcatcggctc ttgcgatcag ataatataaa tacttgatgg gactttaatg 152880
cacagaggcc gtttcggatc gcatcctctt cagccatgtc tatctgatca acctgtcaat 152940
aggcaaaaac ttgtggtgcc ccccagccca ataagcaaa cggattgggc cagtaataca 153000
aattcatcgc cgtaccaccc cacacatgag taggacaaca catcggcgat ggatagaatg 153060
ggacgcacca tgctatccct ggaggaggat gataaggcga tattggttgt gctacccttt 153120
gggtccgttt agtcggcttt tgctttcgca cagatcgccc tattgacttt gttgttttta 153180
```

```
ttggccggtt gtgtggaacg gccttcttca tatatttggc aagcaactga ccaaaagtag   153240
ggccgactct actgagtcgt ccagacgtct tagtagtgtt ttgtttccta acacttgtgt   153300
tggaacgttg tggtccgatg gtctgaggtt gctgcttctg accatctgcg gaccgtccgg   153360
ccatcatagc cggactgtcc gcgcctgtct cggactgttc ggccttagta cccggatcgt   153420
ccggcgtacg catgacaggc gaccgtgatc gggtgtccga tcgtgcttgc ccccggtgc    153480
ctccggtctt tcttttgtcc ggagccttca gagtaaccat tctgcgtgac atatttggtg   153540
tgcgaggatc accaatgacg atatttttat tttactttt atcggccgca caaggccgaa    153600
ttatggcctt tttgctcatg ggctctaatg tggtgacagg aacaggtggc ctgtcaattt   153660
tcacctcttt ttgaaacctc aaccggcctt cgtttatagc cgattgtatt tgccgacgga   153720
agacggcaca atcattggtg ttatggagaa aggagccatg ccatttgcaa taaacacgcc   153780
cttttaattg ttcaaccgga ggaattacat gtgacaattt aatattacca tgtttaagca   153840
actcatcaaa tattttatca catttagtaa tattaaatgt gaacttaacc ttttcctttt   153900
gtttcgagtg cgggtaagag cgaacagaag gtttggcctt agtgggccaa acaagctcag   153960
ggacatgtga cttttttagt tcttggggct tgggtggccg attatattta tgtcggcctt   154020
ccgcactagg tggatcacag gtgacttctg gtgccccgga cggtccgact tgcacagtcg   154080
gacggtctgc gggtggatcg gacggtccgg tactatcctc ggacagtccg gtcacgtcag   154140
gcaacacctg tgacccttgt ggtgggctct gtgtaactcc agactgtccg gcgtagggtg   154200
ccggacggtc cgacagaggg ccggacggtc cgcaattgtg tgcggacggt ccggctgtgc   154260
ccagggttga ctcaccattt agcaaagatg gtgatgacgg tcgtcctaga tatgagtcca   154320
tcggcatacc agaatatggc tggggaaacc catttgccgc cgatgtgttt ggcgcaattg   154380
tttcatcgcc taatttatgt gataaaaaat taggcatgtg agttttttcct aatgcatgtg   154440
tcatcctctc tatatcctcc gtgatacttt taatccgatt atcaaaagaa attttaatag   154500
atggaatatc atcggctgac ctggcatcac ctattgtggg gagctgttgc agcacggcta   154560
acatatactc ggcgtttatc tccctctctt ggacggtctt ctggtggcag tctaccttga   154620
agtgcgagag gtaccacttg tccgccacct tgagcacctg atccttttgt cggtgggcct   154680
cctcgtctat tttcttcatg tcatcttcta atttttatg ctcagcggcc gataaattag    154740
tcagccttgt gttgctgttt ggagaagcac tgttgagatc tttagaatcg gccatgtaag   154800
cctgattttg tagatctgca acttcttccc cagcggagtc gccaaaaagt atgttgacgc   154860
cttttttggag cgccaaacac tcaacaagaa ccgtggcggt gccctctggt caggcgcgga   154920
cggtccgcag ccttgggccg gacggtccgc agccttgggc cggacggtcc gcgacctggg   154980
cgcaggagcg gtgtcttccc tgcgtcacac cggacggtcc gcagctctgg gccggacggt   155040
ccgcgacctg gcgacagggt cgtcttccta ctccttgctg gaatctagat ctcgtcccct   155100
gggggaaag atcttaaggt gctccgggtc gacaggtcac ccggggcgtc cccagacgac    155160
gtggagtcgc ctaggaatta agagatcaaa tcgaggaaga agtcttggat ggacaactag   155220
atcttgcccc ccgggagggg tgagatccta gggtcgtctt gggatcggca ggccacccaa   155280
gacggatcta gacgacgtag agttgaatag gggtggaggt ggatatgtgg aagactacaa   155340
ctagaactat gctacatcta ctcctagggc aggaaaagta aataaggtaa ttggttcgat   155400
tggaatgtgt tcgggggttc tcaatcggcc gtacccctttt atatttatag gggaggaggt  155460
ctggaccttt tcctaagaga tagccaacaa actcccacgt gattagatgg ataaccacgc   155520
```

```
acgagataaa gaaaaacccc cnnnnnnnnn nnnnnnnnnn nnnnnnnnnn nnnnnnnnnn   155580
nnnnnnnnnn nnnnnnnnnn nnnnnnnnnn nnnnnnnnnn nnnnnnnnnn nnnnnnnnnn   155640
ngaattccaa gatttaaata gaagtctttt ataatgagag attaaataaa agaccctcat   155700
ataatttaaa ccaacccttg ttgaataaca tgattagaga tattctccaa aagaattaag   155760
cttaaaaaac cttaataaat actatacaca caaaaaaatc ctctatctta aaaattatga   155820
acataatttt aaatggacta tacattcaaa gaagtaattt ttactctatg tgtgtgcatt   155880
gcatacttaa aatatttgga taaaataaac aaaactaaac agatatatgt aattattgca   155940
tatcatgccg gagttttgga ttgagcattt agattagagt ttaaaataag ggaaagaaat   156000
atgaaaggga agataaaaca gaaaatcatt aaagaataaa gaaaaagggg aagctttctg   156060
cgctatgggc cggatctctg gcttctcggc ccagtttctt tccttcgtta gcgggcccaa   156120
ctctatttcc ctgctccggc gcagcccgct cctgcccact ctcgcgcctg cagccgcgtc   156180
tggcatgtgg gccatggccg tcaagtctat cctccccatg gcgatcctgc tcgtccgctg   156240
caagctcgcc tcctgtaaac tgtgcaacga ccttcgtgcc atggtgcacc cgcccactgc   156300
tagccgtacc cctggccata tataacggac gctccaacct cggccatggg tgcagctcta   156360
gtttcctctc cttcagcatc gtgggctacg ctcggtctgc cgatcgggag agaaggcgcc   156420
atcaccatcg tcgtaaggga gaaggagaac acaggggtg aattgccacc gacggggtt     156480 cccgggcacg ccggtattgc ggtctcggcg tcggttggg tcatccgtgg gacgcgtgca    156540
ggattctaga aggcacctcg tgcgagaaca acgaccagtg catgcttcgc tggtgacccg   156600
cggcgccacg gagcaactgc gtggtggggt caacacttga aacaccgtga tccttggtaa   156660
gaacagccct agcatacttg gagcctcctc ctctccgtga ttcacgtacc cacgctcgat   156720
actaggaaat ggggagccgg gcgggatatc actggtggtg tggtggggca tggccgcggc   156780
gtgcccgcac cagtgctctg ctttccgtcg tgaggtggaa ggaaatgcag cagccgttag   156840
atcatgggtg agcgatcacg atcagggcat ggctgggcct cgcgtgaacc gtggatctgg   156900
gaggtatcgg ctgtgattag atcacacgta acgtttcatc cgaatcgatc cgggtcgtct   156960
gatctggatc ttgcatatga ggatcgatct ctattatttt aagcgtgggc cgtttatcgt   157020
agatccgacg atctaggatg cgtaccggtt cggcgggcaa atcttctact ctgggcgctt   157080
ggctgatgat ccaaggaatt agtcacgtgt acccCttcac cgtgactaac ttataaaaga   157140
gaccccagac ttcttgcaaa tcagcccgca gtccgggtat aggtagaaat cattgcggat   157200
aagtcctaaa tattatatgg agccccctga tcttttatag aatagtgtcc ccaatccaga   157260
aatatttaat aattatagaa ttaaatccta aaacttaata aatacatatc tctttcattt   157320
taactctgat ttaatgtatt catgttgcgt tagcttcgta ataattttgc ctacgcttct   157380
gtaaaattat tttagcaaat agcatgtttc caaaaaataa atattcattt aatatatgct   157440
tagtagatta ttcctactaa tcaaagttag tttgtctatg attataaggt aactaaaata   157500
ttatgtctac tctagtatga tgtagattaa agttatttct ttaatatctt tatcacataa   157560
tttataaaat caacataaag acctagtctc atatttaatc acataggtct tccgaaaacc   157620
acatcttgtt aaccgtaact ccgaatttag tggttctcga acctaggatc tcgttgtggt   157680
gcgtagatca ttattatgca gtttgttctt tatgtttggt gtgatgttaa ttttgcctat   157740
accatgtttg tttgtattgc tatgattagc agcgaggtta cgagaatctt gaagaccaag   157800
ctggtaccta ggaatcttga gtctcagcca agttgtgccc ttgatcactt ttctttaccct  157860 aataatgttc ctattaatca ctgtgacatg ctcaggttaa tttgatggga cccaataggt   157920
```

```
tttcctagta ttgtttatcc cctaccttgc aaacaaaagc actattgggt agtattgcta    157980
ttgctctacc tggttttggg aaattaatgt tacattatga tcatgttaca attcttttgt    158040
tattttaatt attgttcatg ataagattgc tatgttaatt ggaacatgga gcaaccaccc    158100
aggaaaacag tgctaccaca agggtggtat gggacgccct tggctgacta attaagaaag    158160
ctagtggaag actaccttac ccgaaagggg caagggcggt agaggagcat gcgtataggg    158220
aggttctcga gtcgatcatg ctgcgatggc tttttggacg agggattcct atattttcct    158280
tcttagaaac cgtagcgggt tttcggaagc tagtggaagt ttgtaaaggc ctcgtagtgg    158340
taacctacct tgtcttctcg gtagagatga atgagaagtc gcgatccctt ggcaaatagg    158400
taacatgact tgtgggtaaa gatgtgcaac ctgtgcagac tgtaaaactg ttatatcagc    158460
cgtgctcacg gtcatgagca gctcggaccc tcacatgagt aaattatgga actaaactta    158520
aattgtcata tgcattgcat tgtgggtgtt gttattaatt taatctctta tttatttggg    158580
tcggtatcta cttatactta gtaactgcta ataaaatttt gaccaacttt aaaagtcatg    158640
ctcatcttta cccatctcct ttggtaagcc ttacacttca catgagctcc cacctttggt    158700
gagttcatac acattattcc ccacaacttg ttgagcgatg aacgtatgtg agctcaccct    158760
tgctgtactc aaatccccct ggtcaagaac aggtaccgca agatgaggag catgaaggat    158820
gtcgcgatga gttcatgaga ggtctaggcc gtcgtctcac agtaaacttt gggttgatgg    158880
atcgtcgtca tcgtatgatg taattatttta gttattttgt gcagaacttc tattatatag    158940
taaagatgtg acatttgttt ctataccatg agtcatcata tgtgtgagac tcgatcccag    159000
cacttggtga atttcgcgcc tgggttttgg acccctaaaa cccgggtgtg acatgctgct    159060
gttgagggaa ctgcctctgg aattgctact ggtgcgaaca ttggttctgg tgttggtatc    159120
cctgagggtg gatctacttg aactgctagg gtggattgcc agaaacggga gacgactgct    159180
gctcctggcc tagggtccac caatcttgcg cttttggtct tccatctcct ggcgcttcct    159240
ctcagtcatt attgccctat caatcagatg ttggaaggta gggaatgtgt ggttcatcaa    159300
ctagtagtgc aggggtcaac caaccctctc ggaaacctgt agtacctctt agcatcaatg    159360
ttgacatcct cgggtgcatt gtgagatagt tgcaggaatt tgtccatgta ctcactgaca    159420
gacaggggcc cttgcttcag tgccagaaat tcttccttcc tcactatcat caaaccttgt    159480
agaacgtggt acccgcagnn nnnnnnnnn nnnnnnnnn nnnnnnnnnn nnnnnnnnnn    159540
nnnnnnnnnn nnnnnnnnnn nnnnnnnnnn nnnnnnnnnn nnnnnnnnnn nnnnnnnncg    159600
cgcggaggcc ggtttgtcgg tgccggtttc tttcacgcaa cacgcccgct ccttttttgcc    159660
tcggtgggtc ggcctgtcag cgcagaaccg ctcgttcgcg tattcaccct cgctggcaag    159720
cggaccccac ctgtcagcca cctcccccttt ccctaaccac ccgctcgcgc accccgccgt    159780
ggatgcacac atgtcgcgtg ttttcggcc actccccccca cgcgcctgac tttttttggag    159840
cccacactca ctcgctcact cccctcgctc agtagcgtcc cacagccgac cccctcgcac    159900
ctctctctcg caccgagcgc acagccgtgg agcactgccg tagtccaccg tccgttccgt    159960
ggccgtcgtc gagttcctgt cgcgtccatt gccctactga tcttcgcctc ctcgccagca    160020
acacgagaca ccctctggtt ttccccagcc cctctatttc ccttggttcg ctcaccgac    160080
ctatcaccat gcagccgagt ctccgccacc gtccaccagg gccctcgcgg tgtcctcgcc    160140
gttgctcaag cgctctagag tcatctctcg acgtaaccaa cccacccatg cccttaattt    160200
cccatttact gccctgttgt ccatgcaatc gctcgccaga gttaagctgc gccgccgtgg    160260
```

```
ggctgctttg cctcggaccg tgctctctgg tgcctctacg ccggtgtcgt gcccatggct    160320
gagcccgccg tgtcaccctg agctcgcctg agcttttcc cagcgcccag accctcacca    160380
tggccgcgcc acgccgcgaa attgggcggc ggcgccatga gcagcctagc aaccccgccc    160440
gagcttgcca tcagatttca ggcatccatc tgagatctaa cgacctggct tcaattaaac    160500
tcgatctgat cccagctgtc cgatggagat ctggccactc ggatccgcca cctcacccgc    160560
gccctgcagc taggcccggc cagacagtcc gcctcgcccc taggtcgctg actatcctgg    160620
cccacctgtt agctcgtgct cgtgctcgcg ctcaaatcta atcctggccg ttgatctgtg    160680
atcatgcagt cgagatcagc tgataccect ttgcgtggta gttttgttaa aaaggccctc    160740
ggctttctga gaatcaaccc atcgtccctg gttttcgcac gcatgcccct gtactttgc     160800
agaaaggccc ctaatctttt aggttatcac ataattagac ctagttttgt attttgaatt    160860
ccaaaacttg tttatttcat atcttttgca tatgaactcc aaattgagtg attcaaattg    160920
caaaatgttt gtaaggttat tctctacctg tttaaattat aacctttttac tgtctgcatg    160980
tgctaatttt atgcctagac tataggttag tgtaactgat ggcttattta ttaataagaa    161040
ggataaaagg aaaaccataa tggtagttag atgtttaact ttgtgggtta ataatatgta    161100
atatatgaac ctatccctgg tataattctt ttgtctcatt aagataaatg aaattaagtt    161160
atgtaatcta ttgagataag taatacttag agaaccacaa acctatatgt gtattggtcc    161220
accctagacc ctaggcttcg cttgagtttg ttactttctt ttgaattagt gttcacttga    161280
ttgtatattt ttggtgtatt gtttctttat cattatcgaa atgtgttgaa tgcatgatcg    161340
ctttgcgtag acaacaagca gtctatggtt cctgagtgtg ttgccgaaga tcttcctggg    161400
caacaacctg gtgaaggcaa gtgtcctctg acctattatg tcctacttac ttcataattc    161460
actgtcccc tttacttaat tgaaacctaa ggtttgacta gtctgtattt atcttgtcct     161520
tgtttacctt ttgggttatt atggtaagct tcaagctatt gctccacttt aatcaacaaa    161580
catgatgcga atatttatga tatgatgttg ttattatgat tacgatgatg ttcttatggc    161640
actttaggag actcaggcta ttttcctgag taccttttcct ttggacctgc tcgttgagtg   161700
accacccgtg ataacagaac gaatcaagct gattcatcag cggccggg                 161748
```

<210> SEQ ID NO 111  
<211> LENGTH: 1348  
<212> TYPE: DNA  
<213> ORGANISM: Zea mays

<400> SEQUENCE: 111

```
tacaagaata ttgagacgtg agtacatagc attggcattt tcattagcaa gcatttcaaa     60
agaatttaat tttctcatag caatgtgata tctctcctca cgctcaattc tagttccttc    120
atgtagagca catatgtcca tccacaaatc atgacaattt ttatggtttc taactctatt    180
aaacacatct ttgcaaaggc ctctaaaaag ggtgttttg gccttagcat tccatttctc     240
atagttcaac tcttcaccta caagatttgt gggatctcta ggttcgggga atctttgtgt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagcggtt aagctaatct aagagcaaca aggctcttat accaattgaa aggatcacga    480
tgcccaagag ggggggttga attgggcttt tctaaaaatc aacactaact aaaatctaag    540
caagagccca acttcacccc gacaactagc actaagagaa taatactaga aatcaacaa     600
tgctaagata atacttcaaa tacttgctaa acaaatacac aatgtaaaat acttgaatta    660
```

```
agtgcggaat gtaaagcaag gtttagaaga ctcctccaat ttttctagag gtatcaaaga        720
gtcggcactc tcccctagtc ctcgttggag cacctgcgta agggtatcgc tctcccttgg        780
tcatcgcaag aaccaagtgc tcacaacgag atgatcattt gccactccgg cgcggtggat        840
ccctcacgac cgcttacaaa cttgagtcgg gtcaccaaca agatctccac ggtgatcacc        900
gagctcccaa cgccaccaag ccgtctaggt gatgccgatc accaagagta ataagccata        960
gactttcact tgaccaagag aagcctaatg catgcggtgt gtgctctagg tggctctcgc       1020
tagcgttaat gaggtccaaa tgcgggatta agattctcaa gtcacctcac taggctttgt       1080
ggtgcttgca atgctctacc aatgtgtagg agtaaatgtg ggcagcaaga ccatcaatat       1140
ggtaggtgga tggggtataa atagccctca cccaccaact agccattacc aggaatctgc       1200
tgcgcatggg cgcaccggac agtccggtgt gccaccggtg cgccaacggt cgactcaaac       1260
ggctagttct gacagctagc cgttggacag atggcatacc ggacagtccg atacgctgtc       1320
cggtgtgcct ctaaaattca actcacga                                          1348
```